United States Patent [19]

Christensen et al.

[11] Patent Number: 4,877,440
[45] Date of Patent: Oct. 31, 1989

[54] THIOPHENESULFONAMIDE HERBICIDES

[75] Inventors: Joel R. Christensen; John Cuomo, both of Newark; George Levitt, Wilmington, all of Del.

[73] Assignee: E. I. Du Pont de Nemours and Company, Wilmington, Del.

[21] Appl. No.: 158,985

[22] Filed: Feb. 18, 1988

Related U.S. Application Data

[63] Continuation-in-part of Ser. No. 935,504, Nov. 26, 1986, Pat. No. 4,743,290, which is a continuation-in-part of Ser. No. 852,739, Apr. 21, 1986, abandoned, which is a continuation-in-part of Ser. No. 739,074, May 29, 1985, abandoned.

[51] Int. Cl.$^4$ .................... A01N 43/66; C07D 409/12
[52] U.S. Cl. .......................................... 71/90; 71/93; 544/83; 544/113; 544/219; 544/207; 544/209; 544/212; 544/198; 544/195
[58] Field of Search ............... 71/90, 93; 544/83, 113, 544/219, 207, 209, 212, 198, 195

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,398,939 | 8/1983 | Levitt | 71/90 |
| 4,421,550 | 12/1983 | Selby et al. | 71/92 |
| 4,441,910 | 4/1984 | Shapiro | 71/90 |
| 4,481,029 | 11/1984 | Levitt | 71/93 |
| 4,518,776 | 5/1985 | Meyer et al. | 544/206 |
| 4,521,597 | 6/1985 | Kristinsson et al. | 544/3 |
| 4,549,898 | 10/1985 | Böner et al. | 71/90 |
| 4,563,211 | 1/1986 | Wexler et al. | 71/92 |
| 4,629,494 | 12/1986 | Shapiro | 71/92 |
| 4,639,264 | 1/1987 | Töpfl | 71/87 |
| 4,685,961 | 8/1987 | Töpfl et al. | 71/92 |
| 4,822,402 | 4/1989 | Kimura et al. | 71/90 |

FOREIGN PATENT DOCUMENTS

| | | |
|---|---|---|
| 30142 | 6/1981 | European Pat. Off. |
| 41404 | 12/1981 | European Pat. Off. |
| 46677 | 8/1982 | European Pat. Off. |
| 64804 | 11/1982 | European Pat. Off. |
| 73562 | 3/1983 | European Pat. Off. |
| 126711 | 5/1983 | European Pat. Off. |
| 84224 | 7/1983 | European Pat. Off. |
| 101670 | 2/1984 | European Pat. Off. |
| 125864 | 11/1984 | European Pat. Off. |
| 146263 | 6/1985 | European Pat. Off. |
| 161211 | 11/1985 | European Pat. Off. |
| 164269 | 12/1985 | European Pat. Off. |
| 165753 | 12/1985 | European Pat. Off. |
| 177163 | 4/1986 | European Pat. Off. |
| 60-278482 | 7/1986 | Japan . |
| 61-123620 | 1/1987 | Japan . |
| 62-155271 | 7/1987 | Japan . |
| 62-161783 | 7/1987 | Japan . |

Primary Examiner—John M. Ford

[57] ABSTRACT

Thiophenesulfonamides of the formula

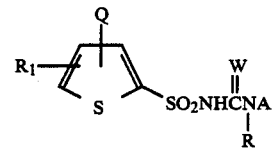

are useful as herbicides.

77 Claims, No Drawings

THIOPHENESULFONAMIDE HERBICIDES

RELATED APPLICATION

This application is a continuation-in-part of copending application U.S. Ser. No. 935,504, filed Nov. 26, 1986; now U.S. Pat. No. 4,743,290, which in turn is a continuation-in-part of U.S. Ser. No. 852,739, filed Apr. 21, 1986, now abandoned, which in turn is a continuation-in-part of U.S. Ser. No. 739,074, filed May 29, 1985, now abandoned.

TECHNICAL FIELD

This invention relates to certain novel thiophenesulfonamide compounds, to compositions containing such compounds, and to a method of use of such compositions to control the growth of undesired vegetation.

BACKGROUND OF THE INVENTION

The presence of undesired vegetation causes substantial damage to agricultural products which helps satisfy man's basic food and fiber needs. The current population explosion and concomitant world food and fiber shortage demand improved productivity in agricultural efforts since virtually all the readily available, relatively fertile cropland in developed countries has already been placed in use [Science 214, 1087, 1089 (1981)]. Preventing or minimizing loss of a portion of such valuable crops, by inhibiting the growth or killing undesired competing vegetation which is potentially damaging to crop yields [Science 215, 324 (1982)], is a significant approach to improving agricultural efficiency.

A wide variety of materials, commonly referred to as herbicides, useful for controlling the growth of undesired vegetation (by killing or inhibiting) is available. There still exists a need, however, for effective herbicides which destroy or control weeds while not significantly damaging useful crops. Efficient production on large acreage requires the extensive use of herbicides, with approximately 625 million lb. of herbicides used by American farmers in 1981 [Chemical Week, July 7, 1982, p. 36]. At the present time, no existing product provides all features deemed advantageous. Greater persistence, less soil residual, reduced application rates, reduced soil binding, greater selectivity or safety margin between weed control and crop injury, and less dependence on rainfall for activation are currently desirable features for herbicides.

U.S. Pat. Nos. 4,127,405 and 4,169,719 disclose herbicidal thiophenesulfonamides, wherein the thiophene ring may be optionally substituted with $CH_3$, Cl or Br.

U.S. Pat. No. 4,398,939 discloses herbicidal thiophenesulfonamides, wherein the thiophene ring is substituted with substituent groups selected from $C_1$-$C_4$ alkyl, $C_3$ alkenyl, $OCH_3$, $NO_2$, Cl, Br, $SO_2N(C_1$-$C_3$ alkyl$)_2$ or $SO_2N(OCH_3)CH_3$.

U.S. Pat. No. 4,481,029 discloses herbicidal thiophenesulfonamides, wherein the thiopehene ring is substituted with carboxylic acid, carboxylic ester and alkylcarbonyl groups or derivatives thereof.

U.S. Pat. No. 4,441,910 discloses herbicidal thiophenesulfonamides, wherein the thiophene ring is substituted with the group represented by $R_6S(O)_n$ wherein $R_6$ is $C_1$-$C_4$ alkyl, $C_3$-$C_4$ alkenyl, cyclopentyl or cyclopropylmethyl.

U.S. Pat. No. 4,518,776 discloses, in part, a process for the preparation of compounds of formula

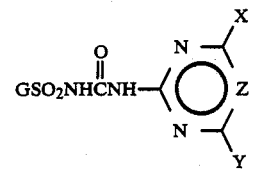

wherein
G is

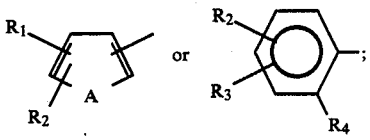

$R_1$ is H, $C_1$-$C_4$ alkyl, halogen, $NO_2$, CN, $NH_2$, $S(O)_n$-$C_1$-$C_4$ alkyl, $SO_2C_1$-$C_4$ alkoxy, $SO_2$-di-$C_1$-$C_4$ alkylamino, CHO, $CONH_2$, $DC_3$-$C_5$ alkynyl, $CODC_3$-$C_5$ alkynyl, $DC_1$-$C_4$ alkyl, $DC_3$-$C_5$ alkenyl, $COC_1$-$C_4$ alkyl, $CODC_1$-$C_4$ alkyl or $CODC_3$-$C_5$ alkenyl;

n is 1 or 2;

D is O, S, NH or $NC_1$-$C_4$ alkyl;

$R_2$ is H, halogen, $CF_3$, $NO_2$, $C_1$-$C_4$ alkyl or $C_1$-$C_4$ alkoxy;

A is O, S, $NR_5$ or —C=N—;

X is $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ alkylamino or di-$C_1$-$C_4$ alkylamino;

Y is $C_1$-$C_4$ alkyl, $C_1$-$C_4$ alkoxy or $C_1$-$C_4$ haloalkoxy; and

Z is CH or N.

EP-A No. 101,670 discloses, in part, a process for the preparation of compounds of formula

GSO$_2$NHCNH—⟨ ⟩— wherein
G is $R_1$ is H, halogen, $NO_2$, $QC_1$-$C_4$ alkyl, $C_1$-$C_4$ alkyl, $CF_3$, $SO_2$-di-$C_1$-$C_4$ alkylamino, $COQC_3$-$C_4$ alkynyl, $COQC_1$-$C_4$ alkyl or $COQC_3$-$C_5$ alkenyl optionally substituted by halogen, CN, $C_1$-$C_4$ alkoxy or $C_1$-$C_4$ alkylthio;

Q is O, $S(O)_n$, NH or $N(C_1$-$C_4$ alkyl);

n is 0, 1 or 2;

$R_2$ is H, halogen, $CF_3$, $NO_2$, $C_1$-$C_4$ alkyl or $C_1$-$C_4$ alkoxy;

A is O, S, $NR_5$ or —C=N—;

X is $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, $C_1$-$C_4$ alkylamino or di-$C_1$-$C_4$ alkylamino;

Y is $C_1$-$C_4$ alkyl, $C_1$-$C_4$ alkoxy or $C_1$-$C_4$ haloalkoxy; and

Z is CH or N.

U.S. Pat. No. 4,521,597 discloses, in part, a process for the preparation of compounds of formula

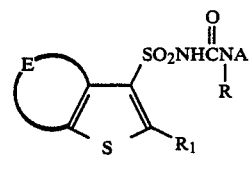

wherein
A is

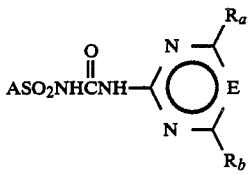

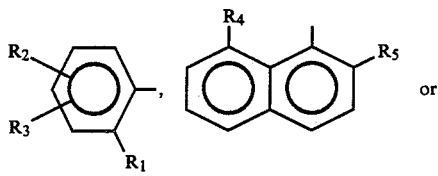

$R_3$ is H, halogen, $NO_2$, $OCH_3$ or $CF_3$;

$R_5$ is H, F, Cl, Br, $NO_2$, $C_1$-$C_5$ alkyl, $C_1$-$C_5$ alkoxy, $CF_3$, $S(O)_m C_1$-$C_5$ alkyl, $COR_7$ or $SO_2NR_8R_9$;

Y is O, S or $C(R_6)=N$;

$R_a$ is H, halogen, $C_1$-$C_5$ alkyl, $C_1$-$C_5$ haloalkyl, $C_1$-$C_5$ alkoxy, $C_1$-$C_5$ haloalkoxy, $C_1$-$C_5$ alkylthio, $C_2$-$C_{10}$ alkoxyalkyl or $C_2$-$C_{10}$ alkoxyalkoxy;

$R_b$ is the same as $R_a$ or $NR_c R_d$; and

E is CH or N.

U.S. Pat. No. 4,549,898 discloses herbicidal sulfonylureas of formula

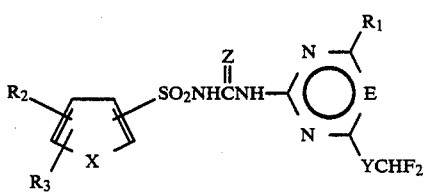

wherein
X is O, S, $NR_4$ or $C(R_5)=N$;
Y is O or S;
Z is O or S;
E is N or CH;
$R_1$ is H, $C_1$-$C_4$ alkyl, $C_1$-$C_4$ haloalkyl, $C_1$-$C_4$ haloalkoxy, $C_1$-$C_4$ alkoxy, halogen, $C_1$-$C_4$ alkylthio, $NR_6R_7$ or alkoxyalkyl containing not more than 4 carbon atoms;
$R_2$ is H, $C_1$-$C_3$ alkyl, $C_1$-$C_3$ haloalkyl, halogen, $NO_2$, $C_1$-$C_3$ alkoxy, $C(W)R_8$, $SO_2NR_6R_7$, $S(O)_n$-$C_1$-$C_3$ alkyl or $COR_9$;
$R_3$ is H, halogen, $C_1$-$C_3$ alkyl, $OCH_3$ or $CF_3$;

$R_5$ is H, $NO_2$, F, Cl, Br, $CH_3$, $CF_3$, $S(O)_n C_1$-$C_3$ alkyl, $COC_1$-$C_4$ alkoxy or $C_1$-$C_3$ alkoxy;
$R_6$ is H, $C_1$-$C_6$ alkyl, $C_1$-$C_4$ cyanoalkyl, methoxy or ethoxy; and
$R_7$ is H, $C_1$-$C_6$ alkyl or $C_3$-$C_6$ alkenyl.

EP-A No. 146,263 published June 26, 1985, discloses herbicidal thiophenesulfonamides represented by the following generic formulae.

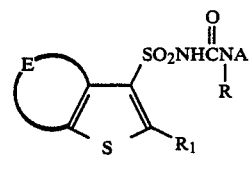

and

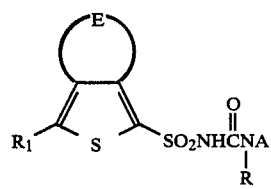

EP-A No. 165,753 published Dec. 27, 1985, discloses herbicidal thiophenesulfonamides substituted with 5- and 6-membered heterocyclic rings.

EP-A No. 177,163 published Apr. 9, 1986 discloses herbicidal thiophenesulfonamides substituted with acetal and ketal groups.

U.S. Pat. No. 4,421,550 discloses in part herbicidal thiophenesulfonamides of the formula

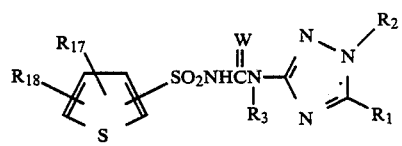

wherein
$R_{17}$ is H, F, Cl, Br, $CH_3$ or $OCH_3$; and
$R_{18}$ is H, $C_1$-$C_4$ alkyl, $C_1$-$C_4$ alkoxy, F, Cl, Br, $NO_2$, $CO_2R_{10}$, $SO_2NR_{10}R_{11}$, $SO_2N(OCH_3)CH_3$ or $S(O)_n R_{13}$.

EP-A No. 84,224 published July 27, 1983 discloses, in part, herbicidal thiophenesulfonamides of the formula

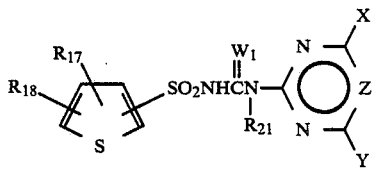

wherein
$R_{17}$ is H, F, Cl, Br, $CH_3$ or $OCH_3$; and
$R_{18}$ is H, $C_1$-$C_4$ alkyl, $C_1$-$C_4$ alkoxy, F, Cl, Br, $NO_2$, $CO_2R_9$, $SO_2NR_{10}R_{11}$, $SO_2N(OCH_3)CH_3$ or $S(O)_n R_{13}$.

SUMMARY OF THE INVENTION

This application pertains to novel compounds of Formula I, agriculturally suitable compositions containing them and their method-of-use as preemergent and/or postemergent herbicides or plant growth regulants.

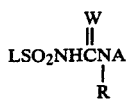

wherein
L is

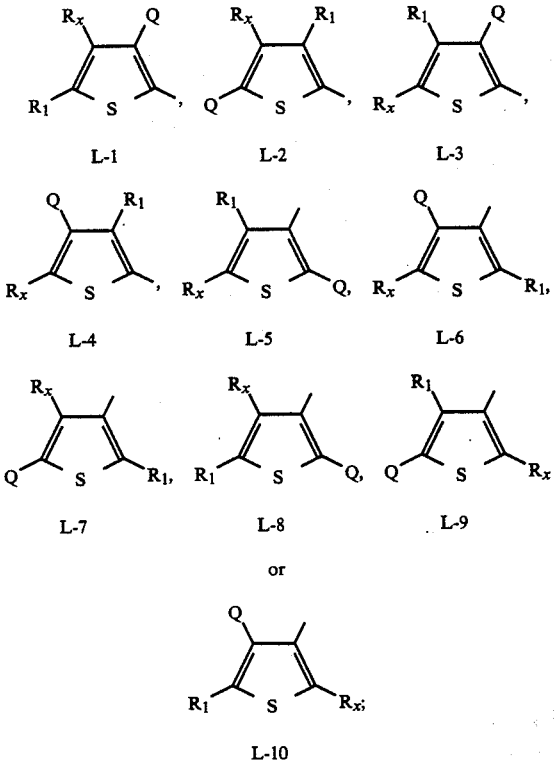

or

R is H or $CH_3$;
W is O or S;
$R_1$ is $R_1'$ or $R_1''$;
$R_x$ is H or halogen;
$R_1'$ is H, $C_1$–$C_3$ alkyl, $C_1$–$C_3$ haloalkyl, halogen, nitro, $C_1$–$C_3$ alkoxy, CN, $C_1$–$C_3$ haloalkoxy or $C_1$–$C_3$ haloalkylthio;
$R_1''$ is $SO_2NR_aR_b$, $C_1$–$C_3$ alkylthio, $C_1$–$C_3$ alkylsulfinyl, $C_1$–$C_3$ alkylsulfonyl, $CO_2R_c$ or $C(O)NR_gR_h$;
$R_a$ is H, $C_1$–$C_4$ alkyl, $C_2$–$C_3$ cyanoalkyl, methoxy, ethoxy or $C_3$–$C_4$ alkenyl;
$R_b$ is H or $C_1$–$C_3$ alkyl; or
$R_a$ and $R_b$ may be taken together to form $(CH_2)_3$, $(CH_2)_4$, $(CH_2)_5$ or $CH_2CH_2OCH_2CH_2$;
$R_c$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, cyclopropylmethyl or $C_2$–$C_4$ alkoxyalkyl;
$R_g$ is H or $C_1$–$C_3$ alkyl;
$R_h$ is $C_1$–$C_3$ alkyl;
Q is $Q_1$ or $Q_2$;
$Q_1$ is $ER_2$, $NR_3R_4$,

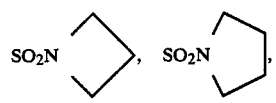

$OSO_2R_7$, $C_1$–$C_4$ haloalkyl, CN, $SO_2NHR_{21}$,

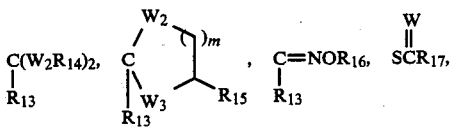

$SO_2NR_{22}NR_{23}R_{24}$ or $C_1$–$C_4$ alkyl substituted with $R_8$;
E is O, S, SO or $SO_2$;
$W_1$ is O or S;
J is O, S, NH, $NCH_3$, $CH_2$ or a single bond;
$Q_2$ is $SO_2NH_2$, $SO_2NR_iR_j$, $CO_2R_k$, $C(O)NR_mR_n$, $C_1$–$C_3$ alkylthio, $C_1$–$C_3$ alkylsulfinyl, $C_1$–$C_3$ alkylsulfonyl, halogen, CHO or $CR_p$=$NOR_q$;
$R_i$ is $C_1$–$C_4$ alkyl, $C_2$–$C_3$ cyanoalkyl, methoxy, ethoxy or $C_3$–$C_4$ alkenyl;
$R_j$ is $C_1$–$C_3$ alkyl or
$R_i$ and $R_j$ may be taken together to form $(CH_2)_5$ or $CH_2CH_2OCH_2CH_2$;
$R_k$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, cyclopropylmethyl or $C_2$–$C_4$ alkoxyalkyl;
$R_m$ is H or $C_1$–$C_3$ alkyl;
$R_n$ is $C_1$–$C_3$ alkyl;
$R_p$ is H, $C_1$–$C_4$ alkyl or $C_1$–$C_4$ haloalkyl;
$R_q$ is H, $C_1$–$C_4$ alkyl, $C_3$–$C_4$ alkenyl or $C_3$–$C_4$ alkynyl;
$R_2$ is $C_1$–$C_6$ alkyl substituted with $R_8$, $C_2$–$C_6$ alkenyl substituted with $R_8$, $C_3$–$C_6$ alkynyl, $C_3$–$C_6$ alkynyl substituted with $R_8$, $C_1$–$C_6$ haloalkyl, $C_2$–$C_6$ haloalkenyl or $C_3$–$C_6$ haloalkynyl;
$R_3$ is $C_1$–$C_4$ alkyl;
$R_4$ is H or $C_1$–$C_4$ alkyl; or
$R_3$ and $R_4$ may be taken together to form $(CH_2)_4$, $(CH_2)_5$ or $CH_2CH_2OCH_2CH_2$;
$R_5$ and $R_6$ are independently $C_1$–$C_2$ alkyl, $C_1$–$C_2$ alkoxy, $C_1$–$C_2$ alkylthio, $C_1$–$C_2$ alkylamino or di($C_1$–$C_2$ alkyl)amino;
$R_7$ is $C_1$–$C_4$ alkyl, $C_1$–$C_4$ haloalkyl, $C_3$–$C_4$ alkenyl, $C_3$–$C_4$ haloalkenyl, $C_3$–$C_4$ alkynyl, $C_3$–$C_4$ haloalkynyl or $NR_{19}R_{20}$;
$R_8$ is $OR_9$, $S(O)_nR_{10}$, $CO_2R_{10}$, $SO_2NR_{11}R_{12}$, $NR_{11}R_{12}$, $CONR_{11}R_{12}$, $C(O)R_{13}$, $C(W_2R_{14})_2$, CN, SCN, SH, $NO_2$ or $N_3$;
$R_9$ is H, $C_1$–$C_4$ alkyl, $C_3$–$C_4$ alkenyl, $C_3$–$C_4$ alkynyl, $C_1$–$C_4$ haloalkyl, $C_3$–$C_4$ haloalkenyl, $C_3$–$C_4$ haloalkynyl, $C_2$–$C_4$ alkylcarbonyl, $C_1$–$C_4$ alkylsulfonyl, $C_2$–$C_4$ alkoxyalkyl, $C_2$–$C_4$ alkylthioalkyl or $C_2$–$C_4$ cyanoalkyl;
$R_{10}$ is $C_1$–$C_4$ alkyl, $C_3$–$C_4$ alkenyl, $C_3$–$C_4$ alkynyl, $C_1$–$C_4$ haloalkyl, $C_3$–$C_4$ haloalkenyl, $C_3$–$C_4$ haloalkynyl, $C_2$–$C_4$ alkoxyalkyl, $C_2$–$C_4$ alkylthioalkyl or $C_2$–$C_4$ cyanoalkyl;
$R_{11}$ is H or $C_1$–$C_3$ alkyl;
$R_{12}$ is H, $C_1$–$C_4$ alkyl, $C_1$–$C_4$ haloalkyl, $C_3$–$C_6$ cycloalkyl, $C_2$–$C_4$ alkoxyalkyl, $C_2$–$C_4$ alkylthioalkyl, $C_2$–$C_4$ cyanoalkyl, $C_1$–$C_3$ alkoxy, $C_3$–$C_4$ alkenyl or $C_3$–$C_4$ alkynyl; or $R_{11}$ and $R_{12}$ may be taken together to form $(CH_2)_3$, $(CH_2)_4$, $(CH_2)_5$ or $CH_2CH_2OCH_2CH_2$;

$R_{13}$ is H, $C_1-C_4$ alkyl or $C_1-C_4$ haloalkyl;

$R_{14}$ is $C_1-C_2$ alkyl;

$R_{15}$ is H or $CH_3$;

$R_{16}$ is H, $C_1-C_4$ alkyl, $C_3-C_4$ alkenyl or $C_3-C_4$ alkynyl;

$R_{17}$ is $C_1-C_4$ alkyl, $C_1-C_4$ alkoxy, $C_1-C_4$ alkylthio, $C_1-C_4$ alkylamino or di($C_1-C_4$ alkyl)amino;

$R_{19}$ is H, $C_1-C_3$ alkyl, $C_3-C_4$ alkenyl or $C_3-C_4$ alkynyl;

$R_{20}$ is H or $C_1-C_3$ alkyl; or $R_{19}$ and $R_{20}$ may be taken together to form $(CH_2)_4$, $(CH_2)_5$ or $CH_2CH_2OCH_2CH_2$;

$R_{21}$ is $C_1-C_4$ alkyl, $C_1-C_3$ haloalkyl, $C_2-C_3$ cyanoalkyl, cyclopropyl, $C_3-C_4$ alkenyl, $C_3-C_4$ alkynyl, $C_2-C_4$ alkoxyalkyl or $C_1-C_2$ alkoxy;

$R_{22}$ is H or $C_1-C_4$ alkyl;

$R_{23}$ is H or $C_1-C_4$ alkyl;

$R_{24}$ is H, $C_1-C_4$ alkyl, $C_3-C_4$ alkenyl, $C_3-C_4$ alkynyl, $C_1-C_4$ haloalkyl or phenyl which may be optionally substituted with $R_{25}$; or $R_{23}$ and $R_{24}$ may be taken together to form $(CH_2)_4$, $(CH_2)_5$ or $CH_2CH_2OCH_2CH_2$;

$R_{25}$ is H, $CH_3$, Cl, F, Br, $NO_2$, $CF_3$, CN or $OCH_3$;

m is 1 or 2;

n is 0, 1 or 2;

$W_2$ and $W_3$ are independently O or S;

A is

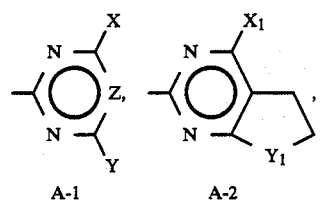

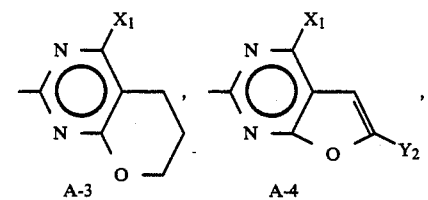

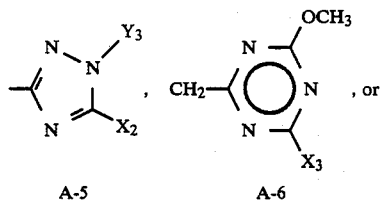

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino or di($C_1-C_3$ alkyl)amino;

Y is H, $C_1-C_4$ alkyl, $C_1-C_4$ alkoxy, $C_1-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_4-C_5$ cycloalkyl, $C_2-C_4$ alkynyl, cyano,

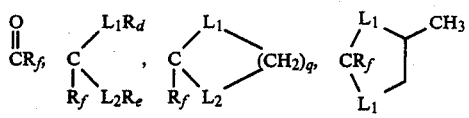

q is 2 or 3;

$L_1$ and $L_2$ are independently O or S;

$R_d$ and $R_e$ are independently $C_1-C_2$ alkyl;

$R_f$ is H or $CH_3$;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$;

$X_3$ is $CH_3$ or $OCH_3$;

$X_4$ is $CH_3$, $OCH_3$, $OC_2H_5$, $CH_2OCH_3$ or Cl; and $Y_4$ is $CH_3$, $OCH_3$, $OC_2H_5$ or Cl;

and their agriculturally suitable salts; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when X or Y is $C_1$ haloalkoxy, then Z is CH;

(c) when $Q_1$ is $CF_3$, then A is A-4, A-5, A-6 or A-7;

(d) when E is O or S and $R_9$ is H, then $R_2$ is other than $CH_2OR_9$;

(e) when W is S, then A is A-1, R is H and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

(f) the total number of carbon atoms in $R_1$ and Q is less than or equal to 10;

(g) when $Q_1$ is $C_1-C_4$ haloalkyl or

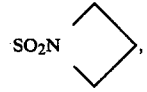

then X and Y are other than $OCF_2H$ or $SCF_2H$;

(h) $X_4$ and $Y_4$ cannot simultaneously be Cl;

(i) when $R_1$ is $R_1'$ then L is L-1, L-3, L-5, L-6, L-8 or L-10;

(j) the total number of carbon atoms in $R_{22}$, $R_{23}$ and $R_{24}$ is less than or equal to 10;

(k) when $R_{21}$ is $C_1-C_4$ alkyl, $C_2-C_3$ cyanoalkyl, $C_1-C_2$ alkoxy or $C_3-C_4$ alkenyl, then X and Y are other than $OCF_2H$ or $SCF_2H$;

(l) when Y is CN and $R_1'$ is H, F, Cl or $CH_3$, then $R_{21}$ is other than $C_1-C_3$ alkyl;

(m) when $R_1$ is $R_1'$ then Q is $Q_1$;

(n) when $R_1$ is $R_1''$ then Q is $Q_1$ or $Q_2$;

(o) when $Q_2$ is halogen then $R_x$ is halogen;

(p) when $R_1''$ is $SO_2NR_aR_b$, $CO_2R_c$ or $C(O)NR_gR_h$ when Q is $SO_2NHR_{21}$,

$SO_2NR_{22}NR_{23}R_{24}$, $SO_2NH_2$, $SO_2NR_iR_j$, $CO_2R_k$, $C(O)NR_mR_n$ or CHO then L is L-1, L-2, L-5 or L-6; and (q) when $Q_2$ is halogen then L is L-2, L-4, L-5, L-6, L-7 or L-9.

Another aspect of this invention relates to a composition suitable for controlling the growth of undesired vegetation which comprises a herbicidally effective amount of a compound of formula I and a diluent, surfactant, or mixture thereof. Yet another aspect of the invention relates to a method for the control of undesired vegetation which comprises applying to the locus of the undesired vegetation a herbicidally effective amount of the compounds of formula I.

Preferred compounds for reasons of their higher herbicidal activity, greater plant growth regulant activity or more favorable ease of synthesis are:

(1) Compounds of Formula I wherein
  R is $R_1'$;
  $R_1'$ is H, $CH_3$, Cl, Br, $OCH_3$ or $C_1$ haloalkyl;
  X is $CH_3$, $OCH_3$, $OCH_2CH_3$, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
  Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $CH_2SCH_2CH_3$, $OCH_2CH_2OCH_3$,

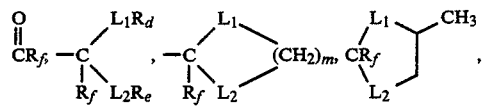

$OCF_2H$, $SCF_2H$, $C\equiv CH$ or $C\equiv CCH_3$.

(2) Compounds of Preferred 1 where A is A-1 and W is 0.

(3) Compounds of Preferred 2 where L is L-1 or L-3.

(4) Compounds of Preferred 2 where L is L-5, L-6, L-8 or L-10.

(5) Compounds of Preferred 3 where
  $Q_1$ is $ER_2$,

$C_1$–$C_2$ alkyl substituted with $R_8$, $C_1$–$C_2$ haloalkyl, CN, $SO_2NHC_1$–$C_2$ alkyl, $SO_2NH$cyclopropyl or

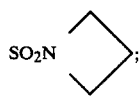

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;
$R_5$ and $R_6$ are independently $CH_3$, $OCH_3$ or $SCH_3$;
$R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl$)_2$, $C(O)CH_3$, CN or $C(O)N(CH_3)_2$; and
$R_9$ is H, $C_1$–$C_2$ alkyl or $C_2$–$C_3$ cyanoalkyl.

(6) Compounds of Preferred 5 where
  X is $CH_3$, $OCH_3$, $OCH_2CH_3$, Cl, $OCF_2H$ or $OCH_2CF_3$;
  Y is $CH_3$, $OCH_3$, $C_2H_5$, $CH_2OCH_3$, $NHCH_3$ or $CH(OCH_3)_2$;
  $Q_1$ is $ER_2$, $C_1$–$C_2$ alkyl substituted with $R_8$ or $C_1$–$C_2$ haloalkyl, CN or $SO_2NHC_1$–$C_2$ alkyl;
  E is S or $SO_2$;
  $R_2$ is $C_1$–$C_2$ alkyl substituted with $R_8$ or $C_1$–$C_2$ haloalkyl; and
  $R_8$ is $CH_3O$, $CH_3CH_2O$, $CH_3S$, $CH_3SO_2$, $SO_2N(CH_3)_2$ or $CO_2CH_3$.

(7) Compounds of Preferred 4 where
  $Q_1$ is $ER_2$,

$C_1$–$C_2$ alkyl substituted with $R_8$, $C_1$–$C_2$ haloalkyl, CN, $SO_2NHC_1$–$C_2$ alkyl, $SO_2NH$cyclopropyl or

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;
$R_5$ and $R_6$ are independently $CH_3$, $OCH_3$ or $SCH_3$;
$R_8$ is $OR_9$, $C_1$–$C_2$ alkylthio, $C_1$–$C_2$ alkylsulfinyl, $C_1$–$C_2$alkylsulfonyl, $CO_2(C_1$–$C_2$ alkyl), $SO_2N(C_1$–$C_2$ alkyl$)_2$, $C(O)CH_3$, CN or $C(O)N(CH_3)_2$; and
$R_9$ is H, $C_1$–$C_2$ alkyl or $C_2$–$C_3$ cyanoalkyl.

(8) Compounds of Preferred 7 where
  X is $CH_3$, $OCH_3$, $OCH_2CH_3$, Cl, $OCF_2H$ or $OCH_2CF_3$;
  Y is $CH_3$, $OCH_3$, $C_2H_5$, $CH_2OCH_3$, $NHCH_3$ or $CH(OCH_3)_2$;
  $Q_1$ is $ER_2$, $C_1$–$C_2$ alkyl substituted with $R_8$ or $C_1$–$C_2$ haloalkyl, CN or $SO_2NHC_1$–$C_2$ alkyl;
  E is S or $SO_2$;
  $R_2$ is $C_1$–$C_2$ alkyl substituted with $R_8$ or $C_1$–$C_2$ haloalkyl; and
  $R_8$ is $CH_3O$, $CH_3CH_2O$, $CH_3S$, $CH_3SO_2$, $SO_2N(CH_3)_2$ or $CO_2CH_3$.

(9) Compounds of Formula I wherein
  $R_1$ is $R_1''$;
  X is $CH_3$, $OCH_3$, $OCH_2CH_3$, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
  Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $CH_2SCH_2CH_3$, $OCH_2CH_2OCH_3$,

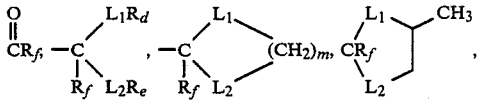

$OCF_2H$, $SCF_2H$, $C\equiv CH$ or $C\equiv CCH_3$.

(10) Compounds of Preferred 9 where W is O.
(11) Compounds of Preferred 10 where L is L-1.
(12) Compounds of Preferred 10 where L is L-2.
(13) Compounds of Preferred 10 where L is L-3.
(14) Compounds of Preferred 10 where L is L-4.
(15) Compounds of Preferred 10 where L is L-5.
(16) Compounds of Preferred 10 where L is L-6.
(17) Compounds of Preferred 10 where L is L-7.
(18) Compounds of Preferred 10 where L is L-8.
(19) Compounds of Preferred 10 where L is L-9.
(20) Compounds of Preferred 10 where L is L-10.
(21) Compounds of Preferred 11 where
   $Q_1$ is $ER_2$, $$\underset{CH_2PR_5R_6,}{\overset{O\quad\ O}{\underset{\|\quad\ \|}{}}} \underset{PR_5R_6,}{\overset{O\quad\ O}{\underset{\|\quad\ \|}{}}}$$

$C_1$–$C_2$ alkyl substituted with $R_8$, $C_1$–$C_2$ haloalkyl, CN, $SO_2NHC_1$–$C_2$ alkyl, $SO_2NH$cyclopropyl or $$SO_2N{\triangleright};$$

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;
   $R_5$ and $R_6$ are independently $CH_3$, $OCH_3$ or $SCH_3$;
   $R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and
   $R_9$ is H, $C_1$–$C_2$ alkyl or $C_2$–$C_3$ cyanoalkyl.
(22) Compounds of Preferred 21 where
   $Q_1$ is $ER_2$, $C_1$–$C_2$ alkyl substituted with $R_8$ or $C_1$–$C_2$ haloalkyl, CN or $SO_2NHC_1$–$C_2$ alkyl;
   E is S or $SO_2$;
   $R_2$ is $C_1$–$C_2$ alkyl substituted with $R_8$ or $C_1$–$C_2$ haloalkyl;
   $R_8$ is $CH_3O$, $CH_3CH_2O$, $CH_3S$, $CH_3SO_2$, $SO_2N(CH_3)_2$ or $CO_2CH_3$;
   $Q_2$ is $SO_2NR_iR_j$, $CO_2R_k$, $C(O)NR_mR_n$, $C_1$–$C_3$ alkylthio, $C_1$–$C_3$ alkylsulfinyl or $C_1$–$C_3$ alkylsulfonyl;
   $R_a$ is H or $C_1$–$C_2$ alkyl;
   $R_b$ is $C_1$–$C_2$ alkyl;
   $R_c$ and $R_k$ are independently $C_1$–$C_3$ alkyl, allyl, $CH_2CH_2Cl$ or $CH_2CH_2OCH_3$;
   $R_g$ is H or $C_1$–$C_2$ alkyl;
   $R_h$ is $CH_3$;
   $R_i$ is $C_1$–$C_2$ alkyl; and
   $R_j$ is $C_1$–$C_2$ alkyl.
(23) Compounds of Preferred 22 where
   A is A-1;
   X is $CH_3$, $OCH_3$, $OCH_2CH_3$, Cl, $OCF_2H$ or $OCH_2CF_3$; and
   Y is $CH_3$, $OCH_3$, $C_2H_5$, $CH_2OCH_3$, $NHCH_3$ or $CH(OCH_3)_2$.
(24) Compounds of Preferred 12 where
   $Q_1$ is $ER_2$, $$\underset{CH_2PR_5R_6,}{\overset{O\quad\ O}{\underset{\|\quad\ \|}{}}} \underset{PR_5R_6,}{\overset{O\quad\ O}{\underset{\|\quad\ \|}{}}}$$

$C_1$–$C_2$ alkyl substituted with $R_8$, $C_1$–$C_2$ haloalkyl, CN, $SO_2NHC_1$–$C_2$ alkyl, $SO_2NH$cyclopropyl or $$SO_2N{\triangleright};$$

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;
   $R_5$ and $R_6$ are independently $CH_3$, $OCH_3$ or $SCH_3$;
   $R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and
   $R_9$ is H, $C_1$–$C_2$ alkyl or $C_2$–$C_3$ cyanoalkyl.
(25) Compounds of Preferred 24 where
   $Q_1$ is $ER_2$, $C_1$–$C_2$ alkyl substituted with $R_8$ or $C_1$–$C_2$ haloalkyl, CN or $SO_2NHC_1$–$C_2$ alkyl;
   E is S or $SO_2$;
   $R_2$ is $C_1$–$C_2$ alkyl substituted with $R_8$ or $C_1$–$C_2$ haloalkyl;
   $R_8$ is $CH_3O$, $CH_3CH_2O$, $CH_3S$, $CH_3SO_2$, $SO_2N(CH_3)_2$ or $CO_2CH_3$;
   $Q_2$ is $SO_2NR_iR_j$, $CO_2R_k$, $C(O)NR_mR_n$, $C_1$–$C_3$ alkylthio, $C_1$–$C_3$ alkylsulfinyl or $C_1$–$C_3$ alkylsulfonyl;
   $R_a$ is H or $C_1$–$C_2$ alkyl;
   $R_b$ is $C_1$–$C_2$ alkyl;
   $R_c$ and $R_k$ are independently $C_1$–$C_3$ alkyl, allyl, $CH_2CH_2Cl$ or $CH_2CH_2OCH_3$;
   $R_g$ is H or $C_1$–$C_2$ alkyl;
   $R_h$ is $CH_3$;
   $R_i$ is $C_1$–$C_2$ alkyl; and
   $R_j$ is $C_1$–$C_2$ alkyl.
(26) Compounds of Preferred 25 where
   A is A-1;
   X is $CH_3$, $OCH_3$, $OCH_2CH_3$, Cl, $OCF_2H$ or $OCH_2CF_3$; and
   Y is $CH_3$, $OCH_3$, $C_2H_5$, $CH_2OCH_3$, $NHCH_3$ or $CH(OCH_3)_2$.
(27) Compounds of Preferred 13 where
   $Q_1$ is $ER_2$, $$\underset{CH_2PR_5R_6,}{\overset{O\quad\ O}{\underset{\|\quad\ \|}{}}} \underset{PR_5R_6,}{\overset{O\quad\ O}{\underset{\|\quad\ \|}{}}}$$

$C_1$–$C_2$ alkyl substituted with $R_8$, $C_1$–$C_2$ haloalkyl, CN, $SO_2NHC_1$–$C_2$ alkyl, $SO_2NH$cyclopropyl or $$SO_2N{\triangleright};$$

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;
   $R_5$ and $R_6$ are independently $CH_3$, $OCH_3$ or $SCH_3$;
   $R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and
   $R_9$ is H, $C_1$–$C_2$ alkyl or $C_2$–$C_3$ cyanoalkyl.
(28) Compounds of Preferred 27 where
   $Q_1$ is $ER_2$, $C_1$–$C_2$ alkyl substituted with $R_8$ or $C_1$–$C_2$ haloalkyl, CN or $SO_2NHC_1$–$C_2$ alkyl;
   E is S or $SO_2$;
   $R_2$ is $C_1$–$C_2$ alkyl substituted with $R_8$ or $C_1$–$C_2$ haloalkyl;
   $R_8$ is $CH_3O$, $CH_3CH_2O$, $CH_3S$, $CH_3SO_2$, $SO_2N(CH_3)_2$ or $CO_2CH_3$;

(29) Compounds of Preferred 28 where
  A is A-1;
  X is $CH_3$, $OCH_3$, $OCH_2CH_3$, Cl, $OCF_2H$ or $OCH_2CF_3$; and
  Y is $CH_3$, $OCH_3$, $C_2H_5$, $CH_2OCH_3$, $NHCH_3$ or $CH(OCH_3)_2$.
(30) Compounds of Preferred 14 where
  $Q_1$ is $ER_2$,

$C_1-C_2$ alkyl substituted with $R_8$, $C_1-C_2$ haloalkyl, CN, $SO_2NHC_1-C_2$ alkyl, $SO_2NH$cyclopropyl or

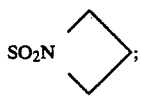

$R_2$ is $C_1-C_3$ alkyl substituted with $R_8$, $C_1-C_3$ haloalkyl, $C_2-C_3$ haloalkenyl or $C_3-C_4$ alkynyl;
  $R_5$ and $R_6$ are independently $CH_3$, $OCH_3$ or $SCH_3$;
  $R_8$ is $OR_9$, $C_1-C_2$ alkylthio, $C_1-C_2$ alkylsulfinyl, $C_1-C_2$ alkylsulfonyl, $CO_2(C_1-C_2$ alkyl), $SO_2N(C_1-C_2$ alkyl$)_2$, $C(O)CH_3$, CN or $C(O)N(CH_3)_2$; and
  $R_9$ is H, $C_1-C_2$ alkyl or $C_2-C_3$ cyanoalkyl.
(31) Compounds of Preferred 30 where
  $Q_1$ is $ER_2$, $C_1-C_2$ alkyl substituted with $R_8$ or $C_1-C_2$ haloalkyl, CN or $SO_2NHC_1-C_2$ alkyl;
  E is S or $SO_2$;
  $R_2$ is $C_1-C_2$ alkyl substituted with $R_8$ or $C_1-C_2$ haloalkyl;
  $R_8$ is $CH_3O$, $CH_3CH_2O$, $CH_3S$, $CH_3SO_2$, $SO_2N(CH_3)_2$ or $CO_2CH_3$;
  $Q_2$ is $SO_2NR_iR_j$, $CO_2R_k$, $C(O)NR_mR_n$, $C_1-C_3$ alkylthio, $C_1-C_3$ alkylsulfinyl or $C_1-C_3$ alkylsulfonyl;
  $R_a$ is H or $C_1-C_2$ alkyl;
  $R_b$ is $C_1-C_2$ alkyl;
  $R_c$ and $R_k$ are independently $C_1-C_3$ alkyl, allyl, $CH_2CH_2Cl$ or $CH_2CH_2OCH_3$;
  $R_g$ is H or $C_1-C_2$ alkyl;
  $R_h$ is $CH_3$;
  $R_i$ is $C_1-C_2$ alkyl; and
  $R_j$ is $C_1-C_2$ alkyl.
(32) Compounds of Preferred 31 where
  A is A-1;
  X is $CH_3$, $OCH_3$, $OCH_2CH_3$, Cl, $OCF_2H$ or $OCH_2CF_3$; and
  Y is $CH_3$, $OCH_3$, $C_2H_5$, $CH_2OCH_3$, $NHCH_3$ or $CH(OCH_3)_2$.
(33) Compounds of Preferred 15 where
  $Q_1$ is $ER_2$,

$C_1-C_2$ alkyl substituted with $R_8$, $C_1-C_2$ haloalkyl, CN, $SO_2NHC_1-C_2$ alkyl. $SO_2NH$cyclopropyl or

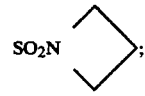

$R_2$ is $C_1-C_3$ alkyl substituted with $R_8$, $C_1-C_3$ haloalkyl, $C_2-C_3$ haloalkenyl or $C_3-C_4$ alkynyl;
  $R_5$ and $R_6$ are independently $CH_3$, $OCH_3$ or $SCH_3$;
  $R_8$ is $OR_9$, $C_1-C_2$ alkylthio, $C_1-C_2$ alkylsulfinyl, $C_1-C_2$ alkylsulfonyl, $CO_2(C_1-C_2$ alkyl), $SO_2N(C_1-C_2$ alkyl$)_2$, $C(O)CH_3$, CN or $C(O)N(CH_3)_2$; and
  $R_9$ is H, $C_1-C_2$ alkyl or $C_2-C_3$ cyanoalkyl.
(34) Compounds of Preferred 33 where
  $Q_1$ is $ER_2$, $C_1-C_2$ alkyl substituted with $R_8$ or $C_1-C_2$ haloalkyl, CN or $SO_2NHC_1-C_2$ alkyl;
  E is S or $SO_2$;
  $R_2$ is $C_1-C_2$ alkyl substituted with $R_8$ or $C_1-C_2$ haloalkyl;
  $R_8$ is $CH_3O$, $CH_3CH_2O$, $CH_3S$, $CH_3SO_2$, $SO_2N(CH_3)_2$ or $CO_2CH_3$;
  $Q_2$ is $SO_2NR_iR_j$, $CO_2R_k$, $C(O)NR_mR_n$, $C_1-C_3$ alkylthio, $C_1-C_3$ alkylsulfinyl or $C_1-C_3$ alkylsulfonyl;
  $R_a$ is H or $C_1-C_2$ alkyl;
  $R_b$ is $C_1-C_2$ alkyl;
  $R_c$ and $R_k$ are independently $C_1-C_3$ alkyl, allyl, $CH_2CH_2Cl$ or $CH_2CH_2OCH_3$;
  $R_g$ is H or $C_1-C_2$ alkyl;
  $R_h$ is $CH_3$;
  $R_i$ is $C_1-C_2$ alkyl; and
  $R_j$ is $C_1-C_2$ alkyl.
(35) Compounds of Preferred 34 where
  A is A-1;
  x is $CH_3$, $OCH_3$, $OCH_2CH_3$, Cl, $OCF_2H$ or $OCH_2CF_3$; and
  Y is $CH_3$, $OCH_3$, $C_2H_5$, $CH_2OCH_3$, $NHCH_3$ or $CH(OCH_3)_2$.
(36) Compounds of Preferred 16 where
  $Q_1$ is $ER_2$,

$C_1-C_2$ alkyl substituted with $R_8$, $C_1-C_2$ haloalkyl, CN, $SO_2NHC_1-C_2$ alkyl, $SO_2NH$cyclopropyl or

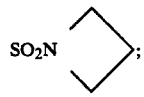

$R_2$ is $C_1-C_3$ alkyl substituted with $R_8$, $C_1-C_3$ haloalkyl, $C_2-C_3$ haloalkenyl or $C_3-C_4$ alkynyl;
  $R_5$ and $R_6$ are independently $CH_3$, $OCH_3$ or $SCH_3$;
  $R_8$ is $OR_9$, $C_1-C_2$ alkylthio, $C_1-C_2$ alkylsulfinyl, $C_1-C_2$ alkylsulfonyl, $CO_2(C_1-C_2$ alkyl), $SO_2N(C_1-C_2$ alkyl$)_2$, $C(O)CH_3$, CN or $C(O)N(CH_3)_2$; and
  $R_9$ is H, $C_1-C_2$ alkyl or $C_2-C_3$ cyanoalkyl.
(37) Compounds of Preferred 36 where $Q_1$ is $ER_2$, $C_1$-$C_2$ alkyl substituted with $R_8$ or $C_1$-$C_2$ haloalkyl, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

(38) Compounds of Preferred 37 where
A is A-1;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

(39) Compounds of Preferred 17 where
$Q_1$ is $ER_2$,

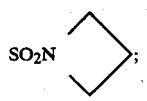

$C_1$-$C_2$ alkyl substituted with $R_8$, $C_1$-$C_2$ haloalkyl, CN, $SO_2NHC_1$-$C_2$ alkyl, $SO_2NH$cyclopropyl or $R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl$)_2$, $C(O)CH_3$, CN or $C(O)N(CH_3)_2$; and
$R_9$ is H, $C_1$-$C_2$ alkyl or $C_2$-$C_3$ cyanoalkyl.

(40) Compounds of Preferred 39 where
$Q_1$ is $ER_2$, $C_1$-$C_2$ alkyl substituted with $R_8$ or $C_1$-$C_2$ haloalkyl, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

(41) Compounds of Preferred 40 where
A is A-1;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

(42) Compounds of Preferred 18 where
$Q_1$ is $ER_2$,

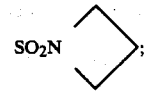

$C_1$-$C_2$ alkyl substituted with $R_8$, $C_1$-$C_2$ haloalkyl, CN, $SO_2NHC_1$-$C_2$ alkyl, $SO_2NH$cyclopropyl or $R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl$)_2$, $C(O)CH_3$, CN or $C(O)N(CH_3)_2$; and
$R_9$ is H, $C_1$-$C_2$ alkyl or $C_2$-$C_3$ cyanoalkyl.

(43) Compounds of Preferred 42 where
$Q_1$ is $ER_2$, $C_1$-$C_2$ alkyl substituted with $R_8$ or $C_1C_2$ haloalkyl, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

(44) Compounds of Preferred 43 where
A is A-1;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

(45) Compounds of Preferred 19 where
$Q_1$ is $ER_2$,

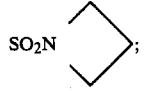

$C_1$-$C_2$ alkyl substituted with $R_8$, $C_1$-$C_2$ haloalkyl, CN, $SO_2NHC_1$-$C_2$ alkyl, $SO_2NH$cyclopropyl or $R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;

$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, $CN$ or $C(O)N(CH_3)_2$; and
$R_9$ is H, $C_1$-$C_2$ alkyl or $C_2$-$C_3$ cyanoalkyl.

(46) Compounds of Preferred 45 where
$Q_1$ is $ER_2$, $C_1$-$C_2$ alkyl substituted with $R_8$ or $C_1$-$C_2$ haloalkyl, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

(47) Compounds of Preferred 46 where
A is A-1;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

(48) Compounds of Preferred 20 where
$Q_1$ is $ER_2$,

$C_1$-$C_2$ alkyl substituted with $R_8$, $C_1$-$C_2$ haloalkyl, CN, $SO_2NHC_1$-$C_2$ alkyl, $SO_2NH$cyclopropyl or

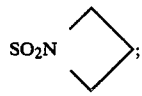

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

(49) Compounds of Preferred 48 where
$Q_1$ is $ER_2$, $C_1$-$C_2$ alkyl substituted with $R_8$ or $C_1$-$C_2$ haloalkyl, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

(50) Compounds of Preferred 49 where
A is A-1;
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.

Specifically preferred for reasons of greatest ease of synthesis and/or greatest herbicidal efficacy are:
N-[(4,6-dimethoxypyrimidin-2-yl)aminocarbonyl]-2-(methoxymethyl)-3-thiophenesulfonamide, m.p. 171°-173° C.;
N-[(4-methoxy-6-methyl-1,3,5-triazin-2-yl)aminocarbonyl]-2-(methoxymethyl)-3-thiophenesulfonamide, m.p. 155°-156° C.;
N-[(4-methoxy-6-methylpyrimidin-2-yl)aminocarbonyl]-4-cyano-3-thiophenesulfonamide, m.p. 189°-192° C.;
N-[(4,6-dimethoxypyrimidin-2-yl)aminocarbonyl]-3-(2-methoxyethyl)-2-thiophenesulfonamide, m.p. 173°-176° C.;
3-[[(4,6-dimethoxypyrimidin-2-yl)aminocarbonyl]aminosulfonyl]-4-(propylsulfinyl)-2-thiophenecarboxylic acid, methyl ester, m.p. 178°-179° C.; and
3-[[(4-methoxy-6-methylpyrimidin-2-yl)aminocarbonyl]aminosulfonyl]-4-(propylsulfinyl)-2-thiophenecarboxylic acid, methyl ester, m.p. 112°-113° C.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl or hexyl isomers.

Alkoxy denotes methoxy, ethoxy, n-propyloxy, isopropyloxy and the different butyl isomers.

Alkenyl denotes straight chain or branched alkenes, e.g. vinyl, 1-propenyl, 2-propenyl, 3-propenyl, isopropenyl and the different butenyl, pentenyl or hexenyl isomers.

Alkynyl denotes straight chain or branched alkynes, e.g. ethynyl, 1-propynyl, 2-propynyl and the different butynyl, pentynyl or hexynyl isomers.

Alkylcarbonyl denotes, e.g., acetyl, propionyl and the different butyryl isomers.

Alkylsulfonyl denotes methylsulfonyl, ethylsulfonyl or the different propylsulfonyl and butylsulfonyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 6. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

DETAILED DESCRIPTION OF THE INVENTION

Synthesis

The compounds of Formula I can be prepared by one or more of the methods described below in Equations 1 through 4.

Many of the compounds of Formula I can be prepared by reaction of a sulfonamide of Formula 2 with an appropriate methyl carbamate of Formula 3 in the presence of at least an equimolar amount of trimethylaluminum, according to Equation 1.

Equation 1

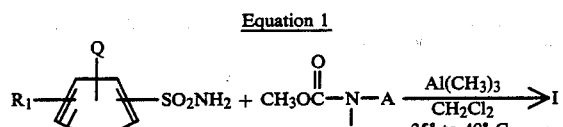

This reaction is carried out at 25° to 40° C. under an inert atmosphere and in an inert, dipolar aprotic solvent such as methylene chloride for 10 to 96 hours. Details of this reaction as well as the preparation of the carbamates of Formula 3 can be found in EPO Publication No. 13,480.

Many of the compounds of Formula I also can be prepared by reacting a sulfonylcarbamate of Formula 4 with an appropriate heterocyclic amine of Formula 5, according to Equation 1a.

Equation 1a

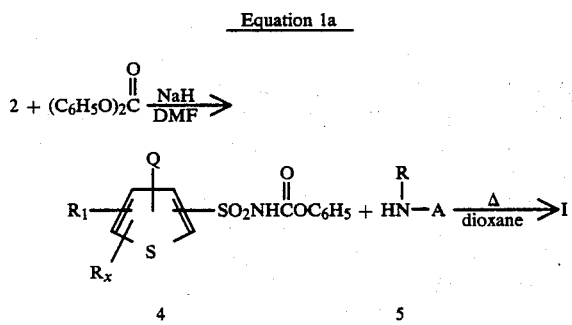

The reaction is carried out at 50° to 100° C. in a solvent such as 1,4-dioxane for 0.5 to 24 hours according to EPO Publication No. 44807. The required carbamates of Formula 4 are prepared by reacting the appropriate sulfonamide, 2, with diphenylcarbonate in the presence of equimolar quantities of a strong base, such as sodium or potassium hydride.

Some of the compounds of Formula I also can be prepared as shown in Equation 2.

Equation 2

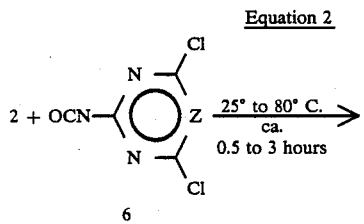 (a)

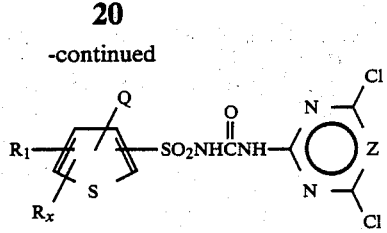

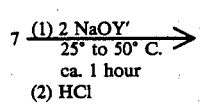 (b)

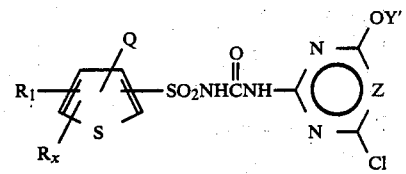

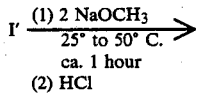 (c)

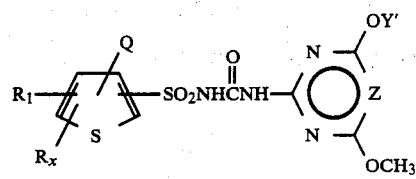

wherein Y' is $CH_3$, $C_2H_5$ or $CH_2CF_3$. This reaction series is performed according to the procedures disclosed by EPO Publication No. 30,140 and the requisite heterocyclic isocyanates of Formula 6 can be prepared according to methods described in Swiss 579,062, U.S. Pat. No. 3,919,228, U.S. Pat. No. 3,732,223 and U. von Gizycki, *Agnew. Chem. Int. Ed. Engl.* 1976, 10, 402 and 403.

Compounds of Formula I also may be prepared by reaction of a thienylsulfonylisocyanate of Formula 8 with the appropriate heterocyclic amine, as shown in Equation 3.

Equation 3

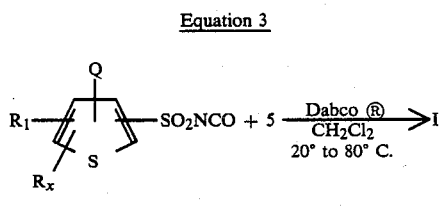

wherein Q, $R_1$ and A are as previously defined provided $R_a$, $R_b$, $R_4$, $R_9$, $R_{11}$, $R_{12}$, $R_{19}$ and $R_{20}$ are not H; J is not NH and $R_5$, $R_6$ and $R_7$ are not alkylamino.

The reaction of Equation 3 is most successful when performed in an inert dipolar aprotic solvent such as methylene chloride, tetrahydrofuran or acetonitrile at temperatures between 20° and 80° C. A catalytic amount of 1,4-diazabicyclo[2.2.2]octane (Dabco®) may be used to accelerate the reaction. In cases where the products are insoluble in the reaction solvent, isolation may be performed by simple filtration; when the products are soluble, isolation may be performed by evaporation of the solvent, trituration with a solvent such as 1-chlorobutane, diethyl ether or methanol and filtration.

Thienylsulfonylisocyanates of Formula 8 can be prepared from sulfonamides of Formula 2 by methods described in U.S. Pat. No. 4,238,621, as indicated in Equation 3a. Alternatively, these sulfonylisocyanates can be synthesized via a two-step procedure, consisting of (1) reacting sulfonamide 2 with n-butylisocyanate in the presence of one molar equivalent of a base such as potassium carbonate in a solvent such as 2-butanone or acetonitrile to form n-butylsulfonylureas of Formula 9, and (2) reaction of 9 with phosgene using Dabaco ® as a catalyst in refluxing xylene as solvent. This method is similar to the preparation found in "Newer Methods of Preparative Organic Chemistry," Forest, W., Ed., Vol. VI, Academic Press, NY. 1967, pp. 223-241. Equation 3b illustrates the procedure.

Equation 3a

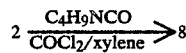

Equation 3b

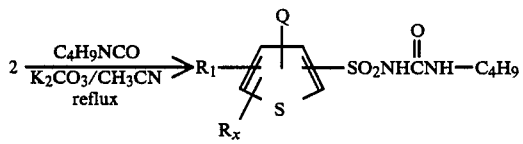

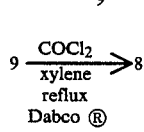

wherein the substituents are as defined for Equation 3 above.

The compunds of Formula I also are available by the methodology described in South African Application No. 830441 and illustrated by Equation 4. Thienylsulfonamides of Formula 2 react with heterocyclic carbamates of Formula 10 in 1,4-dioxane at 20° to 80° C. for periods of 1 to 24 hours when 1 equivalent of 1,8-diazabicyclo[5.4.0]undec-7-ene (DBU) is added to the reaction mixture. The resultant products are isolated by dilution of the reaction mixture with water, acidification and subsequent filtration. Heterocyclic carbamates of Formula 10 in turn are synthesized by reaction of heterocyclic amines of Formula 5 with diphenyl carbonate or phenyl chloroformate in pyridine at temperatures ranging from 20° to 80° C., as indicated in Equation 4a.

Equation 4

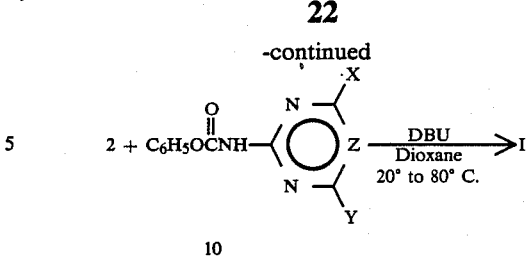

Equation 4a

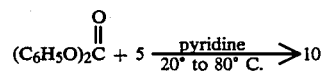

The synthesis of thienylsulfonylureas of Formula I relies upon the requisite intermediate thiophenesulfonamides of Formula 2.

Some of the intermediate sulfonamides of Formula 2 described above can be prepared from amines of Formula 11 by a two-step procedure, as shown in Equation 5. This consists of (5a) diazotizing 11 and coupling the diazonium salt with sulfur dioxide to form a sulfonyl chloride of Formula 12; and (5b) aminating 12 with ammonium hydroxide or anhydrous ammonia to form 2.

Equation 5

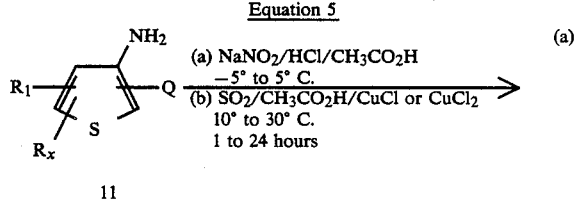

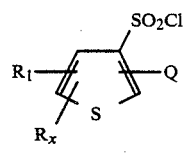

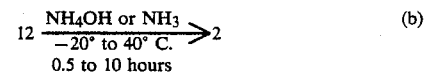

The reaction of Equation 5a is accomplished by treating a solution of amine 11 in a mixture of concentrated hydrochloric acid and glacial acetic acid with a solution of sodium nitrite in water at −5° to 5° C. After being stirred for 10-30 minutes at about 0° C. to insure complete diazotization, the solution is added to a mixture of an excess of sulfur dioxide and a catalytic amount of copper(I) chloride or copper(II) chloride in glacial acetic acid at about 10° C. The temperature is kept at about 10° C. for ¼ to 1 hour, then raised to 20° to 30° C. and held at that temperature for 2 to about 24 hours. This solution is then poured into a large excess of ice water. The sulfonyl chloride 12 can be isolated by filtration or by extraction into a solvent such as ethyl ether, methylene chloride or, preferably, 1-chlorobutane followed by evaporation of the solvent.

The amination described in the reaction of Equation 5b above is conveniently carried out by treating a solution of the sulfonyl chloride 12 with at least two mole equivalents of anhydrous ammonia in a solvent such as ethyl ether or methylene chloride at −20° to 30° C. If the sulfonamide product 2 is insoluble, it may be isolated by filtration followed by washing out the salts with water. If product 2 is soluble in the reaction solvent, it may be isolated by filtering off the precipitated ammonium chloride and evaporation of the solvent. Alternatively, many sulfonamides 2 can be prepared by reaction of corresponding sulfonyl chlorides 12 with excess aqueous ammonium hydroxide in tetrahydrofuran at 0° to about 40° C. for 0.5 to 10 hours. The sulfonamide product 2 is isolated by evaporation of the tetrahydrofuran solvent, addition of water to the residue and filtration.

Alternatively, the intermediate sulfonyl chloride 12 can be prepared as shown below in Equation 6.

Equation 6

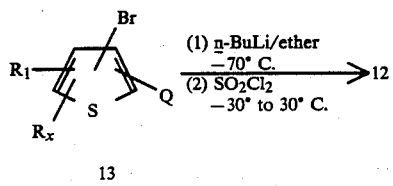

According to Equation 6, a lithium salt, prepared by reaction of 13 with n-butyllithium in ether at about −70° C., is added to sulfuryl chloride in hexane at about −30° to −20° C. and stirred for 0.5 to 10 hours at −30° to 30° C. to yield sulfonyl chloride 12, according to teachings of S. N. Bhattacharya, C. Earborn and D. R. M. Walsh, *J. Chem Soc.* (C) 1968, 1265 and H. Quast and F. Kee, *Synthesis* 1974, 489. Subsequent reaction of 12 with ammonia or ammonium hydroxide as described above provides the corresponding sulfonamide.

Starting with an appropriate bromothiophene, and carrying out the procedures described in Equation 6, or simple modifications thereof, one skilled in the art may prepare some of the other sulfonyl chlorides of Formula 12 described above. Of necessity, the reactions are limited to those cases in which the substituents Q and $R_1$ are inert to lithium reagents under the conditions of the reactions, which will be obvious to one skilled in the art. For reviews of metallation with lithium reagents, see H. W. Gschwend and H. R. Rodriguez, *Org. Reactions* 1979, 26, 1; and N. S. Narasimhan, R. S. Mali, *Synthesis* 1983, 957.

Some sulfonamides 2 are best prepared by the procedure of Equation 7 below.

Equation 7

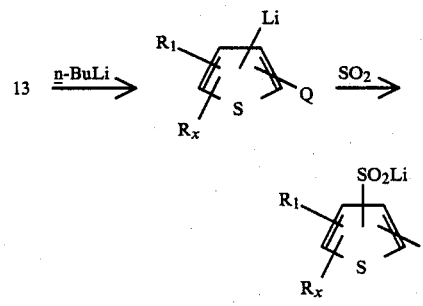

The preparation of sulfinic acid salts 14 by the procedure of Equation 7 is well known in the art; see U.S. Pat. No. 4,441,910 and H. W. Gschwend et al., loc. cit. Sulfonamides 2 can be prepared by treatment of sulfinic acid salts with chloramine. In this procedure an ethereal solution or suspension of the salt 14 is treated at low temperature (25° to −30° C.) with a dry ethereal solution of chloramine. The reaction is stirred for a period of several minutes to several hours. After filtration, the reaction mixture is washed with aqueous bisulfite, dried and the solvent removed on a rotary evaporator. The crude product is further purified by usual methods such as crystallization or chromatography.

In the reaction shown in Equation 8, a thienyl copper compound of Formula 15 is reacted with an iodo or bromo compound QX, where X is I or Br, in a solvent such as pyridine or quinoline. The copper compounds of Formula 15 are prepared by reacting the corresponding lithium compounds with cuprous iodide or cuprous bromide in a solvent such as diethyl ether. Detailed procedures for these reactions are described in the following references: M. Nilsson and C. Ullenius, *Acta Chem. Scand.* 1970, 24, 2379–2388; C. Ullenius, *Acta Chem. Scand.* 1972, 26, 3383–3386.

Equation 8

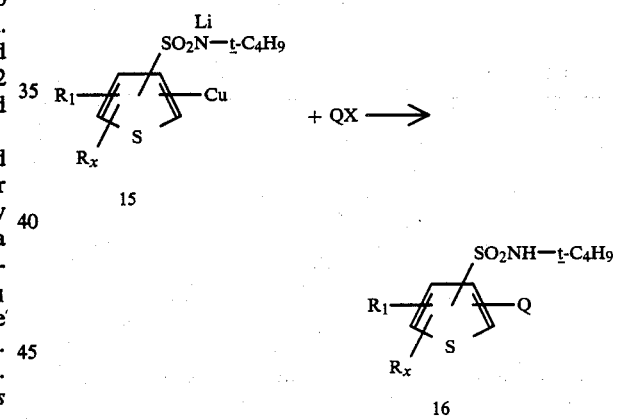

Alternatively, compounds of Formula 16 wherein Q is CN can also be prepared as shown in Equation 8a by the reaction of a bromothiophenesulfonamide of Formula 15a with cuprous cyanide in a solvent such as dimethylformamide at ambient to reflux temperature. Detailed procedures for this reaction are described below.

Equation 8a

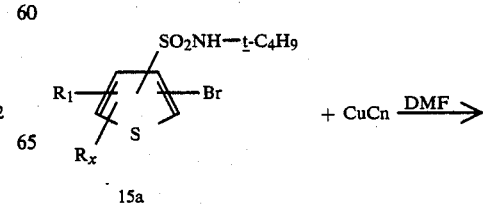

-continued
Equation 8a

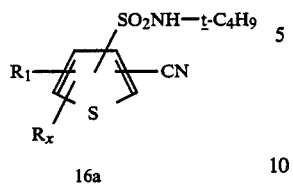

16a

Treatment of the compounds of Formula 16 with an acid catalyst in an alcohol solvent or in trifluoroacetic acid removes the t-butyl group to yield compounds of Formula 2 as shown in Equation 9.

Equation 9

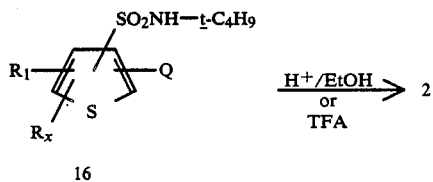

Starting with the appropriate 3-substituted thiophene and following the metallation procedure indicated in Equation 7 or simple modifications thereof, one skilled in the art may prepare many of the sulfonamides of Formula 2. Only those 3-substituents which are inert to metallating reagents relative to the desired 2-metallation of the thiophene nucleus are compatible with this synthetic strategy; such substituents will be obvious to one skilled in the art.

In complement to the metallation-chlorosulfonation sequence illustrated by Equation 6, equivalent metallation-sulfination may be performed to obtain the sulfonamides of Formula 2a. The latter sequence is described by Equation 10 and is entirely analogous to that of Equation 7.

Equation 10

-continued
Equation 10

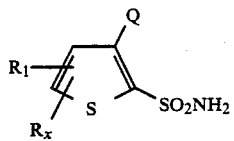

2a

Once sulfinate salts of Formula 18 have been made, they may be transformed into sulfonamides 2a directly by reaction with chloramine as described by G. H. Coleman and C. R. Hauser *J. Am. Chem. Soc.* 1928, 50, 1193. sulfinate salts of Formula 18 also may be converted to 2a in a two-step process: chlorination to afford a sulfonyl chloride, as practiced by J. F. Sculley and E. V. Brown *J. Org. Chem.* 1954, 19, 894; W. E. Trull and E. Wellisch *J. Am. Chem. Soc.* 1952, 74, 5177 and Y. K. Yuriev and N. K. Sadavaya *J. Gen. Chem. USSR* 1964, 34, 1814 and treatment of that sulfonyl chloride with ammonia in an ethereal solvent such as THF. Any of these procedures also are compatible with those sulfinate salts of Formula 14 generated via Equation 7.

The use of the strategy of Equation 11 is especially appealing in those cases where metallation of the 3-substituted thiophene of Formula 17 in the 2-position is not possible due to the reactivity of Q under the conditions of metallation. Formation of the 2-brominated thiophene 19 allows for exceedingly facile, mild halogen-metal exchange conditions as shown in Equation 11.

Equation 11

Electrophilic aromatic bromination of 3-substituted thiophenes of Formula 17 leads to the 2-brominated compounds of Formula 19 selectively, as shown in the teachings of S. Gronowitz, P. Moses and A. B. Hornfeldt *Ark. Kem.* 1962, 17, 165. Subsequent halogen-metal exchange and sulfination with sulfur dioxide gives the sulfinate salts 18, or sulfonation with sulfuryl chloride leads to the sulfonyl chlorides 20.

In still other cases where Q will suffer addition of most nucleophiles. Q can be placed at the 3-position of the thiophene nucleus after the sulfonamide moiety or its synthetic equivalent has been incorporated at the 2-position. This strategy is shown in Equation 12.

Equation 12

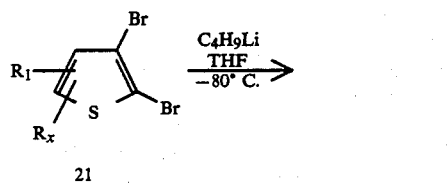

21

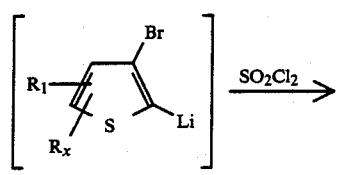

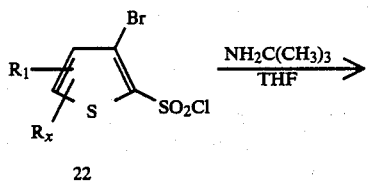

22

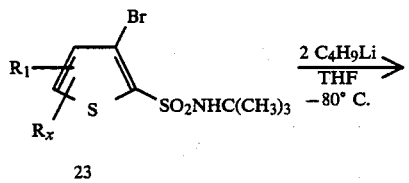

23

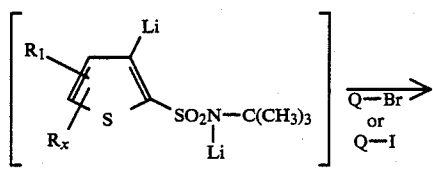

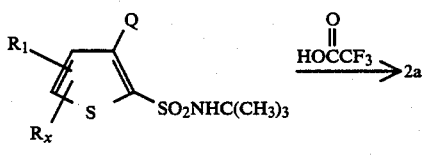

24

2,3-Dibromothiophene 21 can be lithiated preferentially at the 2-position and treated with sulfuryl chloride to give the sulfonyl halide 22. Treatment with tert-butylamine results in the tert-butyl-protected sulfonamide of Formula 23. A second lithium-halogen exchange reaction allows for 3-substitution of the heterocycle. Q, which may be added as in intact entity or as a synthetically equivalent substructure.

Sulfonamides of Formula 2a can also be prepared by the sequence shown in Equation 13.

Equation 13

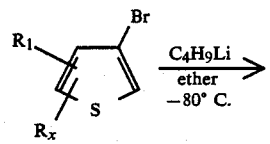

25

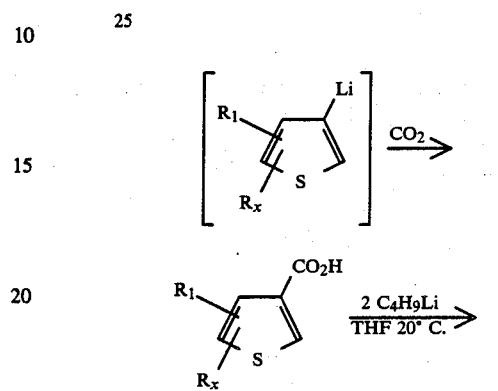

26

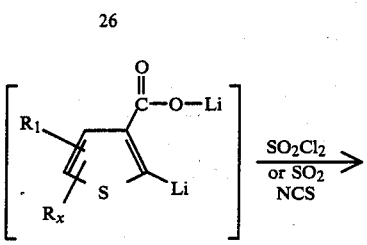

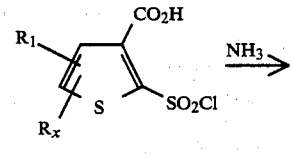

27

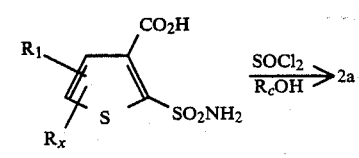

28

Sulfonamides of Formula 2b can be prepared by use of the strategy shown in Equation 14.

Equation 14

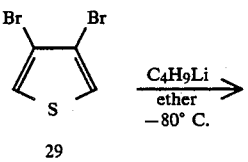

29

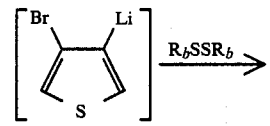

-continued
Equation 14

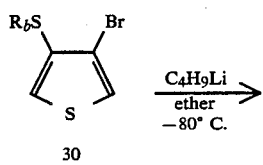

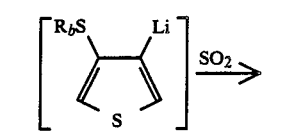

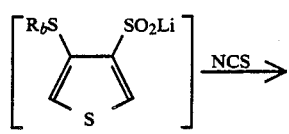

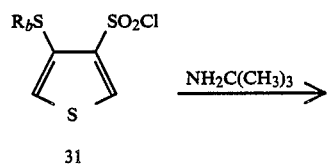

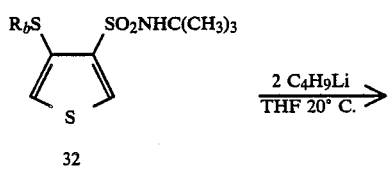

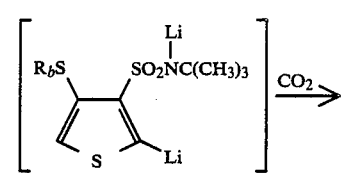

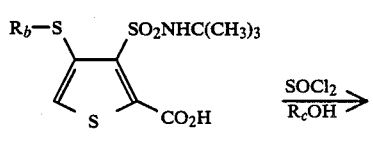

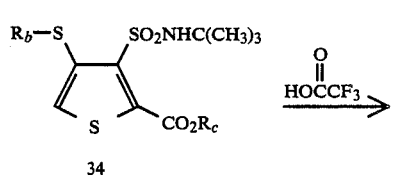

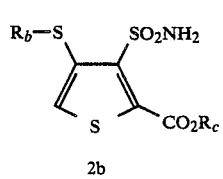

3,4-Dibromothiophene, 29 can be metallated at the 3-position and treated with disulfide to give thio compound 30. A second lithium exchange followed by reaction with sulfur dioxide and N-chlorosuccinimide treatment of the lithium sulfinate salt results in the sulfonyl halide 31. Treatment with tert-butylamine gives the tert-butyl-protected sulfonamide of Formula 32. Reaction with 2 equivalents of butyllithium followed by carbon dioxide treatment yields the 2-substituted acid 33. Esterification, followed by trifluoroacetic acid treatment gives 2b.

Reaction of the dianion from 32 with electrophiles allows for 2-substitution of the thiophene as shown in Equation 15.

Equation 15

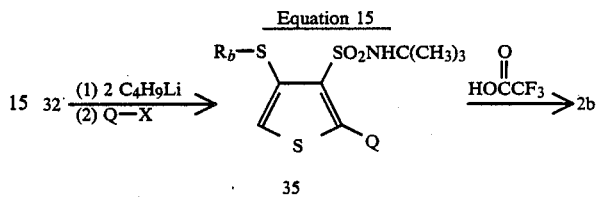

Thio compounds such as 34 or 35 can be oxidized by standard methods known to anyone skilled in the art to prepare sulfinyl and sulfonyl compounds such as 36 and 37 as shown in Equations 16a and 16b.

Equation 16a

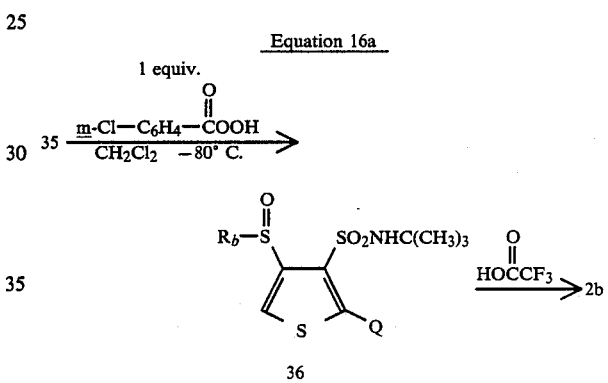

Equation 16b

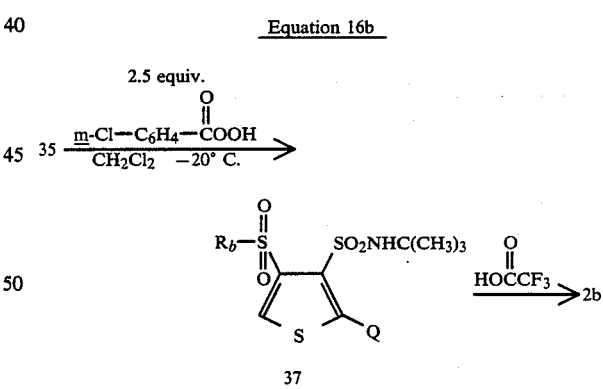

Sulfonamides of Formula 2b can also be prepared by the strategy shown in Equation 17.

Equation 17

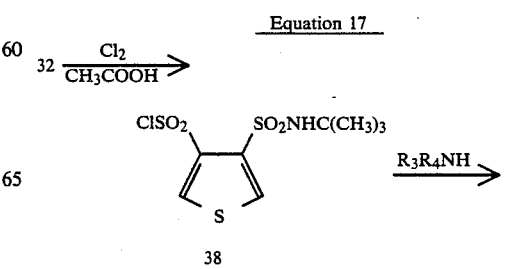

-continued
Equation 17

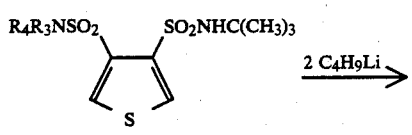

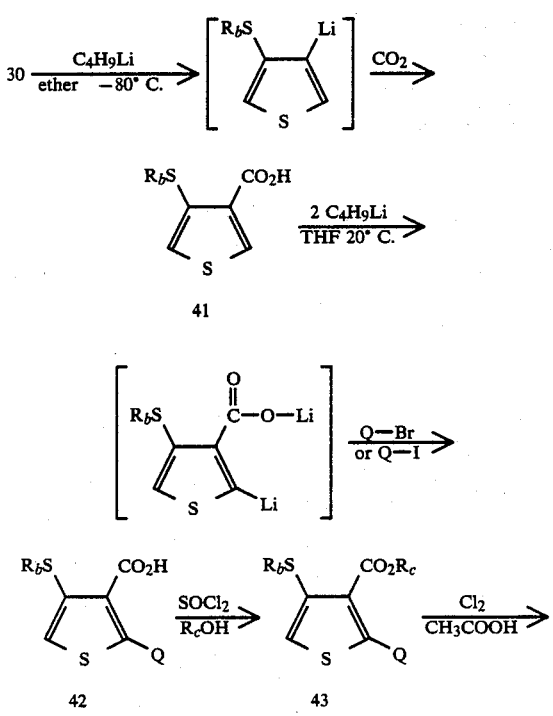

The tert-butyl-protected sulfonamide 32 can be treated with chlorine in acid to give sulfonyl chloride 38. Standard reaction with amines then yields disulfonamide 39 which can be lithiated and reacted with electrophiles to give 2-substituted-disulfonamide 40. The tert-butyl sulfonamide can then be deprotected with trifluoroacetic acid to afford 2b.

Sulfonamides of Formula 2c can be prepared by the strategy shown in Equation 18.

-continued
Equation 18

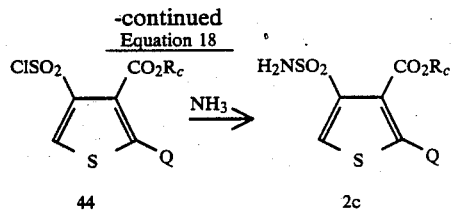

The thio-bromide 30 can be lithiated preferentially at the 3-position and reacted with carbon dioxide to give acid 41. The dianion of this acid can easily be formed and allows for 2-substitution of the heterocycle with Q which may be added as an intact entity or as a synthetically equivalent substructure. Esterification of the acid 42 by standard methods gives 43 which is treated with chlorine in acid to yield sulfonyl chloride 44. Amination then affords sulfonamide of structure 2c.

A judicious choice of the appropriate methods for preparing compounds of Formula 2 must take into account the nature of the substituents Q and $R_1$, and their chemical compatibility with the reaction conditions of Equations 1-18.

The heterocyclic amines of Formula 5 in Equation 1a above can be prepared by methods known in the literature, or simple modifications thereof, by those skilled in the art. For instance, EP-A No. 84,224 (published in July 27, 1983) and W. Braker et al., *J. Am. Chem. Soc.*, 69, 3072 (1947) describe methods for preparing aminopyrimidines and triazines substituted by acetal groups such as dialkoxymethyl or 1,3-dioxolan-yl, among other groups. Also, for example, South African patent application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$, among other groups. South African patent application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidines-2-amines (5, A is A-2) and the 6,7-dihydro-5H-pyrano[2,3-d]pyrimidin-2-amines (5, A is A-3) can be prepared as described in EP-A No. 15,683. The furo[2,3-d]pyrimidin-2-amines (5, A is A-4) are described in EP-A No. 46,677.

Compounds of Formula 5 where A is A-5, are described in EP-A-73,562. Compounds of Formula 5 where A is A-6, are described in EP-A-94,260.

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples.

EXAMPLE 1

3-(Methoxymethyl)thiophene-2-sulfonamide

To 22.3 g of 3-(methoxymethyl)thiophene dissolved in 180 mL of dry ether under nitrogen is added, dropwise with stirring at 0° C., at 120 mL of a 1.6M solution of n-butyllithium in hexane. The mixture is stirred at 0° C. for two hours, and 24.1 g of sulfuryl chloride is added while the temperature is maintained at −40° C. After two hours 5 mL of ethyl acetate is added and the reaction mixture is poured into ice and water. The organic phase is separated and added to 25 mL of concentrated ammonium hydroxide at ambient temperature.

After evaporation of the ether and hexane from the reaction mixture, the desired sulfonamide can be separated from the aqueous residue, washed with water and dried. The product can be purified by chromatography using procedures described by W. C. Still et al., *J. Org. Chem.*, 43, 2923 (1978).

EXAMPLE 2

N-[(4,6-Dimethoxypyrimidin-2-yl)aminocarbonyl]-3-(methoxymethyl)thiophene-2-sulfonamide To 0.41 g of 3-(methoxymethyl)thiophene-2-sulfonamide and 0.55 g of phenyl N-(4,6-dimethoxypyrimidin-2-yl)carbamate in 20 mL of acetonitrile is added 0.3 mL of 1,8-diazabicyclo-[5.4.0]undec-7-ene (DBU). After being stirred for 2 hours at ambient temperature and pressure, the reaction mass is poured onto 25–50 g of ice and the resultant mixture acidified to pH 3 by the addition of hydrochloric acid. The desired solid product can be isolated by filtration. Alternatively, it can be extracted into methylene chloride which is then dried over magnesium sulfate, filtered and evaporated to dryness to yield the desired product in sufficiently pure form for the purposes of this invention.

EXAMPLE 3

N-[(4-Methoxy-6-methylpyrimidin-2-yl)aminocarbonyl]-3-(methoxymethyl)thiophene-2-sulfonamide To 0.41 g of 3-(methoxymethyl)thiophene-2-sulfonamide and 0.52 g of phenyl N-(4-methoxy-6-methylpyrimidin-2-yl)carbamate in 25 mL of 1,4-dioxane is added 0.3 mL of 1,8-diazabicyclo[5.4.0]undec-7-ene. After being stirred for two hours at ambient temperature and pressure, the reaction mixture is poured onto 25–50 g of ice and the resultant mixture is acidified to pH 3 by the addition of hydrochloric acid. The desired solid product can be isolated by filtration. Alternatively, it can be extracted into methylene chloride which is then dried over magnesium sulfate, filtered and evaporated to dryness to yield the desired product in sufficiently pure form for the purposes of this invention.

EXAMPLE 4

3-(2-Methoxyethyl)thiophene-2-sulfonyl chloride

To 56 g of chlorosulfonic acid at −15° C. was added with efficient stirring 14.2 g of 3-(2-methoxyethyl)thiophene. The mixture was stirred for one hour at −10° C. and then cautiously added to ice and the resultant mixture extracted with methylene chloride. The methylene chloride extract was washed with cold water, dried over magnesium sulfate, filtered and concentrated to yield 6.0 g of an oil. Infrared absorption spectroscopy showed peaks at 1160, 1180 and 1360 cm$^{-1}$ consistent for sulfonyl chloride. This product was sufficiently pure for use as an intermediate for the preparation of compounds of this invention.

EXAMPLE 5

3-(2-Methoxyethyl)thiophene-2-sulfonamide

Six grams of crude 3-(2-methoxyethyl)thiophene-2-sulfonyl chloride was dissolved in 25 mL of acetone and added dropwise with stirring at ambient temperature to 25 mL of concentrated aqueous ammonium hydroxide. The reaction mixture was allowed to stand overnight and the acetone removed by evaporation. The aqueous residue was extracted with three 100 mL portions of methylene chloride which were combined, dried over magnesium sulfate, filtered and evaporated to yield a residue which was a mixture of an oil and a solid. The sulfonamide was isolated by passing the residue through a 30 cm high by 80mm diameter column of silica gel using 1:1 ethyl acetate mixed hexanes solvent system and taking 100 mL fractions. The desired product came off in fractions 4 to 12. After evaporation of the solvent 1.84 grams was obtained, m.p. 64°–73° C. Analysis by mass spectroscopy showed a molecular weight of 221 AMU in agreement for the desired sulfonamide.

EXAMPLE 6

N-[(4-Chloro-6-methoxypyrimidin-2-yl)aminocarbonyl[-3-(2-methoxyethyl)thiophene-2-sulfonamide To a solution of 0.33 g of 3-(2-methoxyethyl)thiophene-2-sulfonamide and 0.42 g of phenyl N-(4-chloro-6-methoxypyrimidin-2-yl)carbamate in 20 mL of acetonitrile was added with stirring at ambient temperature 0.23 mL of DBU. After stirring for two hours the mixture was poured into 25 g of ice and water, acidified with 12N hydrochloric acid and the resultant precipitate removed by filtration, washed with cold water and dried to yield 0.37 g of product, m.p. 135°–141° C. It showed peaks by infrared absorption spectroscopy at 1700, 1600 and 1560 cm$^{-1}$ consistent for the desired structure.

NMR (CDCl$_3$) 3.27 δ, s, CH$_3$O; 3.27 δ, t, CH$_2$; 3.65 δ, t, CH$_2$; 4.02 δ, t, CH$_3$O on pyrimidine; 6.49 δ, s, CH of pyrimidine; 7.05 δ, d, 7.60 δ, d, thiophene; 7.05 δ, ws, NH between

and hetero; and 12.0 δ, s, NH (imide).

EXAMPLE 7

N-[(4,6-Dimethoxypyrimidin-2-yl)aminocarbonyl]-3-(2-methoxyethyl)-2-thiophenesulfonamide To a mixture of 0.33 g of 3-(2-methoxyethyl)thiophene-2-sulfonamide and 0.41 of phenyl N-(4,6-dimethoxypyrimidin-2-yl)carbamate in 20 mL of acetonitrile was added 0.23 mL of 1,8-diazabicyclo[5.4.0]undec-7-ene (DBU) at ambient temperature with stirring. After 2 hours the mixture was poured onto ice and acidified with 12N hydrochloric acid. The resultant precipitate was removed by filtration, washed with water and dried to yield 0.42 g, m.p. 173°-176° C.

NMR (CDCl$_3$): 3.268 δ, s, CH$_3$O; 3.27 δ, t, CH$_2$; 3.64 δ, t, CH$_2$; 3.98 δ, s, 2 X CH$_3$O of pyrimidine; 5.78 δ, s, CH of pyrimidine; and 7.2, 7.6 δ, d, 2 X CH of thiophene.

EXAMPLE 8

2-Hydroxymethylthiophene-3-sulfonamide

To 5.0 g of methyl 3-aminosulfonylthiophene-2-carboxylate in 200 mL of tetrahydrofuran was added 0.75 g of lithium borohydride. After heating at reflux for two hours the reaction was quenched with water and acidified with concentrated hydrochloric acid. The desired product was then extracted into methylene chloride which was washed with water, dried over magnesium sulfate, filtered and concentrated in vacuo to yield 1.8 g of a yellow solid, m.p. 85°-89°.

NMR (CDCl$_3$): 7.3 δ, AB quartet, 2H on thiophene; 6.8 δ, sw, 2H of NH$_2$; 5.4 δ, 1H of OH; and 4.95 δ, d, 2H of CH$_2$.

EXAMPLE 9

2-Chloromethylthiophene-3-sulfonamide

To a stirred suspension of 16 g of 2-hydroxymethylthiophene-3-sulfonamide, 150 mL of methylene chloride and 10.5 mL of N,N-dimethylaniline was added 6.0 mL of thionyl chloride. An ice cooling bath was applied when the reaction temperature rose to 40° C. and the mixture was cooled to room temperature. It was then diluted with 50 mL of 1-chlorobutane followed by the addition of 200 mL of ice and water. The precipitate thus formed was isolated by filtration, washed with water and air-dried to yield 12.2 g of white solid, m.p. 100° dec.

NMR (CDCl$_3$-DMSO): 7.4 δ, s, 2H, thiophene; 7.4-5.5 δ, vbs, 2H, NH$_2$; and 5.2 δ, s, 2H, CH$_2$.

EXAMPLE 10

3-Cyano-N-(1,1-dimethylethyl)thiophene-2-sulfonamide

A mixture of 197.7 g of 3-bromo-N-(1,1-dimethylethyl)thiophene-2-sulfonamide, 195.9 g of cuprous cyanide and 500 mL of dimethylformamide was heated to 150° for two and one half hours at which time none of the bromothiophene remained as indicated by thin layer chromatography. The reaction was cooled to room temperature and poured into 1500 mL of 10% aqueous sodium cyanide. The aqueous mixture was extracted with five, 200 mL portions of ethyl ether and the combined extracts were washed with five, 150 mL portions of water followed by one, 200 mL aqueous sodium chloride wash. After drying over magnesium sulfate, filtration and evaporation of the solvent 140.8 g of the desired product was obtained.

EXAMPLE 11

3-Cyanothiophene-2-sulfonamide

Ten grams of 3-cyano-N-(1,1-dimethylethyl)thiophene-2-sulfonamide was dissolved in 500 mL of trifluoroacetic acid and stirred overnight at room temperature. After removal of the solvent by evaporation, the residue was dissolved in ethyl acetate and washed with four portions of 100 mL of water followed by saturated sodium chloride. After drying over magnesium sulfate, the solvent was evaporated in vacuo to yield 6.42 g of white solid, m.p. 152°-155°. It showed peaks by Nuclear Magnetic Resonance consistent for the desired structure.

EXAMPLE 12

4-Propylthio-3-bromothiophene

A solution of 199 mL of 2.18M n-butyllithium in 320 mL ether was cooled to −80° C. and was treated dropwise with a solution of 100 g 3,4-dibromothiophene in 320 mL ether keeping the temperature below −70° C. After stirring another 30 minutes at −80° C. a solution of 94 mL dipropyl disulfide in 120 mL ether was added dropwise. The suspension was stirred at −80° C. for 2 hours, warmed to 20° C., poured into ice and hydrochloric acid and the organic phase was separated. The aqueous phase was extracted 2 times with ethyl acetate and the combined organic phases were washed with brine, dried (MgSO$_4$) and concentrated to an amber oil. The product (90.2 g) was isolated by distillation of the residue; bp 93°-96° C. at 0.5 torr.

EXAMPLE 13

4-Propylthio-N-(1,1-dimethylethyl)-3-thiophenesulfonamide

A solution of 44.7 g 4-propylthio-3-bromothiophene in 250 mL ether was added dropwise to a solution of 85 mL 2.0M n-butyllithium in ether (250 mL) cooled to −80° C. After stirring at −80° C. for an additional 30 minutes, a solution of 21.5 mL sulfur dioxide in 50 mL ether was slowly added keeping the temperature below −60° C. The suspension was warmed to 20° C. and concentrated to a white solid. The solid was dissolved in 300 mL acetic acid and cooled to about 16° while 21.9 g N-chlorosuccinimide was added in portions. After stirring at 20° C. overnight the acetic acid was removed in vacuo and the residue was triturated with 1 l ether, filtered and the ether was washed with saturated aqueous bicarbonate and brine, dried (MgSO$_4$), and concentrated to a dark oil. The oil was dissolved in 600 mL ether, cooled to −10° C. and 50.4 mL t-butyl amine was added. The mixture was warmed to 20°, diluted with ethyl acetate and washed with water and brine, dried (MgSO$_4$) and concentrated to an oil. The product was isolated as a tan solid after chromatography on silica with 10% ethyl acetate in hexane; yield 20.8 g; m.p. 61°-63° C.

EXAMPLE 14

4-Propylthio-3-(N-(1,1-dimethylethyl)aminosulfonyl)-2-thiophenecarboxylic acid A solution of 12.15 g 4-propylthio-3-N-(1,1-dimethylethyl)-3-thiophenesulfonamide in 150 mL THF was cooled to −30° C. and treated dropwise with 31.6 mL 2.69M n-butyllithium in hexane. The solution was warmed to 20° C. for 1.5 hours and then cooled to −80° C. 8.8 g Solid carbon dioxide was added in one portion, the mixture was warmed to 20° C. and poured over ice and hydrochloric acid. The organic layer was separated and the aqueous layer was extracted with ethyl acetate. The combined organic layers were washed with brine, dried and concentrated to a solid. The product was purified by recrystallization from butyl chloride to give 10.4 g of light yellow solid; m.p. 123°-126° C.

EXAMPLE 15

4-Propylthio-3-(N-(1,1-dimethylethyl)aminosulfonyl)-2-thiophenecarboxylic acid, methyl ester Thionyl chloride (2.3 mL) was added dropwise to 110 mL methanol cooled to −10° C. Next 10.4 g 4-propylthio-3-(N-(1,1-dimethylethyl)aminosulfonyl)-2-thiophenecarboxylic acid was added in one portion. The solution was warmed to reflux for 6 hours, then cooled to −45° C., and the product precipitated in sufficiently pure form for the purposes of this invention; yield 8.45 g; m.p. 93°-98° C.

EXAMPLE 16

4-Propylsulfinyl-3-(N-(1,1-dimethylethyl)aminosulfonyl)-2-thiophenecarboxylic acid, methyl ester A solution of 2.32 g 4-propylthio-3-(N-(1,1-dimethylethyl)aminosulfonyl)-2-thiophenecarboxylic acid, methyl ester in 75 mL methylene chloride was cooled to −80° C. and 1.39 g of 80–85% m-chloroperoxybenzoic acid was added in one portion. After stirring at −80° C. for 20 minutes and warming to 20° C. the solution was diluted with more methylene chloride and washed with aqueous sodium bicarbonate, sodium bisulfite, sodium bicarbonate and water, dried and concentrated to 2.2 g of colorless oil in sufficiently pure form for the purposes of this invention.

EXAMPLE 17

4-Propylsulfinyl-3-aminosulfonyl-2-thiophenecarboxylic acid, methyl ester

A solution of 2.2 g of 4-propylsulfinyl-3-(N-1,1-dimethylethyl)aminosulfonyl)-2-thiophenecarboxylic acid, methyl ester in 15 mL methylene chloride was treated with 30 mL trifluoroacetic acid at room temperature for 24 hours. The solvents were removed in vacuo and the residue was crystallized with butyl chloride to give 1.74 g of white solid; m.p. 131°-144° C.

EXAMPLE 18

3-[[(4,6-Dimethoxypyrimidin-2-yl)aminocarbonyl]aminosulfonyl]-4-propylsulfinyl-2-thiophenecarboxylic acid, methyl ester To 0.28 g of 4-propylsulfinyl-3-aminosulfinyl-2-thiophenecarboxylic acid, methyl ester in 5 mL acetonitrile was added 0.32 g (4,6-dimethoxypyrimidin-2-yl)phenylcarbamate and 172 μL 1,8-diazabicyclo[5.4.0]undec-7-ene. After stirring at 20° C. for 30 minutes, 25 mL water was added and the product precipitated by addition of 1N hydrochloric acid, and purified by wasing with water, butyl chloride and ether; yield 0.24 g; m.p. 178°-179° C.

NMR (CDCl₃) 12.95 δ, br s, 1H, NH; 8.25 δ, s, 1H, thiophene; 7.20 δ, br s, 1H, NH; 5.82 δ, s, 1H, pyrimidine; 4.03 δ, s, 6H, pyrimidine OCH₃; 3.87 δ, s, 3H, COOCH₃; 3.5–3.7 δ, m, 1H, S(O)CH$_a$H$_b$—; 2.9–3.1 δ, m, 1H, S(O)CH$_a$H$_b$—; 1.7–2.1 δ, m, 2H, —CH₂—; and 1.09 δ, t, J=7 Hz, 3H, —CH₃.

EXAMPLE 19

3-[[(4-Methoxy-6-methylpyrimidin-2-yl)aminocarbonyl]aminosulfonyl]-4-(propylsulfinyl)-2-thiophenecarboxylic acid, methyl ester To 0.28 g of 4-propylsulfinyl-3-aminosulfinyl-2-thiophenecarboxylic acid, methyl ester in 5 mL acetonitrile was added 0.30 g (4-methoxy-6-methylpyrimidin-2-yl)phenylcarbamate and 172 μL 1,8-diazabicyclo[5.4.0]undec-7-ene. After stirring at 20° C. for 30 minutes, 25 mL water was added and the product precipitated by addition of 1N hydrochloric acid, and purified by washing with water, butyl chloride and ether; yield 0.17 g; m.p. 112°-113° C.

NMR (CDCl₃) 13.50 δ, br s, 1H, NH; 8.23 δ, s, 1H, thiophene; 7.40 δ, br s, 1H, NH; 6.32 δ, s, 1H, pyrimidine; 4.01 δ, s, 3H, OCH₃; 3.86 δ, s, 3H, COOCH₃; 3.7–3.5 δ, m, 1H, S(O)CH$_a$H$_b$; 3.1–2.9 δ, m, 1H, S(O)CH$_a$H$_b$; 2.49 δ, s, 3H, CH₃; 2.0–1.6 δ, m, 2H, —CH₂—; and 1.09 δ, t, J=7 Hz, 3H CH₃.

Following the procedures described earlier and exemplified in Examples 1–18, one skilled in the art can prepare the compounds of Tables Ia–XIa and Ib–XVb.

| General Formula | General Formulas for Tables Ia–XIa |
|---|---|
| Ia | 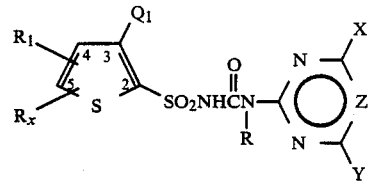 |
| IIa | 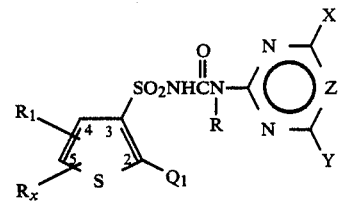 |
| IIIa | 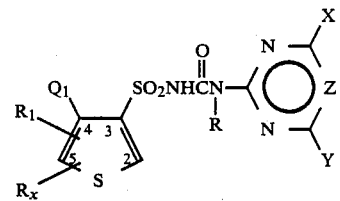 |

-continued
General Formulas for Tables Ia–XIa
| General Formula | |
|---|---|
| IVa | 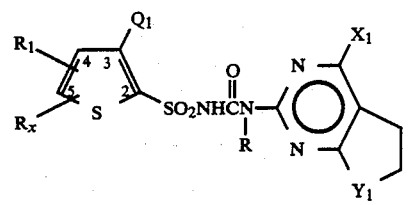 |
| Va | 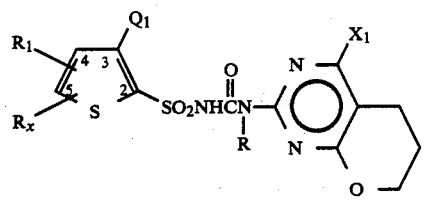 |
| VIa | 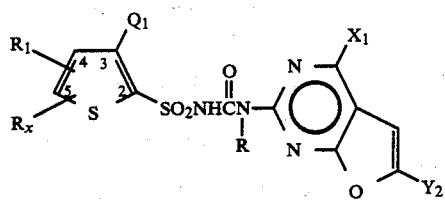 |
| VIIa | 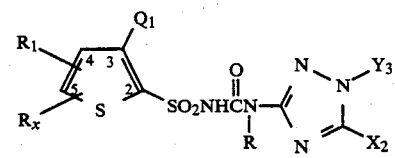 |
| VIIIa | 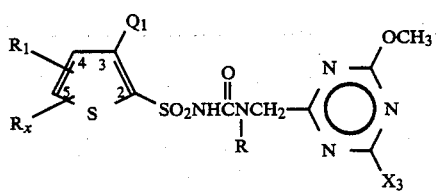 |
| IXa | 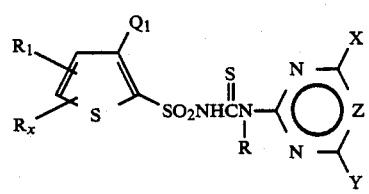 |
| Xa | 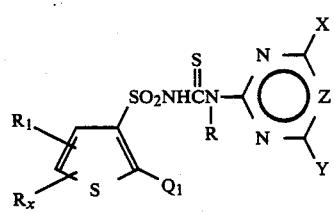 |
-continued
General Formulas for Tables Ia–XIa
| General Formula | |
|---|---|
| XIa | 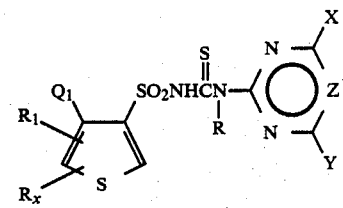 |
| Ib | 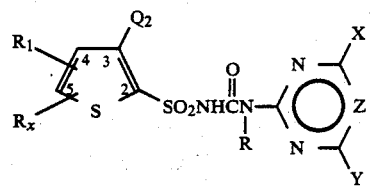 |
| IIb | 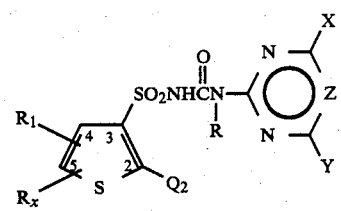 |
| IIIb | 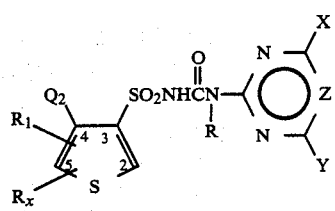 |
| IVb | 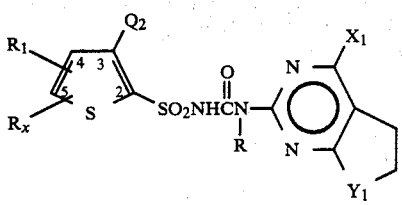 |
| Vb | 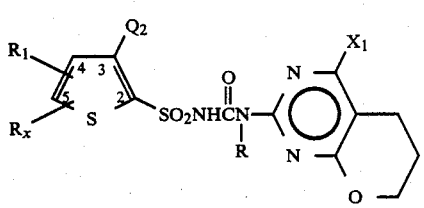 |
| VIb | 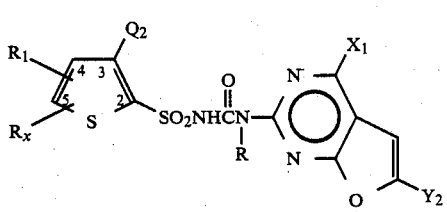 |

-continued

General Formulas for Tables Ia–XIa

| General Formula | |
|---|---|
| VIIb | 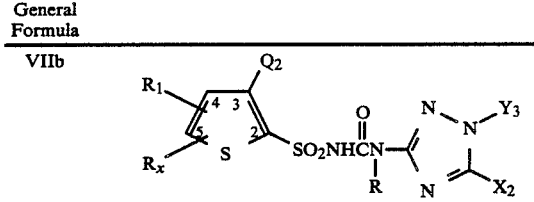 |
| VIIIb | 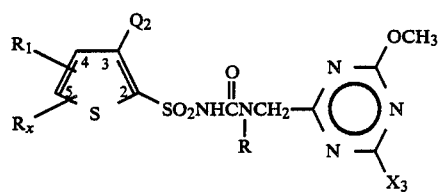 |
| IXb | 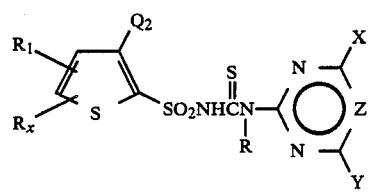 |
| Xb | 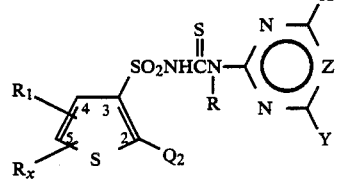 |
| XIb | 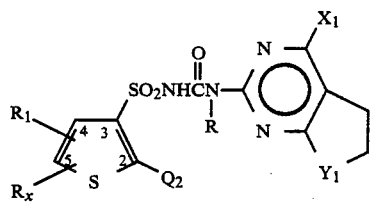 |

General Formulas for Tables Ia–XIa

| General Formula | |
|---|---|
| XIIb | 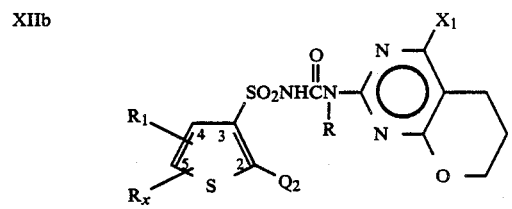 |
| XIIIb | 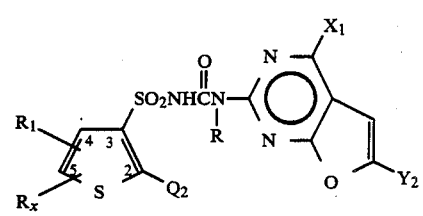 |
| XIVb | 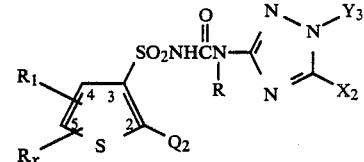 |
| XVb | 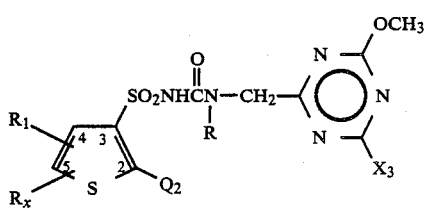 |

TABLE Ia

General Formula Ia

| R | $R_1$ | $R_x$ | $Q_1$ | X | Y | Z | m.p. (°C.) |
|---|---|---|---|---|---|---|---|
| H | H | H | $S(CH_2)_2OCH_3$ | $CH_3$ | $OCH_3$ | CH | |
| H | H | H | $S(CH_2)_2OCH_3$ | $OCH_3$ | $OCH_3$ | CH | |
| H | H | H | $S(CH_2)_2OCH_3$ | Cl | $OCH_3$ | CH | |
| H | H | H | $S(CH_2)_2OCH_3$ | $CH_3$ | $OCH_3$ | N | |
| H | H | H | $S(CH_2)_3OCH_3$ | $CH_3$ | $OCH_3$ | CH | |
| H | H | H | $S(CH_2)_3OCH_3$ | $OCH_3$ | $OCH_3$ | CH | |
| H | H | H | $S(CH_2)_2OCH_2CN$ | $OCH_3$ | $OCH_3$ | CH | |
| H | H | H | $S(CH_2)_2OCH_2CN$ | $CH_3$ | $OCH_3$ | N | |
| H | H | H | $S(CH_2)_2SCH_3$ | $CH_3$ | $CH_3$ | CH | |
| H | H | H | $S(CH_2)_2SCH_3$ | $CH_3$ | $OCH_3$ | CH | |
| H | H | H | $S(CH_2)_2SCH_3$ | $OCH_3$ | $OCH_3$ | CH | |
| H | H | H | $S(CH_2)_2SCH_3$ | $CH_3$ | $OCH_3$ | N | |
| H | H | H | $S(CH_2)_2S(O)CH_3$ | $CH_3$ | $OCH_3$ | CH | |
| H | H | H | $S(CH_2)_2S(O)CH_3$ | $OCH_3$ | $OCH_3$ | CH | |
| H | H | H | $S(CH_2)_2S(O)CH_3$ | Cl | $OCH_3$ | CH | |
| H | H | H | $S(CH_2)_2S(O)CH_3$ | $CH_3$ | $OCH_3$ | N | |
| H | H | H | $S(CH_2)_2S(O)CH_2CH_3$ | $OCH_3$ | $OCH_3$ | CH | |
| H | H | H | $S(CH_2)_2S(O)CH_2CH_3$ | Cl | $OCH_3$ | CH | |
| H | H | H | $S(CH_2)_2SO_2CH_3$ | $OCH_3$ | $OCH_3$ | CH | |
| H | H | H | $S(CH_2)_2SO_2CH_3$ | Cl | $OCH_3$ | CH | |
| H | H | H | $S(CH_2)_2SO_2CH_3$ | $CH_3$ | $OCH_3$ | N | |
| H | H | H | $S(CH_2)_2SO_2CH_2CH_3$ | $CH_3$ | $OCH_3$ | CH | |
| H | H | H | $S(CH_2)_2SO_2CH_2CH_3$ | $OCH_3$ | $OCH_3$ | CH | |
| H | H | H | $SCH_2CO_2CH_3$ | $CH_3$ | $OCH_3$ | CH | |
| H | H | H | $SCH_2CO_2CH_3$ | $OCH_3$ | $OCH_3$ | CH | |

TABLE Ia-continued

General Formula Ia

| R | $R_1$ | $R_x$ | $Q_1$ | X | Y | Z | m.p. (°C.) |
|---|---|---|---|---|---|---|---|
| H | H | H | $SCH_2CO_2CH_3$ | Cl | $OCH_3$ | CH | |
| H | H | H | $SCH_2CO_2CH_3$ | $CH_3$ | $OCH_3$ | N | |
| H | H | H | $S(CH_2)_3SO_2N(CH_3)_2$ | $OCH_3$ | $OCH_3$ | CH | |
| H | H | H | $S(CH_2)_2SO_2N(CH_2CH_3)_2$ | $CH_3$ | $OCH_3$ | CH | |
| H | H | H | $S(CH_2)_2SO_2N(CH_2CH_3)_2$ | $OCH_3$ | $OCH_3$ | CH | |
| H | H | H | $SCH_2C(O)CH_3$ | $OCH_3$ | $OCH_3$ | CH | |
| H | H | H | $SCH_2C(O)CH_3$ | $CH_3$ | $OCH_3$ | N | |
| H | H | H | $S(CH_2)_2CN$ | $CH_3$ | $OCH_3$ | CH | |
| H | H | H | $S(CH_2)_2CN$ | $OCH_3$ | $OCH_3$ | CH | |
| H | H | H | $S(CH_2)_2CN$ | $CH_3$ | $OCH_3$ | N | |
| H | H | H | $SCH_2C(O)N(CH_3)_2$ | $CH_3$ | $OCH_3$ | CH | |
| H | H | H | $SCH_2C(O)N(CH_3)_2$ | $OCH_3$ | $OCH_3$ | CH | |
| H | H | H | $SCH_2C(O)N(CH_3)_2$ | $CH_3$ | $OCH_3$ | N | |
| H | 4-$CH_3$ | H | $S(CH_2)_2C(O)N(CH_3)_2$ | $CH_3$ | $OCH_3$ | CH | |
| H | 4-$CH_3$ | H | $S(CH_2)_2C(O)N(CH_3)_2$ | $OCH_3$ | $OCH_3$ | CH | |
| H | 4-$CH_3$ | H | $S(CH_2)_2C(O)N(CH_3)_2$ | $CH_3$ | $OCH_3$ | N | |
| H | H | H | $S(CH_2)_2Cl$ | $CH_3$ | $CH_3$ | CH | |
| H | H | H | $S(CH_2)_2Cl$ | $CH_3$ | $OCH_3$ | CH | |
| H | H | H | $S(CH_2)_2Cl$ | $OCH_3$ | $OCH_3$ | CH | |
| H | H | H | $S(CH_2)_2Cl$ | Cl | $OCH_3$ | CH | |
| H | H | H | $S(CH_2)_2Cl$ | $CH_3$ | $OCH_3$ | N | |
| H | H | H | $S(CH_2)_2Cl$ | $OCH_3$ | $OCH_3$ | N | |
| H | H | H | $S(CH_2)_3Cl$ | $CH_3$ | $OCH_3$ | CH | |
| H | H | H | $S(CH_2)_3Cl$ | $OCH_3$ | $OCH_3$ | CH | |
| H | H | H | $S(CH_2)_3Cl$ | $CH_3$ | $OCH_3$ | N | |
| H | H | H | $S(CH_2)_2F$ | $OCH_3$ | $OCH_3$ | CH | |
| H | H | H | $S(CH_2)_2F$ | $CH_3$ | $OCH_3$ | N | |
| H | H | H | $S(CH_2)_2Br$ | $CH_3$ | $CH_3$ | CH | |
| H | H | H | $S(CH_2)_2Br$ | $OCH_3$ | $OCH_3$ | CH | |
| H | 4-Cl | H | $SCHClCH=CH_2$ | $CH_3$ | $OCH_3$ | CH | |
| H | 4-Cl | H | $SCHClCH=CH_2$ | $OCH_3$ | $OCH_3$ | CH | |
| H | 4-Cl | H | $SCHClCH=CH_2$ | $CH_3$ | $OCH_3$ | N | |
| H | H | H | $SCH_2C\equiv CH$ | $CH_3$ | $OCH_3$ | CH | |
| H | H | H | $SCH_2C\equiv CH$ | $OCH_3$ | $OCH_3$ | CH | |
| H | H | H | $SCH_2C\equiv CH$ | $CH_3$ | $OCH_3$ | N | |
| H | H | H | $S(CH_2)_2C\equiv CH$ | $CH_3$ | $OCH_3$ | CH | |
| H | H | H | $S(CH_2)_2C\equiv CH$ | $OCH_3$ | $OCH_3$ | CH | |
| H | H | H | $S(CH_2)_2C\equiv CH$ | $CH_3$ | $OCH_3$ | N | |
| H | 4-Cl | H | $SO_2(CH_2)_2OCH_3$ | $OCH_3$ | $OCH_3$ | CH | |
| H | 4-Cl | H | $SO_2(CH_2)_2OCH_3$ | $CH_3$ | $OCH_3$ | N | |
| H | H | H | $SO_2CH_2OCH_2CH_3$ | $OCH_3$ | $OCH_3$ | CH | |
| H | H | H | $SO_2CH_2OCH_2CH_3$ | $CH_3$ | $OCH_3$ | N | |
| H | H | H | $SO_2(CH_2)_2OCH_2CH_3$ | $OCH_3$ | $OCH_3$ | CH | |
| H | H | H | $SO_2(CH_2)_2OCH_2CH_3$ | $CH_3$ | $OCH_3$ | N | |
| H | H | H | $SO_2(CH_2)_2SCH_3$ | $CH_3$ | $OCH_3$ | CH | |
| H | H | H | $SO_2(CH_2)_2SCH_3$ | $OCH_3$ | $OCH_3$ | CH | |
| H | H | H | $SO_2(CH_2)_2SCH_3$ | $CH_3$ | $OCH_3$ | N | |
| H | H | H | $SO_2(CH_2)_2SCH_2CH_3$ | $OCH_3$ | $OCH_3$ | CH | |
| H | H | H | $SO_2(CH_2)_2SCH_2CH_3$ | $CH_3$ | $OCH_3$ | N | |
| H | H | H | $SO_2(CH_2)_2S(O)CH_3$ | $OCH_3$ | $OCH_3$ | CH | |
| H | H | H | $SO_2(CH_2)_2S(O)CH_3$ | $CH_3$ | $OCH_3$ | N | |
| H | H | H | $SO_2(CH_2)_2CO_2CH_3$ | $OCH_3$ | $OCH_3$ | CH | |
| H | H | H | $SO_2(CH_2)_2CO_2CH_3$ | $CH_3$ | $OCH_3$ | N | |
| H | H | H | $SO_2CH_2CO_2CH_2CH_3$ | $CH_3$ | $OCH_3$ | CH | |
| H | H | H | $SO_2CH_2CO_2CH_2CH_3$ | $OCH_3$ | $OCH_3$ | CH | |
| H | H | H | $SO_2CH_2CO_2CH_2CH_3$ | $CH_3$ | $OCH_3$ | N | |
| H | H | H | $SO_2(CH_2)_2C(O)CH_3$ | $CH_3$ | $OCH_3$ | CH | |
| H | H | H | $SO_2(CH_2)_2C(O)CH_3$ | $OCH_3$ | $OCH_3$ | CH | |
| H | H | H | $SO_2(CH_2)_2C(O)CH_3$ | $CH_3$ | $OCH_3$ | N | |
| H | H | H | $SO_2(CH_2)_2C(O)N(CH_3)_2$ | $OCH_3$ | $OCH_3$ | CH | |
| H | H | H | $SO_2(CH_2)_2C(O)N(CH_3)_2$ | $CH_3$ | $OCH_3$ | CH | |
| H | H | H | $SO_2(CH_2)_2Br$ | $OCH_3$ | $OCH_3$ | CH | |
| H | H | H | $SO_2(CH_2)_2Br$ | $CH_3$ | $OCH_3$ | N | |
| H | H | H | $SO_2CH_2F$ | $OCH_3$ | $OCH_3$ | CH | |
| H | H | H | $SO_2CH_2F$ | $CH_3$ | $OCH_3$ | N | |
| H | H | H | $SO_2CHClCH=CH_2$ | $OCH_3$ | $OCH_3$ | CH | |
| H | H | H | $SO_2CHClCH=CH_2$ | $CH_3$ | $OCH_3$ | N | |
| H | 4-$CH_3$ | H | $SO_2CH_2C\equiv CH$ | $OCH_3$ | $OCH_3$ | CH | |
| H | 4-$CH_3$ | H | $SO_2CH_2C\equiv CH$ | $CH_3$ | $OCH_3$ | N | |
| H | H | H | $SO_2(CH_2)_2C\equiv CH$ | $CH_3$ | $OCH_3$ | CH | |
| H | H | H | $SO_2(CH_2)_2C\equiv CH$ | $OCH_3$ | $OCH_3$ | CH | |
| H | H | H | $SO_2(CH_2)_2C\equiv CH$ | $CH_3$ | $OCH_3$ | N | |
| H | H | H | $CH_2P(O)(OCH_3)_2$ | $OCH_3$ | $OCH_3$ | CH | |
| H | H | H | $CH_2P(O)(OCH_3)_2$ | $CH_3$ | $OCH_3$ | N | |
| H | H | H | $P(O)(OCH_3)_2$ | $OCH_3$ | $OCH_3$ | CH | |
| H | H | H | $P(O)(OCH_3)_2$ | $CH_3$ | $OCH_3$ | N | |
| H | H | H | $P(O)(SCH_3)_2$ | $OCH_3$ | $OCH_3$ | CH | |
| H | 4-Cl | H | $CH_2OH$ | $CH_3$ | $CH_3$ | CH | |
| H | 4-Cl | H | $CH_2OH$ | $CH_3$ | $OCH_3$ | CH | |
| H | 4-Cl | H | $CH_2OH$ | $OCH_3$ | $OCH_3$ | CH | |

TABLE Ia-continued

General Formula Ia

| R | R₁ | Rₓ | Q₁ | X | Y | Z | m.p. (°C.) |
|---|---|---|---|---|---|---|---|
| H | 4-Cl | H | CH₂OH | Cl | OCH₃ | CH | |
| H | 4-Cl | H | CH₂OH | CH₃ | OCH₃ | N | |
| H | 4-Cl | H | CH₂OH | OCH₃ | OCH₃ | N | |
| H | H | H | (CH₂)₂OH | CH₃ | CH₃ | CH | |
| H | H | H | (CH₂)₂OH | CH₃ | OCH₃ | CH | |
| H | H | H | (CH₂)₂OH | OCH₃ | OCH₃ | CH | |
| H | H | H | (CH₂)₂OH | Cl | OCH₃ | CH | |
| H | H | H | (CH₂)₂OH | CH₃ | OCH₃ | N | |
| H | H | H | (CH₂)₂OH | OCH₃ | OCH₃ | N | |
| H | H | H | CH₂OCH₃ | CH₃ | CH₃ | CH | |
| H | H | H | CH₂OCH₃ | CH₃ | OCH₃ | CH | |
| H | H | H | CH₂OCH₃ | OCH₃ | OCH₃ | CH | |
| H | H | H | CH₂OCH₃ | Cl | OCH₃ | CH | |
| H | H | H | CH₂OCH₃ | CH₃ | OCH₃ | N | |
| H | H | H | CH₂OCH₃ | OCH₃ | OCH₃ | N | |
| H | H | H | (CH₂)₂OCH₃ | CH₃ | CH₃ | CH | |
| H | H | H | (CH₂)₂OCH₃ | CH₃ | OCH₃ | CH | 135.5–137 |
| H | H | H | (CH₂)₂OCH₃ | OCH₃ | OCH₃ | CH | 168.5–171 |
| H | H | H | (CH₂)₂OCH₃ | Cl | OCH₃ | CH | |
| H | H | H | (CH₂)₂OCH₃ | CH₃ | OCH₃ | N | 146.5–147.5 |
| H | H | H | (CH₂)₂OCH₃ | OCH₃ | OCH₃ | N | 145–148 |
| H | H | H | (CH₂)₂OCH₂CH₃ | CH₃ | CH₃ | CH | |
| H | H | H | (CH₂)₂OCH₂CH₃ | CH₃ | OCH₃ | CH | 147–148.5 |
| H | H | H | (CH₂)₂OCH₂CH₃ | OCH₃ | OCH₃ | CH | |
| H | H | H | (CH₂)₂OCH₂CH₃ | Cl | OCH₃ | CH | |
| H | H | H | (CH₂)₂OCH₂CH₃ | OCH₃ | OCH₃ | N | |
| H | H | H | CH₂O(CH₂)₂CN | CH₃ | CH₃ | CH | |
| H | H | H | CH₂O(CH₂)₂CN | CH₃ | OCH₃ | CH | |
| H | H | H | CH₂O(CH₂)₂CN | OCH₃ | OCH₃ | CH | |
| H | H | H | CH₂O(CH₂)₂CN | Cl | OCH₃ | CH | |
| H | H | H | CH₂O(CH₂)₂CN | CH₃ | OCH₃ | N | |
| H | H | H | CH₂O(CH₂)₂CN | OCH₃ | OCH₃ | N | |
| H | H | H | CH₂SCH₃ | CH₃ | CH₃ | CH | |
| H | H | H | CH₂SCH₃ | CH₃ | OCH₃ | CH | 128–130 |
| H | H | H | CH₂SCH₃ | OCH₃ | OCH₃ | CH | |
| H | H | H | CH₂SCH₃ | Cl | OCH₃ | CH | |
| H | H | H | CH₂SCH₃ | CH₃ | OCH₃ | N | |
| H | H | H | CH₂SCH₃ | OCH₃ | OCH₃ | N | |
| H | H | H | (CH₂)₂SCH₃ | CH₃ | CH₃ | CH | |
| H | H | H | (CH₂)₂SCH₃ | CH₃ | OCH₃ | CH | |
| H | H | H | (CH₂)₂SCH₃ | OCH₃ | OCH₃ | CH | |
| H | H | H | (CH₂)₂SCH₃ | Cl | OCH₃ | CH | |
| H | H | H | (CH₂)₂SCH₃ | CH₃ | OCH₃ | N | |
| H | H | H | (CH₂)₂SCH₃ | OCH₃ | OCH₃ | N | |
| H | H | H | (CH₂)₃SCH₃ | CH₃ | CH₃ | CH | |
| H | H | H | (CH₂)₃SCH₃ | CH₃ | OCH₃ | CH | |
| H | H | H | (CH₂)₃SCH₃ | OCH₃ | OCH₃ | CH | |
| H | H | H | (CH₂)₃SCH₃ | Cl | OCH₃ | CH | |
| H | H | H | (CH₂)₃SCH₃ | CH₃ | OCH₃ | N | |
| H | H | H | (CH₂)₃SCH₃ | OCH₃ | OCH₃ | N | |
| H | H | H | CH₂S(O)CH₃ | CH₃ | CH₃ | CH | |
| H | H | H | CH₂S(O)CH₃ | CH₃ | OCH₃ | CH | |
| H | H | H | CH₂S(O)CH₃ | OCH₃ | OCH₃ | CH | |
| H | H | H | CH₂S(O)CH₃ | Cl | OCH₃ | CH | |
| H | H | H | CH₂S(O)CH₃ | CH₃ | OCH₃ | N | |
| H | H | H | CH₂S(O)CH₃ | OCH₃ | OCH₃ | N | |
| H | H | H | (CH₂)₂S(O)CH₃ | CH₃ | CH₃ | CH | |
| H | H | H | (CH₂)₂S(O)CH₃ | CH₃ | OCH₃ | CH | |
| H | H | H | (CH₂)₂S(O)CH₃ | OCH₃ | OCH₃ | CH | |
| H | H | H | (CH₂)₂S(O)CH₃ | Cl | OCH₃ | CH | |
| H | H | H | (CH₂)₂S(O)CH₃ | CH₃ | OCH₃ | N | |
| H | H | H | (CH₂)₂S(O)CH₃ | OCH₃ | OCH₃ | N | |
| H | H | H | (CH₂)₂S(O)CH₂CH₃ | CH₃ | CH₃ | CH | |
| H | H | H | (CH₂)₂S(O)CH₂CH₃ | CH₃ | OCH₃ | CH | |
| H | H | H | (CH₂)₂S(O)CH₂CH₃ | OCH₃ | OCH₃ | CH | |
| H | H | H | (CH₂)₂S(O)CH₂CH₃ | Cl | OCH₃ | CH | |
| H | H | H | (CH₂)₂S(O)CH₂CH₃ | CH₃ | OCH₃ | N | |
| H | H | H | (CH₂)₂S(O)CH₂CH₃ | OCH₃ | OCH₃ | N | |
| H | 4-CH₃ | H | CH₂SO₂CH₃ | CH₃ | CH₃ | CH | |
| H | 4-CH₃ | H | CH₂SO₂CH₃ | CH₃ | OCH₃ | CH | |
| H | 4-CH₃ | H | CH₂SO₂CH₃ | OCH₃ | OCH₃ | CH | |
| H | 4-CH₃ | H | CH₂SO₂CH₃ | CH₃ | OCH₃ | N | |
| H | H | H | (CH₂)₂SO₂CH₃ | CH₃ | CH₃ | CH | |
| H | H | H | (CH₂)₂SO₂CH₃ | CH₃ | OCH₃ | CH | |
| H | H | H | (CH₂)₂SO₂CH₃ | OCH₃ | OCH₃ | CH | |
| H | H | H | (CH₂)₂SO₂CH₃ | Cl | OCH₃ | CH | |
| H | H | H | (CH₂)₂SO₂CH₃ | CH₃ | OCH₃ | N | |
| H | H | H | (CH₂)₂SO₂CH₃ | OCH₃ | OCH₃ | N | |
| H | H | H | (CH₂)₃SO₂CH₃ | OCH₃ | OCH₃ | CH | |
| H | H | H | (CH₂)₃SO₂CH₃ | CH₃ | OCH₃ | N | |

TABLE Ia-continued

General Formula Ia

| R | R₁ | Rₓ | Q₁ | X | Y | Z | m.p. (°C.) |
|---|---|---|---|---|---|---|---|
| H | H | H | (CH₂)₃SO₂CH₃ | OCH₃ | OCH₃ | N | |
| H | H | H | CH₂SO₂CH₂CH₃ | OCH₃ | OCH₃ | CH | |
| H | H | H | CH₂SO₂CH₂CH₃ | Cl | OCH₃ | CH | |
| H | H | H | CH₂SO₂CH₂CH₃ | CH₃ | OCH₃ | N | |
| H | H | H | CH₂CO₂CH₃ | CH₃ | CH₃ | CH | |
| H | H | H | CH₂CO₂CH₃ | CH₃ | OCH₃ | CH | |
| H | H | H | CH₂CO₂CH₃ | OCH₃ | OCH₃ | CH | |
| H | H | H | CH₂CO₂CH₃ | Cl | OCH₃ | CH | |
| H | H | H | CH₂CO₂CH₃ | CH₃ | OCH₃ | N | |
| H | H | H | CH₂CO₂CH₂CH₃ | CH₃ | CH₃ | CH | |
| H | H | H | CH₂CO₂CH₂CH₃ | CH₃ | OCH₃ | CH | |
| H | H | H | CH₂CO₂CH₂CH₃ | OCH₃ | OCH₃ | CH | |
| H | H | H | CH₂CO₂CH₂CH₃ | Cl | OCH₃ | CH | |
| H | H | H | CH₂CO₂CH₂CH₃ | CH₃ | OCH₃ | N | |
| H | H | H | CH₂SO₂N(CH₃)₂ | CH₃ | CH₃ | CH | |
| H | H | H | CH₂SO₂N(CH₃)₂ | CH₃ | OCH₃ | CH | |
| H | H | H | CH₂SO₂N(CH₃)₂ | OCH₃ | OCH₃ | CH | |
| H | H | H | CH₂SO₂N(CH₃)₂ | Cl | OCH₃ | CH | |
| H | H | H | CH₂SO₂N(CH₃)₂ | CH₃ | OCH₃ | N | |
| H | H | H | CH₂SO₂N(CH₃)₂ | OCH₃ | OCH₃ | N | |
| H | 4-Cl | H | (CH₂)₂SO₂N(CH₃)₂ | CH₃ | OCH₃ | CH | |
| H | 4-Cl | H | (CH₂)₂SO₂N(CH₃)₂ | OCH₃ | OCH₃ | CH | |
| H | 4-Cl | H | (CH₂)₂SO₂N(CH₃)₂ | CH₃ | OCH₃ | N | |
| H | H | H | CH₂SO₂N(CH₂CH₃)₂ | CH₃ | OCH₃ | CH | |
| H | H | H | CH₂SO₂N(CH₂CH₃)₂ | OCH₃ | OCH₃ | CH | |
| H | H | H | CH₂SO₂N(CH₂CH₃)₂ | CH₃ | OCH₃ | N | |
| H | H | H | CH₂C(O)CH₃ | CH₃ | OCH₃ | CH | |
| H | H | H | CH₂C(O)CH₃ | OCH₃ | OCH₃ | CH | |
| H | H | H | CH₂C(O)CH₃ | CH₃ | OCH₃ | N | |
| H | 4-Cl | H | (CH₂)₂C(O)CH₃ | CH₃ | OCH₃ | CH | |
| H | 4-Cl | H | (CH₂)₂C(O)CH₃ | OCH₃ | OCH₃ | CH | |
| H | 4-Cl | H | (CH₂)₂C(O)CH₃ | CH₃ | OCH₃ | N | |
| H | H | H | CH₂CN | CH₃ | CH₃ | CH | |
| H | H | H | CH₂CN | CH₃ | OCH₃ | CH | 127–138 |
| H | H | H | CH₂CN | OCH₃ | OCH₃ | CH | 189–191.5 |
| H | H | H | CH₂CN | Cl | OCH₃ | CH | 181–183 |
| H | H | H | CH₂CN | CH₃ | OCH₃ | N | 155.5–159 |
| H | H | H | CH₂CN | CH₃ | CH₃ | N | 173–176 |
| H | H | H | CH₂CN | OCH₃ | OCH₃ | N | 167.5–169 |
| H | H | H | (CH₂)₂CN | CH₃ | CH₃ | CH | |
| H | H | H | (CH₂)₂CN | CH₃ | OCH₃ | CH | |
| H | H | H | (CH₂)₂CN | OCH₃ | OCH₃ | CH | |
| H | H | H | (CH₂)₂CN | Cl | OCH₃ | CH | |
| H | H | H | (CH₂)₂CN | CH₃ | OCH₃ | N | |
| H | H | H | (CH₂)₂CN | OCH₃ | OCH₃ | N | |
| H | H | H | CH₂C(O)N(CH₃)₂ | CH₃ | OCH₃ | CH | |
| H | H | H | CH₂C(O)N(CH₃)₂ | OCH₃ | OCH₃ | CH | |
| H | H | H | CH₂C(O)N(CH₃)₂ | CH₃ | OCH₃ | N | |
| H | H | H | (CH₂)₂C(O)N(CH₃)₂ | CH₃ | OCH₃ | CH | |
| H | H | H | (CH₂)₂C(O)N(CH₃)₂ | OCH₃ | OCH₃ | CH | |
| H | H | H | (CH₂)₂C(O)N(CH₃)₂ | CH₃ | OCH₃ | N | |
| H | H | H | CH₂Cl | CH₃ | CH₃ | CH | 152–154 |
| H | H | H | CH₂Cl | CH₃ | OCH₃ | CH | 155–156 |
| H | H | H | CH₂Cl | OCH₃ | OCH₃ | CH | 183–184 |
| H | H | H | CH₂Cl | Cl | OCH₃ | CH | 168–170 |
| H | H | H | CH₂Cl | CH₃ | OCH₃ | N | 150–152 |
| H | H | H | CH₂Cl | OCH₃ | OCH₃ | N | 108–110 |
| H | H | H | CH₂Cl | CH₃ | CH₃ | N | 141–146 |
| CH₃ | H | H | CH₂Cl | CH₃ | OCH₃ | N | 125–129 |
| H | H | H | (CH₂)₂Cl | OCH₃ | OCH₃ | CH | |
| H | H | H | (CH₂)₂Cl | Cl | OCH₃ | CH | |
| H | H | H | (CH₂)₂Cl | CH₃ | OCH₃ | N | |
| H | H | H | (CH₂)₂Cl | OCH₃ | OCH₃ | N | |
| H | H | H | CH₂F | CH₃ | CH₃ | CH | |
| H | H | H | CH₂F | CH₃ | OCH₃ | CH | |
| H | H | H | CH₂F | OCH₃ | OCH₃ | CH | |
| H | H | H | CH₂F | Cl | OCH₃ | CH | |
| H | H | H | CH₂F | CH₃ | OCH₃ | N | |
| H | H | H | CH₂F | OCH₃ | OCH₃ | N | |
| H | H | H | (CH₂)₂F | CH₃ | OCH₃ | CH | |
| H | H | H | (CH₂)₂F | OCH₃ | OCH₃ | CH | |
| H | H | H | (CH₂)₂F | CH₃ | OCH₃ | N | |
| H | H | H | CH₂Br | CH₃ | CH₃ | CH | |
| H | H | H | CH₂Br | CH₃ | OCH₃ | CH | |
| H | H | H | CH₂Br | OCH₃ | OCH₃ | CH | |
| H | H | H | CH₂Br | Cl | OCH₃ | CH | |
| H | H | H | CH₂Br | CH₃ | OCH₃ | N | |
| H | H | H | CH₂Br | OCH₃ | OCH₃ | N | |
| H | H | H | (CH₂)₂Br | CH₃ | OCH₃ | CH | |
| H | H | H | (CH₂)₂Br | OCH₃ | OCH₃ | CH | |

TABLE Ia-continued

General Formula Ia

| R | $R_1$ | $R_x$ | $Q_1$ | X | Y | Z | m.p. (°C.) |
|---|---|---|---|---|---|---|---|
| H | H | H | (CH$_2$)$_2$Br | Cl | OCH$_3$ | CH | |
| H | H | H | CH$_2$SCH$_3$ | OCH$_2$CH$_3$ | C$_2$H$_5$ | CH | |
| H | H | H | CH$_2$SCH$_3$ | OCH$_2$CH$_3$ | C$_2$H$_5$ | N | |
| H | H | H | CH$_2$SCH$_3$ | OCH$_2$CH$_3$ | CH$_2$OCH$_3$ | CH | |
| H | H | H | CH$_2$SCH$_3$ | OCH$_2$CH$_3$ | CH$_2$OCH$_3$ | N | |
| H | H | H | CH$_2$SCH$_3$ | OCH$_2$CH$_3$ | NHCH$_3$ | N | |
| H | H | H | CH$_2$SCH$_3$ | OCH$_2$CH$_3$ | CH(OCH$_3$)$_2$ | CH | |
| H | H | H | CH$_2$SCH$_3$ | OCF$_2$H | C$_2$H$_5$ | CH | |
| H | H | H | CH$_2$SCH$_3$ | OCF$_2$H | CH$_2$OCH$_3$ | CH | |
| H | H | H | CH$_2$SCH$_3$ | OCH$_2$CF$_3$ | C$_2$H$_5$ | CH | |
| H | H | H | CH$_2$SCH$_3$ | OCH$_2$CF$_3$ | C$_2$H$_5$ | N | |
| H | H | H | CH$_2$SCH$_3$ | OCH$_2$CF$_3$ | CH$_2$OCH$_3$ | CH | |
| H | H | H | CH$_2$SCH$_3$ | OCH$_2$CF$_3$ | CH$_2$OCH$_3$ | N | |
| H | H | H | CH$_2$SCH$_3$ | OCH$_2$CF$_3$ | NHCH$_3$ | N | |
| H | H | H | CH$_2$SCH$_3$ | OCH$_2$CF$_3$ | CH(OCH$_3$)$_2$ | N | |
| H | H | H | CH$_2$SCH$_3$ | CH$_3$ | C$_2$H$_5$ | N | |
| H | H | H | CH$_2$SCH$_3$ | CH$_3$ | CH$_2$OCH$_3$ | CH | |
| H | H | H | CH$_2$SCH$_3$ | CH$_3$ | CH$_2$OCH$_3$ | N | |
| H | H | H | CH$_2$SCH$_3$ | CH$_3$ | NHCH$_3$ | N | |
| H | H | H | CH$_2$SCH$_3$ | CH$_3$ | CH(OCH$_3$)$_2$ | N | |
| H | H | H | CH$_2$SCH$_3$ | OCH$_3$ | C$_2$H$_5$ | CH | |
| H | H | H | CH$_2$SCH$_3$ | OCH$_3$ | C$_2$H$_5$ | N | |
| H | H | H | CH$_2$SCH$_3$ | OCH$_3$ | CH$_2$OCH$_3$ | CH | |
| H | H | H | CH$_2$SCH$_3$ | OCH$_3$ | CH$_2$OCH$_3$ | N | |
| H | H | H | CH$_2$SCH$_3$ | OCH$_3$ | NHCH$_3$ | N | |
| H | H | H | CH$_2$SCH$_3$ | OCH$_3$ | CH(OCH$_3$)$_2$ | CH | |
| H | H | H | CH$_2$SCH$_3$ | OCH$_3$ | CH(OCH$_3$)$_2$ | N | |
| H | 4-Cl | H | CH$_2$OCH$_3$ | OCH$_2$CH$_3$ | C$_2$H$_5$ | CH | |
| H | 4-Cl | H | CH$_2$OCH$_3$ | OCH$_2$CH$_3$ | C$_2$H$_5$ | N | |
| H | 4-Cl | H | CH$_2$OCH$_3$ | OCH$_2$CH$_3$ | CH$_2$OCH$_3$ | CH | |
| H | 4-Cl | H | CH$_2$OCH$_3$ | OCH$_2$CH$_3$ | CH$_2$OCH$_3$ | N | |
| H | 4-Cl | H | CH$_2$OCH$_3$ | OCH$_2$CH$_3$ | NHCH$_3$ | CH | |
| H | 4-Cl | H | CH$_2$OCH$_3$ | OCH$_2$CH$_3$ | NHCH$_3$ | N | |
| H | 4-Cl | H | CH$_2$OCH$_3$ | OCH$_2$CH$_3$ | CH(OCH$_3$)$_2$ | CH | |
| H | 4-Cl | H | CH$_2$OCH$_3$ | OCH$_2$CH$_3$ | CH(OCH$_3$)$_2$ | N | |
| H | 4-Cl | H | CH$_2$OCH$_3$ | OCF$_2$H | C$_2$H$_5$ | CH | |
| H | 4-Cl | H | CH$_2$OCH$_3$ | OCF$_2$H | CH$_2$OCH$_3$ | CH | |
| H | 4-Cl | H | CH$_2$OCH$_3$ | OCF$_2$H | NHCH$_3$ | CH | |
| H | 4-Cl | H | CH$_2$OCH$_3$ | OCH$_2$CF$_3$ | C$_2$H$_5$ | CH | |
| H | 4-Cl | H | CH$_2$OCH$_3$ | OCH$_2$CF$_3$ | CH$_2$OCH$_3$ | N | |
| H | 4-Cl | H | CH$_2$OCH$_3$ | OCH$_2$CF$_3$ | NHCH$_3$ | CH | |
| H | 4-Cl | H | CH$_2$OCH$_3$ | OCH$_2$CF$_3$ | NHCH$_3$ | N | |
| H | 4-Cl | H | CH$_2$OCH$_3$ | OCH$_2$CF$_3$ | CH(OCH$_3$)$_2$ | CH | |
| H | 4-Cl | H | CH$_2$OCH$_3$ | OCH$_2$CF$_3$ | CH(OCH$_3$)$_2$ | N | |
| H | 4-Cl | H | CH$_2$OCH$_3$ | Cl | NHCH$_3$ | CH | |
| H | 4-Cl | H | CH$_2$OCH$_3$ | CH$_3$ | C$_2$H$_5$ | CH | |
| H | 4-Cl | H | CH$_2$OCH$_3$ | CH$_3$ | C$_2$H$_5$ | N | |
| H | 4-Cl | H | CH$_2$OCH$_3$ | CH$_3$ | CH$_2$OCH$_3$ | CH | |
| H | 4-Cl | H | CH$_2$OCH$_3$ | CH$_3$ | CH$_2$OCH$_3$ | N | |
| H | 4-Cl | H | CH$_2$OCH$_3$ | Cl | NHCH$_3$ | CH | |
| H | 4-Cl | H | CH$_2$OCH$_3$ | CH$_3$ | C$_2$H$_5$ | CH | |
| H | 4-Cl | H | CH$_2$OCH$_3$ | CH$_3$ | C$_2$H$_5$ | N | |
| H | 4-Cl | H | CH$_2$OCH$_3$ | CH$_3$ | CH$_2$OCH$_3$ | CH | |
| H | 4-Cl | H | CH$_2$OCH$_3$ | CH$_3$ | CH$_2$OCH$_3$ | N | |
| H | 4-Cl | H | CH$_2$OCH$_3$ | CH$_3$ | NHCH$_3$ | N | |
| H | 4-Cl | H | CH$_2$OCH$_3$ | CH$_3$ | CH(OCH$_3$)$_2$ | CH | |
| H | 4-Cl | H | CH$_2$OCH$_3$ | CH$_3$ | CH(OCH$_3$)$_2$ | N | |
| H | 4-Cl | H | CH$_2$OCH$_3$ | OCH$_3$ | C$_2$H$_5$ | CH | |
| H | 4-Cl | H | CH$_2$OCH$_3$ | OCH$_3$ | C$_2$H$_5$ | N | |
| H | 4-Cl | H | CH$_2$OCH$_3$ | OCH$_3$ | CH$_2$OCH$_3$ | CH | |
| H | 4-Cl | H | CH$_2$OCH$_3$ | OCH$_3$ | CH$_2$OCH$_3$ | N | |
| H | 4-Cl | H | CH$_2$OCH$_3$ | OCH$_3$ | NHCH$_3$ | CH | |
| H | 4-Cl | H | CH$_2$OCH$_3$ | OCH$_3$ | NHCH$_3$ | N | |
| H | 4-Cl | H | CH$_2$OCH$_3$ | OCH$_3$ | CH(OCH$_3$)$_2$ | CH | |
| H | 4-Cl | H | CH$_2$OCH$_3$ | OCH$_3$ | CH(OCH$_3$)$_2$ | N | |
| H | H | H | CN | CH$_3$ | CH$_3$ | CH | 165–167 |
| H | H | H | CN | CH$_3$ | OCH$_3$ | CH | 166–168 |
| H | H | H | CN | OCH$_3$ | OCH$_3$ | CH | 188–190 |
| H | H | H | CN | Cl | OCH$_3$ | CH | 169–171 |
| H | H | H | CN | CH$_3$ | OCH$_3$ | N | 150–152 |
| H | H | H | CN | OCH$_3$ | OCH$_3$ | N | 176–178 |
| H | H | H | SO$_2$NHCH$_3$ | OCH$_3$ | OCH$_3$ | CH | |
| H | H | H | 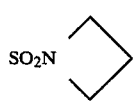 SO$_2$N | OCH$_3$ | OCH$_3$ | CH | |

TABLE Ia-continued

General Formula Ia

| R | R$_1$ | R$_x$ | Q$_1$ | X | Y | Z | m.p. (°C.) |
|---|---|---|---|---|---|---|---|
| H | H | H | SO$_2$NHC$_6$H$_5$ | OCH$_3$ | OCH$_3$ | CH | |

TABLE IIa

General Formula IIa

| R | R$_1$ | R$_x$ | Q$_1$ | X | Y | Z | m.p. (°C.) |
|---|---|---|---|---|---|---|---|
| H | H | H | S(CH$_2$)$_2$OCH$_3$ | CH$_3$ | OCH$_3$ | CH | |
| H | H | H | S(CH$_2$)$_2$OCH$_3$ | OCH$_3$ | OCH$_3$ | CH | |
| H | H | H | S(CH$_2$)$_2$OCH$_3$ | Cl | OCH$_3$ | CH | |
| H | H | H | S(CH$_2$)$_2$OCH$_3$ | CH$_3$ | OCH$_3$ | N | |
| H | H | H | S(CH$_2$)$_3$OCH$_3$ | CH$_3$ | OCH$_3$ | CH | |
| H | H | H | S(CH$_2$)$_3$OCH$_3$ | OCH$_3$ | OCH$_3$ | CH | |
| H | H | H | S(CH$_2$)$_2$OCH$_2$CN | OCH$_3$ | OCH$_3$ | CH | |
| H | H | H | S(CH$_2$)$_2$OCH$_2$CN | CH$_3$ | OCH$_3$ | N | |
| H | H | H | S(CH$_2$)$_2$SCH$_3$ | CH$_3$ | CH$_3$ | CH | |
| H | H | H | S(CH$_2$)$_2$SCH$_3$ | CH$_3$ | OCH$_3$ | CH | |
| H | H | H | S(CH$_2$)$_2$SCH$_3$ | OCH$_3$ | OCH$_3$ | CH | |
| H | H | H | S(CH$_2$)$_2$SCH$_3$ | CH$_3$ | OCH$_3$ | N | |
| H | H | H | S(CH$_2$)$_2$S(O)CH$_3$ | CH$_3$ | OCH$_3$ | CH | |
| H | H | H | S(CH$_2$)$_2$S(O)CH$_3$ | OCH$_3$ | OCH$_3$ | CH | |
| H | H | H | S(CH$_2$)$_2$S(O)CH$_3$ | Cl | OCH$_3$ | CH | |
| H | H | H | S(CH$_2$)$_2$S(O)CH$_3$ | CH$_3$ | OCH$_3$ | N | |
| H | H | H | S(CH$_2$)$_2$S(O)CH$_2$CH$_3$ | OCH$_3$ | OCH$_3$ | CH | |
| H | H | H | S(CH$_2$)$_2$S(O)CH$_2$CH$_3$ | Cl | OCH$_3$ | CH | |
| H | H | H | S(CH$_2$)$_2$SO$_2$CH$_3$ | OCH$_3$ | OCH$_3$ | CH | |
| H | H | H | S(CH$_2$)$_2$SO$_2$CH$_3$ | Cl | OCH$_3$ | CH | |
| H | H | H | S(CH$_2$)$_2$SO$_2$CH$_3$ | CH$_3$ | OCH$_3$ | N | |
| H | H | H | S(CH$_2$)$_2$SO$_2$CH$_2$CH$_3$ | CH$_3$ | OCH$_3$ | CH | |
| H | H | H | S(CH$_2$)$_2$SO$_2$CH$_2$CH$_3$ | OCH$_3$ | OCH$_3$ | CH | |
| H | H | H | SCH$_2$CO$_2$CH$_3$ | CH$_3$ | OCH$_3$ | CH | |
| H | H | H | SCH$_2$CO$_2$CH$_3$ | OCH$_3$ | OCH$_3$ | CH | |
| H | H | H | SCH$_2$CO$_2$CH$_3$ | Cl | OCH$_3$ | CH | |
| H | H | H | SCH$_2$CO$_2$CH$_3$ | CH$_3$ | OCH$_3$ | N | |
| H | H | H | S(CH$_2$)$_3$SO$_2$N(CH$_3$)$_2$ | OCH$_3$ | OCH$_3$ | CH | |
| H | H | H | S(CH$_2$)$_2$SO$_2$N(CH$_2$CH$_3$)$_2$ | CH$_3$ | OCH$_3$ | CH | |
| H | H | H | S(CH$_2$)$_2$SO$_2$N(CH$_2$CH$_3$)$_2$ | OCH$_3$ | OCH$_3$ | CH | |
| H | H | H | SCH$_2$C(O)CH$_3$ | OCH$_3$ | OCH$_3$ | CH | |
| H | H | H | SCH$_2$C(O)CH$_3$ | CH$_3$ | OCH$_3$ | N | |
| H | H | H | S(CH$_2$)$_2$CN | CH$_3$ | CH$_3$ | CH | |
| H | H | H | S(CH$_2$)$_2$CN | CH$_3$ | OCH$_3$ | CH | |
| H | H | H | S(CH$_2$)$_2$CN | OCH$_3$ | OCH$_3$ | CH | |
| H | H | H | S(CH$_2$)$_2$CN | CH$_3$ | OCH$_3$ | N | |
| H | H | H | SCH$_2$C(O)N(CH$_3$)$_2$ | CH$_3$ | OCH$_3$ | CH | |
| H | H | H | SCH$_2$C(O)N(CH$_3$)$_2$ | OCH$_3$ | OCH$_3$ | CH | |
| H | H | H | SCH$_2$C(O)N(CH$_3$)$_2$ | CH$_3$ | OCH$_3$ | N | |
| H | 4-CH$_3$ | H | S(CH$_2$)$_2$C(O)N(CH$_3$)$_2$ | CH$_3$ | OCH$_3$ | CH | |
| H | 4-CH$_3$ | H | S(CH$_2$)$_2$C(O)N(CH$_3$)$_2$ | OCH$_3$ | OCH$_3$ | CH | |
| H | H | H | S(CH$_2$)$_2$Cl | CH$_3$ | CH$_3$ | CH | |
| H | H | H | S(CH$_2$)$_2$Cl | CH$_3$ | OCH$_3$ | CH | |
| H | H | H | S(CH$_2$)$_2$Cl | OCH$_3$ | OCH$_3$ | CH | |
| H | H | H | S(CH$_2$)$_2$Cl | Cl | OCH$_3$ | CH | |
| H | H | H | S(CH$_2$)$_2$Cl | CH$_3$ | OCH$_3$ | N | |
| H | H | H | S(CH$_2$)$_2$Cl | OCH$_3$ | OCH$_3$ | N | |
| H | H | H | S(CH$_2$)$_3$Cl | CH$_3$ | OCH$_3$ | CH | |
| H | H | H | S(CH$_2$)$_3$Cl | OCH$_3$ | OCH$_3$ | CH | |
| H | H | H | S(CH$_2$)$_3$Cl | CH$_3$ | OCH$_3$ | N | |
| H | H | H | S(CH$_2$)$_2$F | OCH$_3$ | OCH$_3$ | CH | |
| H | H | H | S(CH$_2$)$_2$F | CH$_3$ | OCH$_3$ | N | |
| H | H | H | S(CH$_2$)$_2$Br | CH$_3$ | CH$_3$ | CH | |
| H | H | H | S(CH$_2$)$_2$Br | OCH$_3$ | OCH$_3$ | CH | |
| H | 5-Cl | H | S—CHClCH=CH$_2$ | CH$_3$ | OCH$_3$ | CH | |
| H | 5-Cl | H | S—CHClCH=CH$_2$ | OCH$_3$ | OCH$_3$ | CH | |
| H | 5-Cl | H | S—CHClCH=CH$_2$ | CH$_3$ | OCH$_3$ | N | |
| H | H | H | SCH$_2$C≡CH | CH$_3$ | OCH$_3$ | CH | |
| H | H | H | SCH$_2$C≡CH | OCH$_3$ | OCH$_3$ | CH | |
| H | H | H | SCH$_2$C≡CH | CH$_3$ | OCH$_3$ | N | |
| H | H | H | S(CH$_2$)$_2$C≡CH | CH$_3$ | OCH$_3$ | CH | |
| H | H | H | S(CH$_2$)$_2$C≡CH | OCH$_3$ | OCH$_3$ | CH | |
| H | H | H | S(CH$_2$)$_2$C≡CH | CH$_3$ | OCH$_3$ | N | |
| H | 5-Cl | H | SO$_2$(CH$_2$)$_2$OCH$_3$ | OCH$_3$ | OCH$_3$ | CH | |
| H | 5-Cl | H | SO$_2$(CH$_2$)$_2$OCH$_3$ | CH$_3$ | OCH$_3$ | N | |
| H | H | H | SO$_2$CH$_2$OCH$_2$CH$_3$ | OCH$_3$ | OCH$_3$ | CH | |
| H | H | H | SO$_2$CH$_2$OCH$_2$CH$_3$ | CH$_3$ | OCH$_3$ | N | |
| H | H | H | SO$_2$(CH$_2$)$_2$OCH$_2$CH$_3$ | OCH$_3$ | OCH$_3$ | CH | |
| H | H | H | SO$_2$(CH$_2$)$_2$OCH$_2$CH$_3$ | CH$_3$ | OCH$_3$ | N | |
| H | H | H | SO$_2$(CH$_2$)$_2$SCH$_3$ | CH$_3$ | OCH$_3$ | CH | |
| H | H | H | SO$_2$(CH$_2$)$_2$SCH$_3$ | OCH$_3$ | OCH$_3$ | CH | |
| H | H | H | SO$_2$(CH$_2$)$_2$SCH$_3$ | CH$_3$ | OCH$_3$ | N | |

TABLE IIa-continued

General Formula IIa

| R | R$_1$ | R$_x$ | Q$_1$ | X | Y | Z | m.p. (°C.) |
|---|---|---|---|---|---|---|---|
| H | H | H | SO$_2$(CH$_2$)$_2$SCH$_2$CH$_3$ | OCH$_3$ | OCH$_3$ | CH | |
| H | H | H | SO$_2$(CH$_2$)$_2$SCH$_2$CH$_3$ | CH$_3$ | OCH$_3$ | N | |
| H | H | H | SO$_2$(CH$_2$)$_2$S(O)CH$_3$ | OCH$_3$ | OCH$_3$ | CH | |
| H | H | H | SO$_2$(CH$_2$)$_2$S(O)CH$_3$ | CH$_3$ | OCH$_3$ | N | |
| H | H | H | SO$_2$(CH$_2$)$_2$CO$_2$CH$_3$ | OCH$_3$ | OCH$_3$ | CH | |
| H | H | H | SO$_2$(CH$_2$)$_2$CO$_2$CH$_3$ | CH$_3$ | OCH$_3$ | N | |
| H | H | H | SO$_2$CH$_2$CO$_2$CH$_2$CH$_3$ | CH$_3$ | OCH$_3$ | CH | |
| H | H | H | SO$_2$CH$_2$CO$_2$CH$_2$CH$_3$ | OCH$_3$ | OCH$_3$ | CH | |
| H | H | H | SO$_2$CH$_2$CO$_2$CH$_2$CH$_3$ | CH$_3$ | OCH$_3$ | N | |
| H | H | H | SO$_2$(CH$_2$)$_2$C(O)CH$_3$ | CH$_3$ | OCH$_3$ | CH | |
| H | H | H | SO$_2$(CH$_2$)$_2$C(O)CH$_3$ | OCH$_3$ | OCH$_3$ | CH | |
| H | H | H | SO$_2$(CH$_2$)$_2$C(O)CH$_3$ | CH$_3$ | OCH$_3$ | N | |
| H | H | H | SO$_2$(CH$_2$)$_2$C(O)N(CH$_3$)$_2$ | OCH$_3$ | OCH$_3$ | CH | |
| H | H | H | SO$_2$(CH$_2$)$_2$C(O)N(CH$_3$)$_2$ | CH$_3$ | OCH$_3$ | N | |
| H | H | H | SO$_2$(CH$_2$)$_2$Br | OCH$_3$ | OCH$_3$ | CH | |
| H | H | H | SO$_2$(CH$_2$)$_2$Br | CH$_3$ | OCH$_3$ | N | |
| H | H | H | SO$_2$CH$_2$F | CH$_3$ | CH$_3$ | CH | |
| H | H | H | SO$_2$CH$_2$F | Cl | OCH$_3$ | CH | |
| H | H | H | SO$_2$CHClCH=CH$_2$ | OCH$_3$ | OCH$_3$ | CH | |
| H | H | H | SO$_2$CHClCH=CH$_2$ | CH$_3$ | OCH$_3$ | N | |
| H | 5-CH$_3$ | H | SO$_2$CH$_2$C≡CH | OCH$_3$ | OCH$_3$ | CH | |
| H | 5-CH$_3$ | H | SO$_2$CH$_2$C≡CH | CH$_3$ | OCH$_3$ | N | |
| H | H | H | SO$_2$(CH$_2$)$_2$C≡CH | CH$_3$ | OCH$_3$ | CH | |
| H | H | H | SO$_2$(CH$_2$)$_2$C≡CH | OCH$_3$ | OCH$_3$ | CH | |
| H | H | H | SO$_2$(CH$_2$)$_2$C≡CH | CH$_3$ | OCH$_3$ | N | |
| H | H | H | CH$_2$P(O)(OCH$_3$)$_2$ | OCH$_3$ | OCH$_3$ | CH | |
| H | H | H | CH$_2$P(O)(OCH$_3$)$_2$ | CH$_3$ | OCH$_3$ | N | |
| H | H | H | P(O)(OCH$_3$)$_2$ | OCH$_3$ | OCH$_3$ | CH | |
| H | H | H | P(O)(OCH$_3$)$_2$ | CH$_3$ | OCH$_3$ | N | |
| H | H | H | P(O)(SCH$_3$)$_2$ | OCH$_3$ | OCH$_3$ | CH | |
| H | H | H | P(O)(SCH$_3$)$_2$ | CH$_3$ | OCH$_3$ | N | |
| H | 5-Cl | H | CH$_2$OH | CH$_3$ | CH$_3$ | CH | |
| H | 5-Cl | H | CH$_2$OH | CH$_3$ | OCH$_3$ | CH | |
| H | 5-Cl | H | CH$_2$OH | OCH$_3$ | OCH$_3$ | CH | |
| H | 5-Cl | H | CH$_2$OH | Cl | OCH$_3$ | CH | |
| H | 5-Cl | H | CH$_2$OH | CH$_3$ | OCH$_3$ | N | |
| H | 5-Cl | H | CH$_2$OH | OCH$_3$ | OCH$_3$ | N | |
| H | H | H | (CH$_2$)$_2$OH | CH$_3$ | CH$_3$ | CH | |
| H | H | H | (CH$_2$)$_2$OH | CH$_3$ | OCH$_3$ | CH | |
| H | H | H | (CH$_2$)$_2$OH | OCH$_3$ | OCH$_3$ | CH | |
| H | H | H | (CH$_2$)$_2$OH | Cl | OCH$_3$ | CH | |
| H | H | H | (CH$_2$)$_2$OH | CH$_3$ | OCH$_3$ | N | |
| H | H | H | (CH$_2$)$_2$OH | OCH$_3$ | OCH$_3$ | N | |
| H | H | H | CH$_2$OCH$_3$ | CH$_3$ | CH$_3$ | CH | 175–177 |
| H | H | H | CH$_2$OCH$_3$ | CH$_3$ | OCH$_3$ | CH | |
| H | H | H | CH$_2$OCH$_3$ | OCH$_3$ | OCH$_3$ | CH | 171–173 |
| H | H | H | CH$_2$OCH$_3$ | Cl | OCH$_3$ | CH | 154–155 |
| H | H | H | CH$_2$OCH$_3$ | CH$_3$ | OCH$_3$ | N | 155–156 |
| H | H | H | CH$_2$OCH$_3$ | OCH$_3$ | OCH$_3$ | N | 158 |
| H | H | H | (CH$_2$)$_2$OCH$_3$ | CH$_3$ | CH$_3$ | CH | |
| H | H | H | (CH$_2$)$_2$OCH$_3$ | CH$_3$ | OCH$_3$ | CH | |
| H | H | H | (CH$_2$)$_2$OCH$_3$ | OCH$_3$ | OCH$_3$ | CH | |
| H | H | H | (CH$_2$)$_2$OCH$_3$ | Cl | OCH$_3$ | CH | |
| H | H | H | (CH$_2$)$_2$OCH$_3$ | CH$_3$ | OCH$_3$ | N | |
| H | H | H | (CH$_2$)$_2$OCH$_3$ | OCH$_3$ | OCH$_3$ | N | |
| H | H | H | CH$_2$OCH$_2$CH$_3$ | CH$_3$ | CH$_3$ | CH | |
| H | H | H | CH$_2$OCH$_2$CH$_3$ | CH$_3$ | OCH$_3$ | CH | |
| H | H | H | CH$_2$OCH$_2$CH$_3$ | OCH$_3$ | OCH$_3$ | CH | 143–146 |
| H | H | H | CH$_2$OCH$_2$CH$_3$ | Cl | OCH$_3$ | N | |
| H | H | H | CH$_2$OCH$_2$CH$_3$ | OCH$_3$ | OCH$_3$ | N | |
| H | H | H | CH$_2$O(CH$_2$)$_2$CN | CH$_3$ | CH$_3$ | CH | |
| H | H | H | CH$_2$O(CH$_2$)$_2$CN | CH$_3$ | OCH$_3$ | CH | |
| H | H | H | CH$_2$O(CH$_2$)$_2$CN | OCH$_3$ | OCH$_3$ | CH | |
| H | H | H | CH$_2$O(CH$_2$)$_2$CN | Cl | OCH$_3$ | CH | |
| H | H | H | CH$_2$O(CH$_2$)$_2$CN | CH$_3$ | OCH$_3$ | N | |
| H | H | H | CH$_2$O(CH$_2$)$_2$CN | OCH$_3$ | OCH$_3$ | N | |
| H | H | H | CH$_2$SCH$_3$ | CH$_3$ | CH$_3$ | CH | |
| H | H | H | CH$_2$SCH$_3$ | CH$_3$ | OCH$_3$ | CH | |
| H | H | H | CH$_2$SCH$_3$ | OCH$_3$ | OCH$_3$ | CH | 155–159(d) |
| H | H | H | CH$_2$SCH$_3$ | Cl | OCH$_3$ | CH | |
| H | H | H | CH$_2$SCH$_3$ | CH$_3$ | OCH$_3$ | N | |
| H | H | H | CH$_2$SCH$_3$ | OCH$_3$ | OCH$_3$ | N | |
| H | H | H | (CH$_2$)$_2$SCH$_3$ | CH$_3$ | CH$_3$ | CH | |
| H | H | H | (CH$_2$)$_2$SCH$_3$ | CH$_3$ | OCH$_3$ | CH | |
| H | H | H | (CH$_2$)$_2$SCH$_3$ | OCH$_3$ | OCH$_3$ | CH | |
| H | H | H | (CH$_2$)$_2$SCH$_3$ | Cl | OCH$_3$ | CH | |
| H | H | H | (CH$_2$)$_2$SCH$_3$ | CH$_3$ | OCH$_3$ | N | |
| H | H | H | (CH$_2$)$_2$SCH$_3$ | OCH$_3$ | OCH$_3$ | N | |
| H | H | H | (CH$_2$)$_3$SCH$_3$ | CH$_3$ | CH$_3$ | CH | |
| H | H | H | (CH$_2$)$_3$SCH$_3$ | CH$_3$ | OCH$_3$ | CH | |

TABLE IIa-continued

General Formula IIa

| R | $R_1$ | $R_x$ | $Q_1$ | X | Y | Z | m.p. (°C.) |
|---|---|---|---|---|---|---|---|
| H | H | H | $(CH_2)_3SCH_3$ | $OCH_3$ | $OCH_3$ | CH | |
| H | H | H | $(CH_2)_3SCH_3$ | Cl | $OCH_3$ | CH | |
| H | H | H | $(CH_2)_3SCH_3$ | $CH_3$ | $OCH_3$ | N | |
| H | H | H | $(CH_2)_3SCH_3$ | $OCH_3$ | $OCH_3$ | N | |
| H | H | H | $CH_2S(O)CH_3$ | $CH_3$ | $CH_3$ | CH | |
| H | H | H | $CH_2S(O)CH_3$ | $CH_3$ | $OCH_3$ | CH | |
| H | H | H | $CH_2S(O)CH_3$ | $OCH_3$ | $OCH_3$ | CH | |
| H | H | H | $CH_2S(O)CH_3$ | Cl | $OCH_3$ | CH | |
| H | H | H | $CH_2S(O)CH_3$ | $CH_3$ | $OCH_3$ | N | |
| H | H | H | $CH_2S(O)CH_3$ | $OCH_3$ | $OCH_3$ | N | |
| H | H | H | $(CH_2)_2S(O)CH_3$ | $CH_3$ | $CH_3$ | CH | |
| H | H | H | $(CH_2)_2S(O)CH_3$ | $CH_3$ | $OCH_3$ | CH | |
| H | H | H | $(CH_2)_2S(O)CH_3$ | $OCH_3$ | $OCH_3$ | CH | |
| H | H | H | $(CH_2)_2S(O)CH_3$ | Cl | $OCH_3$ | CH | |
| H | H | H | $(CH_2)_2S(O)CH_3$ | $CH_3$ | $OCH_3$ | N | |
| H | H | H | $(CH_2)_2S(O)CH_3$ | $OCH_3$ | $OCH_3$ | N | |
| H | H | H | $(CH_2)_2S(O)CH_2CH_3$ | $CH_3$ | $CH_3$ | CH | |
| H | H | H | $(CH_2)_2S(O)CH_2CH_3$ | $CH_3$ | $OCH_3$ | CH | |
| H | H | H | $(CH_2)_2S(O)CH_2CH_3$ | $OCH_3$ | $OCH_3$ | CH | |
| H | H | H | $(CH_2)_2S(O)CH_2CH_3$ | Cl | $OCH_3$ | CH | |
| H | H | H | $(CH_2)_2S(O)CH_2CH_3$ | $CH_3$ | $OCH_3$ | N | |
| H | H | H | $(CH_2)_2S(O)CH_2CH_3$ | $OCH_3$ | $OCH_3$ | N | |
| H | 4-$CH_3$ | H | $CH_2SO_2CH_3$ | $CH_3$ | $CH_3$ | CH | |
| H | 4-$CH_3$ | H | $CH_2SO_2CH_3$ | $CH_3$ | $OCH_3$ | CH | |
| H | 4-$CH_3$ | H | $CH_2SO_2CH_3$ | $OCH_3$ | $OCH_3$ | CH | |
| H | 4-$CH_3$ | H | $CH_2SO_2CH_3$ | $CH_3$ | $OCH_3$ | N | |
| H | H | H | $(CH_2)_2SO_2CH_3$ | $CH_3$ | $CH_3$ | CH | |
| H | H | H | $(CH_2)_2SO_2CH_3$ | $CH_3$ | $OCH_3$ | CH | |
| H | H | H | $(CH_2)_2SO_2CH_3$ | $OCH_3$ | $OCH_3$ | CH | |
| H | H | H | $(CH_2)_2SO_2CH_3$ | Cl | $OCH_3$ | CH | |
| H | H | H | $(CH_2)_2SO_2CH_3$ | $CH_3$ | $OCH_3$ | N | |
| H | H | H | $(CH_2)_2SO_2CH_3$ | $OCH_3$ | $OCH_3$ | N | |
| H | H | H | $(CH_2)_3SO_2CH_3$ | $OCH_3$ | $OCH_3$ | CH | |
| H | H | H | $(CH_2)_3SO_2CH_3$ | $CH_3$ | $OCH_3$ | N | |
| H | H | H | $CH_2SO_2CH_2CH_3$ | $CH_3$ | $OCH_3$ | CH | |
| H | H | H | $CH_2SO_2CH_2CH_3$ | $OCH_3$ | $OCH_3$ | CH | |
| H | H | H | $CH_2SO_2CH_2CH_3$ | Cl | $OCH_3$ | CH | |
| H | H | H | $CH_2SO_2CH_2CH_3$ | $CH_3$ | $OCH_3$ | N | |
| H | H | H | $CH_2CO_2CH_3$ | $CH_3$ | $CH_3$ | CH | |
| H | H | H | $CH_2CO_2CH_3$ | $CH_3$ | $OCH_3$ | CH | |
| H | H | H | $CH_2CO_2CH_3$ | $OCH_3$ | $OCH_3$ | CH | |
| H | H | H | $CH_2CO_2CH_3$ | Cl | $OCH_3$ | CH | |
| H | H | H | $CH_2CO_2CH_3$ | $CH_3$ | $OCH_3$ | N | |
| H | H | H | $CH_2CO_2CH_2CH_3$ | $CH_3$ | $CH_3$ | CH | |
| H | H | H | $CH_2CO_2CH_2CH_3$ | $CH_3$ | $OCH_3$ | CH | |
| H | H | H | $CH_2CO_2CH_2CH_3$ | $OCH_3$ | $OCH_3$ | CH | |
| H | H | H | $CH_2CO_2CH_2CH_3$ | Cl | $OCH_3$ | CH | |
| H | H | H | $CH_2CO_2CH_2CH_3$ | $CH_3$ | $OCH_3$ | N | |
| H | H | H | $CH_2SO_2N(CH_3)_2$ | $CH_3$ | $CH_3$ | CH | |
| H | H | H | $CH_2SO_2N(CH_3)_2$ | $CH_3$ | $OCH_3$ | CH | |
| H | H | H | $CH_2SO_2N(CH_3)_2$ | $OCH_3$ | $OCH_3$ | CH | |
| H | H | H | $CH_2SO_2N(CH_3)_2$ | Cl | $OCH_3$ | CH | |
| H | H | H | $CH_2SO_2N(CH_3)_2$ | $CH_3$ | $OCH_3$ | N | |
| H | H | H | $CH_2SO_2N(CH_3)_2$ | $OCH_3$ | $OCH_3$ | N | |
| H | 5-Cl | H | $(CH_2)_2SO_2N(CH_3)_2$ | $CH_3$ | $OCH_3$ | CH | |
| H | 5-Cl | H | $(CH_2)_2SO_2N(CH_3)_2$ | $OCH_3$ | $OCH_3$ | CH | |
| H | 5-Cl | H | $(CH_2)_2SO_2N(CH_3)_2$ | $CH_3$ | $OCH_3$ | N | |
| H | H | H | $CH_2SO_2N(CH_2CH_3)_2$ | $CH_3$ | $OCH_3$ | CH | |
| H | H | H | $CH_2SO_2N(CH_2CH_3)_2$ | $OCH_3$ | $OCH_3$ | CH | |
| H | H | H | $CH_2SO_2N(CH_2CH_3)_2$ | $CH_3$ | $OCH_3$ | N | |
| H | H | H | $CH_2C(O)CH_3$ | $CH_3$ | $OCH_3$ | CH | |
| H | H | H | $CH_2C(O)CH_3$ | $OCH_3$ | $OCH_3$ | CH | |
| H | H | H | $CH_2C(O)CH_3$ | $CH_3$ | $OCH_3$ | N | |
| H | 5-Cl | H | $(CH_2)_2C(O)CH_3$ | $CH_3$ | $OCH_3$ | CH | |
| H | 5-Cl | H | $(CH_2)_2C(O)CH_3$ | $OCH_3$ | $OCH_3$ | CH | |
| H | 5-Cl | H | $(CH_2)_2C(O)CH_3$ | $CH_3$ | $OCH_3$ | N | |
| H | H | H | $CH_2CN$ | $CH_3$ | $CH_3$ | CH | |
| H | H | H | $CH_2CN$ | $CH_3$ | $OCH_3$ | CH | |
| H | H | H | $CH_2CN$ | $OCH_3$ | $OCH_3$ | CH | |
| H | H | H | $CH_2CN$ | Cl | $OCH_3$ | CH | |
| H | H | H | $CH_2CN$ | $CH_3$ | $OCH_3$ | N | |
| H | H | H | $CH_2CN$ | $OCH_3$ | $OCH_3$ | N | 105–110 |
| H | H | H | $(CH_2)_2CN$ | $CH_3$ | $CH_3$ | CH | |
| H | H | H | $(CH_2)_2CN$ | $CH_3$ | $OCH_3$ | CH | |
| H | H | H | $(CH_2)_2CN$ | $OCH_3$ | $OCH_3$ | CH | |
| H | H | H | $(CH_2)_2CN$ | Cl | $OCH_3$ | CH | |
| H | H | H | $(CH_2)_2CN$ | $CH_3$ | $OCH_3$ | N | |
| H | H | H | $(CH_2)_2CN$ | $OCH_3$ | $OCH_3$ | N | |
| H | H | H | $CH_2C(O)N(CH_3)_2$ | $CH_3$ | $OCH_3$ | CH | |
| H | H | H | $CH_2C(O)N(CH_3)_2$ | $OCH_3$ | $OCH_3$ | CH | |

TABLE IIa-continued

General Formula IIa

| R | R₁ | Rₓ | Q₁ | X | Y | Z | m.p. (°C.) |
|---|---|---|---|---|---|---|---|
| H | H | H | CH₂C(O)N(CH₃)₂ | CH₃ | OCH₃ | N | |
| H | H | H | (CH₂)₂C(O)N(CH₃)₂ | CH₃ | OCH₃ | CH | |
| H | H | H | (CH₂)₂C(O)N(CH₃)₂ | OCH₃ | OCH₃ | CH | |
| H | H | H | (CH₂)₂C(O)N(CH₃)₂ | CH₃ | OCH₃ | N | |
| H | H | H | CH₂Cl | CH₃ | CH₃ | CH | 186–187 |
| H | H | H | CH₂Cl | CH₃ | OCH₃ | CH | 161.5–163 |
| H | H | H | CH₂Cl | OCH₃ | OCH₃ | CH | 175–177 |
| H | H | H | CH₂Cl | Cl | OCH₃ | CH | 165–167 |
| H | H | H | CH₂Cl | CH₃ | OCH₃ | N | 158–159 |
| H | H | H | CH₂Cl | OCH₃ | OCH₃ | N | 140–143 |
| H | H | H | CH₂Cl | CH₃ | CH₃ | N | 175.5–177 |
| H | H | H | (CH₂)₂Cl | CH₃ | CH₃ | CH | |
| H | H | H | (CH₂)₂Cl | CH₃ | OCH₃ | CH | |
| H | H | H | (CH₂)₂Cl | OCH₃ | OCH₃ | CH | |
| H | H | H | (CH₂)₂Cl | Cl | OCH₃ | CH | |
| H | H | H | (CH₂)₂Cl | CH₃ | OCH₃ | N | |
| H | H | H | (CH₂)₂Cl | OCH₃ | OCH₃ | N | |
| H | H | H | CH₂F | CH₃ | CH₃ | CH | |
| H | H | H | CH₂F | CH₃ | OCH₃ | CH | |
| H | H | H | CH₂F | OCH₃ | OCH₃ | CH | |
| H | H | H | CH₂F | Cl | OCH₃ | CH | |
| H | H | H | CH₂F | CH₃ | OCH₃ | N | |
| H | H | H | CH₂F | OCH₃ | OCH₃ | N | |
| H | H | H | (CH₂)₂F | CH₃ | OCH₃ | CH | |
| H | H | H | (CH₂)₂F | OCH₃ | OCH₃ | CH | |
| H | H | H | (CH₂)₂F | CH₃ | OCH₃ | N | |
| H | H | H | CH₂Br | CH₃ | CH₃ | CH | |
| H | H | H | CH₂Br | CH₃ | OCH₃ | CH | |
| H | H | H | CH₂Br | OCH₃ | OCH₃ | CH | |
| H | H | H | CH₂Br | Cl | OCH₃ | CH | |
| H | H | H | CH₂Br | CH₃ | OCH₃ | N | |
| H | H | H | CH₂Br | OCH₃ | OCH₃ | N | |
| H | H | H | (CH₂)₂Br | CH₃ | OCH₃ | CH | |
| H | H | H | (CH₂)₂Br | OCH₃ | OCH₃ | CH | |
| H | H | H | (CH₂)₂Br | Cl | OCH₃ | CH | |
| H | H | H | CH₂SCH₃ | OCH₂CH₃ | C₂H₅ | CH | |
| H | H | H | CH₂SCH₃ | OCH₂CH₃ | C₂H₅ | N | |
| H | H | H | CH₂SCH₃ | OCH₂CH₃ | CH₂OCH₃ | CH | |
| H | H | H | CH₂SCH₃ | OCH₂CH₃ | CH₂OCH₃ | N | |
| H | H | H | CH₂SCH₃ | OCH₂CH₃ | NHCH₃ | N | |
| H | H | H | CH₂SCH₃ | OCH₂CH₃ | CH(OCH₃)₂ | CH | |
| H | H | H | CH₂SCH₃ | OCF₂H | C₂H₅ | CH | |
| H | H | H | CH₂SCH₃ | OCF₂H | CH₂OCH₃ | CH | |
| H | H | H | CH₂SCH₃ | OCH₂CF₃ | C₂H₅ | CH | |
| H | H | H | CH₂SCH₃ | OCH₂CF₃ | C₂H₅ | N | |
| H | H | H | CH₂SCH₃ | OCH₂CF₃ | CH₂OCH₃ | CH | |
| H | H | H | CH₂SCH₃ | OCH₂CF₃ | CH₂OCH₃ | N | |
| H | H | H | CH₂SCH₃ | OCH₂CF₃ | NHCH₃ | N | |
| H | H | H | CH₂SCH₃ | OCH₂CF₃ | CH(OCH₃)₂ | N | |
| H | H | H | CH₂SCH₃ | CH₃ | C₂H₅ | N | |
| H | H | H | CH₂SCH₃ | CH₃ | CH₂OCH₃ | CH | |
| H | H | H | CH₂SCH₃ | CH₃ | CH₂OCH₃ | N | |
| H | H | H | CH₂SCH₃ | CH₃ | NHCH₃ | N | |
| H | H | H | CH₂SCH₃ | CH₃ | CH(OCH₃)₂ | N | |
| H | H | H | CH₂SCH₃ | OCH₃ | C₂H₅ | CH | |
| H | H | H | CH₂SCH₃ | OCH₃ | C₂H₅ | N | |
| H | H | H | CH₂SCH₃ | OCH₃ | CH₂OCH₃ | CH | |
| H | H | H | CH₂SCH₃ | OCH₃ | CH₂OCH₃ | N | |
| H | H | H | CH₂SCH₃ | OCH₃ | NHCH₃ | N | |
| H | H | H | CH₂SCH₃ | OCH₃ | CH(OCH₃)₂ | CH | |
| H | H | H | CH₂SCH₃ | OCH₃ | CH(OCH₃)₂ | N | |
| H | 5-Cl | H | CH₂OCH₃ | OCH₂CH₃ | C₂H₅ | CH | |
| H | 5-Cl | H | CH₂OCH₃ | OCH₂CH₃ | C₂H₅ | N | |
| H | 5-Cl | H | CH₂OCH₃ | OCH₂CH₃ | CH₂OCH₃ | CH | |
| H | 5-Cl | H | CH₂OCH₃ | OCH₂CH₃ | CH₂OCH₃ | N | |
| H | 5-Cl | H | CH₂OCH₃ | OCH₂CH₃ | NHCH₃ | CH | |
| H | 5-Cl | H | CH₂OCH₃ | OCH₂CH₃ | NHH₃ | N | |
| H | 5-Cl | H | CH₂OCH₃ | OCH₂CH₃ | CH(OCH₃)₂ | CH | |
| H | 5-Cl | H | CH₂OCH₃ | OCH₂CH₃ | CH(OCH₃)₂ | N | |
| H | 5-Cl | H | CH₂OCH₃ | OCF₂H | C₂H₅ | CH | |
| H | 5-Cl | H | CH₂OCH₃ | OCF₂H | CH₂OCH₃ | CH | |
| H | 5-Cl | H | CH₂OCH₃ | OCF₂H | NHCH₃ | CH | |
| H | 5-Cl | H | CH₂OCH₃ | OCH₂CF₃ | C₂H₅ | CH | |
| H | 5-Cl | H | CH₂OCH₃ | OCH₂CF₃ | CH₂OCH₃ | N | |
| H | 5-Cl | H | CH₂OCH₃ | OCH₂CF₃ | NHCH₃ | CH | |
| H | 5-Cl | H | CH₂OCH₃ | OCH₂CF₃ | NHCH₃ | N | |
| H | 5-Cl | H | CH₂OCH₃ | OCH₂CF₃ | CH(OCH₃)₂ | CH | |
| H | 5-Cl | H | CH₂OCH₃ | OCH₂CF₃ | CH(OCH₃)₂ | N | |
| H | 5-Cl | H | CH₂OCH₃ | Cl | NHCH₃ | CH | |
| H | 5-Cl | H | CH₂OCH₃ | CH₃ | C₂H₅ | CH | |

TABLE IIa-continued

General Formula IIa

| R | R₁ | Rₓ | Q₁ | X | Y | Z | m.p. (°C.) |
|---|---|---|---|---|---|---|---|
| H | 5-Cl | H | CH₂OCH₃ | CH₃ | CH₂OCH₃ | CH | |
| H | 5-Cl | H | CH₂OCH₃ | CH₃ | CH₂OCH₃ | N | |
| H | 5-Cl | H | CH₂OCH₃ | Cl | NHCH₃ | CH | |
| H | 5-Cl | H | CH₂OCH₃ | CH₃ | CH₂OCH₃ | CH | |
| H | 5-Cl | H | CH₂OCH₃ | CH₃ | CH₂OCH₃ | N | |
| H | 5-Cl | H | CH₂OCH₃ | CH₃ | NHCH₃ | N | |
| H | 5-Cl | H | CH₂OCH₃ | CH₃ | CH(OCH₃)₂ | CH | |
| H | 5-Cl | H | CH₂OCH₃ | CH₃ | CH(OCH₃)₂ | N | |
| H | 5-Cl | H | CH₂OCH₃ | OCH₃ | C₂H₅ | CH | |
| H | 5-Cl | H | CH₂OCH₃ | OCH₃ | C₂H₅ | N | |
| H | 5-Cl | H | CH₂OCH₃ | OCH₃ | CH₂OCH₃ | CH | |
| H | 5-Cl | H | CH₂OCH₃ | OCH₃ | CH₂OCH₃ | N | |
| H | 5-Cl | H | CH₂OCH₃ | OCH₃ | NHCH₃ | CH | |
| H | 5-Cl | H | CH₂OCH₃ | OCH₃ | NHCH₃ | N | |
| H | 5-Cl | H | CH₂OCH₃ | OCH₃ | CH(OCH₃)₂ | CH | |
| H | 5-Cl | H | CH₂OCH₃ | OCH₃ | CH(OCH₃)₂ | N | |
| H | H | H | CN | CH₃ | CH₃ | CH | |
| H | H | H | CN | CH₃ | OCH₃ | CH | |
| H | H | H | CN | OCH₃ | OCH₃ | CH | |
| H | H | H | CN | Cl | OCH₃ | CH | |
| H | H | H | CN | CH₃ | OCH₃ | N | |
| H | H | H | CN | OCH₃ | OCH₃ | N | |
| CH₃ | H | H | CN | CH₃ | OCH₃ | N | |
| CH₃ | H | H | CH₂OCH₃ | CH₃ | OCH₃ | N | |
| CH₃ | H | H | (CH₂)₂OCH₃ | CH₃ | OCH₃ | N | |
| H | H | H | CH₂OCH₃ | OCH₃ | SCF₂H | CH | |
| H | H | H | CH₂OCH₃ | OCH₃ | SCH₃ | CH | |
| H | H | H | CH₂OCH₃ | OCH₃ | OCH₂C≡CH | CH | |
| H | H | H | CH₂OCH₃ | OCH₃ | OCH₂CH=CH₂ | CH | |
| H | H | H | CH₂OCH₃ | OCH₃ | CH₂SCH₃ | CH | |
| H | H | H | CH₂OCH₃ | OCH₃ | CN | CH | |
| H | 4-SCH₂CH₃ | H | CN | CH₃ | CH₃ | CH | |
| H | 4-SCH₂CH₃ | H | CN | CH₃ | OCH₃ | CH | 231–236 |
| H | 4-SCH₂CH₃ | H | CN | OCH₃ | OCH₃ | CH | 215–221 |
| H | 4-SCH₂CH₃ | H | CN | CH₃ | OCH₃ | N | 203–207 |
| H | 4-SCH₂CH₃ | H | CN | OCH₃ | OCH₃ | N | |
| H | 4-SCH₂CH₃ | H | CN | Cl | OCH₃ | CH | 217–220 |
| H | 4-SCH₂CH₂CH₃ | H | CN | CH₃ | CH₃ | CH | |
| H | 4-SCH₂CH₂CH₃ | H | CN | CH₃ | OCH₃ | CH | |
| H | 4-SCH₂CH₂CH₃ | H | CN | OCH₃ | OCH₃ | CH | |
| H | 4-SCH₂CH₂CH₃ | H | CN | CH₃ | OCH₃ | N | |
| H | 4-SCH₂CH₂CH₃ | H | CN | OCH₃ | OCH₃ | N | |
| H | 4-SCH₂CH₂CH₃ | H | CN | Cl | OCH₃ | CH | |
| H | 4-CH₃ | H | CH₂SCH₃ | CH₃ | CH₃ | CH | |
| H | 4-CH₃ | H | CH₂SCH₃ | CH₃ | OCH₃ | CH | |
| H | 4-CH₃ | H | CH₂SCH₃ | OCH₃ | OCH₃ | CH | |
| H | 4-CH₃ | H | CH₂SCH₃ | CH₃ | OCH₃ | N | |
| H | 4-CH₃ | H | CH₂SCH₃ | OCH₃ | OCH₃ | N | |
| H | 4-CH₃ | H | CH₂SCH₃ | Cl | OCH₃ | CH | |
| H | 4-CH₃ | H | CH₂S(O)CH₃ | CH₃ | CH₃ | CH | |
| H | 4-CH₃ | H | CH₂S(O)CH₃ | CH₃ | OCH₃ | CH | |
| H | 4-CH₃ | H | CH₂S(O)CH₃ | OCH₃ | OCH₃ | CH | |
| H | 4-CH₃ | H | CH₂S(O)CH₃ | CH₃ | OCH₃ | N | |
| H | 4-CH₃ | H | CH₂S(O)CH₃ | OCH₃ | OCH₃ | N | |
| H | 4-CH₃ | H | CH₂S(O)CH₃ | Cl | OCH₃ | CH | |
| H | 4-CH₃ | H | CH₂S(O)₂CH₃ | CH₃ | CH₃ | CH | |
| H | 4-CH₃ | H | CH₂S(O)₂CH₃ | CH₃ | OCH₃ | CH | |
| H | 4-CH₃ | H | CH₂S(O)₂CH₃ | OCH₃ | OCH₃ | CH | |
| H | 4-CH₃ | H | CH₂S(O)₂CH₃ | CH₃ | OCH₃ | N | |
| H | 4-CH₃ | H | CH₂S(O)₂CH₃ | OCH₃ | OCH₃ | N | |
| H | 4-CH₃ | H | CH₂S(O)₂CH₃ | Cl | OCH₃ | CH | |
| H | 4-CH₃ | H | CH₂SCH₂CH₃ | CH₃ | CH₃ | CH | |
| H | 4-CH₃ | H | CH₂SCH₂CH₃ | CH₃ | OCH₃ | CH | |
| H | 4-CH₃ | H | CH₂SCH₂CH₃ | OCH₃ | OCH₃ | CH | |
| H | 4-CH₃ | H | CH₂SCH₂CH₃ | CH₃ | OCH₃ | N | |
| H | 4-CH₃ | H | CH₂SCH₂CH₃ | OCH₃ | OCH₃ | N | |
| H | 4-CH₃ | H | CH₂SCH₂CH₃ | Cl | OCH₃ | CH | |
| H | 4-CH₃ | H | CH₂S(O)CH₂CH₃ | CH₃ | CH₃ | CH | |
| H | 4-CH₃ | H | CH₂S(O)CH₂CH₃ | CH₃ | OCH₃ | CH | 173–176 |
| H | 4-CH₃ | H | CH₂S(O)CH₂CH₃ | OCH₃ | OCH₃ | CH | 160–164 |
| H | 4-CH₃ | H | CH₂S(O)CH₂CH₃ | CH₃ | OCH₃ | N | |
| H | 4-CH₃ | H | CH₂S(O)CH₂CH₃ | OCH₃ | OCH₃ | N | |
| H | 4-CH₃ | H | CH₂S(O)CH₂CH₃ | Cl | OCH₃ | CH | |
| H | 4-CH₃ | H | CH₂S(O)₂CH₂CH₃ | CH₃ | CH₃ | CH | |
| H | 4-CH₃ | H | CH₂S(O)₂CH₂CH₃ | CH₃ | OCH₃ | CH | |
| H | 4-CH₃ | H | CH₂S(O)₂CH₂CH₃ | OCH₃ | OCH₃ | CH | |
| H | 4-CH₃ | H | CH₂S(O)₂CH₂CH₃ | CH₃ | OCH₃ | N | |
| H | 4-CH₃ | H | CH₂S(O)₂CH₂CH₃ | OCH₃ | OCH₃ | N | |
| H | 4-CH₃ | H | CH₂S(O)₂CH₂CH₃ | Cl | OCH₃ | CH | |
| H | 4-CH₃ | H | CH₂SCH₂CH₂CH₃ | CH₃ | CH₃ | CH | |

TABLE IIa-continued

General Formula IIa

| R | R₁ | Rₓ | Q₁ | X | Y | Z | m.p. (°C.) |
|---|---|---|---|---|---|---|---|
| H | 4-CH₃ | H | CH₂SCH₂CH₂CH₃ | CH₃ | OCH₃ | CH | 98–105 |
| H | 4-CH₃ | H | CH₂SCH₂CH₂CH₃ | OCH₃ | OCH₃ | CH | 138–142 |
| H | 4-CH₃ | H | CH₂SCH₂CH₂CH₃ | CH₃ | OCH₃ | N | |
| H | 4-CH₃ | H | CH₂SCH₂CH₂CH₃ | OCH₃ | OCH₃ | N | |
| H | 4-CH₃ | H | CH₂SCH₂CH₂CH₃ | Cl | OCH₃ | CH | |
| H | 4-CH₃ | H | CH₂S(O)CH₂CH₂CH₃ | CH₃ | CH₃ | CH | |
| H | 4-CH₃ | H | CH₂S(O)CH₂CH₂CH₃ | CH₃ | OCH₃ | CH | 109–112 |
| H | 4-CH₃ | H | CH₂S(O)CH₂CH₂CH₃ | OCH₃ | OCH₃ | CH | 123–127 |
| H | 4-CH₃ | H | CH₂S(O)CH₂CH₂CH₃ | CH₃ | OCH₃ | N | 158–161 |
| H | 4-CH₃ | H | CH₂S(O)CH₂CH₂CH₃ | OCH₃ | OCH₃ | N | |
| H | 4-CH₃ | H | CH₂S(O)CH₂CH₂CH₃ | Cl | OCH₃ | CH | |
| H | 4-CH₃ | H | CH₂S(O)₂CH₂CH₂CH₃ | CH₃ | CH₃ | CH | |
| H | 4-CH₃ | H | CH₂S(O)₂CH₂CH₂CH₃ | CH₃ | OCH₃ | CH | |
| H | 4-CH₃ | H | CH₂S(O)₂CH₂CH₂CH₃ | OCH₃ | OCH₃ | CH | |
| H | 4-CH₃ | H | CH₂S(O)₂CH₂CH₂CH₃ | CH₃ | OCH₃ | N | |
| H | 4-CH₃ | H | CH₂S(O)₂CH₂CH₂CH₃ | OCH₃ | OCH₃ | N | |
| H | 4-CH₃ | H | CH₂S(O)₂CH₂CH₂CH₃ | Cl | OCH₃ | CH | |
| H | 4-CH₃ | H | CH₂Cl | CH₃ | CH₃ | CH | |
| H | 4-CH₃ | H | CH₂Cl | CH₃ | OCH₃ | CH | 195–200 |
| H | 4-CH₃ | H | CH₂Cl | OCH₃ | OCH₃ | CH | 134–140 |
| H | 4-CH₃ | H | CH₂Cl | CH₃ | OCH₃ | N | |
| H | 4-CH₃ | H | CH₂Cl | OCH₃ | OCH₃ | N | |
| H | 4-CH₃ | H | CH₂Cl | Cl | OCH₃ | CH | |
| H | 4-CH₃ | H | CH₂Br | CH₃ | CH₃ | CH | |
| H | 4-CH₃ | H | CH₂Br | CH₃ | OCH₃ | CH | |
| H | 4-CH₃ | H | CH₂Br | OCH₃ | OCH₃ | CH | |
| H | 4-CH₃ | H | CH₂Br | CH₃ | OCH₃ | N | |
| H | 4-CH₃ | H | CH₂Br | OCH₃ | OCH₃ | N | |
| H | 4-CH₃ | H | CH₂Br | Cl | OCH₃ | CH | |
| H | 4-CH₃ | H | CH₂F | CH₃ | CH₃ | CH | |
| H | 4-CH₃ | H | CH₂F | CH₃ | OCH₃ | CH | |
| H | 4-CH₃ | H | CH₂F | OCH₃ | OCH₃ | CH | |
| H | 4-CH₃ | H | CH₂F | CH₃ | OCH₃ | N | |
| H | 4-CH₃ | H | CH₂F | OCH₃ | OCH₃ | N | |
| H | 4-CH₃ | H | CH₂F | Cl | OCH₃ | CH | |

TABLE IIIa

General Formula IIIa

| R | R₁ | Rₓ | Q₁ | X | Y | Z | m.p.(°C.) |
|---|---|---|---|---|---|---|---|
| H | H | H | S(CH₂)₂OCH₃ | CH₃ | OCH₃ | CH | |
| H | H | H | S(CH₂)₂OCH₃ | OCH₃ | OCH₃ | CH | |
| H | H | H | S(CH₂)₂OCH₃ | Cl | OCH₃ | CH | |
| H | H | H | S(CH₂)₂OCH₃ | CH₃ | OCH₃ | N | |
| H | H | H | S(CH₂)₃OCH₃ | CH₃ | OCH₃ | CH | |
| H | H | H | S(CH₂)₃OCH₃ | OCH₃ | OCH₃ | CH | |
| H | H | H | S(CH₂)₂OCH₂CN | CH₃ | OCH₃ | CH | |
| H | H | H | S(CH₂)₂OCH₂CN | Cl | OCH₃ | CH | |
| H | H | H | S(CH₂)₂OCH₂CN | OCH₃ | OCH₃ | N | |
| H | H | H | S(CH₂)₂SCH₃ | CH₃ | OCH₃ | CH | |
| H | H | H | S(CH₂)₂SCH₃ | OCH₃ | OCH₃ | CH | |
| H | H | H | S(CH₂)₂SCH₃ | CH₃ | OCH₃ | N | |
| H | H | H | S(CH₂)₂S(O)CH₃ | CH₃ | OCH₃ | CH | |
| H | H | H | S(CH₂)₂S(O)CH₃ | OCH₃ | OCH₃ | CH | |
| H | H | H | S(CH₂)₂S(O)CH₃ | Cl | OCH₃ | CH | |
| H | H | H | S(CH₂)₂S(O)CH₃ | CH₃ | OCH₃ | N | |
| H | H | H | S(CH₂)₂S(O)CH₂CH₃ | OCH₃ | OCH₃ | CH | |
| H | H | H | S(CH₂)₂S(O)CH₂CH₃ | Cl | OCH₃ | CH | |
| H | H | H | S(CH₂)₂SO₂CH₃ | OCH₃ | OCH₃ | CH | |
| H | H | H | S(CH₂)₂SO₂CH₃ | Cl | OCH₃ | CH | |
| H | H | H | S(CH₂)₂SO₂CH₃ | CH₃ | OCH₃ | N | |
| H | H | H | S(CH₂)₂SO₂CH₂CH₃ | CH₃ | OCH₃ | CH | |
| H | H | H | S(CH₂)₂SO₂CH₂CH₃ | OCH₃ | OCH₃ | CH | |
| H | H | H | S(CH₂)₂SO₂CH₂CH₃ | OCH₃ | OCH₃ | N | |
| H | H | H | SCH₂CO₂CH₃ | CH₃ | CH₃ | CH | |
| H | H | H | S(CH₂)₃SO₂N(CH₃)₂ | OCH₃ | OCH₃ | CH | |
| H | H | H | S(CH₂)₃SO₂N(CH₃)₂ | CH₃ | OCH₃ | N | |
| H | H | H | S(CH₂)₂SO₂N(CH₂CH₃)₂ | CH₃ | OCH₃ | CH | |
| H | H | H | S(CH₂)₂SO₂N(CH₂CH₃)₂ | OCH₃ | OCH₃ | CH | |
| H | H | H | SCH₂C(O)CH₃ | OCH₃ | OCH₃ | CH | |
| H | H | H | SCH₂C(O)CH₃ | CH₃ | OCH₃ | N | |
| H | H | H | S(CH₂)₂CN | CH₃ | CH₃ | CH | |
| H | H | H | S(CH₂)₂CN | CH₃ | OCH₃ | CH | |
| H | H | H | S(CH₂)₂CN | OCH₃ | OCH₃ | CH | |
| H | H | H | S(CH₂)₂CN | CH₃ | OCH₃ | N | |
| H | H | H | SCH₂C(O)N(CH₃)₂ | CH₃ | CH₃ | CH | |
| H | H | H | SCH₂C(O)N(CH₃)₂ | CH₃ | OCH₃ | CH | |
| H | H | H | SCH₂C(O)N(CH₃)₂ | OCH₃ | OCH₃ | CH | |

TABLE IIIa-continued

General Formula IIIa

| R | R₁ | Rₓ | Q₁ | X | Y | Z | m.p.(°C.) |
|---|----|----|----|----|---|---|-----------|
| H | H | H | SCH₂C(O)N(CH₃)₂ | CH₃ | OCH₃ | N | |
| H | 2-CH₃ | H | S(CH₂)₂C(O)N(CH₃)₂ | CH₃ | OCH₃ | CH | |
| H | 2-CH₃ | H | S(CH₂)₂C(O)N(CH₃)₂ | OCH₃ | OCH₃ | CH | |
| H | H | H | S(CH₂)₂Cl | CH₃ | CH₃ | CH | |
| H | H | H | S(CH₂)₂Cl | CH₃ | OCH₃ | CH | |
| H | H | H | S(CH₂)₂Cl | OCH₃ | OCH₃ | CH | |
| H | H | H | S(CH₂)₂Cl | Cl | OCH₃ | CH | |
| H | H | H | S(CH₂)₂Cl | CH₃ | OCH₃ | N | |
| H | H | H | S(CH₂)₂Cl | OCH₃ | OCH₃ | N | |
| H | H | H | S(CH₂)₃Cl | CH₃ | OCH₃ | CH | |
| H | H | H | S(CH₂)₃Cl | OCH₃ | OCH₃ | CH | |
| H | H | H | S(CH₂)₃Cl | CH₃ | OCH₃ | N | |
| H | H | H | S(CH₂)₂F | OCH₃ | OCH₃ | CH | |
| H | H | H | S(CH₂)₂F | CH₃ | OCH₃ | N | |
| H | H | H | S(CH₂)₂Br | CH₃ | CH₃ | CH | |
| H | H | H | S(CH₂)₂Br | CH₃ | OCH₃ | CH | |
| H | H | H | S(CH₂)₂Br | OCH₃ | OCH₃ | CH | |
| H | 5-Cl | H | S-CHClCH=CH₂ | CH₃ | OCH₃ | CH | |
| H | 5-Cl | H | S-CHClCH=CH₂ | OCH₃ | OCH₃ | CH | |
| H | 5-Cl | H | S-CHClCH=CH₂ | CH₃ | OCH₃ | N | |
| H | H | H | SCH₂C≡CH | CH₃ | CH₃ | CH | |
| H | H | H | SCH₂C≡CH | CH₃ | OCH₃ | CH | |
| H | H | H | SCH₂C≡CH | OCH₃ | OCH₃ | CH | |
| H | H | H | SCH₂C≡CH | CH₃ | OCH₃ | N | |
| H | H | H | S(CH₂)₂C≡CH | CH₃ | OCH₃ | CH | |
| H | H | H | S(CH₂)₂C≡CH | OCH₃ | OCH₃ | CH | |
| H | H | H | S(CH₂)₂C≡CH | CH₃ | OCH₃ | N | |
| H | 5-Cl | H | SO₂(CH₂)₂OCH₃ | OCH₃ | OCH₃ | CH | |
| H | 5-Cl | H | SO₂(CH₂)₂OCH₃ | CH₃ | OCH₃ | N | |
| H | H | H | SO₂CH₂OCH₂CH₃ | OCH₃ | OCH₃ | CH | |
| H | H | H | SO₂CH₂OCH₂CH₃ | CH₃ | OCH₃ | N | |
| H | H | H | SO₂(CH₂)₂OCH₂CH₃ | CH₃ | CH₃ | CH | |
| H | H | H | SO₂(CH₂)₂OCH₂CH₃ | OCH₃ | OCH₃ | CH | |
| H | H | H | SO₂(CH₂)₂OCH₂CH₃ | CH₃ | OCH₃ | N | |
| H | H | H | SO₂(CH₂)₂SCH₃ | CH₃ | OCH₃ | CH | |
| H | H | H | SO₂(CH₂)₂SCH₃ | OCH₃ | OCH₃ | CH | |
| H | H | H | SO₂(CH₂)₂SCH₃ | CH₃ | OCH₃ | N | |
| H | H | H | SO₂(CH₂)₂SCH₂CH₃ | OCH₃ | OCH₃ | CH | |
| H | H | H | SO₂(CH₂)₂SCH₂CH₃ | CH₃ | OCH₃ | N | |
| H | H | H | SO₂(CH₂)₂S(O)CH₃ | OCH₃ | OCH₃ | CH | |
| H | H | H | SO₂(CH₂)₂S(O)CH₃ | CH₃ | OCH₃ | N | |
| H | H | H | SO₂(CH₂)₂CO₂CH₃ | CH₃ | OCH₃ | CH | |
| H | H | H | SO₂(CH₂)₂CO₂CH₃ | OCH₃ | OCH₃ | CH | |
| H | H | H | SO₂(CH₂)₂CO₂CH₃ | CH₃ | OCH₃ | N | |
| H | H | H | SO₂CH₂CO₂CH₂CH₃ | CH₃ | CH₃ | CH | |
| H | H | H | SO₂CH₂CO₂CH₂CH₃ | CH₃ | OCH₃ | CH | |
| H | H | H | SO₂CH₂CO₂CH₂CH₃ | OCH₃ | OCH₃ | CH | |
| H | H | H | SO₂CH₂CO₂CH₂CH₃ | CH₃ | OCH₃ | N | |
| H | H | H | SO₂(CH₂)₂C(O)CH₃ | CH₃ | OCH₃ | CH | |
| H | H | H | SO₂(CH₂)₂C(O)CH₃ | OCH₃ | OCH₃ | CH | |
| H | H | H | SO₂(CH₂)₂C(O)CH₃ | CH₃ | OCH₃ | N | |
| H | H | H | SO₂(CH₂)₂C(O)N(CH₃)₂ | OCH₃ | OCH₃ | CH | |
| H | H | H | SO₂(CH₂)₂C(O)N(CH₃)₂ | CH₃ | OCH₃ | N | |
| H | H | H | SO₂(CH₂)₂Br | OCH₃ | OCH₃ | CH | |
| H | H | H | SO₂(CH₂)₂Br | CH₃ | OCH₃ | N | |
| H | H | H | SO₂CH₂F | CH₃ | CH₃ | CH | |
| H | H | H | SO₂CH₂F | OCH₃ | OCH₃ | CH | |
| H | H | H | SO₂CH₂F | Cl | OCH₃ | CH | |
| H | H | H | SO₂CH₂F | CH₃ | OCH₃ | N | |
| H | H | H | SO₂CHClCH=CH₂ | OCH₃ | OCH₃ | CH | |
| H | 2-CH₃ | H | SO₂CH₂C≡CH | OCH₃ | OCH₃ | CH | |
| H | 2-CH₃ | H | SO₂CH₂C≡CH | CH₃ | OCH₃ | N | |
| H | H | H | SO₂(CH₂)₂C≡CH | CH₃ | OCH₃ | CH | |
| H | H | H | SO₂(CH₂)₂C≡CH | OCH₃ | OCH₃ | CH | |
| H | H | H | SO₂(CH₂)₂C≡CH | CH₃ | OCH₃ | N | |
| H | H | H | CH₂P(O)(OCH₃)₂ | OCH₃ | OCH₃ | CH | |
| H | H | H | CH₂P(O)(OCH₃)₂ | CH₃ | OCH₃ | N | |
| H | H | H | CH₂P(O)(OCH₃)₂ | OCH₃ | OCH₃ | N | |
| H | H | H | P(O)(OCH₃)₂ | Cl | OCH₃ | CH | |
| H | H | H | P(O)(SCH₃)₂ | CH₃ | OCH₃ | CH | |
| H | H | H | P(O)(SCH₃)₂ | Cl | OCH₃ | CH | |
| H | H | H | P(O)(OCH₃)₂ | OCH₃ | OCH₃ | N | |
| H | 2-Cl | H | CH₂OH | CH₃ | CH₃ | CH | |
| H | 2-Cl | H | CH₂OH | CH₃ | OCH₃ | CH | |
| H | 2-Cl | H | CH₂OH | OCH₃ | OCH₃ | CH | |
| H | 2-Cl | H | CH₂OH | Cl | OCH₃ | CH | |
| H | 2-Cl | H | CH₂OH | CH₃ | OCH₃ | N | |
| H | 2-Cl | H | CH₂OH | OCH₃ | OCH₃ | N | |
| H | H | H | (CH₂)₂OH | CH₃ | CH₃ | CH | |
| H | H | H | (CH₂)₂OH | CH₃ | OCH₃ | CH | |

TABLE IIIa-continued

General Formula IIIa

| R | R₁ | Rₓ | Q₁ | X | Y | Z | m.p.(°C.) |
|---|---|---|---|---|---|---|---|
| H | H | H | (CH₂)₂OH | OCH₃ | OCH₃ | CH | |
| H | H | H | (CH₂)₂OH | Cl | OCH₃ | CH | |
| H | H | H | (CH₂)₂OH | CH₃ | OCH₃ | N | |
| H | H | H | (CH₂)₂OH | OCH₃ | OCH₃ | N | |
| H | H | H | CH₂OCH₃ | CH₃ | CH₃ | CH | |
| H | H | H | CH₂OCH₃ | CH₃ | OC₃ | CH | |
| H | H | H | CH₂OCH₃ | OCH₃ | OCH₃ | CH | |
| H | H | H | CH₂OCH₃ | Cl | OCH₃ | CH | |
| H | H | H | CH₂OCH₃ | CH₃ | OCH₃ | N | |
| H | H | H | CH₂OCH₃ | OCH₃ | OCH₃ | N | |
| H | H | H | (CH₂)₂OCH₃ | CH₃ | CH₃ | CH | |
| H | H | H | (CH₂)₂OCH₃ | CH₃ | OCH₃ | CH | |
| H | H | H | (CH₂)₂OCH₃ | OCH₃ | OCH₃ | CH | |
| H | H | H | (CH₂)₂OCH₃ | Cl | OCH₃ | CH | |
| H | H | H | (CH₂)₂OCH₃ | CH₃ | OCH₃ | N | |
| H | H | H | (CH₂)₂OCH₃ | OCH₃ | OCH₃ | N | |
| H | 5-CH₃ | H | CH₂OCH₂CH₃ | CH₃ | CH₃ | CH | |
| H | 5-CH₃ | H | CH₂OCH₂CH₃ | CH₃ | OCH₃ | CH | |
| H | 5-CH₃ | H | CH₂OCH₂CH₃ | OCH₃ | OCH₃ | CH | |
| H | 5-CH₃ | H | CH₂OCH₂CH₃ | Cl | OCH₃ | CH | |
| H | 5-CH₃ | H | CH₂OCH₂CH₃ | OCH₃ | OCH₃ | N | |
| H | H | H | CH₂O(CH₂)₂CN | CH₃ | CH₃ | CH | |
| H | H | H | CH₂O(CH₂)₂CN | CH₃ | OCH₃ | CH | |
| H | H | H | CH₂O(CH₂)₂CN | OCH₃ | OCH₃ | CH | |
| H | H | H | CH₂O(CH₂)₂CN | Cl | OCH₃ | CH | |
| H | H | H | CH₂O(CH₂)₂CN | CH₃ | OCH₃ | N | |
| H | H | H | CH₂O(CH₂)₂CN | OCH₃ | OCH₃ | N | |
| H | H | H | CH₂SCH₃ | CH₃ | CH₃ | CH | |
| H | H | H | CH₂SCH₃ | CH₃ | OCH₃ | CH | |
| H | H | H | CH₂SCH₃ | OCH₃ | OCH₃ | CH | |
| H | H | H | CH₂SCH₃ | Cl | OCH₃ | CH | |
| H | H | H | CH₂SCH₃ | CH₃ | OCH₃ | N | |
| H | H | H | CH₂SCH₃ | OCH₃ | OCH₃ | N | |
| H | H | H | (CH₂)₂SCH₃ | CH₃ | CH₃ | CH | |
| H | H | H | (CH₂)₂SCH₃ | CH₃ | OCH₃ | CH | |
| H | H | H | (CH₂)₂SCH₃ | OCH₃ | OCH₃ | CH | |
| H | H | H | (CH₂)₂SCH₃ | Cl | OCH₃ | CH | |
| H | H | H | (CH₂)₂SCH₃ | CH₃ | OCH₃ | N | |
| H | H | H | (CH₂)₂SCH₃ | OCH₃ | OCH₃ | N | |
| H | H | H | (CH₂)₃SCH₃ | CH₃ | CH₃ | CH | |
| H | H | H | (CH₂)₃SCH₃ | CH₃ | OCH₃ | CH | |
| H | H | H | (CH₂)₃SCH₃ | OCH₃ | OCH₃ | CH | |
| H | H | H | (CH₂)₃SCH₃ | Cl | OCH₃ | CH | |
| H | H | H | (CH₂)₃SCH₃ | CH₃ | OCH₃ | N | |
| H | H | H | (CH₂)₃SCH₃ | OCH₃ | OCH₃ | N | |
| H | H | H | CH₂S(O)CH₃ | CH₃ | CH₃ | CH | |
| H | H | H | CH₂S(O)CH₃ | CH₃ | OCH₃ | CH | |
| H | H | H | CH₂S(O)CH₃ | OCH₃ | OCH₃ | CH | |
| H | H | H | CH₂S(O)CH₃ | Cl | OCH₃ | CH | |
| H | H | H | CH₂S(O)CH₃ | CH₃ | OCH₃ | N | |
| H | H | H | CH₂S(O)CH₃ | OCH₃ | OCH₃ | N | |
| H | H | H | (CH₂)₂S(O)CH₃ | CH₃ | CH₃ | CH | |
| H | H | H | (CH₂)₂S(O)CH₃ | CH₃ | OCH₃ | CH | |
| H | H | H | (CH₂)₂S(O)CH₃ | OCH₃ | OCH₃ | CH | |
| H | H | H | (CH₂)₂S(O)CH₃ | Cl | OCH₃ | CH | |
| H | H | H | (CH₂)₂S(O)CH₃ | CH₃ | OCH₃ | N | |
| H | H | H | (CH₂)₂S(O)CH₃ | OCH₃ | OCH₃ | N | |
| H | H | H | (CH₂)₂S(O)CH₂CH₃ | CH₃ | CH₃ | CH | |
| H | H | H | (CH₂)₂S(O)CH₂CH₃ | CH₃ | OCH₃ | CH | |
| H | H | H | (CH₂)₂S(O)CH₂CH₃ | OCH₃ | OCH₃ | CH | |
| H | H | H | (CH₂)₂S(O)CH₂CH₃ | Cl | OCH₃ | CH | |
| H | H | H | (CH₂)₂S(O)CH₂CH₃ | CH₃ | OCH₃ | N | |
| H | H | H | (CH₂)₂S(O)CH₂CH₃ | OCH₃ | OCH₃ | N | |
| H | 5-CH₃ | H | CH₂SO₂CH₃ | CH₃ | CH₃ | CH | |
| H | 5-CH₃ | H | CH₂SO₂CH₃ | CH₃ | OCH₃ | CH | |
| H | 5-CH₃ | H | CH₂SO₂CH₃ | OCH₃ | OCH₃ | CH | |
| H | 5-CH₃ | H | CH₂SO₂CH₃ | CH₃ | OCH₃ | N | |
| H | H | H | (CH₂)₂SO₂CH₃ | CH₃ | CH₃ | CH | |
| H | H | H | (CH₂)₂SO₂CH₃ | CH₃ | CH₃ | CH | |
| H | H | H | (CH₂)₂SO₂CH₃ | OCH₃ | OCH₃ | CH | |
| H | H | H | (CH₂)₂SO₂CH₃ | Cl | OCH₃ | CH | |
| H | H | H | (CH₂)₂SO₂CH₃ | CH₃ | OCH₃ | N | |
| H | H | H | (CH₂)₂SO₂CH₃ | OCH₃ | OCH₃ | N | |
| H | H | H | (CH₂)₃SO₂CH₃ | OCH₃ | OCH₃ | CH | |
| H | H | H | (CH₂)₃SO₂CH₃ | Cl | OCH₃ | CH | |
| H | H | H | CH₂SO₂CH₂CH₃ | CH₃ | CH₃ | CH | |
| H | H | H | CH₂SO₂CH₂CH₃ | CH₃ | OCH₃ | CH | |
| H | H | H | CH₂SO₂CH₂CH₃ | OCH₃ | OCH₃ | CH | |
| H | H | H | CH₂SO₂CH₂CH₃ | Cl | OCH₃ | CH | |
| H | H | H | CH₂SO₂CH₂CH₃ | CH₃ | OCH₃ | N | |

TABLE IIIa-continued

General Formula IIIa

| R | R₁ | Rₓ | Q₁ | X | Y | Z | m.p.(°C.) |
|---|---|---|---|---|---|---|---|
| H | H | H | CH$_2$CO$_2$CH$_3$ | CH$_3$ | CH$_3$ | CH | |
| H | H | H | CH$_2$CO$_2$CH$_3$ | CH$_3$ | OCH$_3$ | CH | |
| H | H | H | CH$_2$CO$_2$CH$_3$ | OCH$_3$ | OCH$_3$ | CH | |
| H | H | H | CH$_2$CO$_2$CH$_3$ | Cl | OCH$_3$ | CH | |
| H | H | H | CH$_2$CO$_2$CH$_3$ | CH$_3$ | OCH$_3$ | N | |
| H | H | H | CH$_2$CO$_2$CH$_2$CH$_3$ | CH$_3$ | CH$_3$ | CH | |
| H | H | H | CH$_2$CO$_2$CH$_2$CH$_3$ | CH$_3$ | OCH$_3$ | CH | |
| H | H | H | CH$_2$CO$_2$CH$_2$CH$_3$ | OCH$_3$ | OCH$_3$ | CH | |
| H | H | H | CH$_2$CO$_2$CH$_2$CH$_3$ | Cl | OCH$_3$ | CH | |
| H | H | H | CH$_2$CO$_2$CH$_2$CH$_3$ | CH$_3$ | OCH$_3$ | N | |
| H | H | H | CH$_2$SO$_2$N(CH$_3$)$_2$ | CH$_3$ | CH$_3$ | CH | |
| H | H | H | CH$_2$SO$_2$N(CH$_3$)$_2$ | CH$_3$ | OCH$_3$ | CH | |
| H | H | H | CH$_2$SO$_2$N(CH$_3$)$_2$ | OCH$_3$ | OCH$_3$ | CH | |
| H | H | H | CH$_2$SO$_2$N(CH$_3$)$_2$ | Cl | OCH$_3$ | CH | |
| H | H | H | CH$_2$SO$_2$N(CH$_3$)$_2$ | CH$_3$ | OCH$_3$ | N | |
| H | H | H | CH$_2$SO$_2$N(CH$_3$)$_2$ | OCH$_3$ | OCH$_3$ | N | |
| H | 5-Cl | H | (CH$_2$)$_2$SO$_2$N(CH$_3$)$_2$ | CH$_3$ | OCH$_3$ | CH | |
| H | 5-Cl | H | (CH$_2$)$_2$SO$_2$N(CH$_3$)$_2$ | OCH$_3$ | OCH$_3$ | CH | |
| H | 5-Cl | H | (CH$_2$)$_2$SO$_2$N(CH$_3$)$_2$ | CH$_3$ | OCH$_3$ | N | |
| H | H | H | CH$_2$SO$_2$N(CH$_2$CH$_3$)$_2$ | CH$_3$ | CH$_3$ | CH | |
| H | H | H | CH$_2$SO$_2$N(CH$_2$CH$_3$)$_2$ | CH$_3$ | OCH$_3$ | CH | |
| H | H | H | CH$_2$SO$_2$N(CH$_2$CH$_3$)$_2$ | OCH$_3$ | OCH$_3$ | CH | |
| H | H | H | CH$_2$SO$_2$N(CH$_2$CH$_3$)$_2$ | CH$_3$ | OCH$_3$ | N | |
| H | H | H | CH$_2$C(O)CH$_3$ | CH$_3$ | OCH$_3$ | CH | |
| H | H | H | CH$_2$C(O)CH$_3$ | OCH$_3$ | OCH$_3$ | CH | |
| H | H | H | CH$_2$C(O)CH$_3$ | CH$_3$ | OCH$_3$ | N | |
| H | 2-Cl | H | (CH$_2$)$_2$C(O)CH$_3$ | CH$_3$ | OCH$_3$ | CH | |
| H | 2-Cl | H | (CH$_2$)$_2$C(O)CH$_3$ | OCH$_3$ | OCH$_3$ | CH | |
| H | 2-Cl | H | (CH$_2$)$_2$C(O)CH$_3$ | CH$_3$ | OCH$_3$ | N | |
| H | H | H | CH$_2$CN | CH$_3$ | CH$_3$ | CH | |
| H | H | H | CH$_2$CN | CH$_3$ | OCH$_3$ | CH | |
| H | H | H | CH$_2$CN | OCH$_3$ | OCH$_3$ | CH | |
| H | H | H | CH$_2$CN | Cl | OCH$_3$ | CH | |
| H | H | H | CH$_2$CN | CH$_3$ | OCH$_3$ | N | |
| H | H | H | CH$_2$CN | OCH$_3$ | OCH$_3$ | N | |
| H | H | H | (CH$_2$)$_2$CN | CH$_3$ | CH$_3$ | CH | |
| H | H | H | (CH$_2$)$_2$CN | CH$_3$ | OCH$_3$ | CH | |
| H | H | H | (CH$_2$)$_2$CN | OCH$_3$ | OCH$_3$ | CH | |
| H | H | H | (CH$_2$)$_2$CN | Cl | OCH$_3$ | CH | |
| H | H | H | (CH$_2$)$_2$CN | CH$_3$ | OCH$_3$ | N | |
| H | H | H | (CH$_2$)$_2$CN | OCH$_3$ | OCH$_3$ | N | |
| H | H | H | CH$_2$C(O)N(CH$_3$)$_2$ | CH$_3$ | OCH$_3$ | CH | |
| H | H | H | CH$_2$C(O)N(CH$_3$)$_2$ | OCH$_3$ | OCH$_3$ | CH | |
| H | H | H | CH$_2$C(O)N(CH$_3$)$_2$ | CH$_3$ | OCH$_3$ | N | |
| H | H | H | (CH$_2$)$_2$C(O)N(CH$_3$)$_2$ | CH$_3$ | OCH$_3$ | CH | |
| H | H | H | (CH$_2$)$_2$C(O)N(CH$_3$)$_2$ | OCH$_3$ | OCH$_3$ | CH | |
| H | H | H | (CH$_2$)$_2$C(O)N(CH$_3$)$_2$ | CH$_3$ | OCH$_3$ | N | |
| H | H | H | CH$_2$Cl | CH$_3$ | CH$_3$ | CH | |
| H | H | H | CH$_2$Cl | CH$_3$ | OCH$_3$ | CH | |
| H | H | H | CH$_2$Cl | OCH$_3$ | OCH$_3$ | CH | |
| H | H | H | CH$_2$Cl | Cl | OCH$_3$ | CH | |
| H | H | H | CH$_2$Cl | CH$_3$ | OCH$_3$ | N | |
| H | H | H | CH$_2$Cl | OCH$_3$ | OCH$_3$ | N | |
| H | H | H | (CH$_2$)$_2$Cl | CH$_3$ | CH$_3$ | CH | |
| H | H | H | (CH$_2$)$_2$Cl | CH$_3$ | OCH$_3$ | CH | |
| H | H | H | (CH$_2$)$_2$Cl | OCH$_3$ | OCH$_3$ | CH | |
| H | H | H | (CH$_2$)$_2$Cl | Cl | OCH$_3$ | CH | |
| H | H | H | (CH$_2$)$_2$Cl | CH$_3$ | OCH$_3$ | N | |
| H | H | H | (CH$_2$)$_2$Cl | OCH$_3$ | OCH$_3$ | N | |
| H | H | H | CH$_2$F | CH$_3$ | CH$_3$ | CH | |
| H | H | H | CH$_2$F | CH$_3$ | OCH$_3$ | CH | |
| H | H | H | CH$_2$F | OCH$_3$ | OCH$_3$ | CH | |
| H | H | H | CH$_2$F | Cl | OCH$_3$ | CH | |
| H | H | H | CH$_2$F | CH$_3$ | OCH$_3$ | N | |
| H | H | H | CH$_2$F | OCH$_3$ | OCH$_3$ | N | |
| H | H | H | (CH$_2$)$_2$F | CH$_3$ | OCH$_3$ | CH | |
| H | H | H | (CH$_2$)$_2$F | OCH$_3$ | OCH$_3$ | CH | |
| H | H | H | (CH$_2$)$_2$F | CH$_3$ | OCH$_3$ | N | |
| H | H | H | CH$_2$Br | CH$_3$ | CH$_3$ | CH | |
| H | H | H | CH$_2$Br | CH$_3$ | OCH$_3$ | CH | |
| H | H | H | CH$_2$Br | OCH$_3$ | OCH$_3$ | CH | |
| H | H | H | CH$_2$Br | Cl | OCH$_3$ | CH | |
| H | H | H | CH$_2$Br | CH$_3$ | OCH$_3$ | N | |
| H | H | H | CH$_2$Br | OCH$_3$ | OCH$_3$ | N | |
| H | H | H | (CH$_2$)$_2$Br | CH$_3$ | OCH$_3$ | CH | |
| H | H | H | (CH$_2$)$_2$Br | OCH$_3$ | OCH$_3$ | CH | |
| H | H | H | (CH$_2$)$_2$Br | Cl | OCH$_3$ | CH | |
| H | H | H | CH$_2$SCH$_3$ | OCH$_2$CH$_3$ | C$_2$H$_5$ | CH | |
| H | H | H | CH$_2$SCH$_3$ | OCH$_2$CH$_3$ | C$_2$H$_5$ | N | |
| H | H | H | CH$_2$SCH$_3$ | OCH$_2$CH$_3$ | CH$_2$OCH$_3$ | CH | |

TABLE IIIa-continued

General Formula IIIa

| R | R₁ | R$_x$ | Q₁ | X | Y | Z | m.p.(°C.) |
|---|---|---|---|---|---|---|---|
| H | H | H | CH₂SCH₃ | OCH₂CH₃ | CH₂OCH₃ | N | |
| H | H | H | CH₂SCH₃ | OCH₂CH₃ | NHCH₃ | N | |
| H | H | H | CH₂SCH₃ | OCH₂CH₃ | CH(OCH₃)₂ | CH | |
| H | H | H | CH₂SCH₃ | OCF₂H | C₂H₅ | CH | |
| H | H | H | CH₂SCH₃ | OCF₂H | CH₂OCH₃ | CH | |
| H | H | H | CH₂SCH₃ | OCH₂CF₃ | C₂H₅ | CH | |
| H | H | H | CH₂SCH₃ | OCH₂CF₃ | C₂H₅ | N | |
| H | H | H | CH₂SCH₃ | OCH₂CF₃ | CH₂OCH₃ | CH | |
| H | H | H | CH₂SCH₃ | OCH₂CF₃ | CH₂OCH₃ | N | |
| H | H | H | CH₂SCH₃ | OCH₂CF₃ | NHCH₃ | N | |
| H | H | H | CH₂SCH₃ | OCH₂CF₃ | CH(OCH₃)₂ | N | |
| H | H | H | CH₂SCH₃ | CH₃ | CH₂OCH₃ | CH | |
| H | H | H | CH₂SCH₃ | CH₃ | CH₂OCH₃ | N | |
| H | H | H | CH₂SCH₃ | CH₃ | NHCH₃ | N | |
| H | H | H | CH₂SCH₃ | CH₃ | CH(OCH₃)₂ | N | |
| H | H | H | CH₂SCH₃ | OCH₃ | C₂H₅ | CH | |
| H | H | H | CH₂SCH₃ | OCH₃ | C₂H₅ | N | |
| H | H | H | CH₂SCH₃ | OCH₂ | CH₂OCH₃ | CH | |
| H | H | H | CH₂SCH₃ | OCH₃ | CH₂OCH₃ | N | |
| H | H | H | CH₂SCH₃ | OCH₃ | NHCH₃ | N | |
| H | H | H | CH₂SCH₃ | OCH₃ | CH(OCH₃)₂ | CH | |
| H | H | H | CH₂SCH₃ | OCH₃ | CH(OCH₃)₂ | N | |
| H | 5-Cl | H | CH₂OCH₃ | OCH₂CH₃ | C₂H₅ | CH | |
| H | 5-Cl | H | CH₂OCH₃ | OCH₂CH₃ | C₂H₅ | N | |
| H | 5-Cl | H | CH₂OCH₃ | OCH₂CH₃ | CH₂OCH₃ | CH | |
| H | 5-Cl | H | CH₂OCH₃ | OCH₂CH₃ | CH₂OCH₃ | N | |
| H | 5-Cl | H | CH₂OCH₃ | OCH₂CH₃ | NHCH₃ | CH | |
| H | 5-Cl | H | CH₂OCH₃ | OCH₂CH₃ | NHCH₃ | N | |
| H | 5-Cl | H | CH₂OCH₃ | OCH₂CH₃ | CH(OCH₃)₂ | CH | |
| H | 5-Cl | H | CH₂OCH₃ | OCH₂CH₃ | CH(OCH₃)₂ | N | |
| H | 5-Cl | H | CH₂OCH₃ | OCF₂H | C₂H₅ | CH | |
| H | 5-Cl | H | CH₂OCH₃ | OCF₂H | CH₂OCH₃ | CH | |
| H | 5-Cl | H | CH₂OCH₃ | OCF₂H | NHCH₃ | CH | |
| H | 5-Cl | H | CH₂OCH₃ | OCH₂CF₃ | C₂H₅ | CH | |
| H | 5-Cl | H | CH₂OCH₃ | OCH₂CF₃ | CH₂OCH₃ | N | |
| H | 5-Cl | H | CH₂OCH₃ | OCH₂CF₃ | NHCH₃ | CH | |
| H | 5-Cl | H | CH₂OCH₃ | OCH₂CF₃ | NHCH₃ | N | |
| H | 5-Cl | H | CH₂OCH₃ | OCH₂CF₃ | CH(OCH₃)₂ | CH | |
| H | 5-Cl | H | CH₂OCH₃ | OCH₂CF₃ | CH(OCH₃)₂ | N | |
| H | 5-Cl | H | CH₂OCH₃ | Cl | NHCH₃ | CH | |
| H | 5-Cl | H | CH₂OCH₃ | CH₃ | C₂H₅ | CH | |
| H | 5-Cl | H | CH₂OCH₃ | CH₃ | CH₂OCH₃ | CH | |
| H | 5-Cl | H | CH₂OCH₃ | CH₃ | CH₂OCH₃ | N | |
| H | 5-Cl | H | CH₂OCH₃ | Cl | NHCH₃ | CH | |
| H | 5-Cl | H | CH₂OCH₃ | CH₃ | CH₂OCH₃ | CH | |
| H | 5-Cl | H | CH₂OCH₃ | CH₃ | CH₂OCH₃ | N | |
| H | 5-Cl | H | CH₂OCH₃ | CH₃ | NHCH₃ | N | |
| H | 5-Cl | H | CH₂OCH₃ | CH₃ | CH(OCH₃)₂ | CH | |
| H | 5-Cl | H | CH₂OCH₃ | CH₃ | CH(OCH₃)₂ | N | |
| H | 5-Cl | H | CH₂OCH₃ | OCH₃ | C₂H₅ | CH | |
| H | 5-Cl | H | CH₂OCH₃ | OCH₃ | C₂H₅ | N | |
| H | 5-Cl | H | CH₂OCH₃ | OCH₃ | CH₂OCH₃ | CH | |
| H | 5-Cl | H | CH₂OCH₃ | OCH₃ | CH₂OCH₃ | N | |
| H | 5-Cl | H | CH₂OCH₃ | OCH₃ | NHCH₃ | CH | |
| H | 5-Cl | H | CH₂OCH₃ | OCH₃ | NHCH₃ | N | |
| H | 5-Cl | H | CH₂OCH₃ | OCH₃ | CH(OCH₃)₂ | CH | |
| H | 5-Cl | H | CH₂OCH₃ | OCH₃ | CH(OCH₃)₂ | N | |
| H | H | H | CN | OCH₃ | CH₃ | N | |
| H | H | H | CN | OCH₃ | OCH₃ | N | |
| H | 2-CH₃ | H | CN | CH₃ | CH₃ | CH | |
| H | 2-CH₃ | H | CN | CH₃ | OCH₃ | CH | |
| H | 2-CH₃ | H | CN | OCH₃ | OCH₃ | CH | 191–192 |
| H | 2-CH₃ | H | CN | CH₃ | OCH₃ | N | 183–187 |
| H | 2-CH₃ | H | CN | OCH₃ | OCH₃ | N | |
| H | 2-CH₃ | H | CN | Cl | OCH₃ | CH | |
| H | H | H | S(CH₂)₂OH | CH₃ | CH₃ | CH | |
| H | H | H | S(CH₂)₂OH | CH₃ | OCH₃ | CH | |
| H | H | H | S(CH₂)₂OH | OCH₃ | OCH₃ | CH | |
| H | H | H | S(CH₂)₂OH | CH₃ | OCH₃ | N | |
| H | H | H | S(CH₂)₂OH | OCH₃ | OCH₃ | N | |
| H | H | H | S(CH₂)₂OH | Cl | OCH₃ | CH | |
| H | H | H | S(CH₂)₂OH | CH₃ | CH₃ | CH | |
| H | H | H | S(CH₂)₂OH | CH₃ | OCH₃ | CH | |
| H | H | H | S(CH₂)₂OH | OCH₃ | OCH₃ | CH | |
| H | H | H | S(CH₂)₂OH | CH₃ | OCH₃ | N | |
| H | H | H | S(CH₂)₂OH | OCH₃ | OCH₃ | N | |
| H | H | H | S(CH₂)₂OH | Cl | OCH₃ | CH | |
| H | 2-CO₂CH₃ | H | S(CH₂)₂OH | CH₃ | CH₃ | CH | |
| H | 2-CO₂CH₃ | H | S(CH₂)₂OH | CH₃ | OCH₃ | CH | |
| H | 2-CO₂CH₃ | H | S(CH₂)₂OH | OCH₃ | OCH₃ | CH | |

TABLE IIIa-continued

General Formula IIIa

| R | R₁ | Rₓ | Q₁ | X | Y | Z | m.p.(°C.) |
|---|---|---|---|---|---|---|---|
| H | 2-CO₂CH₃ | H | S(CH₂)₂OH | CH₃ | OCH₃ | N | |
| H | 2-CO₂CH₃ | H | S(CH₂)₂OH | OCH₃ | OCH₃ | N | |
| H | 2-CO₂CH₃ | H | S(CH₂)₂OH | Cl | OCH₃ | CH | |
| H | 2-CH₃ | H | CH₂SCH₃ | CH₃ | CH₃ | CH | |
| H | 2-CH₃ | H | CH₂SCH₃ | CH₃ | OCH₃ | CH | |
| H | 2-CH₃ | H | CH₂SCH₃ | OCH₃ | OCH₃ | CH | |
| H | 2-CH₃ | H | CH₂SCH₃ | CH₃ | OCH₃ | N | |
| H | 2-CH₃ | H | CH₂SCH₃ | OCH₃ | OCH₃ | N | |
| H | 2-CH₃ | H | CH₂SCH₃ | Cl | OCH₃ | CH | |
| H | 2-CH₃ | H | CH₂S(O)CH₃ | CH₃ | CH₃ | CH | |
| H | 2-CH₃ | H | CH₂S(O)CH₃ | CH₃ | OCH₃ | CH | |
| H | 2-CH₃ | H | CH₂S(O)CH₃ | OCH₃ | OCH₃ | CH | |
| H | 2-CH₃ | H | CH₂S(O)CH₃ | CH₃ | OCH₃ | N | |
| H | 2-CH₃ | H | CH₂S(O)CH₃ | OCH₃ | OCH₃ | N | |
| H | 2-CH₃ | H | CH₂S(O)CH₃ | Cl | OCH₃ | CH | |
| H | 2-CH₃ | H | CH₂S(O)₂CH₃ | CH₃ | CH₃ | CH | |
| H | 2-CH₃ | H | CH₂S(O)₂CH₃ | CH₃ | OCH₃ | CH | |
| H | 2-CH₃ | H | CH₂S(O)₂CH₃ | OCH₃ | OCH₃ | CH | |
| H | 2-CH₃ | H | CH₂S(O)₂CH₃ | CH₃ | OCH₃ | N | |
| H | 2-CH₃ | H | CH₂S(O)₂CH₃ | OCH₃ | OCH₃ | N | |
| H | 2-CH₃ | H | CH₂S(O)₂CH₃ | Cl | OCH₃ | CH | |
| H | 2-CH₃ | H | CH₂SCH₂CH₃ | CH₃ | CH₃ | CH | |
| H | 2-CH₃ | H | CH₂SCH₂CH₃ | CH₃ | OCH₃ | CH | |
| H | 2-CH₃ | H | CH₂SCH₂CH₃ | OCH₃ | OCH₃ | CH | |
| H | 2-CH₃ | H | CH₂SCH₂CH₃ | CH₃ | OCH₃ | N | |
| H | 2-CH₃ | H | CH₂SCH₂CH₃ | OCH₃ | OCH₃ | N | |
| H | 2-CH₃ | H | CH₂SCH₂CH₃ | Cl | OCH₃ | CH | |
| H | 2-CH₃ | H | CH₂S(O)CH₂CH₃ | CH₃ | CH₃ | CH | |
| H | 2-CH₃ | H | CH₂S(O)CH₂CH₃ | CH₃ | OCH₃ | CH | |
| H | 2-CH₃ | H | CH₂S(O)CH₂CH₃ | OCH₃ | OCH₃ | CH | |
| H | 2-CH₃ | H | CH₂S(O)CH₂CH₃ | CH₃ | OCH₃ | N | |
| H | 2-CH₃ | H | CH₂S(O)CH₂CH₃ | OCH₃ | OCH₃ | N | |
| H | 2-CH₃ | H | CH₂S(O)CH₂CH₃ | Cl | OCH₃ | CH | |
| H | 2-CH₃ | H | CH₂S(O)₂CH₂CH₃ | CH₃ | CH₃ | CH | |
| H | 2-CH₃ | H | CH₂S(O)₂CH₂CH₃ | CH₃ | OCH₃ | CH | |
| H | 2-CH₃ | H | CH₂S(O)₂CH₂CH₃ | OCH₃ | OCH₃ | CH | |
| H | 2-CH₃ | H | CH₂S(O)₂CH₂CH₃ | CH₃ | OCH₃ | N | |
| H | 2-CH₃ | H | CH₂S(O)₂CH₂CH₃ | OCH₃ | OCH₃ | N | |
| H | 2-CH₃ | H | CH₂S(O)₂CH₂CH₃ | Cl | OCH₃ | CH | |
| H | 2-CH₃ | H | CH₂SCH₂CH₂CH₃ | CH₃ | CH₃ | CH | |
| H | 2-CH₃ | H | CH₂SCH₂CH₂CH₃ | CH₃ | OCH₃ | CH | |
| H | 2-CH₃ | H | CH₂SCH₂CH₂CH₃ | OCH₃ | OCH₃ | CH | |
| H | 2-CH₃ | H | CH₂SCH₂CH₂CH₃ | CH₃ | OCH₃ | N | |
| H | 2-CH₃ | H | CH₂SCH₂CH₂CH₃ | OCH₃ | OCH₃ | N | |
| H | 2-CH₃ | H | CH₂SCH₂CH₂CH₃ | Cl | OCH₃ | CH | |
| H | 2-CH₃ | H | CH₂S(O)CH₂CH₂CH₃ | CH₃ | CH₃ | CH | |
| H | 2-CH₃ | H | CH₂S(O)CH₂CH₂CH₃ | CH₃ | OCH₃ | CH | |
| H | 2-CH₃ | H | CH₂S(O)CH₂CH₂CH₃ | OCH₃ | OCH₃ | CH | |
| H | 2-CH₃ | H | CH₂S(O)CH₂CH₂CH₃ | CH₃ | OCH₃ | N | |
| H | 2-CH₃ | H | CH₂S(O)CH₂CH₂CH₃ | OCH₃ | OCH₃ | N | |
| H | 2-CH₃ | H | CH₂S(O)CH₂CH₂CH₃ | Cl | OCH₃ | CH | |
| H | 2-CH₃ | H | CH₂S(O)₂CH₂CH₂CH₃ | CH₃ | CH₃ | CH | |
| H | 2-CH₃ | H | CH₂S(O)₂CH₂CH₂CH₃ | CH₃ | OCH₃ | CH | |
| H | 2-CH₃ | H | CH₂S(O)₂CH₂CH₂CH₃ | OCH₃ | OCH₃ | CH | |
| H | 2-CH₃ | H | CH₂S(O)₂CH₂CH₂CH₃ | CH₃ | OCH₃ | N | |
| H | 2-CH₃ | H | CH₂S(O)₂CH₂CH₂CH₃ | OCH₃ | OCH₃ | N | |
| H | 2-CH₃ | H | CH₂S(O)₂CH₂CH₂CH₃ | Cl | OCH₃ | CH | |
| H | 2-CH₂CH₃ | H | CH₂—S—CH₃ | CH₃ | CH₃ | CH | |
| H | 2-CH₂CH₃ | H | CH₂—S—CH₃ | CH₃ | OCH₃ | CH | |
| H | 2-CH₂CH₃ | H | CH₂—S—CH₃ | OCH₃ | OCH₃ | CH | |
| H | 2-CH₂CH₃ | H | CH₂—S—CH₃ | CH₃ | OCH₃ | N | |
| H | 2-CH₂CH₃ | H | CH₂——S—CH₃ | OCH₃ | OCH₃ | N | |
| H | 2-CH₂CH₃ | H | CH₂—S—CH₃ | Cl | OCH₃ | CH | |
| H | 2-CH₂CH₃ | H | CH₂—S—CH₂CH₃ | CH₃ | CH₃ | CH | |
| H | 2-CH₂CH₃ | H | CH₂—S—CH₂CH₃ | CH₃ | OCH₃ | CH | |
| H | 2-CH₂CH₃ | H | CH₂—S—CH₂CH₃ | OCH₃ | OCH₃ | CH | |
| H | 2-CH₂CH₃ | H | CH₂—S—CH₂CH₃ | CH₃ | OCH₃ | N | |
| H | 2-CH₂CH₃ | H | CH₂—S—CH₂CH₃ | OCH₃ | OCH₃ | N | |
| H | 2-CH₂CH₃ | H | CH₂—S—CH₂CH₃ | Cl | OCH₃ | CH | |
| H | 2-CH₂CH₃ | H | CH₂—S—CH₂CH₂CH₃ | CH₃ | CH₃ | CH | |
| H | 2-CH₂CH₃ | H | CH₂—S—CH₂CH₂CH₃ | CH₃ | OCH₃ | CH | |
| H | 2-CH₂CH₃ | H | CH₂—S—CH₂CH₂CH₃ | OCH₃ | OCH₃ | CH | |
| H | 2-CH₂CH₃ | H | CH₂—S—CH₂CH₂CH₃ | CH₃ | OCH₃ | N | |
| H | 2-CH₂CH₃ | H | CH₂—S—CH₂CH₂CH₃ | CH₃ | OCH₃ | N | |
| H | 2-CH₂CH₃ | H | CH₂—S—CH₂CH₂CH₃ | Cl | OCH₃ | CH | |
| H | 2-CO₂CH₃ | H | CH₂Br | CH₃ | CH₃ | CH | |
| H | 2-CO₂CH₃ | H | CH₂Br | CH₃ | OCH₃ | CH | 218–223 |
| H | 2-CO₂CH₃ | H | CH₂Br | OCH₃ | OCH₃ | CH | 193–199 |
| H | 2-CO₂CH₃ | H | CH₂Br | CH₃ | OCH₃ | N | 151–156 |
| H | 2-CO₂CH₃ | H | CH₂Br | OCH₃ | OCH₃ | N | |

TABLE IIIa-continued

General Formula IIIa

| R | R₁ | Rₓ | Q₁ | X | Y | Z | m.p.(°C.) |
|---|---|---|---|---|---|---|---|
| H | 2-CO₂CH₃ | H | CH₂Br | Cl | OCH₃ | CH | |
| H | 2-CH₃ | H | CH₂Br | CH₃ | CH₃ | CH | |
| H | 2-CH₃ | H | CH₂Br | CH₃ | OCH₃ | CH | |
| H | 2-CH₃ | H | CH₂Br | OCH₃ | OCH₃ | CH | |
| H | 2-CH₃ | H | CH₂Br | CH₃ | OCH₃ | N | |
| H | 2-CH₃ | H | CH₂Br | OCH₃ | OCH₃ | N | |
| H | 2-CH₃ | H | CH₂Br | Cl | OCH₃ | CH | |
| H | 2-CH₂CH₃ | H | CH₂Br | CH₃ | CH₃ | CH | |
| H | 2-CH₂CH₃ | H | CH₂Br | CH₃ | OCH₃ | CH | |
| H | 2-CH₂CH₃ | H | CH₂Br | OCH₃ | OCH₃ | CH | |
| H | 2-CH₂CH₃ | H | CH₂Br | CH₃ | OCH₃ | N | |
| H | 2-CH₂CH₃ | H | CH₂Br | OCH₃ | OCH₃ | N | |
| H | 2-CH₂CH₃ | H | CH₂Br | Cl | OCH₃ | CH | |
| H | 2-CO₂CH₂CH₃ | H | CH₂Br | CH₃ | CH₃ | CH | |
| H | 2-CO₂CH₂CH₃ | H | CH₂Br | CH₃ | OCH₃ | CH | |
| H | 2-CO₂CH₂CH₃ | H | CH₂Br | OCH₃ | OCH₃ | CH | |
| H | 2-CO₂CH₂CH₃ | H | CH₂Br | CH₃ | OCH₃ | N | |
| H | 2-CO₂CH₂CH₃ | H | CH₂Br | OCH₃ | OCH₃ | N | |
| H | 2-CO₂CH₂CH₃ | H | CH₂Br | Cl | OCH₃ | CH | |
| H | 2-CO₂CH(CH₃)₂ | H | CH₂Br | CH₃ | CH₃ | CH | |
| H | 2-CO₂CH(CH₃)₂ | H | CH₂Br | CH₃ | OCH₃ | CH | |
| H | 2-CO₂CH(CH₃)₂ | H | CH₂Br | OCH₃ | OCH₃ | CH | |
| H | 2-CO₂CH(CH₃)₂ | H | CH₂Br | CH₃ | OCH₃ | N | |
| H | 2-CO₂CH(CH₃)₂ | H | CH₂Br | OCH₃ | OCH₃ | N | |
| H | 2-CO₂CH(CH₃)₂ | H | CH₂Br | Cl | OCH₃ | CH | |
| H | 2-CO₂CH₃ | H | CH₂SCH₃ | CH₃ | CH₃ | CH | |
| H | 2-CO₂CH₃ | H | CH₂SCH₃ | CH₃ | OCH₃ | CH | |
| H | 2-CO₂CH₃ | H | CH₂SCH₃ | OCH₃ | OCH₃ | CH | |
| H | 2-CO₂CH₃ | H | CH₂SCH₃ | CH₃ | OCH₃ | N | |
| H | 2-CO₂CH₃ | H | CH₂SCH₃ | OCH₃ | OCH₃ | N | |
| H | 2-CO₂CH₃ | H | CH₂SCH₃ | Cl | OCH₃ | CH | |
| H | 2-CO₂CH₃ | H | CH₂S(O)CH₃ | CH₃ | CH₃ | CH | |
| H | 2-CO₂CH₃ | H | CH₂S(O)CH₃ | CH₃ | OCH₃ | CH | |
| H | 2-CO₂CH₃ | H | CH₂S(O)CH₃ | OCH₃ | OCH₃ | CH | |
| H | 2-CO₂CH₃ | H | CH₂S(O)CH₃ | CH₃ | OCH₃ | N | |
| H | 2-CO₂CH₃ | H | CH₂S(O)CH₃ | OCH₃ | OCH₃ | N | |
| H | 2-CO₂CH₃ | H | CH₂S(O)CH₃ | Cl | OCH₃ | CH | |
| H | 2-CO₂CH₃ | H | CH₂S(O)₂CH₃ | CH₃ | CH₃ | CH | |
| H | 2-CO₂CH₃ | H | CH₂S(O)₂CH₃ | CH₃ | OCH₃ | CH | |
| H | 2-CO₂CH₃ | H | CH₂S(O)₂CH₃ | OCH₃ | OCH₃ | CH | |
| H | 2-CO₂CH₃ | H | CH₂S(O)₂CH₃ | CH₃ | OCH₃ | N | |
| H | 2-CO₂CH₃ | H | CH₂S(O)₂CH₃ | OCH₃ | OCH₃ | N | |
| H | 2-CO₂CH₃ | H | CH₂S(O)₂CH₃ | Cl | OCH₃ | CH | |
| H | 2-CO₂CH₃ | H | CH₂SCH₂CH₃ | CH₃ | CH₃ | CH | |
| H | 2-CO₂CH₃ | H | CH₂SCH₂CH₃ | CH₃ | OCH₃ | CH | |
| H | 2-CO₂CH₃ | H | CH₂SCH₂CH₃ | OCH₃ | OCH₃ | CH | |
| H | 2-CO₂CH₃ | H | CH₂SCH₂CH₃ | CH₃ | OCH₃ | N | |
| H | 2-CO₂CH₃ | H | CH₂SCH₃CH₃ | OCH₃ | OCH₃ | N | |
| H | 2-CO₂CH₃ | H | CH₂SCH₃CH₃ | Cl | OCH₃ | CH | |
| H | 2-CO₂CH₃ | H | CH₂S(O)CH₂CH₃ | CH₃ | CH₃ | CH | |
| H | 2-CO₂CH₃ | H | CH₂S(O)CH₂CH₃ | CH₃ | OCH₃ | CH | |
| H | 2-CO₂CH₃ | H | CH₂S(O)CH₂CH₃ | OCH₃ | OCH₃ | CH | |
| H | 2-CO₂CH₃ | H | CH₂S(O)CH₂CH₃ | CH₃ | OCH₃ | N | |
| H | 2-CO₂CH₃ | H | CH₂S(O)CH₂CH₃ | OCH₃ | OCH₃ | N | |
| H | 2-CO₂CH₃ | H | CH₂S(O)CH₂CH₃ | Cl | OCH₃ | CH | |
| H | 2-CO₂CH₃ | H | CH₂S(O)₂CH₂CH₃ | CH₃ | CH₃ | CH | |
| H | 2-CO₂CH₃ | H | CH₂S(O)₂CH₂CH₃ | CH₃ | OCH₃ | CH | |
| H | 2-CO₂CH₃ | H | CH₂S(O)₂CH₂CH₃ | OCH₃ | OCH₃ | CH | |
| H | 2-CO₂CH₃ | H | CH₂S(O)₂CH₂CH₃ | CH₃ | OCH₃ | N | |
| H | 2-CO₂CH₃ | H | CH₂S(O)₂CH₂CH₃ | OCH₃ | OCH₃ | N | |
| H | 2-CO₂CH₃ | H | CH₂S(O)₂CH₂CH₃ | Cl | OCH₃ | CH | |
| H | 2-CO₂CH₃ | H | CH₂SCH₂CH₂CH₃ | CH₃ | CH₃ | CH | |
| H | 2-CO₂CH₃ | H | CH₂SCH₂CH₂CH₃ | CH₃ | OCH₃ | CH | |
| H | 2-CO₂CH₃ | H | CH₂SCH₂CH₂CH₃ | OCH₃ | OCH₃ | CH | |
| H | 2-CO₂CH₃ | H | CH₂SCH₂CH₂CH₃ | CH₃ | OCH₃ | N | |
| H | 2-CO₂CH₃ | H | CH₂SCH₂CH₂CH₃ | OCH₃ | OCH₃ | N | |
| H | 2-CO₂CH₃ | H | CH₂SCH₂CH₂CH₃ | Cl | OCH₃ | CH | |
| H | 2-CO₂CH₃ | H | CH₂S(O)CH₂CH₂CH₃ | CH₃ | CH₃ | CH | |
| H | 2-CO₂CH₃ | H | CH₂S(O)CH₂CH₂CH₃ | CH₃ | OCH₃ | CH | |
| H | 2-CO₂CH₃ | H | CH₂S(O)CH₂CH₂CH₃ | OCH₃ | OCH₃ | CH | |
| H | 2-CO₂CH₃ | H | CH₂S(O)CH₂CH₂CH₃ | CH₃ | OCH₃ | N | |
| H | 2-CO₂CH₃ | H | CH₂S(O)CH₂CH₂CH₃ | OCH₃ | OCH₃ | N | |
| H | 2-CO₂CH₃ | H | CH₂S(O)CH₂CH₂CH₃ | Cl | OCH₃ | CH | |
| H | 2-CO₂CH₃ | H | CH₂S(O)₂CH₂CH₂CH₃ | CH₃ | CH₃ | CH | |
| H | 2-CO₂CH₃ | H | CH₂S(O)₂CH₂CH₂CH₃ | CH₃ | OCH₃ | CH | |
| H | 2-CO₂CH₃ | H | CH₂S(O)₂CH₂CH₂CH₃ | OCH₃ | OCH₃ | CH | |
| H | 2-CO₂CH₃ | H | CH₂S(O)₂CH₂CH₂CH₃ | CH₃ | OCH₃ | N | |
| H | 2-CO₂CH₃ | H | CH₂S(O)₂CH₂CH₂CH₃ | OCH₃ | OCH₃ | N | |

TABLE IIIa-continued

General Formula IIIa

| R | R$_1$ | R$_x$ | Q$_1$ | X | Y | Z | m.p.(°C.) |
|---|---|---|---|---|---|---|---|
| H | 2-CO$_2$CH$_3$ | H | CH$_2$S(O)$_2$CH$_2$CH$_2$CH$_3$ | Cl | OCH$_3$ | CH | |

TABLE IVa

General Formula IVa

| R | R$_1$ | R$_x$ | Q$_1$ | X$_1$ | Y$_1$ | m.p. (°C.) |
|---|---|---|---|---|---|---|
| H | H | H | CH$_2$OCH$_3$ | CH$_3$ | O | |
| H | H | H | CH$_2$OCH$_3$ | OCH$_3$ | O | |
| H | H | H | CH$_2$OCH$_3$ | OC$_2$H$_5$ | O | |
| H | H | H | CH$_2$OCH$_3$ | OCF$_2$H | O | |
| H | H | H | CH$_2$OCH$_3$ | CH$_3$ | CH$_2$ | |
| H | H | H | CH$_2$OCH$_3$ | OCH$_3$ | CH$_2$ | |
| H | H | H | CH$_2$OCH$_3$ | OC$_2$H$_5$ | CH$_2$ | |
| H | H | H | CH$_2$OCH$_3$ | OCF$_2$H | CH$_2$ | |
| H | H | H | SCH$_2$CH$_2$OCH$_3$ | OCH$_3$ | O | |
| H | H | H | SCH$_2$CH$_2$OCH$_3$ | CH$_3$ | O | |
| H | H | H | S(CH$_2$)$_3$Cl | CH$_3$ | O | |
| H | H | H | S(CH$_2$)$_3$Cl | OCH$_3$ | O | |
| H | H | H | SCH$_2$C≡CH | OCH$_3$ | O | |
| H | H | H | SCH$_2$C≡CH | CH$_3$ | O | |
| H | H | H | CH$_2$Cl | OCH$_3$ | O | |
| H | H | H | CHClCH$_3$ | OCH$_3$ | O | |

TABLE Va

General Formula Va

| R | R$_1$ | R$_x$ | Q$_1$ | X$_1$ | m.p. (°C.) |
|---|---|---|---|---|---|
| H | H | H | SCH$_2$CH=CH$_2$ | CH$_3$ | |
| H | H | H | SCH$_2$CH=CH$_2$ | OCH$_3$ | |
| H | H | H | SCH$_2$CH=CH$_2$ | OCF$_2$H | |
| H | H | H | CH$_2$OCH$_3$ | OCH$_3$ | |
| H | H | H | CH$_2$OCH$_3$ | CH$_3$ | |
| H | H | H | S(CH$_2$)$_2$SCH$_3$ | OCH$_3$ | |
| H | H | H | S(CH$_2$)$_2$SCH$_3$ | CH$_3$ | |
| H | H | H | O(CH$_2$)$_2$OCH$_3$ | OCH$_3$ | |
| H | H | H | O(CH$_2$)$_2$OCH$_3$ | CH$_3$ | |

TABLE VIa

General Formula VIa

| R | R$_1$ | R$_x$ | Q$_1$ | X$_1$ | Y$_2$ | m.p. (°C.) |
|---|---|---|---|---|---|---|
| H | H | H | S(CH$_2$)$_2$SCH$_3$ | CH$_3$ | H | |
| H | H | H | S(CH$_2$)$_2$SCH$_3$ | OCH$_3$ | H | |
| H | H | H | S(CH$_2$)$_2$SCH$_3$ | OC$_2$H$_5$ | H | |
| H | H | H | S(CH$_2$)$_2$SCH$_3$ | OCF$_2$H | H | |
| H | H | H | S(CH$_2$)$_2$SCH$_3$ | CH$_3$ | CH$_3$ | |
| H | H | H | S(CH$_2$)$_2$SCH$_3$ | OCH$_3$ | CH$_3$ | |
| H | H | H | S(CH$_2$)$_2$SCH$_3$ | OC$_2$H$_5$ | CH$_3$ | |
| H | H | H | S(CH$_2$)$_2$SCH$_3$ | OCF$_2$H | CH$_3$ | |
| H | H | H | S(CH$_2$)$_3$Cl | OCH$_3$ | H | |
| H | H | H | S(CH$_2$)$_3$Cl | CH$_3$ | H | |
| H | H | H | SCH$_2$CO$_2$CH$_3$ | OCH$_3$ | H | |
| H | H | H | SCH$_2$CO$_2$CH$_3$ | CH$_3$ | H | |
| H | H | H | SO$_2$CH$_2$C≡CH | OCH$_3$ | H | |
| H | H | H | SO$_2$CH$_2$C≡CH | CH$_3$ | H | |

TABLE VIIa

General Formula VIIa

| R | R$_1$ | R$_x$ | Q$_1$ | X$_2$ | Y$_3$ | m.p. (°C.) |
|---|---|---|---|---|---|---|
| H | H | H | (CH$_2$)$_2$OCH$_3$ | CH$_3$ | CH$_3$ | |
| H | H | H | (CH$_2$)$_2$OCH$_3$ | OCH$_3$ | CH$_3$ | |
| H | H | H | (CH$_2$)$_2$OCH$_3$ | SCH$_3$ | CH$_3$ | |
| H | H | H | (CH$_2$)$_2$OCH$_3$ | CH$_3$ | CH$_2$CH$_3$ | |
| H | H | H | (CH$_2$)$_2$OCH$_3$ | SCH$_3$ | CH$_2$CH$_3$ | |
| H | H | H | (CH$_2$)$_2$OCH$_3$ | SCH$_3$ | CH$_2$CF$_3$ | |
| H | H | H | (CH$_2$)$_2$OCH$_3$ | CH$_3$ | CH$_2$CF$_3$ | |
| H | H | H | (CH$_2$)$_2$OCH$_3$ | OCH$_3$ | CH$_2$CF$_3$ | |
| H | H | H | CH$_2$CN | SCH$_3$ | CH$_2$CH$_3$ | |
| H | H | H | CH$_2$CN | OCH$_3$ | CH$_3$ | |

TABLE VIIIa

General Formula VIIIa

| R | R$_1$ | R$_x$ | Q$_1$ | X$_3$ | m.p. (°C.) |
|---|---|---|---|---|---|
| H | H | H | CH$_2$OCH$_3$ | CH$_3$ | |
| H | H | H | CH$_2$OCH$_3$ | OCH$_3$ | |
| H | H | H | S(CH$_2$)$_2$SCH$_3$ | OCH$_3$ | |
| H | H | H | SCH$_2$CO$_2$CH$_3$ | OCH$_3$ | |
| H | H | H | (CH$_2$)$_2$Br | OCH$_3$ | |
| H | H | H | CH$_2$F | OCH$_3$ | |
| H | H | H | CH$_2$CO$_2$CH$_3$ | OCH$_3$ | |
| H | H | H | CH$_2$SO$_2$N(CH$_3$)$_2$ | OCH$_3$ | |

TABLE IXa

General Formula IXa

| R | R$_1$ | R$_x$ | Q$_1$ | X | Y | Z | m.p. (°C.) |
|---|---|---|---|---|---|---|---|
| H | H | H | CH$_2$OCH$_3$ | CH$_3$ | CH$_3$ | CH | |
| H | H | H | CH$_2$OCH$_3$ | OCH$_3$ | OCH$_3$ | CH | |
| H | H | H | CH$_2$OCH$_3$ | Cl | OCH$_3$ | CH | |
| H | H | H | CH$_2$OCH$_3$ | CH$_3$ | OCH$_3$ | N | |
| H | H | H | (CH$_2$)$_2$OCH$_3$ | OCH$_3$ | OCH$_3$ | CH | |
| H | H | H | (CH$_2$)$_2$OCH$_3$ | Cl | OCH$_3$ | CH | |
| H | H | H | (CH$_2$)$_2$OCH$_3$ | CH$_3$ | OCH$_3$ | N | |
| H | H | H | (CH$_2$)$_2$OCH$_3$ | CH$_3$ | CH$_3$ | CH | |
| H | H | H | CH$_2$Cl | CH$_3$ | CH$_3$ | CH | |
| H | H | H | CH$_2$Cl | CH$_3$ | OCH$_3$ | CH | |
| H | H | H | CH$_2$Cl | Cl | OCH$_3$ | CH | |
| H | H | H | CH$_2$Cl | CH$_3$ | OCH$_3$ | CH | |
| H | H | H | CH$_2$OH | CH$_3$ | CH$_3$ | CH | |
| H | H | H | CH$_2$OH | CH$_3$ | OCH$_3$ | CH | |
| H | H | H | CH$_2$OH | OCH$_3$ | OCH$_3$ | CH | |
| H | H | H | CH$_2$OH | Cl | OCH$_3$ | CH | |
| H | H | H | CN | CH$_3$ | CH$_3$ | CH | |
| H | H | H | CN | CH$_3$ | OCH$_3$ | CH | |
| H | H | H | CN | Cl | OCH$_3$ | CH | |
| H | H | H | CH$_2$CN | CH$_3$ | OCH$_3$ | CH | |
| H | H | H | CH$_2$CN | Cl | OCH$_3$ | CH | |
| H | H | H | CH$_2$CN | OCH$_3$ | OCH$_3$ | CH | |
| H | H | H | CH$_2$SCH$_3$ | CH$_3$ | CH$_3$ | CH | |
| H | H | H | CH$_2$SCH$_3$ | Cl | OCH$_3$ | CH | |
| H | H | H | CH$_2$SCH$_3$ | OCH$_3$ | OCH$_3$ | CH | |
| H | H | H | CH$_2$SCH$_3$ | CH$_3$ | OCH$_3$ | N | |

TABLE Xa

General Formula Xa

| R | R$_1$ | R$_x$ | Q$_1$ | X | Y | Z | m.p. (°C.) |
|---|---|---|---|---|---|---|---|
| H | H | H | CH$_2$OCH$_3$ | CH$_3$ | CH$_3$ | CH | |
| H | H | H | CH$_2$OCH$_3$ | OCH$_3$ | OCH$_3$ | CH | |
| H | H | H | CH$_2$OCH$_3$ | Cl | OCH$_3$ | CH | |
| H | H | H | CH$_2$OCH$_3$ | CH$_3$ | OCH$_3$ | N | |
| H | H | H | (CH$_2$)$_2$OCH$_3$ | OCH$_3$ | OCH$_3$ | CH | |
| H | H | H | (CH$_2$)$_2$OCH$_3$ | Cl | OCH$_3$ | CH | |
| H | H | H | (CH$_2$)$_2$OCH$_3$ | CH$_3$ | OCH$_3$ | N | |
| H | H | H | (CH$_2$)$_2$OCH$_3$ | CH$_3$ | CH$_3$ | CH | |
| H | H | H | CH$_2$Cl | CH$_3$ | CH$_3$ | CH | |
| H | H | H | CH$_2$Cl | OCH$_3$ | OCH$_3$ | CH | |
| H | H | H | CH$_2$Cl | Cl | OCH$_3$ | CH | |
| H | H | H | CH$_2$Cl | CH$_3$ | OCH$_3$ | CH | |
| H | H | H | CH$_2$OH | CH$_3$ | CH$_3$ | CH | |
| H | H | H | CH$_2$OH | CH$_3$ | OCH$_3$ | CH | |
| H | H | H | CH$_2$OH | OCH$_3$ | OCH$_3$ | CH | |
| H | H | H | CH$_2$OH | Cl | OCH$_3$ | CH | |
| H | H | H | CN | CH$_3$ | CH$_3$ | CH | |
| H | H | H | CN | CH$_3$ | OCH$_3$ | CH | |
| H | H | H | CN | Cl | OCH$_3$ | CH | |
| H | H | H | CH$_2$CN | CH$_3$ | OCH$_3$ | CH | |
| H | H | H | CH$_2$CN | Cl | OCH$_3$ | CH | |
| H | H | H | CH$_2$CN | OCH$_3$ | OCH$_3$ | CH | |
| H | H | H | CH$_2$SCH$_3$ | CH$_3$ | CH$_3$ | CH | |
| H | H | H | CH$_2$SCH$_3$ | Cl | OCH$_3$ | CH | |

TABLE Xa-continued

General Formula Xa

| R | R₁ | Rₓ | Q₁ | X | Y | Z | m.p. (°C.) |
|---|----|----|-----|----|----|----|-----|
| H | H | H | CH₂SCH₃ | OCH₃ | OCH₃ | CH | |
| H | H | H | CH₂SCH₃ | CH₃ | OCH₃ | N | |

TABLE XIa

General Formula XIa

| R | R₁ | Rₓ | Q₁ | X | Y | Z | m.p. (°C.) |
|---|----|----|-----|----|----|----|-----|
| H | H | H | CH₂OCH₃ | CH₃ | CH₃ | CH | |
| H | H | H | CH₂OCH₃ | OCH₃ | OCH₃ | CH | |
| H | H | H | CH₂OCH₃ | Cl | OCH₃ | CH | |
| H | H | H | CH₂OCH₃ | CH₃ | OCH₃ | N | |
| H | H | H | (CH₂)₂OCH₃ | OCH₃ | OCH₃ | CH | |
| H | H | H | (CH₂)₂OCH₃ | Cl | OCH₃ | CH | |
| H | H | H | (CH₂)₂OCH₃ | CH₃ | OCH₃ | N | |
| H | H | H | (CH₂)₂OCH₃ | CH₃ | CH₃ | CH | |
| H | H | H | CH₂Cl | CH₃ | CH₃ | CH | |

TABLE XIa-continued

General Formula XIa

| R | R₁ | Rₓ | Q₁ | X | Y | Z | m.p. (°C.) |
|---|----|----|-----|----|----|----|-----|
| H | H | H | CH₂Cl | OCH₃ | OCH₃ | CH | |
| H | H | H | CH₂Cl | Cl | OCH₃ | CH | |
| H | H | H | CH₂Cl | CH₃ | OCH₃ | CH | |
| H | H | H | CH₂OH | CH₃ | CH₃ | CH | |
| H | H | H | CH₂OH | CH₃ | OCH₃ | CH | |
| H | H | H | CH₂OH | OCH₃ | OCH₃ | CH | |
| H | H | H | CH₂OH | Cl | OCH₃ | CH | |
| H | H | H | CN | CH₃ | CH₃ | CH | |
| H | H | H | CN | CH₃ | OCH₃ | CH | |
| H | H | H | CN | Cl | OCH₃ | CH | |
| H | H | H | CH₂CN | CH₃ | OCH₃ | CH | |
| H | H | H | CH₂CN | Cl | OCH₃ | CH | |
| H | H | H | CH₂CN | OCH₃ | OCH₃ | CH | |
| H | H | H | CH₂SCH₃ | CH₃ | CH₃ | CH | |
| H | H | H | CH₂SCH₃ | Cl | OCH₃ | CH | |
| H | H | H | CH₂SCH₃ | OCH₃ | OCH₃ | CH | |
| H | H | H | CH₂SCH₃ | CH₃ | OCH₃ | N | |

TABLE Ib

General Formula Ib

| R | R₁ | Rₓ | Q₂ | X | Y | Z | m.p. (°C.) |
|---|----|----|-----|----|----|----|-----|
| H | 4-SCH₃ | H | CO₂CH₃ | CH₃ | CH₃ | CH | |
| H | 4-SCH₃ | H | CO₂CH₃ | CH₃ | OCH₃ | CH | |
| H | 4-SCH₃ | H | CO₂CH₃ | OCH₃ | OCH₃ | CH | |
| H | 4-SCH₃ | H | CO₂CH₃ | CH₃ | OCH₃ | N | |
| H | 4-SCH₃ | H | CO₂CH₃ | OCH₃ | OCH₃ | N | |
| H | 4-SCH₃ | H | CO₂CH₃ | Cl | OCH₃ | CH | |
| H | 4-S(O)CH₃ | H | CO₂CH₃ | CH₃ | CH₃ | CH | |
| H | 4-S(O)CH₃ | H | CO₂CH₃ | CH₃ | OCH₃ | CH | |
| H | 4-S(O)CH₃ | H | CO₂CH₃ | OCH₃ | OCH₃ | CH | |
| H | 4-S(O)CH₃ | H | CO₂CH₃ | CH₃ | OCH₃ | N | |
| H | 4-S(O)CH₃ | H | CO₂CH₃ | OCH₃ | OCH₃ | N | |
| H | 4-S(O)CH₃ | H | CO₂CH₃ | Cl | OCH₃ | CH | |
| H | 4-S(O)₂CH₃ | H | CO₂CH₃ | CH₃ | CH₃ | CH | |
| H | 4-S(O)₂CH₃ | H | CO₂CH₃ | CH₃ | OCH₃ | CH | |
| H | 4-S(O)₂CH₃ | H | CO₂CH₃ | OCH₃ | OCH₃ | CH | |
| H | 4-S(O)₂CH₃ | H | CO₂CH₃ | CH₃ | OCH₃ | N | |
| H | 4-S(O)₂CH₃ | H | CO₂CH₃ | OCH₃ | OCH₃ | N | |
| H | 4-S(O)₂CH₃ | H | CO₂CH₃ | Cl | OCH₃ | CH | |
| H | 4-SCH₂CH₃ | H | CO₂CH₃ | CH₃ | CH₃ | CH | |
| H | 4-SCH₂CH₃ | H | CO₂CH₃ | CH₃ | OCH₃ | CH | |
| H | 4-SCH₂CH₃ | H | CO₂CH₃ | OCH₃ | OCH₃ | CH | |
| H | 4-SCH₂CH₃ | H | CO₂CH₃ | CH₃ | OCH₃ | N | |
| H | 4-SCH₂CH₃ | H | CO₂CH₃ | OCH₃ | OCH₃ | N | |
| H | 4-SCH₂CH₃ | H | CO₂CH₃ | Cl | OCH₃ | CH | |
| H | 4-S(O)CH₂CH₃ | H | CO₂CH₃ | CH₃ | CH₃ | CH | |
| H | 4-S(O)CH₂CH₃ | H | CO₂CH₃ | CH₃ | OCH₃ | CH | |
| H | 4-S(O)CH₂CH₃ | H | CO₂CH₃ | OCH₃ | OCH₃ | CH | |
| H | 4-S(O)CH₂CH₃ | H | CO₂CH₃ | CH₃ | OCH₃ | N | |
| H | 4-S(O)CH₂CH₃ | H | CO₂CH₃ | OCH₃ | OCH₃ | N | |
| H | 4-S(O)CH₂CH₃ | H | CO₂CH₃ | Cl | OCH₃ | CH | |
| H | 4-S(O)₂CH₂CH₃ | H | CO₂CH₃ | CH₃ | CH₃ | CH | |
| H | 4-S(O)₂CH₂CH₃ | H | CO₂CH₃ | CH₃ | OCH₃ | CH | |
| H | 4-S(O)₂CH₂CH₃ | H | CO₂CH₃ | OCH₃ | OCH₃ | CH | |
| H | 4-S(O)₂CH₂CH₃ | H | CO₂CH₃ | CH₃ | OCH₃ | N | |
| H | 4-S(O)₂CH₂CH₃ | H | CO₂CH₃ | OCH₃ | OCH₃ | N | |
| H | 4-S(O)₂CH₂CH₃ | H | CO₂CH₃ | Cl | OCH₃ | CH | |
| H | 4-SCH₂CH₂CH₃ | H | CH₃ | CH₃ | CH | | |
| H | 4-SCH₂CH₂CH₃ | H | CO₂CH₃ | CH₃ | OCH₃ | CH | 137–140 |
| H | 4-SCH₂CH₂CH₃ | H | CO₂CH₃ | OCH₃ | OCH₃ | CH | 134–136 |
| H | 4-SCH₂CH₂CH₃ | H | CO₂CH₃ | CH₃ | OCH₃ | N | |
| H | 4-SCH₂CH₂CH₃ | H | CO₂CH₃ | OCH₃ | OCH₃ | N | 147–149 |
| H | 4-SCH₂CH₂CH₃ | H | CO₂CH₃ | Cl | OCH₃ | CH | 124–129 |
| H | 4-S(O)CH₂CH₂CH₃ | H | CO₂CH₃ | CH₃ | CH₃ | CH | |
| H | 4-S(O)CH₂CH₂CH₃ | H | CO₂CH₃ | CH₃ | OCH₃ | CH | |
| H | 4-S(O)CH₂CH₂CH₃ | H | CO₂CH₃ | OCH₃ | OCH₃ | CH | |
| H | 4-S(O)CH₂CH₂CH₃ | H | CO₂CH₃ | CH₃ | OCH₃ | N | |
| H | 4-S(O)CH₂CH₂CH₃ | H | CO₂CH₃ | OCH₃ | OCH₃ | N | |
| H | 4-S(O)CH₂CH₂CH₃ | H | CO₂CH₃ | Cl | OCH₃ | CH | |
| H | 4-S(O)₂CH₂CH₂CH₃ | H | CO₂CH₃ | CH₃ | CH₃ | CH | |
| H | 4-S(O)₂CH₂CH₂CH₃ | H | CO₂CH₃ | CH₃ | OCH₃ | CH | |
| H | 4-S(O)₂CH₂CH₂CH₃ | H | CO₂CH₃ | OCH₃ | OCH₃ | CH | |
| H | 4-S(O)₂CH₂CH₂CH₃ | H | CO₂CH₃ | CH₃ | OCH₃ | N | |
| H | 4-S(O)₂CH₂CH₂CH₃ | H | CO₂CH₃ | OCH₃ | OCH₃ | N | |
| H | 4-S(O)₂CH₂CH₂CH₃ | H | CO₂CH₃ | Cl | OCH₃ | CH | |
| H | 4-SCH(CH₃)₂ | H | CO₂CH₃ | CH₃ | CH₃ | CH | |
| H | 4-SCH(CH₃)₂ | H | CO₂CH₃ | CH₃ | OCH₃ | CH | |

TABLE Ib-continued

General Formula Ib

| R | $R_1$ | $R_x$ | $Q_2$ | X | Y | Z | m.p. (°C) |
|---|---|---|---|---|---|---|---|
| H | 4-SCH(CH$_3$)$_2$ | H | CO$_2$CH$_3$ | OCH$_3$ | OCH$_3$ | CH | |
| H | 4-SCH(CH$_3$)$_2$ | H | CO$_2$CH$_3$ | CH$_3$ | OCH$_3$ | N | |
| H | 4-SCH(CH$_3$)$_2$ | H | CO$_2$CH$_3$ | OCH$_3$ | OCH$_3$ | N | |
| H | 4-SCH(CH$_3$)$_2$ | H | CO$_2$CH$_3$ | Cl | OCH$_3$ | CH | |
| H | 4-S(O)CH(CH$_3$)$_2$ | H | CO$_2$CH$_3$ | CH$_3$ | CH$_3$ | CH | |
| H | 4-S(O)CH(CH$_3$)$_2$ | H | CO$_2$CH$_3$ | CH$_3$ | OCH$_3$ | CH | |
| H | 4-S(O)CH(CH$_3$)$_2$ | H | CO$_2$CH$_3$ | OCH$_3$ | OCH$_3$ | CH | |
| H | 4-S(O)CH(CH$_3$)$_2$ | H | CO$_2$CH$_3$ | CH$_3$ | OCH$_3$ | N | |
| H | 4-S(O)CH(CH$_3$)$_2$ | H | CO$_2$CH$_3$ | OCH$_3$ | OCH$_3$ | N | |
| H | 4-S(O)CH(CH$_3$)$_2$ | H | CO$_2$CH$_3$ | Cl | OCH$_3$ | CH | |
| H | 4-S(O)$_2$CH(CH$_3$)$_2$ | H | CO$_2$CH$_3$ | CH$_3$ | CH$_3$ | CH | |
| H | 4-S(O)$_2$CH(CH$_3$)$_2$ | H | CO$_2$CH$_3$ | CH$_3$ | OCH$_3$ | CH | |
| H | 4-S(O)$_2$CH(CH$_3$)$_2$ | H | CO$_2$CH$_3$ | OCH$_3$ | OCH$_3$ | CH | |
| H | 4-S(O)$_2$CH(CH$_3$)$_2$ | H | CO$_2$CH$_3$ | CH$_3$ | OCH$_3$ | N | |
| H | 4-S(O)$_2$CH(CH$_3$)$_2$ | H | CO$_2$CH$_3$ | OCH$_3$ | OCH$_3$ | N | |
| H | 4-S(O)$_2$CH(CH$_3$)$_2$ | H | CO$_2$CH$_3$ | Cl | OCH$_3$ | CH | |
| CH$_3$ | 4-SCH$_3$ | H | CO$_2$CH$_3$ | CH$_3$ | OCH$_3$ | N | |
| CH$_3$ | 4-SCH$_3$ | H | CO$_2$CH$_3$ | OCH$_3$ | OCH$_3$ | N | |
| CH$_3$ | 4-SCH$_3$ | H | CO$_2$CH$_3$ | CH$_3$ | OCH$_3$ | CH | |
| CH$_3$ | 4-SCH$_3$ | H | CO$_2$CH$_3$ | OCH$_3$ | OCH$_3$ | CH | |
| CH$_3$ | 4-S(O)CH$_3$ | H | CO$_2$CH$_3$ | CH$_3$ | OCH$_3$ | N | |
| CH$_3$ | 4-S(O)CH$_3$ | H | CO$_2$CH$_3$ | OCH$_3$ | OCH$_3$ | N | |
| CH$_3$ | 4-S(O)CH$_3$ | H | CO$_2$CH$_3$ | CH$_3$ | OCH$_3$ | CH | |
| CH$_3$ | 4-S(O)CH$_3$ | H | CO$_2$CH$_3$ | OCH$_3$ | OCH$_3$ | CH | |
| CH$_3$ | 4-S(O)$_2$CH$_3$ | H | CO$_2$CH$_3$ | CH$_3$ | OCH$_3$ | N | |
| CH$_3$ | 4-S(O)$_2$CH$_3$ | H | CO$_2$CH$_3$ | OCH$_3$ | OCH$_3$ | N | |
| CH$_3$ | 4-S(O)$_2$CH$_3$ | H | CO$_2$CH$_3$ | CH$_3$ | OCH$_3$ | CH | |
| CH$_3$ | 4-S(O)$_2$CH$_3$ | H | CO$_2$CH$_3$ | OCH$_3$ | OCH$_3$ | CH | |
| CH$_3$ | 4-SCH$_2$CH$_3$ | H | CO$_2$CH$_3$ | CH$_3$ | OCH$_3$ | N | |
| CH$_3$ | 4-SCH$_2$CH$_3$ | H | CO$_2$CH$_3$ | OCH$_3$ | OCH$_3$ | N | |
| CH$_3$ | 4-SCH$_2$CH$_3$ | H | CO$_2$CH$_3$ | CH$_3$ | OCH$_3$ | CH | |
| CH$_3$ | 4-SCH$_2$CH$_3$ | H | CO$_2$CH$_3$ | OCH$_3$ | OCH$_3$ | CH | |
| CH$_3$ | 4-S(O)CH$_2$CH$_3$ | H | CO$_2$CH$_3$ | CH$_3$ | OCH$_3$ | N | |
| CH$_3$ | 4-S(O)CH$_2$CH$_3$ | H | CO$_2$CH$_3$ | OCH$_3$ | OCH$_3$ | N | |
| CH$_3$ | 4-S(O)CH$_2$CH$_3$ | H | CO$_2$CH$_3$ | CH$_3$ | OCH$_3$ | CH | |
| CH$_3$ | 4-S(O)CH$_2$CH$_3$ | H | CO$_2$CH$_3$ | OCH$_3$ | OCH$_3$ | CH | |
| CH$_3$ | 4-S(O)$_2$CH$_2$CH$_3$ | H | CO$_2$CH$_3$ | CH$_3$ | OCH$_3$ | N | |
| CH$_3$ | 4-S(O)$_2$CH$_2$CH$_3$ | H | CO$_2$CH$_3$ | OCH$_3$ | OCH$_3$ | N | |
| CH$_3$ | 4-S(O)$_2$CH$_2$CH$_3$ | H | CO$_2$CH$_3$ | CH$_3$ | OCH$_3$ | CH | |
| CH$_3$ | 4-S(O)$_2$CH$_2$CH$_3$ | H | CO$_2$CH$_3$ | OCH$_3$ | OCH$_3$ | CH | |
| CH$_3$ | 4-SCH$_2$CH$_2$CH$_3$ | H | CO$_2$CH$_3$ | CH$_3$ | OCH$_3$ | N | |
| CH$_3$ | 4-SCH$_2$CH$_2$CH$_3$ | H | CO$_2$CH$_3$ | OCH$_3$ | OCH$_3$ | N | |
| CH$_3$ | 4-SCH$_2$CH$_2$CH$_3$ | H | CO$_2$CH$_3$ | CH$_3$ | OCH$_3$ | CH | |
| CH$_3$ | 4-SCH$_2$CH$_2$CH$_3$ | H | CO$_2$CH$_3$ | OCH$_3$ | OCH$_3$ | CH | |
| CH$_3$ | 4-S(O)CH$_2$CH$_2$CH$_3$ | H | CO$_2$CH$_3$ | CH$_3$ | OCH$_3$ | N | |
| CH$_3$ | 4-S(O)CH$_2$CH$_2$CH$_3$ | H | CO$_2$CH$_3$ | OCH$_3$ | OCH$_3$ | N | |
| CH$_3$ | 4-S(O)CH$_2$CH$_2$CH$_3$ | H | CO$_2$CH$_3$ | CH$_3$ | OCH$_3$ | CH | |
| CH$_3$ | 4-S(O)CH$_2$CH$_2$CH$_3$ | H | CO$_2$CH$_3$ | OCH$_3$ | OCH$_3$ | CH | |
| CH$_3$ | 4-S(O)$_2$CH$_2$CH$_2$CH$_3$ | H | CO$_2$CH$_3$ | CH$_3$ | OCH$_3$ | N | |
| CH$_3$ | 4-S(O)$_2$CH$_2$CH$_2$CH$_3$ | H | CO$_2$CH$_3$ | OCH$_3$ | OCH$_3$ | N | |
| CH$_3$ | 4-S(O)$_2$CH$_2$CH$_2$CH$_3$ | H | CO$_2$CH$_3$ | CH$_3$ | OCH$_3$ | CH | |
| CH$_3$ | 4-S(O)$_2$CH$_2$CH$_2$CH$_3$ | H | CO$_2$CH$_3$ | OCH$_3$ | OCH$_3$ | CH | |
| H | 5-CO$_2$CH$_3$ | H | CO$_2$CH$_3$ | CH$_3$ | CH$_3$ | CH | |
| H | 5-CO$_2$CH$_3$ | H | CO$_2$CH$_3$ | CH$_3$ | OCH$_3$ | CH | |
| H | 5-CO$_2$CH$_3$ | H | CO$_2$CH$_3$ | OCH$_3$ | OCH$_3$ | CH | |
| H | 5-CO$_2$CH$_3$ | H | CO$_2$CH$_3$ | CH$_3$ | OCH$_3$ | N | |
| H | 5-CO$_2$CH$_3$ | H | CO$_2$CH$_3$ | OCH$_3$ | OCH$_3$ | N | |
| H | 5-CO$_2$CH$_3$ | H | CO$_2$CH$_3$ | Cl | OCH$_3$ | CH | |
| CH$_3$ | 5-CO$_2$CH$_3$ | H | CO$_2$CH$_3$ | CH$_3$ | OCH$_3$ | N | |
| CH$_3$ | 5-CO$_2$CH$_3$ | H | CO$_2$CH$_3$ | OCH$_3$ | OCH$_3$ | N | |
| CH$_3$ | 5-CO$_2$CH$_3$ | H | CO$_2$CH$_3$ | CH$_3$ | OCH$_3$ | CH | |
| CH$_3$ | 5-CO$_2$CH$_3$ | H | CO$_2$CH$_3$ | OCH$_3$ | OCH$_3$ | CH | |
| H | 5-S(O$_2$)N(CH$_3$)$_2$ | H | CO$_2$CH$_3$ | CH$_3$ | CH$_3$ | CH | |
| H | 5-S(O$_2$)N(CH$_3$)$_2$ | H | CO$_2$CH$_3$ | CH$_3$ | OCH$_3$ | CH | |
| H | 5-S(O$_2$)N(CH$_3$)$_2$ | H | CO$_2$CH$_3$ | OCH$_3$ | OCH$_3$ | CH | |
| H | 5-S(O$_2$)N(CH$_3$)$_2$ | H | CO$_2$CH$_3$ | CH$_3$ | OCH$_3$ | N | |
| H | 5-S(O$_2$)N(CH$_3$)$_2$ | H | CO$_2$CH$_3$ | OCH$_3$ | OCH$_3$ | N | |
| H | 5-S(O$_2$)N(CH$_3$)$_2$ | H | CO$_2$CH$_3$ | Cl | OCH$_3$ | CH | |
| H | 5-C(O)N(CH$_3$)$_2$ | H | CO$_2$CH$_3$ | CH$_3$ | CH$_3$ | CH | |
| H | 5-C(O)N(CH$_3$)$_2$ | H | CO$_2$CH$_3$ | CH$_3$ | OCH$_3$ | CH | |
| H | 5-C(O)N(CH$_3$)$_2$ | H | CO$_2$CH$_3$ | OCH$_3$ | OCH$_3$ | CH | |
| H | 5-C(O)N(CH$_3$)$_2$ | H | CO$_2$CH$_3$ | CH$_3$ | OCH$_3$ | N | |
| H | 5-C(O)N(CH$_3$)$_2$ | H | CO$_2$CH$_3$ | OCH$_3$ | OCH$_3$ | N | |
| H | 5-C(O)N(CH$_3$)$_2$ | H | CO$_2$CH$_3$ | Cl | OCH$_3$ | CH | |
| H | 4-SCH$_3$ | H | CO$_2$CH$_2$CH$_3$ | CH$_3$ | CH$_3$ | CH | |
| H | 4-SCH$_3$ | H | CO$_2$CH$_2$CH$_3$ | CH$_3$ | OCH$_3$ | CH | |
| H | 4-SCH$_3$ | H | CO$_2$CH$_2$CH$_3$ | OCH$_3$ | OCH$_3$ | CH | |
| H | 4-SCH$_3$ | H | CO$_2$CH$_2$CH$_3$ | CH$_3$ | OCH$_3$ | N | |
| H | 4-SCH$_3$ | H | CO$_2$CH$_2$CH$_3$ | OCH$_3$ | OCH$_3$ | N | |
| H | 4-SCH$_3$ | H | CO$_2$CH$_2$CH$_3$ | Cl | OCH$_3$ | CH | |

TABLE Ib-continued

General Formula Ib

| R | R₁ | Rₓ | Q₂ | X | Y | Z | m.p. (°C.) |
|---|---|---|---|---|---|---|---|
| H | 4-SCH₂CH₃ | H | CO₂CH₂CH₃ | CH₃ | CH₃ | CH | |
| H | 4-SCH₂CH₃ | H | CO₂CH₂CH₃ | CH₃ | OCH₃ | CH | |
| H | 4-SCH₂CH₃ | H | CO₂CH₂CH₃ | OCH₃ | OCH₃ | CH | |
| H | 4-SCH₂CH₃ | H | CO₂CH₂CH₃ | CH₃ | OCH₃ | N | |
| H | 4-SCH₂CH₃ | H | CO₂CH₂CH₃ | OCH₃ | OCH₃ | N | |
| H | 4-SCH₂CH₃ | H | CO₂CH₂CH₃ | Cl | OCH₃ | CH | |
| H | 4-SCH₂CH₂CH₃ | H | CO₂CH₂CH₃ | CH₃ | CH₃ | CH | |
| H | 4-SCH₂CH₂CH₃ | H | CO₂CH₂CH₃ | CH₃ | OCH₃ | CH | |
| H | 4-SCH₂CH₂CH₃ | H | CO₂CH₂CH₃ | OCH₃ | OCH₃ | CH | |
| H | 4-SCH₂CH₂CH₃ | H | CO₂CH₂CH₃ | CH₃ | OCH₃ | N | |
| H | 4-SCH₂CH₂CH₃ | H | CO₂CH₂CH₃ | OCH₃ | OCH₃ | N | |
| H | 4-SCH₂CH₂CH₃ | H | CO₂CH₂CH₃ | Cl | OCH₃ | CH | |
| H | 5-CO₂CH₂CH₃ | H | CO₂CH₂CH₃ | CH₃ | CH₃ | CH | |
| H | 5-CO₂CH₂CH₃ | H | CO₂CH₂CH₃ | CH₃ | OCH₃ | CH | |
| H | 5-CO₂CH₂CH₃ | H | CO₂CH₂CH₃ | OCH₃ | OCH₃ | CH | |
| H | 5-CO₂CH₂CH₃ | H | CO₂CH₂CH₃ | CH₃ | OCH₃ | N | |
| H | 5-CO₂CH₂CH₃ | H | CO₂CH₂CH₃ | OCH₃ | OCH₃ | N | |
| H | 5-CO₂CH₂CH₃ | H | CO₂CH₂CH₃ | Cl | OCH₃ | CH | |
| H | 5-SO₂N(CH₃)₂ | H | CO₂CH₂CH₃ | CH₃ | CH₃ | CH | |
| H | 5-SO₂N(CH₃)₂ | H | CO₂CH₂CH₃ | CH₃ | OCH₃ | CH | |
| H | 5-SO₂N(CH₃)₂ | H | CO₂CH₂CH₃ | OCH₃ | OCH₃ | CH | |
| H | 5-SO₂N(CH₃)₂ | H | CO₂CH₂CH₃ | CH₃ | OCH₃ | N | |
| H | 5-SO₂N(CH₃)₂ | H | CO₂CH₂CH₃ | OCH₃ | OCH₃ | N | |
| H | 5-SO₂N(CH₃)₂ | H | CO₂CH₂CH₃ | Cl | OCH₃ | CH | |

TABLE IIb

General Formula IIb

| R | R₁ | Rₓ | Q₂ | X | Y | Z | m.p.(°C.) |
|---|---|---|---|---|---|---|---|
| H | 4-S(O)₂N(CH₃)₂ | H | CO₂CH₃ | CH₃ | CH₃ | CH | |
| H | 4-S(O)₂N(CH₃)₂ | H | CO₂CH₃ | CH₃ | OCH₃ | CH | |
| H | 4-S(O)₂N(CH₃)₂ | H | CO₂CH₃ | OCH₃ | OCH₃ | CH | 184–186 |
| H | 4-S(O)₂N(CH₃)₂ | H | CO₂CH₃ | CH₃ | OCH₃ | N | 176–179 |
| H | 4-S(O)₂N(CH₃)₂ | H | CO₂CH₃ | OCH₃ | OCH₃ | N | |
| H | 4-S(O)₂N(CH₃)₂ | H | CO₂CH₃ | Cl | OCH₃ | CH | |
| H | 4-S(O)₂N-piperidinyl | H | CO₂CH₃ | CH₃ | CH₃ | CH | |
| H | 4-S(O)₂N-piperidinyl | H | CO₂CH₃ | CH₃ | OCH₃ | CH | |
| H | 4-S(O)₂N-piperidinyl | H | CO₂CH₃ | OCH₃ | OCH₃ | CH | |
| H | 4-S(O)₂N-piperidinyl | H | CO₂CH₃ | CH₃ | OCH₃ | N | |
| H | 4-S(O)₂N-piperidinyl | H | CO₂CH₃ | OCH₃ | OCH₃ | N | |
| H | 4-S(O)₂N-piperidinyl | H | CO₂CH₃ | Cl | OCH₃ | CH | |
| H | 4-SCH₃ | H | CO₂CH₃ | CH₃ | CH₃ | CH | |
| H | 4-SCH₃ | H | CO₂CH₃ | CH₃ | OCH₃ | CH | |
| H | 4-SCH₃ | H | CO₂CH₃ | OCH₃ | OCH₃ | CH | |
| H | 4-SCH₃ | H | CO₂CH₃ | CH₃ | OCH₃ | N | |
| H | 4-SCH₃ | H | CO₂CH₃ | OCH₃ | OCH₃ | N | |
| H | 4-SCH₃ | H | CO₂CH₃ | Cl | OCH₃ | CH | |

TABLE IIb-continued

General Formula IIb

| R | R₁ | Rₓ | Q₂ | X | Y | Z | m.p.(°C.) |
|---|---|---|---|---|---|---|---|
| H | 4-S(O)CH₃ | H | CO₂CH₃ | CH₃ | CH₃ | CH | |
| H | 4-S(O)CH₃ | H | CO₂CH₃ | CH₃ | OCH₃ | CH | |
| H | 4-S(O)CH₃ | H | CO₂CH₃ | OCH₃ | OCH₃ | CH | |
| H | 4-S(O)CH₃ | H | CO₂CH₃ | CH₃ | OCH₃ | N | |
| H | 4-S(O)CH₃ | H | CO₂CH₃ | OCH₃ | OCH₃ | N | |
| H | 4-S(O)CH₃ | H | CO₂CH₃ | Cl | OCH₃ | CH | |
| H | 4-S(O)₂CH₃ | H | CO₂CH₃ | CH₃ | CH₃ | CH | |
| H | 4-S(O)₂CH₃ | H | CO₂CH₃ | CH₃ | OCH₃ | CH | |
| H | 4-S(O)₂CH₃ | H | CO₂CH₃ | OCH₃ | OCH₃ | CH | |
| H | 4-S(O)₂CH₃ | H | CO₂CH₃ | CH₃ | OCH₃ | N | |
| H | 4-S(O)₂CH₃ | H | CO₂CH₃ | OCH₃ | OCH₃ | N | |
| H | 4-S(O)₂CH₃ | H | CO₂CH₃ | Cl | OCH₃ | CH | |
| H | 4-SCH₂CH₃ | H | CO₂CH₃ | CH₃ | CH₃ | CH | 149–153 |
| H | 4-SCH₂CH₃ | H | CO₂CH₃ | CH₃ | OCH₃ | CH | 148–150 |
| H | 4-SCH₂CH₃ | H | CO₂CH₃ | OCH₃ | OCH₃ | CH | 98–100 |
| H | 4-SCH₂CH₃ | H | CO₂CH₃ | CH₃ | OCH₃ | N | 144–148 |
| H | 4-SCH₂CH₃ | H | CO₂CH₃ | OCH₃ | OCH₃ | N | 136–139 |
| H | 4-SCH₂CH₃ | H | CO₂CH₃ | Cl | OCH₃ | CH | 126–130 |
| H | 4-S(O)CH₂CH₃ | H | CO₂CH₃ | CH₃ | CH₃ | CH | 103–105 |
| H | 4-S(O)CH₂CH₃ | H | CO₂CH₃ | CH₃ | OCH₃ | CH | 158–165 |
| H | 4-S(O)CH₂CH₃ | H | CO₂CH₃ | OCH₃ | OCH₃ | CH | 203–205 |
| H | 4-S(O)CH₂CH₃ | H | CO₂CH₃ | CH₃ | OCH₃ | N | 181–184 |
| H | 4-S(O)CH₂CH₃ | H | CO₂CH₃ | OCH₃ | OCH₃ | N | 179–182 |
| H | 4-S(O)CH₂CH₃ | H | CO₂CH₃ | Cl | OCH₃ | CH | 157–163 |
| H | 4-S(O)₂CH₂CH₃ | H | CO₂CH₃ | CH₃ | CH₃ | CH | 126–130 |
| H | 4-S(O)₂CH₂CH₃ | H | CO₂CH₃ | CH₃ | OCH₃ | CH | 145–148 |
| H | 4-S(O)₂CH₂CH₃ | H | CO₂CH₃ | OCH₃ | OCH₃ | CH | 151–157 |
| H | 4-S(O)₂CH₂CH₃ | H | CO₂CH₃ | CH₃ | OCH₃ | N | 136–142 |
| H | 4-S(O)₂CH₂CH₃ | H | CO₂CH₃ | OCH₃ | OCH₃ | N | 130–133 |
| H | 4-S(O)₂CH₂CH₃ | H | CO₂CH₃ | Cl | OCH₃ | CH | 158–164 |
| H | 4-SCH₂CH₂CH₃ | H | CO₂CH₃ | CH₃ | CH₃ | CH | 155–162 |
| H | 4-SCH₂CH₂CH₃ | H | CO₂CH₃ | CH₃ | OCH₃ | CH | 147–150 |
| H | 4-SCH₂CH₂CH₃ | H | CO₂CH₃ | OCH₃ | OCH₃ | CH | 139–142 |
| H | 4-SCH₂CH₂CH₃ | H | CO₂CH₃ | CH₃ | OCH₃ | N | 154–164 |
| H | 4-SCH₂CH₂CH₃ | H | CO₂CH₃ | OCH₃ | OCH₃ | N | 159–166 |
| H | 4-SCH₂CH₂CH₃ | H | CO₂CH₃ | Cl | OCH₃ | CH | 139–142 |
| H | 4-S(O)CH₂CH₂CH₃ | H | CO₂CH₃ | CH₃ | CH₃ | CH | 113–114 |
| H | 4-S(O)CH₂CH₂CH₃ | H | CO₂CH₃ | CH₃ | OCH₃ | CH | 112–113 |
| H | 4-S(O)CH₂CH₂CH₃ | H | CO₂CH₃ | OCH₃ | OCH₃ | CH | 178–179 |
| H | 4-S(O)CH₂CH₂CH₃ | H | CO₂CH₃ | CH₃ | OCH₃ | N | 193–194 |
| H | 4-S(O)CH₂CH₂CH₃ | H | CO₂CH₃ | OCH₃ | OCH₃ | N | 201–204 |
| H | 4-S(O)CH₂CH₂CH₃ | H | CO₂CH₃ | Cl | OCH₃ | CH | 187–190 |
| H | 4-S(O)₂CH₂CH₂CH₃ | H | CO₂CH₃ | CH₃ | CH₃ | CH | 103–106 |
| H | 4-S(O)₂CH₂CH₂CH₃ | H | CO₂CH₃ | CH₃ | OCH₃ | CH | 92–94 |
| H | 4-S(O)₂CH₂CH₂CH₃ | H | CO₂CH₃ | OCH₃ | OCH₃ | CH | 96–101 |
| H | 4-S(O)₂CH₂CH₂CH₃ | H | CO₂CH₃ | CH₃ | OCH₃ | N | 153–161 |
| H | 4-S(O)₂CH₂CH₂CH₃ | H | CO₂CH₃ | OCH₃ | OCH₃ | N | 153–160 |
| H | 4-S(O)₂CH₂CH₂CH₃ | H | CO₂CH₃ | Cl | OCH₃ | CH | 111–113 |
| H | 4-SCH(CH₃)₂ | H | CO₂CH₃ | CH₃ | CH₃ | CH | |
| H | 4-SCH(CH₃)₂ | H | CO₂CH₃ | CH₃ | OCH₃ | CH | |
| H | 4-SCH(CH₃)₂ | H | CO₂CH₃ | OCH₃ | OCH₃ | CH | |
| H | 4-SCH(CH₃)₂ | H | CO₂CH₃ | CH₃ | OCH₃ | N | |
| H | 4-SCH(CH₃)₂ | H | CO₂CH₃ | OCH₃ | OCH₃ | N | |
| H | 4-SCH(CH₃)₂ | H | CO₂CH₃ | Cl | OCH₃ | CH | |
| H | 4-S(O)CH(CH₃)₂ | H | CO₂CH₃ | CH₃ | CH₃ | CH | |
| H | 4-S(O)CH(CH₃)₂ | H | CO₂CH₃ | CH₃ | OCH₃ | CH | |
| H | 4-S(O)CH(CH₃)₂ | H | CO₂CH₃ | OCH₃ | OCH₃ | CH | |
| H | 4-S(O)CH(CH₃)₂ | H | CO₂CH₃ | CH₃ | OCH₃ | N | |
| H | 4-S(O)CH(CH₃)₂ | H | CO₂CH₃ | OCH₃ | OCH₃ | N | |
| H | 4-S(O)CH(CH₃)₂ | H | CO₂CH₃ | Cl | OCH₃ | CH | |
| H | 4-S(O)₂CH(CH₃)₂ | H | CO₂CH₃ | CH₃ | CH₃ | CH | |
| H | 4-S(O)₂CH(CH₃)₂ | H | CO₂CH₃ | CH₃ | OCH₃ | CH | |
| H | 4-S(O)₂CH(CH₃)₂ | H | CO₂CH₃ | OCH₃ | OCH₃ | CH | |
| H | 4-S(O)₂CH(CH₃)₂ | H | CO₂CH₃ | CH₃ | OCH₃ | N | |
| H | 4-S(O)₂CH(CH₃)₂ | H | CO₂CH₃ | OCH₃ | OCH₃ | N | |
| H | 4-S(O)₂CH(CH₃)₂ | H | CO₂CH₃ | Cl | OCH₃ | CH | |
| H | 4-S(O)₂N(CH₃)₂ | Br | Br | CH₃ | CH₃ | CH | 163–167 |
| H | 4-S(O)₂N(CH₃)₂ | Br | Br | CH₃ | OCH₃ | CH | 175–179 |
| H | 4-S(O)₂N(CH₃)₂ | Br | Br | OCH₃ | OCH₃ | CH | 183–186 |
| H | 4-S(O)₂N(CH₃)₂ | Br | Br | CH₃ | OCH₃ | N | 108–112 |
| H | 4-S(O)₂N(CH₃)₂ | Br | Br | OCH₃ | OCH₃ | N | 184–188 |
| H | 4-S(O)₂N(CH₃)₂ | Br | Br | Cl | OCH₃ | CH | 186–189 |
| H | 4-S(O)₂N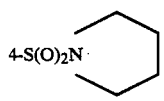 | Br | Br | CH₃ | CH₃ | CH | |

TABLE IIb-continued

General Formula IIb

| R | R₁ | Rₓ | Q₂ | X | Y | Z | m.p.(°C.) |
|---|---|---|---|---|---|---|---|
| H | 4-S(O)₂N⟨⟩ | Br | Br | CH₃ | OCH₃ | CH | |
| H | 4-S(O)₂N⟨⟩ | Br | Br | OCH₃ | OCH₃ | CH | |
| H | 4-S(O)₂N⟨⟩ | Br | Br | CH₃ | OCH₃ | N | |
| H | 4-S(O)₂N⟨⟩ | Br | Br | OCH₃ | OCH₃ | N | |
| H | 4-S(O)₂N⟨⟩ | Br | Br | Cl | OCH₃ | CH | |
| H | 4-SCH₃ | Br | Br | CH₃ | CH₃ | CH | |
| H | 4-SCH₃ | Br | Br | CH₃ | OCH₃ | CH | |
| H | 4-SCH₃ | Br | Br | OCH₃ | OCH₃ | CH | |
| H | 4-SCH₃ | Br | Br | CH₃ | OCH₃ | N | |
| H | 4-SCH₃ | Br | Br | OCH₃ | OCH₃ | N | |
| H | 4-SCH₃ | Br | Br | Cl | OCH₃ | CH | |
| H | 4-S(O)CH₃ | Br | Br | CH₃ | CH₃ | CH | |
| H | 4-S(O)CH₃ | Br | Br | CH₃ | OCH₃ | CH | |
| H | 4-S(O)CH₃ | Br | Br | OCH₃ | OCH₃ | CH | |
| H | 4-S(O)CH₃ | Br | Br | CH₃ | OCH₃ | N | |
| H | 4-S(O)CH₃ | Br | Br | OCH₃ | OCH₃ | N | |
| H | 4-S(O)CH₃ | Br | Br | Cl | OCH₃ | CH | |
| H | 4-S(O)₂CH₃ | Br | Br | CH₃ | CH₃ | CH | |
| H | 4-S(O)₂CH₃ | Br | Br | CH₃ | OCH₃ | CH | |
| H | 4-S(O)₂CH₃ | Br | Br | OCH₃ | OCH₃ | CH | |
| H | 4-S(O)₂CH₃ | Br | Br | CH₃ | OCH₃ | N | |
| H | 4-S(O)₂CH₃ | Br | Br | OCH₃ | OCH₃ | N | |
| H | 4-S(O)₂CH₃ | Br | Br | Cl | OCH₃ | CH | |
| H | 4-SCH₂CH₃ | Br | Br | CH₃ | CH₃ | CH | 161–165 |
| H | 4-SCH₂CH₃ | Br | Br | CH₃ | OCH₃ | CH | 162–164 |
| H | 4-SCH₂CH₃ | Br | Br | OCH₃ | OCH₃ | CH | 165–170 |
| H | 4-SCH₂CH₃ | Br | Br | CH₃ | OCH₃ | N | 112–115 |
| H | 4-SCH₂CH₃ | Br | Br | OCH₃ | OCH₃ | N | 97–101 |
| H | 4-SCH₂CH₃ | Br | Br | Cl | OCH₃ | CH | 124–128 |
| H | 4-S(O)CH₂CH₃ | Br | Br | CH₃ | CH₃ | CH | |
| H | 4-S(O)CH₂CH₃ | Br | Br | CH₃ | OCH₃ | CH | |
| H | 4-S(O)CH₂CH₃ | Br | Br | OCH₃ | OCH₃ | CH | |
| H | 4-S(O)CH₂CH₃ | Br | Br | CH₃ | OCH₃ | N | |
| H | 4-S(O)CH₂CH₃ | Br | Br | OCH₃ | OCH₃ | N | |
| H | 4-S(O)CH₂CH₃ | Br | Br | Cl | OCH₃ | CH | |
| H | 4-S(O)₂CH₂CH₃ | Br | Br | CH₃ | CH₃ | CH | |
| H | 4-S(O)₂CH₂CH₃ | Br | Br | CH₃ | OCH₃ | CH | |
| H | 4-S(O)₂CH₂CH₃ | Br | Br | OCH₃ | OCH₃ | CH | |
| H | 4-S(O)₂CH₂CH₃ | Br | Br | CH₃ | OCH₃ | N | |
| H | 4-S(O)₂CH₂CH₃ | Br | Br | OCH₃ | OCH₃ | N | |
| H | 4-S(O)₂CH₂CH₃ | Br | Br | Cl | OCH₃ | CH | |
| H | 4-SCH₂CH₂CH₃ | Br | Br | CH₃ | CH₃ | CH | |
| H | 4-SCH₂CH₂CH₃ | Br | Br | CH₃ | OCH₃ | CH | |
| H | 4-SCH₂CH₂CH₃ | Br | Br | OCH₃ | OCH₃ | CH | |
| H | 4-SCH₂CH₂CH₃ | Br | Br | CH₃ | OCH₃ | N | |
| H | 4-SCH₂CH₂CH₃ | Br | Br | OCH₃ | OCH₃ | N | |
| H | 4-SCH₂CH₂CH₃ | Br | Br | Cl | OCH₃ | CH | |
| H | 4-S(O)CH₂CH₂CH₃ | Br | Br | CH₃ | CH₃ | CH | |
| H | 4-S(O)CH₂CH₂CH₃ | Br | Br | CH₃ | OCH₃ | CH | |
| H | 4-S(O)CH₂CH₂CH₃ | Br | Br | OCH₃ | OCH₃ | CH | |
| H | 4-S(O)CH₂CH₂CH₃ | Br | Br | CH₃ | OCH₃ | N | |
| H | 4-S(O)CH₂CH₂CH₃ | Br | Br | OCH₃ | OCH₃ | N | |
| H | 4-S(O)CH₂CH₂CH₃ | Br | Br | Cl | OCH₃ | CH | |
| H | 4-S(O)₂CH₂CH₂CH₃ | Br | Br | CH₃ | CH₃ | CH | |
| H | 4-S(O)₂CH₂CH₂CH₃ | Br | Br | CH₃ | OCH₃ | CH | |

TABLE IIb-continued

General Formula IIb

| R | R₁ | Rₓ | Q₂ | X | Y | Z | m.p.(°C.) |
|---|---|---|---|---|---|---|---|
| H | 4-S(O)₂CH₂CH₂CH₃ | Br | Br | OCH₃ | OCH₃ | CH | |
| H | 4-S(O)₂CH₂CH₂CH₃ | Br | Br | CH₃ | OCH₃ | N | |
| H | 4-S(O)₂CH₂CH₂CH₃ | Br | Br | OCH₃ | OCH₃ | N | |
| H | 4-S(O)₂CH₂CH₂CH₃ | Br | Br | Cl | OCH₃ | CH | |
| H | 4-SO₂N(CH₃)₂ | H | SO₂N(CH₃)₂ | CH₃ | CH₃ | CH | |
| H | 4-SO₂N(CH₃)₂ | H | SO₂N(CH₃)₂ | CH₃ | OCH₃ | CH | |
| H | 4-SO₂N(CH₃)₂ | H | SO₂N(CH₃)₂ | OCH₃ | OCH₃ | CH | |
| H | 4-SO₂N(CH₃)₂ | H | SO₂N(CH₃)₂ | CH₃ | OCH₃ | N | |
| H | 4-SO₂N(CH₃)₂ | H | SO₂N(CH₃)₂ | OCH₃ | OCH₃ | N | |
| H | 4-SO₂N(CH₃)₂ | H | SO₂N(CH₃)₂ | Cl | OCH₃ | CH | |
| H | 4-SCH₃ | H | SO₂N(CH₃)₂ | CH₃ | CH₃ | CH | |
| H | 4-SCH₃ | H | SO₂N(CH₃)₂ | CH₃ | OCH₃ | CH | |
| H | 4-SCH₃ | H | SO₂N(CH₃)₂ | OCH₃ | OCH₃ | CH | |
| H | 4-SCH₃ | H | SO₂N(CH₃)₂ | CH₃ | OCH₃ | N | |
| H | 4-SCH₃ | H | SO₂N(CH₃)₂ | OCH₃ | OCH₃ | N | |
| H | 4-SCH₃ | H | SO₂N(CH₃)₂ | Cl | OCH₃ | CH | |
| H | 4-S(O)₂CH₃ | H | SO₂N(CH₃)₂ | CH₃ | CH₃ | CH | |
| H | 4-S(O)₂CH₃ | H | SO₂N(CH₃)₂ | CH₃ | OCH₃ | CH | |
| H | 4-S(O)₂CH₃ | H | SO₂N(CH₃)₂ | OCH₃ | OCH₃ | CH | |
| H | 4-S(O)₂CH₃ | H | SO₂N(CH₃)₂ | CH₃ | OCH₃ | N | |
| H | 4-S(O)₂CH₃ | H | SO₂N(CH₃)₂ | OCH₃ | OCH₃ | N | |
| H | 4-S(O)₂CH₃ | H | SO₂N(CH₃)₂ | Cl | OCH₃ | CH | |
| H | 4-SCH₂CH₃ | H | SO₂N(CH₃)₂ | CH₃ | CH₃ | CH | |
| H | 4-SCH₂CH₃ | H | SO₂N(CH₃)₂ | CH₃ | OCH₃ | CH | |
| H | 4-SCH₂CH₃ | H | SO₂N(CH₃)₂ | OCH₃ | OCH₃ | CH | |
| H | 4-SHC₂CH₃ | H | SO₂N(CH₃)₂ | CH₃ | OCH₃ | N | |
| H | 4-SCH₂CH₃ | H | SO₂N(CH₃)₂ | OCH₃ | OCH₃ | N | |
| H | 4-SCH₂HC₃ | H | SO₂N(CH₃)₂ | Cl | OCH₃ | CH | |
| H | 4-S(O)₂CH₂CH₃ | H | SO₂N(CH₃)₂ | CH₃ | CH₃ | CH | |
| H | 4-S(O)₂CH₂CH₃ | H | SO₂N(CH₃)₂ | CH₃ | OCH₃ | CH | |
| H | 4-S(O)₂CH₂CH₃ | H | SO₂N(CH₃)₂ | OCH₃ | OCH₃ | CH | |
| H | 4-S(O)₂CH₂CH₃ | H | SO₂N(CH₃)₂ | CH₃ | OCH₃ | N | |
| H | 4-S(O)₂CH₂CH₃ | H | SO₂N(CH₃)₂ | OCH₃ | OCH₃ | N | |
| H | 4-S(O)₂CH₂CH₃ | H | SO₂N(CH₃)₂ | Cl | OCH₃ | CH | |
| H | 4-SCH₂CH₂CH₃ | H | SO₂N(CH₃)₂ | CH₃ | C₃ | CH | |
| H | 4-SCH₂CH₂CH₃ | H | SO₂N(CH₃)₂ | CH₃ | OCH₃ | CH | |
| H | 4-SCH₂CH₂CH₃ | H | SO₂N(CH₃)₂ | OCH₃ | OCH₃ | CH | |
| H | 4-SCH₂CH₂CH₃ | H | SO₂N(CH₃)₂ | CH₃ | OCH₃ | N | |
| H | 4-SCH₂CH₂CH₃ | H | SO₂N(CH₃)₂ | OCH₃ | OCH₃ | N | |
| H | 4-SCH₂CH₂CH₃ | H | SO₂N(CH₃)₂ | Cl | OCH₃ | CH | |
| H | 4-S(O)₂CH₂CH₂CH₃ | H | SO₂N(CH₃)₂ | CH₃ | CH₃ | CH | |
| H | 4-S(O)₂CH₂CH₂CH₃ | H | SO₂N(CH₃)₂ | CH₃ | OCH₃ | CH | |
| H | 4-S(O)₂CH₂CH₂CH₃ | H | SO₂N(CH₃)₂ | OCH₃ | OCH₃ | CH | |
| H | 4-S(O)₂CH₂CH₂CH₃ | H | SO₂N(CH₃)₂ | CH₃ | OCH₃ | N | |
| H | 4-S(O)₂CH₂CH₂CH₃ | H | SO₂N(CH₃)₂ | OCH₃ | OCH₃ | N | |
| H | 4-S(O)₂CH₂CH₂CH₃ | H | SO₂N(CH₃)₂ | Cl | OCH₃ | CH | |
| H | 4-SCH(CH₃)₂ | H | SO₂N(CH₃)₂ | CH₃ | CH₃ | CH | |
| H | 4-SCH(CH₃)₂ | H | SO₂N(CH₃)₂ | CH₃ | OCH₃ | CH | |
| H | 4-SCH(CH₃)₂ | H | SO₂N(CH₃)₂ | OCH₃ | OCH₃ | CH | |
| H | 4-SCH(CH₃)₂ | H | SO₂N(CH₃)₂ | CH₃ | OCH₃ | N | |
| H | 4-SCH(CH₃)₂ | H | SO₂N(CH₃)₂ | OCH₃ | OCH₃ | N | |
| H | 4-SCH(CH₃)₂ | H | SO₂N(CH₃)₂ | Cl | OCH₃ | CH | |
| H | 4-CO₂CH₃ | H | CO₂CH₃ | CH₃ | CH₃ | CH | |
| H | 4-CO₂CH₃ | H | CO₂CH₃ | CH₃ | OCH₃ | CH | |
| H | 4-CO₂CH₃ | H | CO₂CH₃ | OCH₃ | OCH₃ | CH | |
| H | 4-CO₂CH₃ | H | CO₂CH₃ | CH₃ | OCH₃ | N | |
| H | 4-CO₂CH₃ | H | CO₂CH₃ | OCH₃ | OCH₃ | N | |
| H | 4-CO₂CH₃ | H | CO₂CH₃ | Cl | OCH₃ | CH | |
| H | 4-C(O)N(CH₃)₂ | H | CO₂CH₃ | CH₃ | CH₃ | CH | |
| H | 4-C(O)N(CH₃)₂ | H | CO₂CH₃ | CH₃ | OCH₃ | CH | |
| H | 4-C(O)N(CH₃)₂ | H | CO₂CH₃ | OCH₃ | OCH₃ | CH | |
| H | 4-C(O)N(CH₃)₂ | H | CO₂CH₃ | CH₃ | OCH₃ | N | |
| H | 4-C(O)N(CH₃)₂ | H | CO₂CH₃ | OCH₃ | OCH₃ | N | |
| H | 4-C(O)N(CH₃)₂ | H | CO₂CH₃ | Cl | OCH₃ | CH | |
| H | 4-SCH₃ | H | CO₂CH₂CH₃ | CH₃ | CH₃ | CH | |
| H | 4-SCH₃ | H | CO₂CH₂CH₃ | CH₃ | OCH₃ | CH | |
| H | 4-SCH₃ | H | CO₂CH₂CH₃ | OCH₃ | OCH₃ | CH | |
| H | 4-SCH₃ | H | CO₂CH₂CH₃ | CH₃ | OCH₃ | N | |
| H | 4-SCH₃ | H | CO₂CH₂CH₃ | OCH₃ | OCH₃ | N | |
| H | 4-SCH₃ | H | CO₂CH₂CH₃ | Cl | OCH₃ | CH | |
| H | 4-S(O)CH₃ | H | CO₂CH₂CH₃ | CH₃ | CH₃ | CH | |
| H | 4-S(O)CH₃ | H | CO₂CH₂CH₃ | CH₃ | OCH₃ | CH | |
| H | 4-S(O)CH₃ | H | CO₂CH₂CH₃ | OCH₃ | OCH₃ | CH | |
| H | 4-S(O)CH₃ | H | CO₂CH₂CH₃ | CH₃ | OCH₃ | N | |
| H | 4-S(O)CH₃ | H | CO₂CH₂CH₃ | OCH₃ | OCH₃ | N | |
| H | 4-S(O)CH₃ | H | CO₂CH₂CH₃ | Cl | OCH₃ | CH | |
| H | 4-S(O)₂CH₃ | H | CO₂CH₂CH₃ | CH₃ | CH₃ | CH | |
| H | 4-S(O)₂CH₃ | H | CO₂CH₂CH₃ | CH₃ | OCH₃ | CH | |
| H | 4-S(O)₂CH₃ | H | CO₂CH₂CH₃ | OCH₃ | OCH₃ | CH | |
| H | 4-S(O)₂CH₃ | H | CO₂CH₂CH₃ | CH₃ | OCH₃ | N | |

TABLE IIb-continued

General Formula IIb

| R | R₁ | Rₓ | Q₂ | X | Y | Z | m.p.(°C.) |
|---|---|---|---|---|---|---|---|
| H | 4-S(O)₂CH₃ | H | CO₂CH₂CH₃ | OCH₃ | OCH₃ | N | |
| H | 4-S(O)₂CH₃ | H | CO₂CH₂CH₃ | Cl | OCH₃ | CH | |
| H | 4-SCH₂CH₃ | H | CO₂CH₂CH₃ | CH₃ | CH₃ | CH | |
| H | 4-SCH₂CH₃ | H | CO₂CH₂CH₃ | CH₃ | OCH₃ | CH | |
| H | 4-SCH₂CH₃ | H | CO₂CH₂CH₃ | OCH₃ | OCH₃ | CH | |
| H | 4-SCH₂CH₃ | H | CO₂CH₂CH₃ | CH₃ | OCH₃ | N | |
| H | 4-SCH₂CH₃ | H | CO₂CH₂CH₃ | OCH₃ | OCH₃ | N | |
| H | 4-SCH₂CH₃ | H | CO₂CH₂CH₃ | Cl | OCH₃ | CH | |
| H | 4-S(O)CH₂CH₃ | H | CO₂CH₂CH₃ | CH₃ | CH₃ | CH | |
| H | 4-S(O)CH₂CH₃ | H | CO₂CH₂CH₃ | CH₃ | OCH₃ | CH | |
| H | 4-S(O)CH₂CH₃ | H | CO₂CH₂CH₃ | OCH₃ | OCH₃ | CH | |
| H | 4-S(O)CH₂CH₃ | H | CO₂CH₂CH₃ | CH₃ | OCH₃ | N | |
| H | 4-S(O)CH₂CH₃ | H | CO₂CH₂CH₃ | OCH₃ | OCH₃ | N | |
| H | 4-S(O)CH₂CH₃ | H | CO₂CH₂CH₃ | Cl | OCH₃ | CH | |
| H | 4-S(O)₂CH₂CH₃ | H | CO₂CH₂CH₃ | CH₃ | CH₃ | CH | |
| H | 4-S(O)₂CH₂CH₃ | H | CO₂CH₂CH₃ | CH₃ | OCH₃ | CH | |
| H | 4-S(O)₂CH₂CH₃ | H | CO₂CH₂CH₃ | OCH₃ | OCH₃ | CH | |
| H | 4-S(O)₂CH₂CH₃ | H | CO₂CH₂CH₃ | CH₃ | OCH₃ | N | |
| H | 4-S(O)₂CH₂CH₃ | H | CO₂CH₂CH₃ | OCH₃ | OCH₃ | N | |
| H | 4-S(O)₂CH₂CH₃ | H | CO₂CH₂CH₃ | Cl | OCH₃ | CH | |
| H | 4-SCH₂CH₂CH₃ | H | CO₂CH₂CH₃ | CH₃ | CH₃ | CH | |
| H | 4-SCH₂CH₂CH₃ | H | CO₂CH₂CH₃ | CH₃ | OCH₃ | CH | |
| H | 4-SCH₂CH₂CH₃ | H | CO₂CH₂CH₃ | OCH₃ | OCH₃ | CH | |
| H | 4-SCH₂CH₂CH₃ | H | CO₂CH₂CH₃ | CH₃ | OCH₃ | N | |
| H | 4-SCH₂CH₂CH₃ | H | CO₂CH₂CH₃ | OCH₃ | OCH₃ | N | |
| H | 4-SCH₂CH₂CH₃ | H | CO₂CH₂CH₃ | Cl | OCH₃ | CH | |
| H | 4-S(O)CH₂CH₂CH₃ | H | CO₂CH₂CH₃ | CH₃ | CH₃ | CH | |
| H | 4-S(O)CH₂CH₂CH₃ | H | CO₂CH₂CH₃ | CH₃ | OCH₃ | CH | |
| H | 4-S(O)CH₂CH₂CH₃ | H | CO₂CH₂CH₃ | OCH₃ | OCH₃ | CH | |
| H | 4-S(O)CH₂CH₂CH₃ | H | CO₂CH₂CH₃ | CH₃ | OCH₃ | N | |
| H | 4-S(O)CH₂CH₂CH₃ | H | CO₂CH₂CH₃ | OCH₃ | OCH₃ | N | |
| H | 4-S(O)CH₂CH₂CH₃ | H | CO₂CH₂CH₃ | Cl | OCH₃ | CH | |
| H | 4-S(O)₂CH₂CH₂CH₃ | H | CO₂CH₂CH₃ | CH₃ | CH₃ | CH | |
| H | 4-S(O)₂CH₂CH₂CH₃ | H | CO₂CH₂CH₃ | CH₃ | OCH₃ | CH | |
| H | 4-S(O)₂CH₂CH₂CH₃ | H | CO₂CH₂CH₃ | OCH₃ | OCH₃ | CH | |
| H | 4-S(O)₂CH₂CH₂CH₃ | H | CO₂CH₂CH₃ | CH₃ | OCH₃ | N | |
| H | 4-S(O)₂CH₂CH₂CH₃ | H | CO₂CH₂CH₃ | OCH₃ | OCH₃ | N | |
| H | 4-S(O)₂CH₂CH₂CH₃ | H | CO₂CH₂CH₃ | Cl | OCH₃ | CH | |
| H | 4-SCH₃ | H | CO₂CH(CH₃)₂ | CH₃ | CH₃ | CH | |
| H | 4-SCH₃ | H | CO₂CH(CH₃)₂ | CH₃ | OCH₃ | CH | |
| H | 4-SCH₃ | H | CO₂CH(CH₃)₂ | OCH₃ | OCH₃ | CH | |
| H | 4-SCH₃ | H | CO₂CH(CH₃)₂ | CH₃ | OCH₃ | N | |
| H | 4-SCH₃ | H | CO₂CH(CH₃)₂ | OCH₃ | OCH₃ | N | |
| H | 4-SCH₃ | H | CO₂CH(CH₃)₂ | Cl | OCH₃ | CH | |
| H | 4-SCH₂CH₃ | H | CO₂CH(CH₃)₂ | CH₃ | CH₃ | CH | |
| H | 4-SCH₂CH₃ | H | CO₂CH(CH₃)₂ | CH₃ | OCH₃ | CH | |
| H | 4-SCH₂CH₃ | H | CO₂CH(CH₂)₂ | OCH₃ | OCH₃ | CH | |
| H | 4-SCH₂CH₃ | H | CO₂CH(CH₃)₂ | CH₃ | OCH₃ | N | |
| H | 4-SCH₂CH₃ | H | CO₂CH(CH₃)₂ | OCH₃ | OCH₃ | N | |
| H | 4-SCH₂CH₃ | H | CO₂CH(CH₃)₂ | Cl | OCH₃ | CH | |
| H | 4-SCH₂CH₂CH₃ | H | CO₂CH(CH₃)₂ | CH₃ | CH₃ | CH | |
| H | 4-SCH₂CH₂CH₃ | H | CO₂CH(CH₃)₂ | CH₃ | OCH₃ | CH | |
| H | 4-SCH₂CH₂CH₃ | H | CO₂CH(CH₃)₂ | OCH₃ | OCH₃ | CH | |
| H | 4-SCH₂CH₂CH₃ | H | CO₂CH(CH₃)₂ | CH₃ | OCH₃ | N | |
| H | 4-SCH₂CH₂CH₃ | H | CO₂CH(CH₃)₂ | OCH₃ | OCH₃ | N | |
| H | 4-SCH₂CH₂CH₃ | H | CO₂CH(CH₃)₂ | Cl | OCH₃ | CH | |
| H | 4-SCH₃ | H | CO₂CH₂CH₂OCH₃ | CH₃ | CH₃ | CH | |
| H | 4-SCH₃ | H | CO₂CH₂CH₂OCH₃ | CH₃ | OCH₃ | CH | |
| H | 4-SCH₃ | H | CO₂CH₂CH₂OCH₃ | OCH₃ | OCH₃ | CH | |
| H | 4-SCH₃ | H | CO₂CH₂CH₂OCH₃ | CH₃ | OCH₃ | N | |
| H | 4-SCH₃ | H | CO₂CH₂CH₂OCH₃ | OCH₃ | OCH₃ | N | |
| H | 4-SCH₃ | H | CO₂CH₂CH₂OCH₃ | Cl | OCH₃ | CH | |
| H | 4-SCH₂CH₃ | H | CO₂CH₂CH₂OCH₃ | CH₃ | CH₃ | CH | |
| H | 4-SCH₂CH₃ | H | CO₂CH₂CH₂OCH₃ | CH₃ | OCH₃ | CH | |
| H | 4-SCH₂CH₃ | H | CO₂CH₂CH₂OCH₃ | OCH₃ | OCH₃ | CH | |
| H | 4-SCH₂CH₃ | H | CO₂CH₂CH₂OCH₃ | CH₃ | OCH₃ | N | |
| H | 4-SCH₂CH₃ | H | CO₂CH₂CH₂OCH₃ | OCH₃ | OCH₃ | N | |
| H | 4-SCH₂CH₃ | H | CO₂CH₂CH₂OCH₃ | Cl | OCH₃ | CH | |
| H | 4-SCH₂CH₂CH₃ | H | CO₂CH₂CH₂OCH₃ | CH₃ | CH₃ | CH | |
| H | 4-SCH₂CH₂CH₃ | H | CO₂CH₂CH₂OCH₃ | CH₃ | OCH₃ | CH | |
| H | 4-SCH₂CH₂CH₃ | H | CO₂CH₂CH₂OCH₃ | OCH₃ | OCH₃ | CH | |
| H | 4-SCH₂CH₂CH₃ | H | CO₂CH₂CH₂OCH₃ | CH₃ | OCH₃ | N | |
| H | 4-SCH₂CH₂CH₃ | H | CO₂CH₂CH₂OCH₃ | OCH₃ | OCH₃ | N | |
| H | 4-SCH₂CH₂CH₃ | H | CO₂CH₂CH₂OCH₃ | Cl | OCH₃ | CH | |
| H | 4-SCH₃ | H | CO₂CH₂CH₂Cl | CH₃ | CH₃ | CH | |
| H | 4-SCH₃ | H | CO₂CH₂CH₂Cl | CH₃ | OCH₃ | CH | |
| H | 4-SCH₃ | H | CO₂CH₂CH₂Cl | OCH₃ | OCH₃ | CH | |
| H | 4-SCH₃ | H | CO₂CH₂CH₂Cl | CH₃ | OCH₃ | N | |
| H | 4-SCH₃ | H | CO₂CH₂CH₂Cl | OCH₃ | OCH₃ | N | |
| H | 4-SCH₃ | H | CO₂CH₂CH₂Cl | Cl | OCH₃ | CH | |

TABLE IIb-continued

General Formula IIb

| R | R₁ | Rₓ | Q₂ | X | Y | Z | m.p.(°C.) |
|---|---|---|---|---|---|---|---|
| H | 4-SCH₂CH₃ | H | CO₂CH₂CH₂Cl | CH₃ | CH₃ | CH | |
| H | 4-SCH₂CH₃ | H | CO₂CH₂CH₂Cl | CH₃ | OCH₃ | CH | |
| H | 4-SCH₂CH₃ | H | CO₂CH₂CH₂Cl | OCH₃ | OCH₃ | CH | |
| H | 4-SCH₂CH₃ | H | CO₂CH₂CH₂Cl | CH₃ | OCH₃ | N | |
| H | 4-SCH₂CH₃ | H | CO₂CH₂CH₂Cl | OCH₃ | OCH₃ | N | |
| H | 4-SCH₂CH₃ | H | CO₂CH₂CH₂Cl | Cl | OCH₃ | CH | |
| H | 4-SCH₂CH₂CH₃ | H | CO₂CH₂CH₂Cl | CH₃ | CH₃ | CH | |
| H | 4-SCH₂CH₂CH₃ | H | CO₂CH₂CH₂Cl | CH₃ | OCH₃ | CH | |
| H | 4-SCH₂CH₂CH₃ | H | CO₂CH₂CH₂Cl | OCH₃ | OCH₃ | CH | |
| H | 4-SCH₂CH₂CH₃ | H | CO₂CH₂CH₂Cl | CH₃ | OCH₃ | N | |
| H | 4-SCH₂CH₂CH₃ | H | CO₂CH₂CH₂Cl | OCH₃ | OCH₃ | N | |
| H | 4-SCH₂CH₂CH₃ | H | CO₂CH₂CH₂Cl | Cl | OCH₃ | CH | |
| H | 4-SCH₃ | H | CO₂CH₂−▷ | CH₃ | CH₃ | OH | |
| H | 4-SCH₃ | H | CO₂CH₂−▷ | CH₃ | OCH₃ | CH | |
| H | 4-SCH₃ | H | CO₂CH₂−▷ | OCH₃ | OCH₃ | CH | |
| H | 4-SCH₃ | H | CO₂CH₂−▷ | CH₃ | OCH₃ | N | |
| H | 4-SCH₃ | H | CO₂CH₂−▷ | OCH₃ | OCH₃ | N | |
| H | 4-SCH₃ | H | CO₂CH₂−▷ | Cl | OCH₃ | CH | |
| H | 4-SCH₂CH₃ | H | CO₂CH₂−▷ | CH₃ | CH₃ | CH | |
| H | 4-SCH₂CH₃ | H | CO₂CH₂−▷ | CH₃ | OCH₃ | CH | |
| H | 4-SCH₂CH₃ | H | CO₂CH₂−▷ | OCH₃ | OCH₃ | CH | |
| H | 4-SCH₂CH₃ | H | CO₂CH₂−▷ | CH₃ | OCH₃ | N | |
| H | 4-SCH₂CH₃ | H | CO₂CH₂−▷ | OCH₃ | OCH₃ | N | |
| H | 4-SCH₂CH₃ | H | CO₂CH₂−▷ | Cl | OCH₃ | CH | |
| H | 4-SCH₂CH₂CH₃ | H | CO₂CH₂−▷ | CH₃ | CH₃ | CH | |
| H | 4-SCH₂CH₂CH₃ | H | CO₂CH₂−▷ | CH₃ | OCH₃ | CH | |
| H | 4-SCH₂CH₂CH₃ | H | CO₂CH₂−▷ | OCH₃ | OCH₃ | CH | |
| H | 4-SCH₂CH₂CH₃ | H | CO₂CH₂−▷ | CH₃ | OCH₃ | N | |
| H | 4-SCH₂CH₂CH₃ | H | CO₂CH₂−▷ | OCH₃ | OCH₃ | N | |

TABLE IIb-continued

General Formula IIb

| R | R₁ | Rₓ | Q₂ | X | Y | Z | m.p.(°C.) |
|---|---|---|---|---|---|---|---|
| H | 4-SCH₂CH₂CH₃ | H | CO₂CH₂—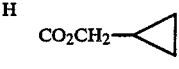 | Cl | OCH₃ | CH | |
| H | 4-SCH₃ | H | C(O)N(CH₃)₂ | CH₃ | CH₃ | CH | |
| H | 4-SCH₃ | H | C(O)N(CH₃)₂ | CH₃ | OCH₃ | CH | |
| H | 4-SCH₃ | H | C(O)N(CH₃)₂ | OCH₃ | OCH₃ | CH | |
| H | 4-SCH₃ | H | C(O)N(CH₃)₂ | CH₃ | OCH₃ | N | |
| H | 4-SCH₃ | H | C(O)N(CH₃)₂ | OCH₃ | OCH₃ | N | |
| H | 4-SCH₃ | H | C(O)N(CH₃)₂ | Cl | OCH₃ | CH | |
| H | 4-S(O)CH₃ | H | C(O)N(CH₃)₂ | CH₃ | CH₃ | CH | |
| H | 4-S(O)CH₃ | H | C(O)N(CH₃)₂ | CH₃ | OCH₃ | CH | |
| H | 4-S(O)CH₃ | H | C(O)N(CH₃)₂ | OCH₃ | OCH₃ | CH | |
| H | 4-S(O)CH₃ | H | C(O)N(CH₃)₂ | CH₃ | OCH₃ | N | |
| H | 4-S(O)CH₃ | H | C(O)N(CH₃)₂ | OCH₃ | OCH₃ | N | |
| H | 4-S(O)CH₃ | H | C(O)N(CH₃)₂ | Cl | OCH₃ | CH | |
| H | 4-S(O)₂CH₃ | H | C(O)N(CH₃)₂ | CH₃ | CH₃ | CH | |
| H | 4-S(O)₂CH₃ | H | C(O)N(CH₃)₂ | CH₃ | OCH₃ | CH | |
| H | 4-S(O)₂CH₃ | H | C(O)N(CH₃)₂ | OCH₃ | OCH₃ | CH | |
| H | 4-S(O)₂CH₃ | H | C(O)N(CH₃)₂ | CH₃ | OCH₃ | N | |
| H | 4-S(O)₂CH₃ | H | C(O)N(CH₃)₂ | OCH₃ | OCH₃ | N | |
| H | 4-S(O)₂CH₃ | H | C(O)N(CH₂)₂ | Cl | OCH₃ | CH | |
| H | 4-SCH₂CH₃ | H | C(O)N(CH₃)₂ | CH₃ | CH₃ | CH | |
| H | 4-SCH₂CH₃ | H | C(O)N(CH₃)₂ | CH₃ | OCH₃ | CH | |
| H | 4-SCH₂CH₃ | H | C(O)N(CH₃)₂ | OCH₃ | OCH₃ | CH | |
| H | 4-SCH₂CH₃ | H | C(O)N(CH₃)₂ | CH₃ | OCH₃ | N | |
| H | 4-SCH₂CH₃ | H | C(O)N(CH₃)₂ | OCH₃ | OCH₃ | N | |
| H | 4-SCH₂CH₃ | H | C(O)N(CH₃)₂ | Cl | OCH₃ | CH | |
| H | 4-S(O)CH₂CH₃ | H | C(O)N(CH₃)₂ | CH₃ | CH₃ | CH | |
| H | 4-S(O)CH₂CH₃ | H | C(O)N(CH₃)₂ | CH₃ | OCH₃ | CH | |
| H | 4-S(O)CH₂CH₃ | H | C(O)N(CH₃)₂ | OCH₃ | OCH₃ | CH | |
| H | 4-S(O)CH₂CH₃ | H | C(O)N(CH₃)₂ | CH₃ | OCH₃ | N | |
| H | 4-S(O)CH₂CH₃ | H | C(O)N(CH₃)₂ | OCH₃ | OCH₃ | N | |
| H | 4-S(O)CH₂CH₃ | H | C(O)N(CH₃)₂ | Cl | OCH₃ | CH | |
| H | 4-S(O)₂CH₂CH₃ | H | C(O)N(CH₃)₂ | CH₃ | CH₃ | CH | |
| H | 4-S(O)₂CH₂CH₃ | H | C(O)N(CH₃)₂ | CH₃ | OCH₃ | CH | |
| H | 4-S(O)₂CH₂CH₃ | H | C(O)N(CH₃)₂ | OCH₃ | OCH₃ | CH | |
| H | 4-S(O)₂CH₂CH₃ | H | C(O)N(CH₃)₂ | CH₃ | OCH₃ | N | |
| H | 4-S(O)₂CH₂CH₃ | H | C(O)N(CH₃)₂ | OCH₃ | OCH₃ | N | |
| H | 4-S(O)₂CH₂CH₃ | H | C(O)N(CH₃)₂ | Cl | OCH₃ | CH | |
| H | 4-SCH₂CH₂CH₃ | H | C(O)N(CH₃)₂ | CH₃ | CH₃ | CH | |
| H | 4-SCH₂CH₂CH₃ | H | C(O)N(CH₃)₂ | CH₃ | OCH₃ | CH | |
| H | 4-SCH₂CH₂CH₃ | H | C(O)N(CH₃)₂ | OCH₃ | OCH₃ | CH | |
| H | 4-SCH₂CH₂CH₃ | H | C(O)N(CH₃)₂ | CH₃ | OCH₃ | N | |
| H | 4-SCH₂CH₂CH₃ | H | C(O)N(CH₃)₂ | OCH₃ | OCH₃ | N | |
| H | 4-SCH₂CH₂CH₃ | H | C(O)N(CH₃)₂ | Cl | OCH₃ | CH | |
| H | 4-S(O)CH₂CH₂CH₃ | H | C(O)N(CH₃)₂ | CH₃ | CH₃ | CH | |
| H | 4-S(O)CH₂CH₂CH₃ | H | C(O)N(CH₃)₂ | CH₃ | OCH₃ | CH | |
| H | 4-S(O)CH₂CH₂CH₃ | H | C(O)N(CH₂)₂ | OCH₃ | OCH₃ | CH | |
| H | 4-S(O)CH₂CH₂CH₃ | H | C(O)N(CH₃)₂ | CH₃ | OCH₃ | N | |
| H | 4-S(O)CH₂CH₂CH₃ | H | C(O)N(CH₃)₂ | OCH₃ | OCH₃ | N | |
| H | 4-S(O)CH₂CH₂CH₃ | H | C(O)N(CH₃)₂ | Cl | OCH₃ | CH | |
| H | 4-S(O)₂CH₂CH₂CH₃ | H | C(O)N(CH₃)₂ | CH₃ | CH₃ | CH | |
| H | 4-S(O)₂CH₂CH₂CH₃ | H | C(O)N(CH₃)₂ | CH₃ | OCH₃ | CH | |
| H | 4-S(O)₂CH₂CH₂CH₃ | H | C(O)N(CH₂)₂ | OCH₃ | OCH₃ | CH | |
| H | 4-S(O)₂CH₂CH₂CH₃ | H | C(O)N(CH₃)₂ | CH₃ | OCH₃ | N | |
| H | 4-S(O)₂CH₂CH₂CH₃ | H | C(O)N(CH₃)₂ | OCH₃ | OCH₃ | N | |
| H | 4-S(O)₂CH₂CH₂CH₃ | H | C(O)N(CH₃)₂ | Cl | OCH₃ | CH | |
| H | 4-SCH₃ | H | SCH₃ | CH₃ | CH₃ | CH | |
| H | 4-SCH₃ | H | SCH₃ | CH₃ | OCH₃ | CH | |
| H | 4-SCH₃ | H | SCH₃ | OCH₃ | OCH₃ | CH | |
| H | 4-SCH₃ | H | SCH₃ | CH₃ | OCH₃ | N | |
| H | 4-SCH₃ | H | SCH₃ | OCH₃ | OCH₃ | N | |
| H | 4-SCH₃ | H | SCH₃ | Cl | OCH₃ | CH | |
| H | 4-SCH₂CH₃ | H | SCH₃ | CH₃ | CH₃ | CH | |
| H | 4-SCH₂CH₃ | H | SCH₃ | CH₃ | OCH₃ | CH | |
| H | 4-SCH₂CH₃ | H | SCH₃ | OCH₃ | OCH₃ | CH | |
| H | 4-SCH₂CH₃ | H | SCH₃ | CH₃ | OCH₃ | N | |
| H | 4-SCH₂CH₃ | H | SCH₃ | OCH₃ | OCH₃ | N | |
| H | 4-SCH₂CH₃ | H | SCH₃ | Cl | OCH₃ | CH | |
| H | 4-SCH₂CH₂CH₃ | H | SCH₃ | CH₃ | CH₃ | CH | |
| H | 4-SCH₂CH₂CH₃ | H | SCH₃ | CH₃ | OCH₃ | CH | |
| H | 4-SCH₂CH₂CH₃ | H | SCH₃ | OCH₃ | OCH₃ | CH | |
| H | 4-SCH₂CH₂CH₃ | H | SCH₃ | CH₃ | OCH₃ | N | |
| H | 4-SCH₂CH₂CH₃ | H | SCH₃ | OCH₃ | OCH₃ | N | |
| H | 4-SCH₂CH₂CH₃ | H | SCH₃ | Cl | OCH₃ | CH | |
| H | 4-SCH₃ | H | SCH₂CH₃ | CH₃ | CH₃ | CH | |
| H | 4-SCH₃ | H | SCH₂CH₃ | CH₃ | OCH₃ | CH | |
| H | 4-SCH₃ | H | SCH₂CH₃ | OCH₃ | OCH₃ | CH | |

TABLE IIb-continued

General Formula IIb

| R | R₁ | Rₓ | Q₂ | X | Y | Z | m.p.(°C.) |
|---|---|---|---|---|---|---|---|
| H | 4-SCH₃ | H | SCH₂CH₃ | CH₃ | OCH₃ | N | |
| H | 4-SCH₃ | H | SCH₂CH₃ | OCH₃ | OCH₃ | N | |
| H | 4-SCH₃ | H | SCH₂CH₃ | Cl | OCH₃ | CH | |
| H | 4-SCH₂CH₃ | H | SCH₂CH₃ | CH₃ | CH₃ | CH | |
| H | 4-SCH₂CH₃ | H | SCH₂CH₃ | CH₃ | OCH₃ | CH | |
| H | 4-SCH₂CH₃ | H | SCH₂CH₃ | OCH₃ | OCH₃ | CH | |
| H | 4-SCH₂CH₃ | H | SCH₂CH₃ | CH₃ | OCH₃ | N | |
| H | 4-SCH₂CH₃ | H | SCH₂CH₃ | OCH₃ | OCH₃ | N | |
| H | 4-SCH₂CH₃ | H | SCH₂CH₃ | Cl | OCH₃ | CH | |
| H | 4-SCH₂CH₂CH₃ | H | SCH₂CH₃ | CH₃ | CH₃ | CH | |
| H | 4-SCH₂CH₂CH₃ | H | SCH₂CH₃ | CH₃ | OCH₃ | CH | |
| H | 4-SCH₂CH₂CH₃ | H | SCH₂CH₃ | OCH₃ | OCH₃ | CH | |
| H | 4-SCH₂CH₂CH₃ | H | SCH₂CH₃ | CH₃ | OCH₃ | N | |
| H | 4-SCH₂CH₂CH₃ | H | SCH₂CH₃ | OCH₃ | OCH₃ | N | |
| H | 4-SCH₂CH₂CH₃ | H | SCH₂CH₃ | Cl | OCH₃ | CH | |
| H | 4-SCH₃ | H | SCH₂CH₂CH₃ | CH₃ | CH₃ | CH | |
| H | 4-SCH₃ | H | SCH₂CH₂CH₃ | CH₃ | OCH₃ | CH | |
| H | 4-SCH₃ | H | SCH₂CH₂CH₃ | OCH₃ | OCH₃ | CH | |
| H | 4-SCH₃ | H | SCH₂CH₂CH₃ | CH₃ | OCH₃ | N | |
| H | 4-SCH₃ | H | SCH₂CH₂CH₃ | OCH₃ | OCH₃ | N | |
| H | 4-SCH₃ | H | SCH₂CH₂CH₃ | Cl | OCH₃ | CH | |
| H | 4-SCH₂CH₃ | H | SCH₂CH₂CH₃ | CH₃ | CH₃ | CH | |
| H | 4-SCH₂CH₃ | H | SCH₂CH₂CH₃ | CH₃ | OCH₃ | CH | |
| H | 4-SCH₂CH₃ | H | SCH₂CH₂CH₃ | OCH₃ | OCH₃ | CH | |
| H | 4-SCH₂CH₃ | H | SCH₂CH₂CH₃ | CH₃ | OCH₃ | N | |
| H | 4-SCH₂CH₃ | H | SCH₂CH₂CH₃ | OCH₃ | OCH₃ | N | |
| H | 4-SCH₂CH₃ | H | SCH₂CH₂CH₃ | Cl | OCH₃ | CH | |
| H | 4-SCH₂CH₂CH₃ | H | SCH₂CH₂CH₃ | CH₃ | CH₃ | CH | |
| H | 4-SCH₂CH₂CH₃ | H | SCH₂CH₂CH₃ | CH₃ | OCH₃ | CH | |
| H | 4-SCH₂CH₂CH₃ | H | SCH₂CH₂CH₃ | OCH₃ | OCH₃ | CH | |
| H | 4-SCH₂CH₂CH₃ | H | SCH₂CH₂CH₃ | CH₃ | OCH₃ | N | |
| H | 4-SCH₂CH₂CH₃ | H | SCH₂CH₂CH₃ | OCH₃ | OCH₃ | N | |
| H | 4-SCH₂CH₂CH₃ | H | SCH₂CH₂CH₃ | Cl | OCH₃ | CH | |
| H | 4-SCH₃ | H | S(O)CH₂CH₃ | CH₃ | CH₃ | CH | |
| H | 4-SCH₃ | H | S(O)CH₂CH₃ | CH₃ | OCH₃ | CH | |
| H | 4-SCH₃ | H | S(O)CH₂CH₃ | OCH₃ | OCH₃ | CH | |
| H | 4-SCH₃ | H | S(O)CH₂CH₃ | CH₃ | OCH₃ | N | |
| H | 4-SCH₃ | H | S(O)CH₂CH₃ | OCH₃ | OCH₃ | N | |
| H | 4-SCH₃ | H | S(O)CH₂CH₃ | Cl | OCH₃ | CH | |
| H | 4-S(O)CH₃ | H | S(O)CH₂CH₃ | CH₃ | CH₃ | CH | |
| H | 4-S(O)CH₃ | H | S(O)CH₂CH₃ | CH₃ | OCH₃ | CH | |
| H | 4-S(O)CH₃ | H | S(O)CH₂CH₃ | OCH₃ | OCH₃ | CH | |
| H | 4-S(O)CH₃ | H | S(O)CH₂CH₃ | CH₃ | OCH₃ | N | |
| H | 4-S(O)CH₃ | H | S(O)CH₂CH₃ | OCH₃ | OCH₃ | N | |
| H | 4-S(O)CH₃ | H | S(O)CH₂CH₃ | Cl | OCH₃ | CH | |
| H | 4-S(O)₂CH₃ | H | S(O)CH₂CH₃ | CH₃ | CH₃ | CH | |
| H | 4-S(O)₂CH₃ | H | S(O)CH₂CH₃ | CH₃ | OCH₃ | CH | |
| H | 4-S(O)₂CH₃ | H | S(O)CH₂CH₃ | OCH₃ | OCH₃ | CH | |
| H | 4-S(O)₂CH₃ | H | S(O)CH₂CH₃ | CH₃ | OCH₃ | N | |
| H | 4-S(O)₂CH₃ | H | S(O)CH₂CH₃ | OCH₃ | OCH₃ | N | |
| H | 4-S(O)₂CH₃ | H | S(O)CH₂CH₃ | Cl | OCH₃ | CH | |
| H | 4-SCH₃ | H | S(O)₂CH₂CH₃ | CH₃ | CH₃ | CH | |
| H | 4-SCH₃ | H | S(O)₂CH₂CH₃ | CH₃ | OCH₃ | CH | |
| H | 4-SCH₃ | H | S(O)₂CH₂CH₃ | OCH₃ | OCH₃ | CH | |
| H | 4-SCH₃ | H | S(O)₂CH₂CH₃ | CH₃ | OCH₃ | N | |
| H | 4-SCH₃ | H | S(O)₂CH₂CH₃ | OCH₃ | OCH₃ | N | |
| H | 4-SCH₃ | H | S(O)₂CH₂CH₃ | Cl | OCH₃ | CH | |
| H | 4-S(O)CH₃ | H | S(O)₂CH₂CH₃ | CH₃ | CH₃ | CH | |
| H | 4-S(O)CH₃ | H | S(O)₂CH₂CH₃ | CH₃ | OCH₃ | CH | |
| H | 4-S(O)CH₃ | H | S(O)₂CH₂CH₃ | OCH₃ | OCH₃ | CH | |
| H | 4-S(O)CH₃ | H | S(O)₂CH₂CH₃ | CH₃ | OCH₃ | N | |
| H | 4-S(O)CH₃ | H | S(O)₂CH₂CH₃ | OCH₃ | OCH₃ | N | |
| H | 4-S(O)CH₃ | H | S(O)₂CH₂CH₃ | Cl | OCH₃ | CH | |
| H | 4-S(O)₂CH₃ | H | S(O)₂CH₂CH₃ | CH₃ | CH₃ | CH | |
| H | 4-S(O)₂CH₃ | H | S(O)₂CH₂CH₃ | CH₃ | OCH₃ | CH | |
| H | 4-S(O)₂CH₃ | H | S(O)₂CH₂CH₃ | OCH₃ | OCH₃ | CH | |
| H | 4-S(O)₂CH₃ | H | S(O)₂CH₂CH₃ | CH₃ | OCH₃ | N | |
| H | 4-S(O)₂CH₃ | H | S(O)₂CH₂CH₃ | OCH₃ | OCH₃ | N | |
| H | 4-S(O)₂CH₃ | H | S(O)₂CH₂CH₃ | Cl | OCH₃ | CH | |
| H | 4-SCH₃ | H | CHO | CH₃ | CH₃ | CH | |
| H | 4-SCH₃ | H | CHO | CH₃ | OCH₃ | CH | |
| H | 4-SCH₃ | H | CHO | OCH₃ | OCH₃ | CH | |
| H | 4-SCH₃ | H | CHO | CH₃ | OCH₃ | N | |
| H | 4-SCH₃ | H | CHO | OCH₃ | OCH₃ | N | |
| H | 4-SCH₃ | H | CHO | Cl | OCH₃ | CH | |
| H | 4-S(O)CH₃ | H | CHO | CH₃ | CH₃ | CH | |
| H | 4-S(O)CH₃ | H | CHO | CH₃ | OCH₃ | CH | |
| H | 4-S(O)CH₃ | H | CHO | OCH₃ | OCH₃ | CH | |
| H | 4-S(O)CH₃ | H | CHO | CH₃ | OCH₃ | N | |
| H | 4-S(O)CH₃ | H | CHO | OCH₃ | OCH₃ | N | |

TABLE IIb-continued

General Formula IIb

| R | R₁ | Rₓ | Q₂ | X | Y | Z | m.p.(°C.) |
|---|---|---|---|---|---|---|---|
| H | 4-S(O)CH₃ | H | CHO | Cl | OCH₃ | CH | |
| H | 4-S(O)₂CH₃ | H | CHO | CH₃ | CH₃ | CH | |
| H | 4-S(O)₂CH₃ | H | CHO | CH₃ | OCH₃ | CH | |
| H | 4-S(O)₂CH₃ | H | CHO | OCH₃ | OCH₃ | CH | |
| H | 4-S(O)₂CH₃ | H | CHO | CH₃ | OCH₃ | N | |
| H | 4-S(O)₂CH₃ | H | CHO | OCH₃ | OCH₃ | N | |
| H | 4-S(O)₂CH₃ | H | CHO | Cl | OCH₃ | CH | |
| H | 4-SCH₂CH₃ | H | CHO | CH₃ | CH₃ | CH | |
| H | 4-SCH₂CH₃ | H | CHO | CH₃ | OCH₃ | CH | |
| H | 4-SCH₂CH₃ | H | CHO | OCH₃ | OCH₃ | CH | |
| H | 4-SCH₂CH₃ | H | CHO | CH₃ | OCH₃ | N | |
| H | 4-SCH₂CH₃ | H | CHO | OCH₃ | OCH₃ | N | |
| H | 4-SCH₂CH₃ | H | CHO | Cl | OCH₃ | CH | |
| H | 4-S(O)CH₂CH₃ | H | CHO | CH₃ | CH₃ | CH | |
| H | 4-S(O)CH₂CH₃ | H | CHO | CH₃ | OCH₃ | CH | |
| H | 4-S(O)CH₂CH₃ | H | CHO | OCH₃ | OCH₃ | CH | |
| H | 4-S(O)CH₂CH₃ | H | CHO | CH₃ | OCH₃ | N | |
| H | 4-S(O)CH₂CH₃ | H | CHO | OCH₃ | OCH₃ | N | |
| H | 4-S(O)CH₂CH₃ | H | CHO | Cl | OCH₃ | CH | |
| H | 4-S(O)₂CH₂CH₃ | H | CHO | CH₃ | CH₃ | CH | |
| H | 4-S(O)₂CH₂CH₃ | H | CHO | CH₃ | OCH₃ | CH | |
| H | 4-S(O)₂CH₂CH₃ | H | CHO | OCH₃ | OCH₃ | CH | |
| H | 4-S(O)₂CH₂CH₃ | H | CHO | CH₃ | OCH₃ | N | |
| H | 4-S(O)₂CH₂CH₃ | H | CHO | OCH₃ | OCH₃ | N | |
| H | 4-S(O)₂CH₂CH₃ | H | CHO | Cl | OCH₃ | CH | |
| H | 4-SCH₂CH₂CH₃ | H | CHO | CH₃ | CH₃ | CH | |
| H | 4-SCH₂CH₂CH₃ | H | CHO | CH₃ | OCH₃ | CH | |
| H | 4-SCH₂CH₂CH₃ | H | CHO | OCH₃ | OCH₃ | CH | |
| H | 4-SCH₂CH₂CH₃ | H | CHO | CH₃ | OCH₃ | N | |
| H | 4-SCH₂CH₂CH₃ | H | CHO | OCH₃ | OCH₃ | N | |
| H | 4-SCH₂CH₂CH₃ | H | CHO | Cl | OCH₃ | CH | |
| H | 4-S(O)CH₂CH₂CH₃ | H | CHO | CH₃ | CH₃ | CH | |
| H | 4-S(O)CH₂CH₂CH₃ | H | CHO | CH₃ | OCH₃ | CH | |
| H | 4-S(O)CH₂CH₂CH₃ | H | CHO | OCH₃ | OCH₃ | CH | |
| H | 4-S(O)CH₂CH₂CH₃ | H | CHO | CH₃ | OCH₃ | N | |
| H | 4-S(O)CH₂CH₂CH₃ | H | CHO | OCH₃ | OCH₃ | N | |
| H | 4-S(O)CH₂CH₂CH₃ | H | CHO | Cl | OCH₃ | CH | |
| H | 4-S(O)₂CH₂CH₂CH₃ | H | CHO | CH₃ | CH₃ | CH | |
| H | 4-S(O)₂CH₂CH₂CH₃ | H | CHO | CH₃ | OCH₃ | CH | |
| H | 4-S(O)₂CH₂CH₂CH₃ | H | CHO | OCH₃ | OCH₃ | CH | |
| H | 4-S(O)₂CH₂CH₂CH₃ | H | CHO | CH₃ | OCH₃ | N | |
| H | 4-S(O)₂CH₂CH₂CH₃ | H | CHO | OCH₃ | OCH₃ | N | |
| H | 4-S(O)₂CH₂CH₂CH₃ | H | CHO | Cl | OCH₃ | CH | |
| H | 4-SCH₃ | H | CH=NOH | CH₃ | CH₃ | CH | |
| H | 4-SCH₃ | H | CH=NOH | CH₃ | OCH₃ | CH | |
| H | 4-SCH₃ | H | CH=NOH | OCH₃ | OCH₃ | CH | |
| H | 4-SCH₃ | H | CH=NOH | CH₃ | OCH₃ | N | |
| H | 4-SCH₃ | H | CH=NOH | OCH₃ | OCH₃ | N | |
| H | 4-SCH₃ | H | CH=NOH | Cl | OCH₃ | CH | |
| H | 4-SCH₂CH₃ | H | CH=NOH | CH₃ | CH₃ | CH | |
| H | 4-SCH₂CH₃ | H | CH=NOH | CH₃ | OCH₃ | CH | |
| H | 4-SCH₂CH₃ | H | CH=NOH | OCH₃ | OCH₃ | CH | |
| H | 4-SCH₂CH₃ | H | CH=NOH | CH₃ | OCH₃ | N | |
| H | 4-SCH₂CH₃ | H | CH=NOH | OCH₃ | OCH₃ | N | |
| H | 4-SCH₂CH₃ | H | CH=NOH | Cl | OCH₃ | CH | |
| H | 4-SCH₂CH₂CH₃ | H | CH=NOH | CH₃ | CH₃ | CH | |
| H | 4-SCH₂CH₂CH₃ | H | CH=NOH | CH₃ | OCH₃ | CH | |
| H | 4-SCH₂CH₂CH₃ | H | CH=NOH | OCH₃ | OCH₃ | CH | |
| H | 4-SCH₂CH₂CH₃ | H | CH=NOH | CH₃ | OCH₃ | N | |
| H | 4-SCH₂CH₂CH₃ | H | CH=NOH | OCH₃ | OCH₃ | N | |
| H | 4-SCH₂CH₂CH₃ | H | CH=NOH | Cl | OCH₃ | CH | |
| H | 4-SCH₃ | H | CH=NOCH₃ | CH₃ | CH₃ | CH | |
| H | 4-SHC₃ | H | CH=NOCH₃ | CH₃ | OCH₃ | CH | |
| H | 4-SCH₃ | H | CH=NOCH₃ | OCH₃ | OCH₃ | CH | |
| H | 4-SCH₃ | H | CH=NOCH₃ | CH₃ | OCH₃ | N | |
| H | 4-SCH₃ | H | CH=NOCH₃ | OCH₃ | OCH₃ | N | |
| H | 4-SCH₃ | H | CH=NOCH₃ | Cl | OCH₃ | CH | |
| H | 4-SCH₂CH₃ | H | CH=NOCH₃ | CH₃ | CH₃ | CH | |
| H | 4-SCH₂CH₃ | H | CH=NOCH₃ | CH₃ | OCH₃ | CH | |
| H | 4-SCH₂CH₃ | H | CH=NOCH₃ | OCH₃ | OCH₃ | CH | |
| H | 4-SCH₂CH₃ | H | CH=NOCH₃ | CH₃ | OCH₃ | N | |
| H | 4-SCH₂CH₃ | H | CH=NOCH₃ | OCH₃ | OCH₃ | N | |
| H | 4-SCH₂CH₃ | H | CH=NOCH₃ | Cl | OCH₃ | CH | |
| H | 4-SCH₂CH₂CH₃ | H | CH=NOCH₃ | CH₃ | CH₃ | CH | |
| H | 4-SCH₂CH₂CH₃ | H | CH=NOCH₃ | CH₃ | OCH₃ | CH | |
| H | 4-SCH₂CH₂CH₃ | H | CH=NOCH₃ | OCH₃ | OCH₃ | CH | |
| H | 4-SCH₂CH₂CH₃ | H | CH=NOCH₃ | CH₃ | OCH₃ | N | |
| H | 4-SCH₂CH₂CH₃ | H | CH=NOCH₃ | OCH₃ | OCH₃ | N | |
| H | 4-SCH₂CH₂CH₃ | H | CH=NOCH₃ | Cl | OCH₃ | CH | |
| H | 4-CO₂CH₃ | H | CO₂CH₂CH₃ | CH₃ | CH₃ | CH | |

TABLE IIb-continued

General Formula IIb

| R | R$_1$ | R$_x$ | Q$_2$ | X | Y | Z | m.p.(°C.) |
|---|---|---|---|---|---|---|---|
| H | 4-CO$_2$CH$_3$ | H | CO$_2$CH$_2$CH$_3$ | CH$_3$ | OCH$_3$ | CH | |
| H | 4-CO$_2$CH$_3$ | H | CO$_2$CH$_2$CH$_3$ | OCH$_3$ | OCH$_3$ | CH | |
| H | 4-CO$_2$CH$_3$ | H | CO$_2$CH$_2$CH$_3$ | CH$_3$ | OCH$_3$ | N | |
| H | 4-CO$_2$CH$_3$ | H | CO$_2$CH$_2$CH$_3$ | OCH$_3$ | OCH$_3$ | N | |
| H | 4-CO$_2$CH$_3$ | H | CO$_2$CH$_2$CH$_3$ | Cl | OCH$_3$ | CH | |
| H | 4-CO$_2$CH$_2$CH$_3$ | H | CO$_2$CH$_2$CH$_3$ | CH$_3$ | CH$_3$ | CH | |
| H | 4-CO$_2$CH$_2$CH$_3$ | H | CO$_2$CH$_2$CH$_3$ | CH$_3$ | OCH$_3$ | CH | |
| H | 4-CO$_2$CH$_2$CH$_3$ | H | CO$_2$CH$_2$CH$_3$ | OCH$_3$ | OCH$_3$ | CH | |
| H | 4-CO$_2$CH$_2$CH$_3$ | H | CO$_2$CH$_2$CH$_3$ | CH$_3$ | OCH$_3$ | N | |
| H | 4-CO$_2$CH$_2$CH$_3$ | H | CO$_2$CH$_2$CH$_3$ | OCH$_3$ | OCH$_3$ | N | |
| H | 4-CO$_2$CH$_2$CH$_3$ | H | CO$_2$CH$_2$CH$_3$ | Cl | OCH$_3$ | CH | |
| H | 4-CO$_2$CH$_3$ | H | C(O)N(CH$_3$)$_2$ | CH$_3$ | CH$_3$ | CH | |
| H | 4-CO$_2$CH$_3$ | H | C(O)N(CH$_3$)$_2$ | CH$_3$ | OCH$_3$ | CH | |
| H | 4-CO$_2$CH$_3$ | H | C(O)N(CH$_3$)$_2$ | OCH$_3$ | OCH$_3$ | CH | |
| H | 4-CO$_2$CH$_3$ | H | C(O)N(CH$_3$)$_2$ | CH$_3$ | OCH$_3$ | N | |
| H | 4-CO$_2$CH$_3$ | H | C(O)N(CH$_3$)$_2$ | OCH$_3$ | OCH$_3$ | N | |
| H | 4-CO$_2$CH$_3$ | H | C(O)N(CH$_3$)$_2$ | Cl | OCH$_3$ | CH | |
| H | 4-CO$_2$CH$_2$CH$_3$ | H | C(O)N(CH$_3$)$_2$ | CH$_3$ | CH$_3$ | CH | |
| H | 4-CO$_2$CH$_2$CH$_3$ | H | C(O)N(CH$_3$)$_2$ | CH$_3$ | OCH$_3$ | CH | |
| H | 4-CO$_2$CH$_2$CH$_3$ | H | C(O)N(CH$_3$)$_2$ | OCH$_3$ | OCH$_3$ | CH | |
| H | 4-CO$_2$CH$_2$CH$_3$ | H | C(O)N(CH$_3$)$_2$ | CH$_3$ | OCH$_3$ | N | |
| H | 4-CO$_2$CH$_2$CH$_3$ | H | C(O)N(CH$_2$)$_2$ | OCH$_3$ | OCH$_3$ | N | |
| H | 4-CO$_2$CH$_2$CH$_3$ | H | C(O)N(CH$_3$)$_2$ | Cl | OCH$_3$ | CH | |
| H | 4-C(O)N(CH$_3$)$_2$ | H | C(O)N(CH$_3$)$_2$ | CH$_3$ | CH$_3$ | CH | |
| H | 4-C(O)N(CH$_3$)$_2$ | H | C(O)N(CH$_3$)$_2$ | CH$_3$ | OCH$_3$ | CH | |
| H | 4-C(O)N(CH$_3$)$_2$ | H | C(O)N(CH$_3$)$_2$ | OCH$_3$ | OCH$_3$ | CH | |
| H | 4-C(O)N(CH$_3$)$_2$ | H | C(O)N(CH$_3$)$_2$ | CH$_3$ | OCH$_3$ | N | |
| H | 4-C(O)N(CH$_3$)$_2$ | H | C(O)N(CH$_3$)$_2$ | OCH$_3$ | OCH$_3$ | N | |
| H | 4-C(O)N(CH$_3$)$_2$ | H | C(O)N(CH$_3$)$_2$ | Cl | OCH$_3$ | CH | |
| CH$_3$ | 4-S(O)$_2$N(CH$_3$)$_2$ | H | CO$_2$CH$_3$ | CH$_3$ | OCH$_3$ | N | |
| CH$_3$ | 4-S(O)$_2$N(CH$_3$)$_2$ | H | CO$_2$CH$_3$ | OCH$_3$ | OCH$_3$ | N | |
| CH$_3$ | 4-S(O)$_2$N(CH$_3$)$_2$ | H | CO$_2$CH$_3$ | CH$_3$ | OCH$_3$ | CH | |
| CH$_3$ | 4-S(O)$_2$N(CH$_3$)$_2$ | H | CO$_2$CH$_3$ | OCH$_3$ | OCH$_3$ | CH | |
| CH$_3$ | 4-SCH$_3$ | H | CO$_2$CH$_3$ | CH$_3$ | OCH$_3$ | N | |
| CH$_3$ | 4-SCH$_3$ | H | CO$_2$CH$_3$ | OCH$_3$ | OCH$_3$ | N | |
| CH$_3$ | 4-SCH$_3$ | H | CO$_2$CH$_3$ | CH$_3$ | OCH$_3$ | CH | |
| CH$_3$ | 4-SCH$_3$ | H | CO$_2$CH$_3$ | OCH$_3$ | OCH$_3$ | CH | |
| CH$_3$ | 4-S(O)CH$_3$ | H | CO$_2$CH$_3$ | CH$_3$ | OCH$_3$ | N | |
| CH$_3$ | 4-S(O)CH$_3$ | H | CO$_2$CH$_3$ | OCH$_3$ | OCH$_3$ | N | |
| CH$_3$ | 4-S(O)CH$_3$ | H | CO$_2$CH$_3$ | CH$_3$ | OCH$_3$ | CH | |
| CH$_3$ | 4-S(O)CH$_3$ | H | CO$_2$CH$_3$ | OCH$_3$ | OCH$_3$ | CH | |
| CH$_3$ | 4-S(O)$_2$CH$_3$ | H | CO$_2$CH$_3$ | CH$_3$ | OCH$_3$ | N | |
| CH$_3$ | 4-S(O)$_2$CH$_3$ | H | CO$_2$CH$_3$ | OCH$_3$ | OCH$_3$ | N | |
| CH$_3$ | 4-S(O)$_2$CH$_3$ | H | CO$_2$CH$_3$ | CH$_3$ | OCH$_3$ | CH | |
| CH$_3$ | 4-S(O)$_2$CH$_3$ | H | CO$_2$CH$_3$ | OCH$_3$ | OCH$_3$ | CH | |
| CH$_3$ | 4-SCH$_2$CH$_3$ | H | CO$_2$CH$_3$ | CH$_3$ | OCH$_3$ | N | |
| CH$_3$ | 4-SCH$_2$CH$_3$ | H | CO$_2$CH$_3$ | OCH$_3$ | OCH$_3$ | N | |
| CH$_3$ | 4-SCH$_2$CH$_3$ | H | CO$_2$CH$_3$ | CH$_3$ | OCH$_3$ | CH | |
| CH$_3$ | 4-SCH$_2$CH$_3$ | H | CO$_2$CH$_3$ | OCH$_3$ | OCH$_3$ | CH | |
| CH$_3$ | 4-S(O)CH$_2$CH$_3$ | H | CO$_2$CH$_3$ | CH$_3$ | OCH$_3$ | N | |
| CH$_3$ | 4-S(O)CH$_2$CH$_3$ | H | CO$_2$CH$_3$ | OCH$_3$ | OCH$_3$ | N | |
| CH$_3$ | 4-S(O)CH$_2$CH$_3$ | H | CO$_2$CH$_3$ | CH$_3$ | OCH$_3$ | CH | |
| CH$_3$ | 4-S(O)CH$_2$CH$_3$ | H | CO$_2$CH$_3$ | OCH$_3$ | OCH$_3$ | CH | |
| CH$_3$ | 4-S(O)$_2$CH$_2$CH$_3$ | H | CO$_2$CH$_3$ | CH$_3$ | OCH$_3$ | N | |
| CH$_3$ | 4-S(O)$_2$CH$_2$CH$_3$ | H | CO$_2$CH$_3$ | OCH$_3$ | OCH$_3$ | N | |
| CH$_3$ | 4-S(O)$_2$CH$_2$CH$_3$ | H | CO$_2$CH$_3$ | CH$_3$ | OCH$_3$ | CH | |
| CH$_3$ | 4-S(O)$_2$CH$_2$CH$_3$ | H | CO$_2$CH$_3$ | OCH$_3$ | OCH$_3$ | CH | |
| CH$_3$ | 4-SCH$_2$CH$_2$CH$_3$ | H | CO$_2$CH$_3$ | CH$_3$ | OCH$_3$ | N | |
| CH$_3$ | 4-SCH$_2$CH$_2$CH$_3$ | H | CO$_2$CH$_3$ | OCH$_3$ | OCH$_3$ | N | |
| CH$_3$ | 4-SCH$_2$CH$_2$CH$_3$ | H | CO$_2$CH$_3$ | CH$_3$ | OCH$_3$ | CH | |
| CH$_3$ | 4-SCH$_2$CH$_2$CH$_3$ | H | CO$_2$CH$_3$ | OCH$_3$ | OCH$_3$ | CH | |
| CH$_3$ | 4-S(O)CH$_2$CH$_2$CH$_3$ | H | CO$_2$CH$_3$ | CH$_3$ | OCH$_3$ | N | |
| CH$_3$ | 4-S(O)CH$_2$CH$_2$CH$_3$ | H | CO$_2$CH$_3$ | OCH$_3$ | OCH$_3$ | N | |
| CH$_3$ | 4-S(O)CH$_2$CH$_2$CH$_3$ | H | CO$_2$CH$_3$ | CH$_3$ | OCH$_3$ | CH | |
| CH$_3$ | 4-S(O)CH$_2$CH$_2$CH$_3$ | H | CO$_2$CH$_3$ | OCH$_3$ | OCH$_3$ | CH | |
| CH$_3$ | 4-S(O)$_2$CH$_2$CH$_2$CH$_3$ | H | CO$_2$CH$_3$ | CH$_3$ | OCH$_3$ | N | |
| CH$_3$ | 4-S(O)$_2$CH$_2$CH$_2$CH$_3$ | H | CO$_2$CH$_3$ | OCH$_3$ | OCH$_3$ | N | |
| CH$_3$ | 4-S(O)$_2$CH$_2$CH$_2$CH$_3$ | H | CO$_2$CH$_3$ | CH$_3$ | OCH$_3$ | CH | |
| CH$_3$ | 4-S(O)$_2$CH$_2$CH$_2$CH$_3$ | H | CO$_2$CH$_3$ | OCH$_3$ | OCH$_3$ | CH | |
| CH$_3$ | 4-S(O)$_2$N(CH$_3$)$_2$ | Br | Br | CH$_3$ | OCH$_3$ | N | |
| CH$_3$ | 4-S(O)$_2$N(CH$_3$)$_2$ | Br | Br | OCH$_3$ | OCH$_3$ | N | |
| CH$_3$ | 4-S(O)$_2$N(CH$_3$)$_2$ | Br | Br | CH$_3$ | OCH$_3$ | CH | |
| CH$_3$ | 4-S(O)$_2$N(CH$_3$)$_2$ | Br | Br | OCH$_3$ | OCH$_3$ | CH | |
| CH$_3$ | 4-SCH$_3$ | Br | Br | CH$_3$ | OCH$_3$ | N | |
| CH$_3$ | 4-SCH$_3$ | Br | Br | OCH$_3$ | OCH$_3$ | N | |
| CH$_3$ | 4-SCH$_3$ | Br | Br | CH$_3$ | OCH$_3$ | CH | |
| CH$_3$ | 4-SCH$_3$ | Br | Br | OCH$_3$ | OCH$_3$ | CH | |
| CH$_3$ | 4-SCH$_2$CH$_3$ | Br | Br | CH$_3$ | OCH$_3$ | N | |
| CH$_3$ | 4-SCH$_2$CH$_3$ | Br | Br | OCH$_3$ | OCH$_3$ | N | |
| CH$_3$ | 4-SCH$_2$CH$_3$ | Br | Br | CH$_3$ | OCH$_3$ | CH | |

TABLE IIb-continued

General Formula IIb

| R | R₁ | Rₓ | Q₂ | X | Y | Z | m.p.(°C.) |
|---|---|---|---|---|---|---|---|
| CH₃ | 4-SCH₂CH₃ | Br | Br | OCH₃ | OCH₃ | CH | |
| CH₃ | 4-SCH₂CH₂CH₃ | Br | Br | CH₃ | OCH₃ | N | |
| CH₃ | 4-SCH₂CH₂CH₃ | Br | Br | OCH₃ | OCH₃ | N | |
| CH₃ | 4-SCH₂CH₂CH₃ | Br | Br | CH₃ | OCH₃ | CH | |
| CH₃ | 4-SCH₂CH₂CH₃ | Br | Br | OCH₃ | OCH₃ | CH | |
| CH₃ | 4-S(O)₂N(CH₃)₂ | H | S(O)₂N(CH₃)₂ | CH₃ | OCH₃ | N | |
| CH₃ | 4-S(O)₂N(CH₃)₂ | H | S(O)₂N(CH₃)₂ | OCH₃ | OCH₃ | N | |
| CH₃ | 4-S(O)₂N(CH₃)₂ | H | S(O)₂N(CH₃)₂ | CH₃ | OCH₃ | CH | |
| CH₃ | 4-S(O)₂N(CH₃)₂ | H | S(O)₂N(CH₃)₂ | OCH₃ | OCH₃ | CH | |
| CH₃ | 4-SCH₃ | H | S(O)₂N(CH₃)₂ | CH₃ | OCH₃ | N | |
| CH₃ | 4-SCH₃ | H | S(O)₂N(CH₃)₂ | OCH₃ | OCH₃ | N | |
| CH₃ | 4-SCH₃ | H | S(O)₂N(CH₃)₂ | CH₃ | OCH₃ | CH | |
| CH₃ | 4-SCH₃ | H | S(O)₂N(CH₃)₂ | OCH₃ | OCH₃ | CH | |
| CH₃ | 4-SCH₂CH₃ | H | S(O)₂N(CH₃)₂ | CH₃ | OCH₃ | N | |
| CH₃ | 4-SCH₂CH₃ | H | S(O)₂N(CH₃)₂ | OCH₃ | OCH₃ | N | |
| CH₃ | 4-SCH₂CH₃ | H | S(O)₂N(CH₃)₂ | CH₃ | OCH₃ | CH | |
| CH₃ | 4-SCH₂CH₃ | H | S(O)₂N(CH₃)₂ | OCH₃ | OCH₃ | CH | |
| CH₃ | 4-SCH₂CH₂CH₃ | H | S(O)₂N(CH₃)₂ | CH₃ | OCH₃ | N | |
| CH₃ | 4-SCH₂CH₂CH₃ | H | S(O)₂N(CH₃)₂ | OCH₃ | OCH₃ | N | |
| CH₃ | 4-SCH₂CH₂CH₃ | H | S(O)₂N(CH₃)₂ | CH₃ | OCH₃ | CH | |
| CH₃ | 4-SCH₂CH₂CH₃ | H | S(O)₂N(CH₃)₂ | OCH₃ | OCH₃ | CH | |
| CH₃ | 4-CO₂CH₃ | H | CO₂CH₃ | CH₃ | OCH₃ | N | |
| CH₃ | 4-CO₂CH₃ | H | CO₂CH₃ | OCH₃ | OCH₃ | N | |
| CH₃ | 4-CO₂CH₃ | H | CO₂CH₃ | CH₃ | OCH₃ | CH | |
| CH₃ | 4-CO₂CH₃ | H | CO₂CH₃ | OCH₃ | OCH₃ | CH | |
| CH₃ | 4-C(O)₂N(CH₃)₂ | H | CO₂CH₃ | CH₃ | OCH₃ | N | |
| CH₃ | 4-C(O)₂N(CH₃)₂ | H | CO₂CH₃ | OCH₃ | OCH₃ | N | |
| CH₃ | 4-C(O)₂N(CH₃)₂ | H | CO₂CH₃ | CH₃ | OCH₃ | CH | |
| CH₃ | 4-C(O)₂N(CH₃)₂ | H | CO₂CH₃ | OCH₃ | OCH₃ | CH | |
| CH₃ | 4-SCH₃ | H | CO₂CH₂CH₃ | CH₃ | OCH₃ | N | |
| CH₃ | 4-SCH₃ | H | CO₂CH₂CH₃ | OCH₃ | OCH₃ | N | |
| CH₃ | 4-SCH₃ | H | CO₂CH₂CH₃ | CH₃ | OCH₃ | CH | |
| CH₃ | 4-SCH₃ | H | CO₂CH₂CH₃ | OCH₃ | OCH₃ | CH | |
| CH₃ | 4-SCH₂CH₃ | H | CO₂CH₂CH₃ | CH₃ | OCH₃ | N | |
| CH₃ | 4-SCH₂CH₃ | H | CO₂CH₂CH₃ | OCH₃ | OCH₃ | N | |
| CH₃ | 4-SCH₂CH₃ | H | CO₂CH₂CH₃ | CH₃ | OCH₃ | CH | |
| CH₃ | 4-SCH₂CH₃ | H | CO₂CH₂CH₃ | OCH₃ | OCH₃ | CH | |
| CH₃ | 4-SCH₂CH₂CH₃ | H | CO₂CH₂CH₃ | CH₃ | OCH₃ | N | |
| CH₃ | 4-SCH₂CH₂CH₃ | H | CO₂CH₂CH₃ | OCH₃ | OCH₃ | N | |
| CH₃ | 4-SCH₂CH₂CH₃ | H | CO₂CH₂CH₃ | CH₃ | OCH₃ | CH | |
| CH₃ | 4-SCH₂CH₂CH₃ | H | CO₂CH₂CH₃ | OCH₃ | OCH₃ | CH | |
| CH₃ | 4-SCH₃ | H | C(O)N(CH₃)₂ | CH₃ | OCH₃ | N | |
| CH₃ | 4-SCH₃ | H | C(O)N(CH₃)₂ | OCH₃ | OCH₃ | N | |
| CH₃ | 4-SCH₃ | H | C(O)N(CH₃)₂ | CH₃ | OCH₃ | CH | |
| CH₃ | 4-SCH₃ | H | C(O)N(CH₃)₂ | OCH₃ | OCH₃ | CH | |
| CH₃ | 4-SCH₂CH₃ | H | C(O)N(CH₃)₂ | CH₃ | OCH₃ | N | |
| CH₃ | 4-SCH₂CH₃ | H | C(O)N(CH₃)₂ | OCH₃ | OCH₃ | N | |
| CH₃ | 4-SCH₂CH₃ | H | C(O)N(CH₃)₂ | CH₃ | OCH₃ | CH | |
| CH₃ | 4-SCH₂CH₃ | H | C(O)N(CH₃)₂ | OCH₃ | OCH₃ | CH | |
| CH₃ | 4-SCH₂CH₂CH₃ | H | C(O)N(CH₃)₂ | CH₃ | OCH₃ | N | |
| CH₃ | 4-SCH₂CH₂CH₃ | H | C(O)N(CH₃)₂ | OCH₃ | OCH₃ | N | |
| CH₃ | 4-SCH₂CH₂CH₃ | H | C(O)N(CH₃)₂ | CH₃ | OCH₃ | CH | |
| CH₃ | 4-SCH₂CH₂CH₃ | H | C(O)N(CH₃)₂ | OCH₂ | OCH₃ | CH | |
| CH₃ | 4-SCH₃ | H | SCH₃ | CH₃ | OCH₃ | N | |
| CH₃ | 4-SCH₃ | H | SCH₃ | OCH₃ | OCH₃ | N | |
| CH₃ | 4-SCH₃ | H | SCH₃ | CH₃ | OCH₃ | CH | |
| CH₃ | 4-SCH₃ | H | SCH₃ | OCH₃ | OCH₃ | CH | |
| CH₃ | 4-SCH₂CH₃ | H | SCH₃ | CH₃ | OCH₃ | N | |
| CH₃ | 4-SCH₂CH₃ | H | SCH₃ | OCH₃ | OCH₃ | N | |
| CH₃ | 4-SCH₂CH₃ | H | SCH₃ | CH₃ | OCH₃ | CH | |
| CH₃ | 4-SCH₂CH₃ | H | SCH₃ | OCH₃ | OCH₃ | CH | |
| CH₃ | 4-SCH₂CH₂CH₃ | H | SCH₃ | CH₃ | OCH₃ | N | |
| CH₃ | 4-SCH₂CH₂CH₃ | H | SCH₃ | OCH₃ | OCH₃ | N | |
| CH₃ | 4-SCH₂CH₂CH₃ | H | SCH₃ | CH₃ | OCH₃ | CH | |
| CH₃ | 4-SCH₂CH₂CH₃ | H | SCH₃ | OCH₃ | OCH₃ | CH | |
| CH₃ | 4-SCH₃ | H | SCH₂CH₃ | CH₃ | OCH₃ | N | |
| CH₃ | 4-SCH₃ | H | SCH₂CH₃ | OCH₃ | OCH₃ | N | |
| CH₃ | 4-SCH₃ | H | SCH₂CH₃ | CH₃ | OCH₃ | CH | |
| CH₃ | 4-SCH₃ | H | SCH₂CH₃ | OCH₃ | OCH₃ | CH | |
| CH₃ | 4-SCH₂CH₃ | H | SCH₂CH₃ | CH₃ | OCH₃ | N | |
| CH₃ | 4-SCH₂CH₃ | H | SCH₂CH₃ | OCH₃ | OCH₃ | N | |
| CH₃ | 4-SCH₂CH₃ | H | SCH₂CH₃ | CH₃ | OCH₃ | CH | |
| CH₃ | 4-SCH₂CH₃ | H | SCH₂CH₃ | OCH₃ | OCH₃ | CH | |
| CH₃ | 4-SCH₂CH₂CH₃ | H | SCH₂CH₃ | CH₃ | OCH₃ | N | |
| CH₃ | 4-SCH₂CH₂CH₃ | H | SCH₂CH₃ | OCH₃ | OCH₃ | N | |
| CH₃ | 4-SCH₂CH₂CH₃ | H | SCH₂CH₃ | CH₃ | OCH₃ | CH | |
| CH₃ | 4-SCH₂CH₂CH₃ | H | SCH₂CH₃ | OCH₃ | OCH₃ | CH | |
| CH₃ | 4-SCH₃ | H | S(O)₂CH₃ | CH₃ | OCH₃ | N | |
| CH₃ | 4-SCH₃ | H | S(O)₂CH₃ | OCH₃ | OCH₃ | N | |
| CH₃ | 4-SCH₃ | H | S(O)₂CH₃ | CH₃ | OCH₃ | CH | |

TABLE IIb-continued

General Formula IIb

| R | R₁ | Rₓ | Q₂ | X | Y | Z | m.p.(°C.) |
|---|---|---|---|---|---|---|---|
| CH₃ | 4-SCH₃ | H | S(O)₂CH₃ | OCH₃ | OCH₃ | CH | |
| CH₃ | 4-S(O)CH₃ | H | S(O)₂CH₃ | CH₃ | OCH₃ | N | |
| CH₃ | 4-S(O)CH₃ | H | S(O)₂CH₃ | OCH₃ | OCH₃ | N | |
| CH₃ | 4-S(O)CH₃ | H | S(O)₂CH₃ | CH₃ | OCH₃ | CH | |
| CH₃ | 4-S(O)CH₃ | H | S(O)₂CH₃ | OCH₃ | OCH₃ | CH | |
| CH₃ | 4-S(O)₂CH₃ | H | S(O)₂CH₃ | CH₃ | OCH₃ | N | |
| CH₃ | 4-S(O)₂CH₃ | H | S(O)₂CH₃ | OCH₃ | OCH₃ | N | |
| CH₃ | 4-S(O)₂CH₃ | H | S(O)₂CH₃ | CH₃ | OCH₃ | CH | |
| CH₃ | 4-S(O)₂CH₃ | H | S(O)₂CH₃ | OCH₃ | OCH₃ | CH | |
| CH₃ | 4-SCH₃ | H | CHO | CH₃ | OCH₃ | N | |
| CH₃ | 4-SCH₃ | H | CHO | OCH₃ | OCH₃ | N | |
| CH₃ | 4-SCH₃ | H | CHO | CH₃ | OCH₃ | CH | |
| CH₃ | 4-SCH₃ | H | CHO | OCH₃ | OCH₃ | CH | |
| CH₃ | 4-SCH₂CH₃ | H | CHO | CH₃ | OCH₃ | N | |
| CH₃ | 4-SCH₂CH₃ | H | CHO | OCH₃ | OCH₃ | N | |
| CH₃ | 4-SCH₂CH₃ | H | CHO | CH₃ | OCH₃ | CH | |
| CH₃ | 4-SCH₂CH₃ | H | CHO | OCH₃ | OCH₃ | CH | |
| CH₃ | 4-SCH₂CH₂CH₃ | H | CHO | CH₃ | OCH₃ | N | |
| CH₃ | 4-SCH₂CH₂CH₃ | H | CHO | OCH₃ | OCH₃ | N | |
| CH₃ | 4-SCH₂CH₂CH₃ | H | CHO | CH₃ | OCH₃ | CH | |
| CH₃ | 4-SCH₂CH₂CH₃ | H | CHO | OCH₃ | OCH₃ | CH | |
| CH₃ | 4-SCH₃ | H | CH=NOH | CH₃ | OCH₃ | N | |
| CH₃ | 4-SCH₃ | H | CH=NOH | OCH₃ | OCH₃ | N | |
| CH₃ | 4-SCH₃ | H | CH=NOH | CH₃ | OCH₃ | CH | |
| CH₃ | 4-SCH₃ | H | CH=NOH | OCH₃ | OCH₃ | CH | |
| CH₃ | 4-SCH₂CH₃ | H | CH=NOH | CH₃ | OCH₃ | N | |
| CH₃ | 4-SCH₂CH₃ | H | CH=NOH | OCH₃ | OCH₃ | N | |
| CH₃ | 4-SCH₂CH₃ | H | CH=NOH | CH₃ | OCH₃ | CH | |
| CH₃ | 4-SCH₂CH₃ | H | CH=NOH | OCH₃ | OCH₃ | CH | |
| CH₃ | 4-SCH₂CH₂CH₃ | H | CH=NOH | CH₃ | OCH₃ | N | |
| CH₃ | 4-SCH₂CH₂CH₃ | H | CH=NOH | OCH₃ | OCH₃ | N | |
| CH₃ | 4-SCH₂CH₂CH₃ | H | CH=NOH | CH₃ | OCH₃ | CH | |
| CH₃ | 4-SCH₂CH₂CH₃ | H | CH=NOH | OCH₃ | OCH₃ | CH | |

TABLE IIIb

General Formula IIIb

| R | R₁ | Rₓ | Q₂ | X | Y | Z | m.p. (°C.) |
|---|---|---|---|---|---|---|---|
| H | 2-SCH₃ | H | CO₂CH₃ | CH₃ | CH₃ | CH | |
| H | 2-SCH₃ | H | CO₂CH₃ | CH₃ | OCH₃ | CH | |
| H | 2-SCH₃ | H | CO₂CH₃ | OCH₃ | OCH₃ | CH | |
| H | 2-SCH₃ | H | CO₂CH₃ | CH₃ | OCH₃ | N | |
| H | 2-SCH₃ | H | CO₂CH₃ | OCH₃ | OCH₃ | N | |
| H | 2-SCH₃ | H | CO₂CH₃ | Cl | OCH₃ | CH | |
| H | 2-SCH₂CH₃ | H | CO₂CH₃ | CH₃ | CH₃ | CH | |
| H | 2-SCH₂CH₃ | H | CO₂CH₃ | CH₃ | OCH₃ | CH | |
| H | 2-SCH₂CH₃ | H | CO₂CH₃ | OCH₃ | OCH₃ | CH | |
| H | 2-SCH₂CH₃ | H | CO₂CH₃ | CH₃ | OCH₃ | N | |
| H | 2-SCH₂CH₃ | H | CO₂CH₃ | OCH₃ | OCH₃ | N | |
| H | 2-SCH₂CH₃ | H | CO₂CH₃ | Cl | OCH₃ | CH | |
| H | 2-SCH₂CH₂CH₃ | H | CO₂CH₃ | CH₃ | CH₃ | CH | |
| H | 2-SCH₂CH₂CH₃ | H | CO₂CH₃ | CH₃ | OCH₃ | CH | |
| H | 2-SCH₂CH₂CH₃ | H | CO₂CH₃ | OCH₃ | OCH₃ | CH | |
| H | 2-SCH₂CH₂CH₃ | H | CO₂CH₃ | CH₃ | OCH₃ | N | |
| H | 2-SCH₂CH₂CH₃ | H | CO₂CH₃ | OCH₃ | OCH₃ | N | |
| H | 2-SCH₂CH₂CH₃ | H | CO₂CH₃ | Cl | OCH₃ | CH | |
| H | 2-S(O)CH₃ | H | CO₂CH₃ | CH₃ | CH₃ | CH | |
| H | 2-S(O)CH₃ | H | CO₂CH₃ | CH₃ | OCH₃ | CH | |
| H | 2-S(O)CH₃ | H | CO₂CH₃ | OCH₃ | OCH₃ | CH | |
| H | 2-S(O)CH₃ | H | CO₂CH₃ | CH₃ | OCH₃ | N | |
| H | 2-S(O)CH₃ | H | CO₂CH₃ | OCH₃ | OCH₃ | N | |
| H | 2-S(O)CH₃ | H | CO₂CH₃ | Cl | OCH₃ | CH | |
| H | 2-S(O)₂CH₃ | H | CO₂CH₃ | CH₃ | CH₃ | CH | |
| H | 2-S(O)₂CH₃ | H | CO₂CH₃ | CH₃ | OCH₃ | CH | |
| H | 2-S(O)₂CH₃ | H | CO₂CH₃ | OCH₃ | OCH₃ | CH | |
| H | 2-S(O)₂CH₃ | H | CO₂CH₃ | CH₃ | OCH₃ | N | |
| H | 2-S(O)₂CH₃ | H | CO₂CH₃ | OCH₃ | OCH₃ | N | |
| H | 2-S(O)₂CH₃ | H | CO₂CH₃ | Cl | OCH₃ | CH | |
| H | 5-SCH₃ | H | CO₂CH₃ | CH₃ | CH₃ | CH | |
| H | 5-SCH₃ | H | CO₂CH₃ | CH₃ | OCH₃ | CH | |
| H | 5-SCH₃ | H | CO₂CH₃ | OCH₃ | OCH₃ | CH | |
| H | 5-SCH₃ | H | CO₂CH₃ | CH₃ | OCH₃ | N | |
| H | 5-SCH₃ | H | CO₂CH₃ | OCH₃ | OCH₃ | N | |
| H | 5-SCH₃ | H | CO₂CH₃ | Cl | OCH₃ | CH | |
| H | 5-S(O)CH₃ | H | CO₂CH₃ | CH₃ | CH₃ | CH | |
| H | 5-S(O)CH₃ | H | CO₂CH₃ | CH₃ | OCH₃ | CH | |
| H | 5-S(O)CH₃ | H | CO₂CH₃ | OCH₃ | OCH₃ | CH | |
| H | 5-S(O)CH₃ | H | CO₂CH₃ | CH₃ | OCH₃ | N | |

TABLE IIIb-continued

General Formula IIIb

| R | R₁ | Rₓ | Q₂ | X | Y | Z | m.p. (°C.) |
|---|----|----|----|---|---|---|---|
| H | 5-S(O)CH₃ | H | CO₂CH₃ | OCH₃ | OCH₃ | N | |
| H | 5-S(O)CH₃ | H | CO₂CH₃ | Cl | OCH₃ | CH | |
| H | 5-S(O)₂CH₃ | H | CO₂CH₃ | CH₃ | CH₃ | CH | |
| H | 5-S(O)₂CH₃ | H | CO₂CH₃ | CH₃ | OCH₃ | CH | |
| H | 5-S(O)₂CH₃ | H | CO₂CH₃ | OCH₃ | OCH₃ | CH | |
| H | 5-S(O)₂CH₃ | H | CO₂CH₃ | CH₃ | OCH₃ | N | |
| H | 5-S(O)₂CH₃ | H | CO₂CH₃ | OCH₃ | OCH₃ | N | |
| H | 5-S(O)₂CH₃ | H | CO₂CH₃ | Cl | OCH₃ | CH | |
| H | 5-SCH₂CH₃ | H | CO₂CH₃ | CH₃ | CH₃ | CH | |
| H | 5-SCH₂CH₃ | H | CO₂CH₃ | CH₃ | OCH₃ | CH | |
| H | 5-SCH₂CH₃ | H | CO₂CH₃ | OCH₃ | OCH₃ | CH | |
| H | 5-SCH₂CH₃ | H | CO₂CH₃ | CH₃ | OCH₃ | N | |
| H | 5-SCH₂CH₃ | H | CO₂CH₃ | OCH₃ | OCH₃ | N | |
| H | 5-SCH₂CH₃ | H | CO₂CH₃ | Cl | OCH₃ | CH | |
| H | 5-S(O)CH₂CH₃ | H | CO₂CH₃ | CH₃ | CH₃ | CH | |
| H | 5-S(O)CH₂CH₃ | H | CO₂CH₃ | CH₃ | OCH₃ | CH | |
| H | 5-S(O)CH₂CH₃ | H | CO₂CH₃ | OCH₃ | OCH₃ | CH | |
| H | 5-S(O)CH₂CH₃ | H | CO₂CH₃ | CH₃ | OCH₃ | N | |
| H | 5-S(O)CH₂CH₃ | H | CO₂CH₃ | OCH₃ | OCH₃ | N | |
| H | 5-S(O)CH₂CH₃ | H | CO₂CH₃ | Cl | OCH₃ | CH | |
| H | 5-S(O)₂CH₂CH₃ | H | CO₂CH₃ | CH₃ | CH₃ | CH | |
| H | 5-S(O)₂CH₂CH₃ | H | CO₂CH₃ | CH₃ | OCH₃ | CH | |
| H | 5-S(O)₂CH₂CH₃ | H | CO₂CH₃ | OCH₃ | OCH₃ | CH | |
| H | 5-S(O)₂CH₂CH₃ | H | CO₂CH₃ | CH₃ | OCH₃ | N | |
| H | 5-S(O)₂CH₂CH₃ | H | CO₂CH₃ | OCH₃ | OCH₃ | N | |
| H | 5-S(O)₂CH₂CH₃ | H | CO₂CH₃ | Cl | OCH₃ | CH | |
| H | 5-SCH₂CH₂CH₃ | H | CO₂CH₃ | CH₃ | CH₃ | CH | |
| H | 5-SCH₂CH₂CH₃ | H | CO₂CH₃ | CH₃ | OCH₃ | CH | |
| H | 5-SCH₂CH₂CH₃ | H | CO₂CH₃ | OCH₃ | OCH₃ | CH | |
| H | 5-SCH₂CH₂CH₃ | H | CO₂CH₃ | CH₃ | OCH₃ | N | |
| H | 5-SCH₂CH₂CH₃ | H | CO₂CH₃ | OCH₃ | OCH₃ | N | |
| H | 5-SCH₂CH₂CH₃ | H | CO₂CH₃ | Cl | OCH₃ | CH | |
| H | 5-S(O)CH₂CH₂CH₃ | H | CO₂CH₃ | CH₃ | CH₃ | CH | |
| H | 5-S(O)CH₂CH₂CH₃ | H | CO₂CH₃ | CH₃ | OCH₃ | CH | |
| H | 5-S(O)CH₂CH₂CH₃ | H | CO₂CH₃ | OCH₃ | OCH₃ | CH | |
| H | 5-S(O)CH₂CH₂CH₃ | H | CO₂CH₃ | CH₃ | OCH₃ | N | |
| H | 5-S(O)CH₂CH₂CH₃ | H | CO₂CH₃ | OCH₃ | OCH₃ | N | |
| H | 5-S(O)CH₂CH₂CH₃ | H | CO₂CH₃ | Cl | OCH₃ | CH | |
| H | 5-S(O)₂CH₂CH₂CH₃ | H | CO₂CH₃ | CH₃ | CH₃ | CH | |
| H | 5-S(O)₂CH₂CH₂CH₃ | H | CO₂CH₃ | CH₃ | OCH₃ | CH | |
| H | 5-S(O)₂CH₂CH₂CH₃ | H | CO₂CH₃ | OCH₃ | OCH₃ | CH | |
| H | 5-S(O)₂CH₂CH₂CH₃ | H | CO₂CH₃ | CH₃ | OCH₃ | N | |
| H | 5-S(O)₂CH₂CH₂CH₃ | H | CO₂CH₃ | OCH₃ | OCH₃ | N | |
| H | 5-S(O)₂CH₂CH₂CH₃ | H | CO₂CH₃ | Cl | OCH₃ | CH | |
| H | 5-SCH(CH₃)₂ | H | CO₂CH₃ | CH₃ | CH₃ | CH | |
| H | 5-SCH(CH₃)₂ | H | CO₂CH₃ | CH₃ | OCH₃ | CH | |
| H | 5-SCH(CH₃)₂ | H | CO₂CH₃ | OCH₃ | OCH₃ | CH | |
| H | 5-SCH(CH₃)₂ | H | CO₂CH₃ | CH₃ | OCH₃ | N | |
| H | 5-SCH(CH₃)₂ | H | CO₂CH₃ | OCH₃ | OCH₃ | N | |
| H | 5-SCH(CH₃)₂ | H | CO₂CH₃ | Cl | OCH₃ | CH | |
| H | 5-S(O)CH(CH₃)₂ | H | CO₂CH₃ | CH₃ | CH₃ | CH | |
| H | 5-S(O)CH(CH₃)₂ | H | CO₂CH₃ | CH₃ | OCH₃ | CH | |
| H | 5-S(O)CH(CH₃)₂ | H | CO₂CH₃ | OCH₃ | OCH₃ | CH | |
| H | 5-S(O)CH(CH₃)₂ | H | CO₂CH₃ | CH₃ | OCH₃ | N | |
| H | 5-S(O)CH(CH₃)₂ | H | CO₂CH₃ | OCH₃ | OCH₃ | N | |
| H | 5-S(O)CH(CH₃)₂ | H | CO₂CH₃ | Cl | OCH₃ | CH | |
| H | 5-S(O)₂CH(CH₃)₂ | H | CO₂CH₃ | CH₃ | CH₃ | CH | |
| H | 5-S(O)₂CH(CH₃)₂ | H | CO₂CH₃ | CH₃ | OCH₃ | CH | |
| H | 5-S(O)₂CH(CH₃)₂ | H | CO₂CH₃ | OCH₃ | OCH₃ | CH | |
| H | 5-S(O)₂CH(CH₃)₂ | H | CO₂CH₃ | CH₃ | OCH₃ | N | |
| H | 5-S(O)₂CH(CH₃)₂ | H | CO₂CH₃ | OCH₃ | OCH₃ | N | |
| H | 5-S(O)₂CH(CH₃)₂ | H | CO₂CH₃ | Cl | OCH₃ | CH | |
| H | 2-SO₂N(CH₃)₂ | H | CO₂CH₃ | CH₃ | CH₃ | CH | |
| H | 2-SO₂N(CH₃)₂ | H | CO₂CH₃ | CH₃ | OCH₃ | CH | |
| H | 2-SO₂N(CH₃)₂ | H | CO₂CH₃ | OCH₃ | OCH₃ | CH | |
| H | 2-SO₂N(CH₃)₂ | H | CO₂CH₃ | CH₃ | OCH₃ | N | |
| H | 2-SO₂N(CH₃)₂ | H | CO₂CH₃ | OCH₃ | OCH₃ | N | |
| H | 2-SO₂N(CH₃)₂ | H | CO₂CH₃ | Cl | OCH₃ | CH | |
| H | 2-CO₂CH₃ | H | CO₂CH₃ | CH₃ | CH₃ | CH | |
| H | 2-CO₂CH₃ | H | CO₂CH₃ | CH₃ | OCH₃ | CH | |
| H | 2-CO₂CH₃ | H | CO₂CH₃ | OCH₃ | OCH₃ | CH | |
| H | 2-CO₂CH₃ | H | CO₂CH₃ | CH₃ | OCH₃ | N | |
| H | 2-CO₂CH₃ | H | CO₂CH₃ | OCH₃ | OCH₃ | N | |
| H | 2-CO₂CH₃ | H | CO₂CH₃ | Cl | OCH₃ | CH | |
| H | 2-C(O)N(CH₃)₂ | H | CO₂CH₃ | CH₃ | CH₃ | CH | |
| H | 2-C(O)N(CH₃)₂ | H | CO₂CH₃ | CH₃ | OCH₃ | CH | |
| H | 2-C(O)N(CH₃)₂ | H | CO₂CH₃ | OCH₃ | OCH₃ | CH | |
| H | 2-C(O)N(CH₃)₂ | H | CO₂CH₃ | CH₃ | OCH₃ | N | |
| H | 2-C(O)N(CH₃)₂ | H | CO₂CH₃ | OCH₃ | OCH₃ | N | |
| H | 2-C(O)N(CH₃)₂ | H | CO₂CH₃ | Cl | OCH₃ | CH | |

TABLE IIIb-continued

General Formula IIIb

| R | R$_1$ | R$_x$ | Q$_2$ | X | Y | Z | m.p. (°C.) |
|---|---|---|---|---|---|---|---|
| H | 5-SCH$_3$ | H | CO$_2$CH$_2$CH$_3$ | CH$_3$ | CH$_3$ | CH | |
| H | 5-SCH$_3$ | H | CO$_2$CH$_2$CH$_3$ | CH$_3$ | OCH$_3$ | CH | |
| H | 5-SCH$_3$ | H | CO$_2$CH$_2$CH$_3$ | OCH$_3$ | OCH$_3$ | CH | |
| H | 5-SCH$_3$ | H | CO$_2$CH$_2$CH$_3$ | CH$_3$ | OCH$_3$ | N | |
| H | 5-SCH$_3$ | H | CO$_2$CH$_2$CH$_3$ | OCH$_3$ | OCH$_3$ | N | |
| H | 5-SCH$_3$ | H | CO$_2$CH$_2$CH$_3$ | Cl | OCH$_3$ | CH | |
| H | 5-SCH$_2$CH$_3$ | H | CO$_2$CH$_2$CH$_3$ | CH$_3$ | CH$_3$ | CH | |
| H | 5-SCH$_2$CH$_3$ | H | CO$_2$CH$_2$CH$_3$ | CH$_3$ | OCH$_3$ | CH | |
| H | 5-SCH$_2$CH$_3$ | H | CO$_2$CH$_2$CH$_3$ | OCH$_3$ | OCH$_3$ | CH | |
| H | 5-SCH$_2$CH$_3$ | H | CO$_2$CH$_2$CH$_3$ | CH$_3$ | OCH$_3$ | N | |
| H | 5-SCH$_2$CH$_3$ | H | CO$_2$CH$_2$CH$_3$ | OCH$_3$ | OCH$_3$ | N | |
| H | 5-SCH$_2$CH$_3$ | H | CO$_2$CH$_2$CH$_3$ | Cl | OCH$_3$ | CH | |
| H | 5-SCH$_2$CH$_2$CH$_3$ | H | CO$_2$CH$_2$CH$_3$ | CH$_3$ | CH$_3$ | CH | |
| H | 5-SCH$_2$CH$_2$CH$_3$ | H | CO$_2$CH$_2$CH$_3$ | CH$_3$ | OCH$_3$ | CH | |
| H | 5-SCH$_2$CH$_2$CH$_3$ | H | CO$_2$CH$_2$CH$_3$ | OCH$_3$ | OCH$_3$ | CH | |
| H | 5-SCH$_2$CH$_2$CH$_3$ | H | CO$_2$CH$_2$CH$_3$ | CH$_3$ | OCH$_3$ | N | |
| H | 5-SCH$_2$CH$_2$CH$_3$ | H | CO$_2$CH$_2$CH$_3$ | OCH$_3$ | OCH$_3$ | N | |
| H | 5-SCH$_2$CH$_2$CH$_3$ | H | CO$_2$CH$_2$CH$_3$ | Cl | OCH$_3$ | CH | |
| H | 5-S(O)CH$_3$ | H | CO$_2$CH$_2$CH$_3$ | CH$_3$ | CH$_3$ | CH | |
| H | 5-S(O)CH$_3$ | H | CO$_2$CH$_2$CH$_3$ | CH$_3$ | OCH$_3$ | CH | |
| H | 5-S(O)CH$_3$ | H | CO$_2$CH$_2$CH$_3$ | OCH$_3$ | OCH$_3$ | CH | |
| H | 5-S(O)CH$_3$ | H | CO$_2$CH$_2$CH$_3$ | CH$_3$ | OCH$_3$ | N | |
| H | 5-S(O)CH$_3$ | H | CO$_2$CH$_2$CH$_3$ | OCH$_3$ | OCH$_3$ | N | |
| H | 5-S(O)CH$_3$ | H | CO$_2$CH$_2$CH$_3$ | Cl | OCH$_3$ | CH | |
| H | 5-S(O)$_2$CH$_3$ | H | CO$_2$CH$_2$CH$_3$ | CH$_3$ | CH$_3$ | CH | |
| H | 5-S(O)$_2$CH$_3$ | H | CO$_2$CH$_2$CH$_3$ | CH$_3$ | OCH$_3$ | CH | |
| H | 5-S(O)$_2$CH$_3$ | H | CO$_2$CH$_2$CH$_3$ | OCH$_3$ | OCH$_3$ | CH | |
| H | 5-S(O)$_2$CH$_3$ | H | CO$_2$CH$_2$CH$_3$ | CH$_3$ | OCH$_3$ | N | |
| H | 5-S(O)$_2$CH$_3$ | H | CO$_2$CH$_2$CH$_3$ | OCH$_3$ | OCH$_3$ | N | |
| H | 5-S(O)$_2$CH$_3$ | H | CO$_2$CH$_2$CH$_3$ | Cl | OCH$_3$ | CH | |
| H | 5-SCH$_3$ | H | CHO | CH$_3$ | CH$_3$ | CH | |
| H | 5-SCH$_3$ | H | CHO | CH$_3$ | OCH$_3$ | CH | |
| H | 5-SCH$_3$ | H | CHO | OCH$_3$ | OCH$_3$ | CH | |
| H | 5-SCH$_3$ | H | CHO | CH$_3$ | OCH$_3$ | N | |
| H | 5-SCH$_3$ | H | CHO | OCH$_3$ | OCH$_3$ | N | |
| H | 5-SCH$_3$ | H | CHO | Cl | OCH$_3$ | CH | |
| H | 5-SCH$_2$CH$_3$ | H | CHO | CH$_3$ | CH$_3$ | CH | |
| H | 5-SCH$_2$CH$_3$ | H | CHO | CH$_3$ | OCH$_3$ | CH | |
| H | 5-SCH$_2$CH$_3$ | H | CHO | OCH$_3$ | OCH$_3$ | CH | |
| H | 5-SCH$_2$CH$_3$ | H | CHO | CH$_3$ | OCH$_3$ | N | |
| H | 5-SCH$_2$CH$_3$ | H | CHO | OCH$_3$ | OCH$_3$ | N | |
| H | 5-SCH$_2$CH$_3$ | H | CHO | Cl | OCH$_3$ | CH | |
| H | 5-SCH$_2$CH$_2$CH$_3$ | H | CHO | CH$_3$ | CH$_3$ | CH | |
| H | 5-SCH$_2$CH$_2$CH$_3$ | H | CHO | CH$_3$ | OCH$_3$ | CH | |
| H | 5-SCH$_2$CH$_2$CH$_3$ | H | CHO | OCH$_3$ | OCH$_3$ | CH | |
| H | 5-SCH$_2$CH$_2$CH$_3$ | H | CHO | CH$_3$ | OCH$_3$ | N | |
| H | 5-SCH$_2$CH$_2$CH$_3$ | H | CHO | OCH$_3$ | OCH$_3$ | N | |
| H | 5-SCH$_2$CH$_2$CH$_3$ | H | CHO | Cl | OCH$_3$ | CH | |
| H | 2-CO$_2$CH$_3$ | H | CHO | CH$_3$ | CH$_3$ | CH | |
| H | 2-CO$_2$CH$_3$ | H | CHO | CH$_3$ | OCH$_3$ | CH | |
| H | 2-CO$_2$CH$_3$ | H | CHO | OCH$_3$ | OCH$_3$ | CH | |
| H | 2-CO$_2$CH$_3$ | H | CHO | CH$_3$ | OCH$_3$ | N | |
| H | 2-CO$_2$CH$_3$ | H | CHO | OCH$_3$ | OCH$_3$ | N | |
| H | 2-CO$_2$CH$_3$ | H | CHO | Cl | OCH$_3$ | CH | |
| H | 2-C(O)N(CH$_3$)$_2$ | H | CHO | CH$_3$ | CH$_3$ | CH | |
| H | 2-C(O)N(CH$_3$)$_2$ | H | CHO | CH$_3$ | OCH$_3$ | CH | |
| H | 2-C(O)N(CH$_3$)$_2$ | H | CHO | OCH$_3$ | OCH$_3$ | CH | |
| H | 2-C(O)N(CH$_3$)$_2$ | H | CHO | CH$_3$ | OCH$_3$ | N | |
| H | 2-C(O)N(CH$_3$)$_2$ | H | CHO | OCH$_3$ | OCH$_3$ | N | |
| H | 2-C(O)N(CH$_3$)$_2$ | H | CHO | Cl | OCH$_3$ | CH | |
| H | 5-SCH$_3$ | H | C(O)N(CH$_3$)$_2$ | CH$_3$ | CH$_3$ | CH | |
| H | 5-SCH$_3$ | H | C(O)N(CH$_3$)$_2$ | CH$_3$ | OCH$_3$ | CH | |
| H | 5-SCH$_3$ | H | C(O)N(CH$_3$)$_2$ | OCH$_3$ | OCH$_3$ | CH | |
| H | 5-SCH$_3$ | H | C(O)N(CH$_3$)$_2$ | CH$_3$ | OCH$_3$ | N | |
| H | 5-SCH$_3$ | H | C(O)N(CH$_3$)$_2$ | OCH$_3$ | OCH$_3$ | N | |
| H | 5-SCH$_3$ | H | C(O)N(CH$_3$)$_2$ | Cl | OCH$_3$ | CH | |
| H | 5-SCH$_2$CH$_3$ | H | C(O)N(CH$_3$)$_2$ | CH$_3$ | CH$_3$ | CH | |
| H | 5-SCH$_2$CH$_3$ | H | C(O)N(CH$_3$)$_2$ | CH$_3$ | OCH$_3$ | CH | |
| H | 5-SCH$_2$CH$_3$ | H | C(O)N(CH$_3$)$_2$ | OCH$_3$ | OCH$_3$ | CH | |
| H | 5-SCH$_2$CH$_3$ | H | C(O)N(CH$_3$)$_2$ | CH$_3$ | OCH$_3$ | N | |
| H | 5-SCH$_2$CH$_3$ | H | C(O)N(CH$_3$)$_2$ | OCH$_3$ | OCH$_3$ | N | |
| H | 5-SCH$_2$CH$_3$ | H | C(O)N(CH$_3$)$_2$ | Cl | OCH$_3$ | CH | |
| H | 5-SCH$_2$CH$_2$CH$_3$ | H | C(O)N(CH$_3$)$_2$ | CH$_3$ | CH$_3$ | CH | |
| H | 5-SCH$_2$CH$_2$CH$_3$ | H | C(O)N(CH$_3$)$_2$ | CH$_3$ | OCH$_3$ | CH | |
| H | 5-SCH$_2$CH$_2$CH$_3$ | H | C(O)N(CH$_3$)$_2$ | OCH$_3$ | OCH$_3$ | CH | |
| H | 5-SCH$_2$CH$_2$CH$_3$ | H | C(O)N(CH$_3$)$_2$ | CH$_3$ | OCH$_3$ | N | |
| H | 5-SCH$_2$CH$_2$CH$_3$ | H | C(O)N(CH$_3$)$_2$ | OCH$_3$ | OCH$_3$ | N | |
| H | 5-SCH$_2$CH$_2$CH$_3$ | H | C(O)N(CH$_3$)$_2$ | Cl | OCH$_3$ | CH | |
| H | 2-CO$_2$CH$_3$ | H | C(O)N(CH$_3$)$_2$ | CH$_3$ | CH$_3$ | CH | |
| H | 2-CO$_2$CH$_3$ | H | C(O)N(CH$_3$)$_2$ | CH$_3$ | OCH$_3$ | CH | |

TABLE IIIb-continued

General Formula IIIb

| R | R₁ | Rₓ | Q₂ | X | Y | Z | m.p. (°C.) |
|---|---|---|---|---|---|---|---|
| H | 2-CO₂CH₃ | H | C(O)N(CH₃)₂ | OCH₃ | OCH₃ | CH | |
| H | 2-CO₂CH₃ | H | C(O)N(CH₃)₂ | CH₃ | OCH₃ | N | |
| H | 2-CO₂CH₃ | H | C(O)N(CH₃)₂ | OCH₃ | OCH₃ | N | |
| H | 2-CO₂CH₃ | H | C(O)N(CH₃)₂ | Cl | OCH₃ | CH | |
| H | 2-C(O)N(CH₃)₂ | H | C(O)N(CH₃)₂ | CH₃ | CH₃ | CH | |
| H | 2-C(O)N(CH₃)₂ | H | C(O)N(CH₃)₂ | CH₃ | OCH₃ | CH | |
| H | 2-C(O)N(CH₃)₂ | H | C(O)N(CH₃)₂ | OCH₃ | OCH₃ | CH | |
| H | 2-C(O)N(CH₃)₂ | H | C(O)N(CH₃)₂ | CH₃ | OCH₃ | N | |
| H | 2-C(O)N(CH₃)₂ | H | C(O)N(CH₃)₂ | OCH₃ | OCH₃ | N | |
| H | 2-C(O)N(CH₃)₂ | H | C(O)N(CH₃)₂ | Cl | OCH₃ | CH | |
| H | 5-SCH₃ | H | SCH₃ | CH₃ | CH₃ | CH | |
| H | 5-SCH₃ | H | SCH₃ | CH₃ | OCH₃ | CH | |
| H | 5-SCH₃ | H | SCH₃ | OCH₃ | OCH₃ | CH | |
| H | 5-SCH₃ | H | SCH₃ | CH₃ | OCH₃ | N | |
| H | 5-SCH₃ | H | SCH₃ | OCH₃ | OCH₃ | N | |
| H | 5-SCH₃ | H | SCH₃ | Cl | OCH₃ | CH | |
| H | 5-SCH₂CH₃ | H | SCH₂CH₃ | CH₃ | CH₃ | CH | |
| H | 5-SCH₂CH₃ | H | SCH₂CH₃ | CH₃ | OCH₃ | CH | |
| H | 5-SCH₂CH₃ | H | SCH₂CH₃ | OCH₃ | OCH₃ | CH | |
| H | 5-SCH₂CH₃ | H | SCH₂CH₃ | CH₃ | OCH₃ | N | |
| H | 5-SCH₂CH₃ | H | SCH₂CH₃ | OCH₃ | OCH₃ | N | |
| H | 5-SCH₂CH₃ | H | SCH₂CH₃ | Cl | OCH₃ | CH | |
| H | 5-SCH₂CH₂CH₃ | H | SCH₂CH₂CH₃ | CH₃ | CH₃ | CH | |
| H | 5-SCH₂CH₂CH₃ | H | SCH₂CH₂CH₃ | CH₃ | OCH₃ | CH | |
| H | 5-SCH₂CH₂CH₃ | H | SCH₂CH₂CH₃ | OCH₃ | OCH₃ | CH | |
| H | 5-SCH₂CH₂CH₃ | H | SCH₂CH₂CH₃ | CH₃ | OCH₃ | N | |
| H | 5-SCH₂CH₂CH₃ | H | SCH₂CH₂CH₃ | OCH₃ | OCH₃ | N | |
| H | 5-SCH₂CH₂CH₃ | H | SCH₂CH₂CH₃ | Cl | OCH₃ | CH | |
| H | 5-SCH₃ | H | CH=NOH | CH₃ | CH₃ | CH | |
| H | 5-SCH₃ | H | CH=NOH | CH₃ | OCH₃ | CH | |
| H | 5-SCH₃ | H | CH=NOH | OCH₃ | OCH₃ | CH | |
| H | 5-SCH₃ | H | CH=NOH | CH₃ | OCH₃ | N | |
| H | 5-SCH₃ | H | CH=NOH | OCH₃ | OCH₃ | N | |
| H | 5-SCH₃ | H | CH=NOH | Cl | OCH₃ | CH | |
| H | 5-SCH₂CH₃ | H | CH=NOH | CH₃ | CH₃ | CH | |
| H | 5-SCH₂CH₃ | H | CH=NOH | CH₃ | OCH₃ | CH | |
| H | 5-SCH₂CH₃ | H | CH=NOH | OCH₃ | OCH₃ | CH | |
| H | 5-SCH₂CH₃ | H | CH=NOH | CH₃ | OCH₃ | N | |
| H | 5-SCH₂CH₃ | H | CH=NOH | OCH₃ | OCH₃ | N | |
| H | 5-SCH₂CH₃ | H | CH=NOH | Cl | OCH₃ | CH | |
| H | 5-SCH₂CH₂CH₃ | H | CH=NOH | CH₃ | CH₃ | CH | |
| H | 5-SCH₂CH₂CH₃ | H | CH=NOH | CH₃ | OCH₃ | CH | |
| H | 5-SCH₂CH₂CH₃ | H | CH=NOH | OCH₃ | OCH₃ | CH | |
| H | 5-SCH₂CH₂CH₃ | H | CH=NOH | CH₃ | OCH₃ | N | |
| H | 5-SCH₂CH₂CH₃ | H | CH=NOH | OCH₃ | OCH₃ | N | |
| H | 5-SCH₂CH₂CH₃ | H | CH=NOH | Cl | OCH₃ | CH | |
| H | 5-CO₂CH₃ | H | CH=NOH | CH₃ | CH₃ | CH | |
| H | 5-CO₂CH₃ | H | CH=NOH | CH₃ | OCH₃ | CH | |
| H | 5-CO₂CH₃ | H | CH=NOH | OCH₃ | OCH₃ | CH | |
| H | 5-CO₂CH₃ | H | CH=NOH | CH₃ | OCH₃ | N | |
| H | 5-CO₂CH₃ | H | CH=NOH | OCH₃ | OCH₃ | N | |
| H | 5-CO₂CH₃ | H | CH=NOH | Cl | OCH₃ | CH | |
| CH₃ | 5-SCH₃ | H | CO₂CH₃ | CH₃ | OCH₃ | N | |
| CH₃ | 5-SCH₃ | H | CO₂CH₃ | OCH₃ | OCH₃ | N | |
| CH₃ | 5-SCH₃ | H | CO₂CH₃ | CH₃ | OCH₃ | CH | |
| CH₃ | 5-SCH₃ | H | CO₂CH₃ | OCH₃ | OCH₃ | CH | |
| CH₃ | 5-SCH₂CH₃ | H | CO₂CH₃ | CH₃ | OCH₃ | N | |
| CH₃ | 5-SCH₂CH₃ | H | CO₂CH₃ | OCH₃ | OCH₃ | N | |
| CH₃ | 5-SCH₂CH₃ | H | CO₂CH₃ | CH₃ | OCH₃ | CH | |
| CH₃ | 5-SCH₂CH₃ | H | CO₂CH₃ | OCH₃ | OCH₃ | CH | |
| CH₃ | 5-SCH₂CH₂CH₃ | H | CO₂CH₃ | CH₃ | OCH₃ | N | |
| CH₃ | 5-SCH₂CH₂CH₃ | H | CO₂CH₃ | OCH₃ | OCH₃ | N | |
| CH₃ | 5-SCH₂CH₂CH₃ | H | CO₂CH₃ | CH₃ | OCH₃ | CH | |
| CH₃ | 5-SCH₂CH₂CH₃ | H | CO₂CH₃ | OCH₃ | OCH₃ | CH | |
| CH₃ | 5-S(O)CH₃ | H | CO₂CH₃ | CH₃ | OCH₃ | N | |
| CH₃ | 5-S(O)CH₃ | H | CO₂CH₃ | OCH₃ | OCH₃ | N | |
| CH₃ | 5-S(O)CH₃ | H | CO₂CH₃ | CH₃ | OCH₃ | CH | |
| CH₃ | 5-S(O)CH₃ | H | CO₂CH₃ | OCH₃ | OCH₃ | CH | |
| CH₃ | 5-S(O)₂CH₃ | H | CO₂CH₃ | CH₃ | OCH₃ | N | |
| CH₃ | 5-S(O)₂CH₃ | H | CO₂CH₃ | OCH₃ | OCH₃ | N | |
| CH₃ | 5-S(O)₂CH₃ | H | CO₂CH₃ | CH₃ | OCH₃ | CH | |
| CH₃ | 5-S(O)₂CH₃ | H | CO₂CH₃ | OCH₃ | OCH₃ | CH | |
| CH₃ | 2-SO₂N(CH₃)₂ | H | CO₂CH₃ | CH₃ | OCH₃ | N | |
| CH₃ | 2-SO₂N(CH₃)₂ | H | CO₂CH₃ | OCH₃ | OCH₃ | N | |
| CH₃ | 2-SO₂N(CH₃)₂ | H | CO₂CH₃ | CH₃ | OCH₃ | CH | |
| CH₃ | 2-SO₂N(CH₃)₂ | H | CO₂CH₃ | OCH₃ | OCH₃ | CH | |
| CH₃ | 2-CO₂CH₃ | H | CO₂CH₃ | CH₃ | OCH₃ | N | |
| CH₃ | 2-CO₂CH₃ | H | CO₂CH₃ | OCH₃ | OCH₃ | N | |
| CH₃ | 2-CO₂CH₃ | H | CO₂CH₃ | CH₃ | OCH₃ | CH | |
| CH₃ | 2-CO₂CH₃ | H | CO₂CH₃ | OCH₃ | OCH₃ | CH | |

TABLE IIIb-continued

General Formula IIIb

| R | R₁ | Rₓ | Q₂ | X | Y | Z | m.p. (°C.) |
|---|---|---|---|---|---|---|---|
| CH₃ | 2-C(O)N(CH₃)₂ | H | CO₂CH₃ | CH₃ | OCH₃ | N | |
| CH₃ | 2-C(O)N(CH₃)₂ | H | CO₂CH₃ | OCH₃ | OCH₃ | N | |
| CH₃ | 2-C(O)N(CH₃)₂ | H | CO₂CH₃ | CH₃ | OCH₃ | CH | |
| CH₃ | 2-C(O)N(CH₃)₂ | H | CO₂CH₃ | OCH₃ | OCH₃ | CH | |
| CH₃ | 5-SCH₃ | H | CHO | CH₃ | OCH₃ | N | |
| CH₃ | 5-SCH₃ | H | CHO | OCH₃ | OCH₃ | N | |
| CH₃ | 5-SCH₃ | H | CHO | CH₃ | OCH₃ | CH | |
| CH₃ | 5-SCH₃ | H | CHO | OCH₃ | OCH₃ | CH | |
| CH₃ | 5-SCH₂CH₃ | H | CHO | CH₃ | OCH₃ | N | |
| CH₃ | 5-SCH₂CH₃ | H | CHO | OCH₃ | OCH₃ | N | |
| CH₃ | 5-SCH₂CH₃ | H | CHO | CH₃ | OCH₃ | CH | |
| CH₃ | 5-SCH₂CH₃ | H | CHO | OCH₃ | OCH₃ | CH | |
| CH₃ | 5-SCH₂CH₂CH₃ | H | CHO | CH₃ | OCH₃ | N | |
| CH₃ | 5-SCH₂CH₂CH₃ | H | CHO | OCH₃ | OCH₃ | N | |
| CH₃ | 5-SCH₂CH₂CH₃ | H | CHO | CH₃ | OCH₃ | CH | |
| CH₃ | 5-SCH₂CH₂CH₃ | H | CHO | OCH₃ | OCH₃ | CH | |
| CH₃ | 2-CO₂CH₃ | H | CHO | CH₃ | OCH₃ | N | |
| CH₃ | 2-CO₂CH₃ | H | CHO | OCH₃ | OCH₃ | N | |
| CH₃ | 2-CO₂CH₃ | H | CHO | CH₃ | OCH₃ | CH | |
| CH₃ | 2-CO₂CH₃ | H | CHO | OCH₃ | OCH₃ | CH | |
| CH₃ | 5-SCH₃ | H | C(O)N(CH₃)₂ | CH₃ | OCH₃ | N | |
| CH₃ | 5-SCH₃ | H | C(O)N(CH₃)₂ | OCH₃ | OCH₃ | N | |
| CH₃ | 5-SCH₃ | H | C(O)N(CH₃)₂ | CH₃ | OCH₃ | CH | |
| CH₃ | 5-SCH₃ | H | C(O)N(CH₃)₂ | OCH₃ | OCH₃ | CH | |
| CH₃ | 5-SCH₂CH₃ | H | C(O)N(CH₃)₂ | CH₃ | OCH₃ | N | |
| CH₃ | 5-SCH₂CH₃ | H | C(O)N(CH₃)₂ | OCH₃ | OCH₃ | N | |
| CH₃ | 5-SCH₂CH₃ | H | C(O)N(CH₃)₂ | CH₃ | OCH₃ | CH | |
| CH₃ | 5-SCH₂CH₃ | H | C(O)N(CH₃)₂ | OCH₃ | OCH₃ | CH | |
| CH₃ | 5-SCH₂CH₂CH₃ | H | C(O)N(CH₃)₂ | CH₃ | OCH₃ | N | |
| CH₃ | 5-SCH₂CH₂CH₃ | H | C(O)N(CH₃)₂ | OCH₃ | OCH₃ | N | |
| CH₃ | 5-SCH₂CH₂CH₃ | H | C(O)N(CH₃)₂ | CH₃ | OCH₃ | CH | |
| CH₃ | 5-SCH₂CH₂CH₃ | H | C(O)N(CH₃)₂ | OCH₃ | OCH₃ | CH | |
| CH₃ | 2-CO₂CH₃ | H | C(O)N(CH₃)₂ | CH₃ | OCH₃ | N | |
| CH₃ | 2-CO₂CH₃ | H | C(O)N(CH₃)₂ | OCH₃ | OCH₃ | N | |
| CH₃ | 2-CO₂CH₃ | H | C(O)N(CH₃)₂ | CH₃ | OCH₃ | CH | |
| CH₃ | 2-CO₂CH₃ | H | C(O)N(CH₃)₂ | OCH₃ | OCH₃ | CH | |
| CH₃ | 5-SCH₃ | H | CH=NOH | CH₃ | OCH₃ | N | |
| CH₃ | 5-SCH₃ | H | CH=NOH | OCH₃ | OCH₃ | N | |
| CH₃ | 5-SCH₃ | H | CH=NOH | CH₃ | OCH₃ | CH | |
| CH₃ | 5-SCH₃ | H | CH=NOH | OCH₃ | OCH₃ | CH | |
| CH₃ | 5-SCH₂CH₃ | H | CH=NOH | CH₃ | OCH₃ | N | |
| CH₃ | 5-SCH₂CH₃ | H | CH=NOH | OCH₃ | OCH₃ | N | |
| CH₃ | 5-SCH₂CH₃ | H | CH=NOH | CH₃ | OCH₃ | CH | |
| CH₃ | 5-SCH₂CH₃ | H | CH=NOH | OCH₃ | OCH₃ | CH | |
| CH₃ | 5-SCH₂CH₂CH₃ | H | CH=NOH | CH₃ | OCH₃ | N | |
| CH₃ | 5-SCH₂CH₂CH₃ | H | CH=NOH | OCH₃ | OCH₃ | N | |
| CH₃ | 5-SCH₂CH₂CH₃ | H | CH=NOH | CH₃ | OCH₃ | CH | |
| CH₃ | 5-SCH₂CH₂CH₃ | H | CH=NOH | OCH₃ | OCH₃ | CH | |
| CH₃ | 5-CO₂CH₃ | H | CH=NOH | CH₃ | OCH₃ | N | |
| CH₃ | 5-CO₂CH₃ | H | CH=NOH | OCH₃ | OCH₃ | N | |
| CH₃ | 5-CO₂CH₃ | H | CH=NOH | CH₃ | OCH₃ | CH | |
| CH₃ | 5-CO₂CH₃ | H | CH=NOH | OCH₃ | OCH₃ | CH | |

TABLE IVb

General Formula IVb

| R | R₁ | Rₓ | Q₂ | X | Y | m.p. (°C.) |
|---|---|---|---|---|---|---|
| H | 4-SCH₃ | H | CO₂CH₃ | CH₃ | O | |
| H | 4-SCH₃ | H | CO₂CH₃ | OCH₃ | O | |
| H | 4-SCH₃ | H | CO₂CH₃ | OCH₂CH₃ | O | |
| H | 4-SCH₃ | H | CO₂CH₃ | OCF₂H | O | |
| H | 4-SCH₃ | H | CO₂CH₃ | CH₃ | CH₂ | |
| H | 4-SCH₃ | H | CO₂CH₃ | OCH₃ | CH₂ | |
| H | 4-SCH₃ | H | CO₂CH₃ | OCH₂CH₃ | CH₂ | |
| H | 4-SCH₃ | H | CO₂CH₃ | OCF₂H | CH₂ | |
| H | 4-SCH₂CH₃ | H | CO₂CH₃ | CH₃ | O | |
| H | 4-SCH₂CH₃ | H | CO₂CH₃ | OCH₃ | O | |
| H | 4-SCH₂CH₃ | H | CO₂CH₃ | OCH₂CH₃ | O | |
| H | 4-SCH₂CH₃ | H | CO₂CH₃ | OCF₂H | O | |
| H | 4-SCH₂CH₃ | H | CO₂CH₃ | CH₃ | CH₂ | |
| H | 4-SCH₂CH₃ | H | CO₂CH₃ | OCH₃ | CH₂ | |
| H | 4-SCH₂CH₃ | H | CO₂CH₃ | OCH₂CH₃ | CH₂ | |
| H | 4-SCH₂CH₃ | H | CO₂CH₃ | OCF₂H | CH₂ | |
| H | 4-SCH₂CH₂CH₃ | H | CO₂CH₃ | CH₃ | O | |
| H | 4-SCH₂CH₂CH₃ | H | CO₂CH₃ | OCH₃ | O | |
| H | 4-SCH₂CH₂CH₃ | H | CO₂CH₃ | OCH₂CH₃ | O | |
| H | 4-SCH₂CH₂CH₃ | H | CO₂CH₃ | OCF₂H | O | |
| H | 4-SCH₂CH₂CH₃ | H | CO₂CH₃ | CH₃ | CH₂ | |
| H | 4-SCH₂CH₂CH₃ | H | CO₂CH₃ | OCH₃ | CH₂ | |
| H | 4-SCH₂CH₂CH₃ | H | CO₂CH₃ | OCH₂CH₃ | CH₂ | |
| H | 4-SCH₂CH₂CH₃ | H | CO₂CH₃ | OCF₂H | CH₂ | |
| H | 4-S(O)CH₂CH₂CH₃ | H | CO₂CH₃ | CH₃ | O | |
| H | 4-S(O)CH₂CH₂CH₃ | H | CO₂CH₃ | OCH₃ | O | |
| H | 4-S(O)CH₂CH₂CH₃ | H | CO₂CH₃ | OCH₂CH₃ | O | |
| H | 4-S(O)CH₂CH₂CH₃ | H | CO₂CH₃ | OCF₂H | O | |
| H | 4-S(O)CH₂CH₂CH₃ | H | CO₂CH₃ | CH₃ | CH₂ | |
| H | 4-S(O)CH₂CH₂CH₃ | H | CO₂CH₃ | OCH₃ | CH₂ | |
| H | 4-S(O)CH₂CH₂CH₃ | H | CO₂CH₃ | OCH₂CH₃ | CH₂ | |
| H | 4-S(O)CH₂CH₂CH₃ | H | CO₂CH₃ | OCF₂H | CH₂ | |
| H | 4-S(O)₂CH₂CH₂CH₃ | H | CO₂CH₃ | CH₃ | O | |
| H | 4-S(O)₂CH₂CH₂CH₃ | H | CO₂CH₃ | OCH₃ | O | |
| H | 4-S(O)₂CH₂CH₂CH₃ | H | CO₂CH₃ | OCH₂CH₃ | O | |
| H | 4-S(O)₂CH₂CH₂CH₃ | H | CO₂CH₃ | OCF₂H | O | |
| H | 4-S(O)₂CH₂CH₂CH₃ | H | CO₂CH₃ | CH₃ | CH₂ | |
| H | 4-S(O)₂CH₂CH₂CH₃ | H | CO₂CH₃ | OCH₃ | CH₂ | |
| H | 4-S(O)₂CH₂CH₂CH₃ | H | CO₂CH₃ | OCH₂CH₃ | CH₂ | |

TABLE IVb-continued

General Formula IVb

| R | R₁ | Rₓ | Q₂ | X | Y | m.p. (°C.) |
|---|---|---|---|---|---|---|
| H | 4-S(O)₂CH₂CH₂CH₃ | H | CO₂CH₃ | OCF₂H | CH₂ | |

TABLE Vb

General Formula Vb

| R | R₁ | Rₓ | Q₂ | X₁ | m.p. (°C.) |
|---|---|---|---|---|---|
| H | 4-SCH₃ | H | CO₂CH₃ | CH₃ | |
| H | 4-SCH₃ | H | CO₂CH₃ | OCH₃ | |
| H | 4-SCH₃ | H | CO₂CH₃ | OCF₂CH₃ | |
| H | 4-SCH₂CH₃ | H | CO₂CH₃ | CH₃ | |
| H | 4-SCH₂CH₃ | H | CO₂CH₃ | OCH₃ | |
| H | 4-SCH₂CH₃ | H | CO₂CH₃ | OCF₂CH₃ | |
| H | 4-S(O)CH₂CH₃ | H | CO₂CH₃ | CH₃ | |
| H | 4-S(O)CH₂CH₃ | H | CO₂CH₃ | OCH₃ | |
| H | 4-S(O)CH₂CH₃ | H | CO₂CH₃ | OCF₂CH₃ | |
| H | 4-S(O)₂CH₂CH₃ | H | CO₂CH₃ | CH₃ | |
| H | 4-S(O)₂CH₂CH₃ | H | CO₂CH₃ | OCH₃ | |
| H | 4-S(O)₂CH₂CH₃ | H | CO₂CH₃ | OCF₂CH₃ | |
| H | 4-SCH₂CH₂CH₃ | H | CO₂CH₃ | CH₃ | |
| H | 4-SCH₂CH₂CH₃ | H | CO₂CH₃ | OCH₃ | |
| H | 4-SCH₂CH₂CH₃ | H | CO₂CH₃ | OCF₂CH₃ | |
| H | 4-S(O)CH₂CH₂CH₃ | H | CO₂CH₃ | CH₃ | |
| H | 4-S(O)CH₂CH₂CH₃ | H | CO₂CH₃ | OCH₃ | |
| H | 4-S(O)CH₂CH₂CH₃ | H | CO₂CH₃ | OCF₂CH₃ | |
| H | 4-S(O)₂CH₂CH₂CH₃ | H | CO₂CH₃ | CH₃ | |
| H | 4-S(O)₂CH₂CH₂CH₃ | H | CO₂CH₃ | OCH₃ | |
| H | 4-S(O)₂CH₂CH₂CH₃ | H | CO₂CH₃ | OCF₂CH₃ | |

TABLE VIb

General Formula VIb

| R | R₁ | Rₓ | Q₂ | X₁ | Y₂ | m.p. (°C.) |
|---|---|---|---|---|---|---|
| H | 4-SCH₃ | H | CO₂CH₃ | CH₃ | H | |
| H | 4-SCH₃ | H | CO₂CH₃ | OCH₃ | H | |
| H | 4-SCH₃ | H | CO₂CH₃ | OCH₂CH₃ | H | |
| H | 4-SCH₃ | H | CO₂CH₃ | OCF₂H | H | |
| H | 4-SCH₃ | H | CO₂CH₃ | CH₃ | CH₃ | |
| H | 4-SCH₃ | H | CO₂CH₃ | OCH₃ | CH₃ | |
| H | 4-SCH₃ | H | CO₂CH₃ | OCH₂CH₃ | CH₃ | |
| H | 4-SCH₃ | H | CO₂CH₃ | OCF₂H | CH₃ | |
| H | 4-SCH₂CH₃ | H | CO₂CH₃ | CH₃ | H | |
| H | 4-SCH₂CH₃ | H | CO₂CH₃ | OCH₃ | H | |
| H | 4-SCH₂CH₃ | H | CO₂CH₃ | OCH₂CH₃ | H | |
| H | 4-SCH₂CH₃ | H | CO₂CH₃ | OCF₂H | H | |
| H | 4-SCH₂CH₃ | H | CO₂CH₃ | CH₃ | CH₃ | |
| H | 4-SCH₂CH₃ | H | CO₂CH₃ | OCH₃ | CH₃ | |
| H | 4-SCH₂CH₃ | H | CO₂CH₃ | OCH₂CH₃ | CH₃ | |
| H | 4-SCH₂CH₃ | H | CO₂CH₃ | OCF₂H | CH₃ | |
| H | 4-SCH₂CH₂CH₃ | H | CO₂CH₃ | CH₃ | H | |
| H | 4-SCH₂CH₂CH₃ | H | CO₂CH₃ | OCH₃ | H | |
| H | 4-SCH₂CH₂CH₃ | H | CO₂CH₃ | OCH₂CH₃ | H | |
| H | 4-SCH₂CH₂CH₃ | H | CO₂CH₃ | OCF₂H | H | |
| H | 4-SCH₂CH₂CH₃ | H | CO₂CH₃ | CH₃ | CH₃ | |
| H | 4-SCH₂CH₂CH₃ | H | CO₂CH₃ | OCH₃ | CH₃ | |
| H | 4-SCH₂CH₂CH₃ | H | CO₂CH₃ | OCH₂CH₃ | CH₃ | |
| H | 4-SCH₂CH₂CH₃ | H | CO₂CH₃ | OCF₂H | CH₃ | |
| H | 4-S(O)CH₂CH₂CH₃ | H | CO₂CH₃ | CH₃ | H | |
| H | 4-S(O)CH₂CH₂CH₃ | H | CO₂CH₃ | OCH₃ | H | |
| H | 4-S(O)CH₂CH₂CH₃ | H | CO₂CH₃ | OCH₂CH₃ | H | |
| H | 4-S(O)CH₂CH₂CH₃ | H | CO₂CH₃ | OCF₂H | H | |
| H | 4-S(O)CH₂CH₂CH₃ | H | CO₂CH₃ | CH₃ | CH₃ | |
| H | 4-S(O)CH₂CH₂CH₃ | H | CO₂CH₃ | OCH₃ | CH₃ | |
| H | 4-S(O)CH₂CH₂CH₃ | H | CO₂CH₃ | OCH₂CH₃ | CH₃ | |
| H | 4-S(O)CH₂CH₂CH₃ | H | CO₂CH₃ | OCF₂H | CH₃ | |
| H | 4-S(O)₂CH₂CH₂CH₃ | H | CO₂CH₃ | CH₃ | H | |
| H | 4-S(O)₂CH₂CH₂CH₃ | H | CO₂CH₃ | OCH₃ | H | |
| H | 4-S(O)₂CH₂CH₂CH₃ | H | CO₂CH₃ | OCH₂CH₃ | H | |
| H | 4-S(O)₂CH₂CH₂CH₃ | H | CO₂CH₃ | OCF₂H | H | |
| H | 4-S(O)₂CH₂CH₂CH₃ | H | CO₂CH₃ | CH₃ | CH₃ | |
| H | 4-S(O)₂CH₂CH₂CH₃ | H | CO₂CH₃ | OCH₃ | CH₃ | |
| H | 4-S(O)₂CH₂CH₂CH₃ | H | CO₂CH₃ | OCH₂CH₃ | CH₃ | |

TABLE VIb-continued

General Formula VIb

| R | R₁ | Rₓ | Q₂ | X₁ | Y₂ | m.p. (°C.) |
|---|---|---|---|---|---|---|
| H | 4-S(O)₂CH₂CH₂CH₃ | H | CO₂CH₃ | OCF₂H | CH₃ | |

TABLE VIIb

General Formula VIIb

| R | R₁ | Rₓ | Q₂ | X₁ | Y₃ | m.p. (°C.) |
|---|---|---|---|---|---|---|
| H | 4-SCH₃ | H | CO₂CH₃ | CH₃ | CH₃ | |
| H | 4-SCH₃ | H | CO₂CH₃ | OCH₃ | CH₃ | |
| H | 4-SCH₃ | H | CO₂CH₃ | SCH₃ | CH₃ | |
| H | 4-SCH₃ | H | CO₂CH₃ | CH₃ | CH₂CH₃ | |
| H | 4-SCH₃ | H | CO₂CH₃ | SCH₃ | CH₂CH₃ | |
| H | 4-SCH₃ | H | CO₂CH₃ | SCH₃ | CH₂CF₃ | |
| H | 4-SCH₃ | H | CO₂CH₃ | CH₃ | CH₂CF₃ | |
| H | 4-SCH₃ | H | CO₂CH₃ | OCH₃ | CH₂CF₃ | |
| H | 4-SCH₂CH₃ | H | CO₂CH₃ | CH₃ | CH₃ | |
| H | 4-SCH₂CH₃ | H | CO₂CH₃ | OCH₃ | CH₃ | |
| H | 4-SCH₂CH₃ | H | CO₂CH₃ | SCH₃ | CH₃ | |
| H | 4-SCH₂CH₃ | H | CO₂CH₃ | CH₃ | CH₂CH₃ | |
| H | 4-SCH₂CH₃ | H | CO₂CH₃ | SCH₃ | CH₂CH₃ | |
| H | 4-SCH₂CH₃ | H | CO₂CH₃ | SCH₃ | CH₂CF₃ | |
| H | 4-SCH₂CH₃ | H | CO₂CH₃ | CH₃ | CH₂CF₃ | |
| H | 4-SCH₂CH₃ | H | CO₂CH₃ | OCH₃ | CH₂CF₃ | |
| H | 4-SCH₂CH₂CH₃ | H | CO₂CH₃ | CH₃ | CH₃ | |
| H | 4-SCH₂CH₂CH₃ | H | CO₂CH₃ | OCH₃ | CH₃ | |
| H | 4-SCH₂CH₂CH₃ | H | CO₂CH₃ | SCH₃ | CH₃ | |
| H | 4-SCH₂CH₂CH₃ | H | CO₂CH₃ | CH₃ | CH₂CH₃ | |
| H | 4-SCH₂CH₂CH₃ | H | CO₂CH₃ | SCH₃ | CH₂CH₃ | |
| H | 4-SCH₂CH₂CH₃ | H | CO₂CH₃ | SCH₃ | CH₂CF₃ | |
| H | 4-SCH₂CH₂CH₃ | H | CO₂CH₃ | CH₃ | CH₂CF₃ | |
| H | 4-SCH₂CH₂CH₃ | H | CO₂CH₃ | OCH₃ | CH₂CF₃ | |
| H | 4-S(O)CH₂CH₂CH₃ | H | CO₂CH₃ | CH₃ | CH₃ | |
| H | 4-S(O)CH₂CH₂CH₃ | H | CO₂CH₃ | OCH₃ | CH₃ | |
| H | 4-S(O)CH₂CH₂CH₃ | H | CO₂CH₃ | SCH₃ | CH₃ | |
| H | 4-S(O)CH₂CH₂CH₃ | H | CO₂CH₃ | CH₃ | CH₂CH₃ | |
| H | 4-S(O)CH₂CH₂CH₃ | H | CO₂CH₃ | SCH₃ | CH₂CH₃ | |
| H | 4-S(O)CH₂CH₂CH₃ | H | CO₂CH₃ | SCH₃ | CH₂CF₃ | |
| H | 4-S(O)CH₂CH₂CH₃ | H | CO₂CH₃ | CH₃ | CH₂CF₃ | |
| H | 4-S(O)CH₂CH₂CH₃ | H | CO₂CH₃ | OCH₃ | CH₂CF₃ | |
| H | 4-S(O)₂CH₂CH₂CH₃ | H | CO₂CH₃ | CH₃ | CH₃ | |
| H | 4-S(O)₂CH₂CH₂CH₃ | H | CO₂CH₃ | OCH₃ | CH₃ | |
| H | 4-S(O)₂CH₂CH₂CH₃ | H | CO₂CH₃ | SCH₃ | CH₃ | |
| H | 4-S(O)₂CH₂CH₂CH₃ | H | CO₂CH₃ | CH₃ | CH₂CH₃ | |
| H | 4-S(O)₂CH₂CH₂CH₃ | H | CO₂CH₃ | SCH₃ | CH₂CH₃ | |
| H | 4-S(O)₂CH₂CH₂CH₃ | H | CO₂CH₃ | SCH₃ | CH₂CF₃ | |
| H | 4-S(O)₂CH₂CH₂CH₃ | H | CO₂CH₃ | CH₃ | CH₂CF₃ | |
| H | 4-S(O)₂CH₂CH₂CH₃ | H | CO₂CH₃ | OCH₃ | CH₂CF₃ | |

TABLE VIIIb

General Formula VIIIb

| R | R₁ | Rₓ | Q₂ | X₃ | m.p. (°C.) |
|---|---|---|---|---|---|
| H | 4-SCH₃ | H | CO₂CH₃ | CH₃ | |
| H | 4-SCH₃ | H | CO₂CH₃ | OCH₃ | |
| H | 4-SCH₂CH₃ | H | CO₂CH₃ | CH₃ | |
| H | 4-SCH₂CH₃ | H | CO₂CH₃ | OCH₃ | |
| H | 4-SCH₂CH₂CH₃ | H | CO₂CH₃ | CH₃ | |
| H | 4-SCH₂CH₂CH₃ | H | CO₂CH₃ | OCH₃ | |
| H | 4-S(O)CH₂CH₂CH₃ | H | CO₂CH₃ | CH₃ | |
| H | 4-S(O)CH₂CH₂CH₃ | H | CO₂CH₃ | OCH₃ | |
| H | 4-S(O)₂CH₂CH₂CH₃ | H | CO₂CH₃ | CH₃ | |
| H | 4-S(O)₂CH₂CH₂CH₃ | H | CO₂CH₃ | OCH₃ | |
| H | 4-SCH₃ | H | CO₂CH₂CH₃ | CH₃ | |
| H | 4-SCH₃ | H | CO₂CH₂CH₃ | OCH₃ | |
| H | 4-SCH₂CH₃ | H | CO₂CH₂CH₃ | CH₃ | |
| H | 4-SCH₂CH₃ | H | CO₂CH₂CH₃ | OCH₃ | |
| H | 4-SCH₂CH₂CH₃ | H | CO₂CH₂CH₃ | CH₃ | |
| H | 4-SCH₂CH₂CH₃ | H | CO₂CH₂CH₃ | OCH₃ | |
| H | 4-S(O)CH₂CH₂CH₃ | H | CO₂CH₂CH₃ | CH₃ | |
| H | 4-S(O)CH₂CH₂CH₃ | H | CO₂CH₂CH₃ | OCH₃ | |
| H | 4-S(O)₂CH₂CH₂CH₃ | H | CO₂CH₂CH₃ | CH₃ | |
| H | 4-S(O)₂CH₂CH₂CH₃ | H | CO₂CH₂CH₃ | OCH₃ | |

TABLE IXb

General Formula IXb

| R | R₁ | Rₓ | Q₂ | X | Y | Z | m.p. (°C.) |
|---|---|---|---|---|---|---|---|
| H | 4-SCH₃ | H | CO₂CH₃ | CH₃ | CH₃ | CH | |
| H | 4-SCH₃ | H | CO₂CH₃ | OCH₃ | OCH₃ | CH | |
| H | 4-SCH₃ | H | CO₂CH₃ | Cl | OCH₃ | CH | |
| H | 4-SCH₃ | H | CO₂CH₃ | CH₃ | OCH₃ | N | |
| H | 4-SCH₂CH₃ | H | CO₂CH₃ | CH₃ | CH₃ | CH | |
| H | 4-SCH₂CH₃ | H | CO₂CH₃ | OCH₃ | OCH₃ | CH | |
| H | 4-SCH₂CH₃ | H | CO₂CH₃ | Cl | OCH₃ | CH | |
| H | 4-SCH₂CH₃ | H | CO₂CH₃ | CH₃ | OCH₃ | N | |
| H | 4-SCH₂CH₂CH₃ | H | CO₂CH₃ | CH₃ | CH₃ | CH | |
| H | 4-SCH₂CH₂CH₃ | H | CO₂CH₃ | OCH₃ | OCH₃ | CH | |
| H | 4-SCH₂CH₂CH₃ | H | CO₂CH₃ | Cl | OCH₃ | CH | |
| H | 4-SCH₂CH₂CH₃ | H | CO₂CH₃ | CH₃ | OCH₃ | N | |
| H | 4-S(O)CH₂CH₂CH₃ | H | CO₂CH₃ | CH₃ | CH₃ | CH | |
| H | 4-S(O)CH₂CH₂CH₃ | H | CO₂CH₃ | OCH₃ | OCH₃ | CH | |
| H | 4-S(O)CH₂CH₂CH₃ | H | CO₂CH₃ | Cl | OCH₃ | CH | |
| H | 4-S(O)CH₂CH₂CH₃ | H | CO₂CH₃ | CH₃ | OCH₃ | N | |
| H | 4-S(O)₂CH₂CH₂CH₃ | H | CO₂CH₃ | CH₃ | CH₃ | CH | |
| H | 4-S(O)₂CH₂CH₂CH₃ | H | CO₂CH₃ | OCH₃ | OCH₃ | CH | |
| H | 4-S(O)₂CH₂CH₂CH₃ | H | CO₂CH₃ | Cl | OCH₃ | CH | |
| H | 4-S(O)₂CH₂CH₂CH₃ | H | CO₂CH₃ | CH₃ | OCH₃ | N | |

TABLE Xb

General Formula Xb

| R | R₁ | Rₓ | Q₂ | X | Y | Z | m.p. (°C.) |
|---|---|---|---|---|---|---|---|
| H | 4-SCH₃ | H | CO₂CH₃ | CH₃ | CH₃ | CH | |
| H | 4-SCH₃ | H | CO₂CH₃ | OCH₃ | OCH₃ | CH | |
| H | 4-SCH₃ | H | CO₂CH₃ | Cl | OCH₃ | CH | |
| H | 4-SCH₃ | H | CO₂CH₃ | CH₃ | OCH₃ | N | |
| H | 4-SCH₂CH₃ | H | CO₂CH₃ | CH₃ | CH₃ | CH | |
| H | 4-SCH₂CH₃ | H | CO₂CH₃ | OCH₃ | OCH₃ | CH | |
| H | 4-SCH₂CH₃ | H | CO₂CH₃ | Cl | OCH₃ | CH | |
| H | 4-SCH₂CH₃ | H | CO₂CH₃ | CH₃ | OCH₃ | N | |
| H | 4-SCH₂CH₂CH₃ | H | CO₂CH₃ | CH₃ | CH₃ | CH | |
| H | 4-SCH₂CH₂CH₃ | H | CO₂CH₃ | OCH₃ | OCH₃ | CH | |
| H | 4-SCH₂CH₂CH₃ | H | CO₂CH₃ | Cl | OCH₃ | CH | |
| H | 4-SCH₂CH₂CH₃ | H | CO₂CH₃ | CH₃ | OCH₃ | N | |
| H | 4-S(O)CH₂CH₂CH₃ | H | CO₂CH₃ | CH₃ | CH₃ | CH | |
| H | 4-S(O)CH₂CH₂CH₃ | H | CO₂CH₃ | OCH₃ | OCH₃ | CH | |
| H | 4-S(O)CH₂CH₂CH₃ | H | CO₂CH₃ | Cl | OCH₃ | CH | |
| H | 4-S(O)CH₂CH₂CH₃ | H | CO₂CH₃ | CH₃ | OCH₃ | N | |
| H | 4-S(O)₂CH₂CH₂CH₃ | H | CO₂CH₃ | CH₃ | CH₃ | CH | |
| H | 4-S(O)₂CH₂CH₂CH₃ | H | CO₂CH₃ | OCH₃ | OCH₃ | CH | |
| H | 4-S(O)₂CH₂CH₂CH₃ | H | CO₂CH₃ | Cl | OCH₃ | CH | |
| H | 4-S(O)₂CH₂CH₂CH₃ | H | CO₂CH₃ | CH₃ | OCH₃ | N | |
| H | 4-CO₂CH₃ | H | SCH₃ | CH₃ | CH₃ | CH | |
| H | 4-CO₂CH₃ | H | SCH₃ | OCH₃ | OCH₃ | CH | |
| H | 4-CO₂CH₃ | H | SCH₃ | Cl | OCH₃ | CH | |
| H | 4-CO₂CH₃ | H | SCH₃ | CH₃ | OCH₃ | N | |
| H | 4-CO₂CH₃ | H | SCH₂CH₃ | CH₃ | CH₃ | CH | |
| H | 4-CO₂CH₃ | H | SCH₂CH₃ | OCH₃ | OCH₃ | CH | |
| H | 4-CO₂CH₃ | H | SCH₂CH₃ | Cl | OCH₃ | CH | |
| H | 4-CO₂CH₃ | H | SCH₂CH₃ | CH₃ | OCH₃ | N | |
| H | 4-CO₂CH₃ | H | SCH₂CH₂CH₃ | CH₃ | CH₃ | CH | |
| H | 4-CO₂CH₃ | H | SCH₂CH₂CH₃ | OCH₃ | OCH₃ | CH | |
| H | 4-CO₂CH₃ | H | SCH₂CH₂CH₃ | Cl | OCH₃ | CH | |
| H | 4-CO₂CH₃ | H | SCH₂CH₂CH₃ | CH₃ | OCH₃ | N | |

TABLE XIb

General Formula XIb

| R | R₁ | Rₓ | Q₂ | X | Y | m.p. (°C.) |
|---|---|---|---|---|---|---|
| H | 4-SCH₃ | H | CO₂CH₃ | CH₃ | O | |
| H | 4-SCH₃ | H | CO₂CH₃ | OCH₃ | O | |
| H | 4-SCH₃ | H | CO₂CH₃ | OCH₂CH₃ | O | |
| H | 4-SCH₃ | H | CO₂CH₃ | OCF₂H | O | |
| H | 4-SCH₃ | H | CO₂CH₃ | CH₃ | CH₂ | |
| H | 4-SCH₃ | H | CO₂CH₃ | OCH₃ | CH₂ | |
| H | 4-SCH₃ | H | CO₂CH₃ | OCH₂CH₃ | CH₂ | |
| H | 4-SCH₃ | H | CO₂CH₃ | OCF₂H | CH₂ | |
| H | 4-SCH₂CH₃ | H | CO₂CH₃ | CH₃ | O | |
| H | 4-SCH₂CH₃ | H | CO₂CH₃ | OCH₃ | O | |
| H | 4-SCH₂CH₃ | H | CO₂CH₃ | OCH₂CH₃ | O | |
| H | 4-SCH₂CH₃ | H | CO₂CH₃ | OCF₂H | O | |
| H | 4-SCH₂CH₃ | H | CO₂CH₃ | CH₃ | CH₂ | |
| H | 4-SCH₂CH₃ | H | CO₂CH₃ | OCH₃ | CH₂ | |

TABLE XIb-continued

General Formula XIb

| R | R₁ | Rₓ | Q₂ | X | Y | m.p. (°C.) |
|---|---|---|---|---|---|---|
| H | 4-SCH₂CH₃ | H | CO₂CH₃ | OCH₂CH₃ | CH₂ | |
| H | 4-SCH₂CH₃ | H | CO₂CH₃ | OCF₂H | CH₂ | |
| H | 4-SCH₂CH₂CH₃ | H | CO₂CH₃ | CH₃ | O | |
| H | 4-SCH₂CH₂CH₃ | H | CO₂CH₃ | OCH₃ | O | |
| H | 4-SCH₂CH₂CH₃ | H | CO₂CH₃ | OCH₂CH₃ | O | |
| H | 4-SCH₂CH₂CH₃ | H | CO₂CH₃ | OCF₂H | O | |
| H | 4-SCH₂CH₂CH₃ | H | CO₂CH₃ | CH₃ | CH₂ | |
| H | 4-SCH₂CH₂CH₃ | H | CO₂CH₃ | OCH₃ | CH₂ | |
| H | 4-SCH₂CH₂CH₃ | H | CO₂CH₃ | OCH₂CH₃ | CH₂ | |
| H | 4-SCH₂CH₂CH₃ | H | CO₂CH₃ | OCF₂H | CH₂ | |
| H | 4-S(O)CH₂CH₂CH₃ | H | CO₂CH₃ | CH₃ | O | |
| H | 4-S(O)CH₂CH₂CH₃ | H | CO₂CH₃ | OCH₃ | O | |
| H | 4-S(O)CH₂CH₂CH₃ | H | CO₂CH₃ | OCH₂CH₃ | O | |
| H | 4-S(O)CH₂CH₂CH₃ | H | CO₂CH₃ | OCF₂H | O | |
| H | 4-S(O)CH₂CH₂CH₃ | H | CO₂CH₃ | CH₃ | CH₂ | |
| H | 4-S(O)CH₂CH₂CH₃ | H | CO₂CH₃ | OCH₃ | CH₂ | |
| H | 4-S(O)CH₂CH₂CH₃ | H | CO₂CH₃ | OCH₂CH₃ | CH₂ | |
| H | 4-S(O)CH₂CH₂CH₃ | H | CO₂CH₃ | OCF₂H | CH₂ | |
| H | 4-S(O)₂CH₂CH₂CH₃ | H | CO₂CH₃ | CH₃ | O | |
| H | 4-S(O)₂CH₂CH₂CH₃ | H | CO₂CH₃ | OCH₃ | O | |
| H | 4-S(O)₂CH₂CH₂CH₃ | H | CO₂CH₃ | OCH₂CH₃ | O | |
| H | 4-S(O)₂CH₂CH₂CH₃ | H | CO₂CH₃ | OCF₂H | O | |
| H | 4-S(O)₂CH₂CH₂CH₃ | H | CO₂CH₃ | CH₃ | CH₂ | |
| H | 4-S(O)₂CH₂CH₂CH₃ | H | CO₂CH₃ | OCH₃ | CH₂ | |
| H | 4-S(O)₂CH₂CH₂CH₃ | H | CO₂CH₃ | OCH₂CH₃ | CH₂ | |
| H | 4-S(O)₂CH₂CH₂CH₃ | H | CO₂CH₃ | OCF₂H | CH₂ | |
| H | 4-CO₂CH₃ | H | SCH₃ | CH₃ | O | |
| H | 4-CO₂CH₃ | H | SCH₃ | OCH₃ | O | |
| H | 4-CO₂CH₃ | H | SCH₃ | OCH₂CH₃ | O | |
| H | 4-CO₂CH₃ | H | SCH₃ | OCF₂H | O | |
| H | 4-CO₂CH₃ | H | SCH₃ | CH₃ | CH₂ | |
| H | 4-CO₂CH₃ | H | SCH₃ | OCH₃ | CH₂ | |
| H | 4-CO₂CH₃ | H | SCH₃ | OCH₂CH₃ | CH₂ | |
| H | 4-CO₂CH₃ | H | SCH₃ | OCF₂H | CH₂ | |
| H | 4-CO₂CH₃ | H | SCH₂CH₃ | CH₃ | O | |
| H | 4-CO₂CH₃ | H | SCH₂CH₃ | OCH₃ | O | |
| H | 4-CO₂CH₃ | H | SCH₂CH₃ | OCH₂CH₃ | O | |
| H | 4-CO₂CH₃ | H | SCH₂CH₃ | OCF₂H | O | |
| H | 4-CO₂CH₃ | H | SCH₂CH₃ | CH₃ | CH₂ | |
| H | 4-CO₂CH₃ | H | SCH₂CH₃ | OCH₃ | CH₂ | |
| H | 4-CO₂CH₃ | H | SCH₂CH₃ | OCH₂CH₃ | CH₂ | |
| H | 4-CO₂CH₃ | H | SCH₂CH₃ | OCF₂H | CH₂ | |
| H | 4-CO₂CH₃ | H | SCH₂CH₂CH₃ | CH₃ | O | |
| H | 4-CO₂CH₃ | H | SCH₂CH₂CH₃ | OCH₃ | O | |
| H | 4-CO₂CH₃ | H | SCH₂CH₂CH₃ | OCH₂CH₃ | O | |
| H | 4-CO₂CH₃ | H | SCH₂CH₂CH₃ | OCF₂H | O | |
| H | 4-CO₂CH₃ | H | SCH₂CH₂CH₃ | CH₃ | CH₂ | |
| H | 4-CO₂CH₃ | H | SCH₂CH₂CH₃ | OCH₃ | CH₂ | |
| H | 4-CO₂CH₃ | H | SCH₂CH₂CH₃ | OCH₂CH₃ | CH₂ | |
| H | 4-CO₂CH₃ | H | SCH₂CH₂CH₃ | OCF₂H | CH₂ | |

TABLE XIIb

General Formula XIIb

| R | R₁ | Rₓ | Q₂ | X₁ | m.p. (°C.) |
|---|---|---|---|---|---|
| H | 4-SCH₃ | H | CO₂CH₃ | CH₃ | |
| H | 4-SCH₃ | H | CO₂CH₃ | OCH₃ | |
| H | 4-SCH₃ | H | CO₂CH₃ | OCF₂CH₃ | |
| H | 4-SCH₂CH₃ | H | CO₂CH₃ | CH₃ | |
| H | 4-SCH₂CH₃ | H | CO₂CH₃ | OCH₃ | |
| H | 4-SCH₂CH₃ | H | CO₂CH₃ | OCF₂CH₃ | |
| H | 4-SCH₂CH₂CH₃ | H | CO₂CH₃ | CH₃ | |
| H | 4-SCH₂CH₂CH₃ | H | CO₂CH₃ | OCH₃ | |
| H | 4-SCH₂CH₂CH₃ | H | CO₂CH₃ | OCF₂CH₃ | |
| H | 4-S(O)CH₂CH₃ | H | CO₂CH₃ | CH₃ | |
| H | 4-S(O)CH₂CH₃ | H | CO₂CH₃ | OCH₃ | |
| H | 4-S(O)CH₂CH₃ | H | CO₂CH₃ | OCF₂CH₃ | |
| H | 4-S(O)₂CH₂CH₃ | H | CO₂CH₃ | CH₃ | |
| H | 4-S(O)₂CH₂CH₃ | H | CO₂CH₃ | OCH₃ | |
| H | 4-S(O)₂CH₂CH₃ | H | CO₂CH₃ | OCF₂CH₃ | |
| H | 4-S(O)CH₂CH₂CH₃ | H | CO₂CH₃ | CH₃ | |
| H | 4-S(O)CH₂CH₂CH₃ | H | CO₂CH₃ | OCH₃ | |
| H | 4-S(O)CH₂CH₂CH₃ | H | CO₂CH₃ | OCF₂CH₃ | |
| H | 4-S(O)₂CH₂CH₂CH₃ | H | CO₂CH₃ | CH₃ | |
| H | 4-S(O)₂CH₂CH₂CH₃ | H | CO₂CH₃ | OCH₃ | |
| H | 4-S(O)₂CH₂CH₂CH₃ | H | CO₂CH₃ | OCF₂CH₃ | |
| H | 4-CO₂CH₃ | H | SCH₃ | CH₃ | |
| H | 4-CO₂CH₃ | H | SCH₃ | OCH₃ | |

TABLE XIIb-continued

General Formula XIIb

| R | R$_1$ | R$_x$ | Q$_2$ | X$_1$ | m.p. (°C.) |
|---|---|---|---|---|---|
| H | 4-CO$_2$CH$_3$ | H | SCH$_3$ | OCF$_2$CH$_3$ | |
| H | 4-CO$_2$CH$_3$ | H | SCH$_2$CH$_3$ | CH$_3$ | |
| H | 4-CO$_2$CH$_3$ | H | SCH$_2$CH$_3$ | OCH$_3$ | |
| H | 4-CO$_2$CH$_3$ | H | SCH$_2$CH$_3$ | OCF$_2$CH$_3$ | |
| H | 4-CO$_2$CH$_3$ | H | SCH$_2$CH$_2$CH$_3$ | CH$_3$ | |
| H | 4-CO$_2$CH$_3$ | H | SCH$_2$CH$_2$CH$_3$ | OCH$_3$ | |
| H | 4-CO$_2$CH$_3$ | H | SCH$_2$CH$_2$CH$_3$ | OCF$_2$CH$_3$ | |
| H | 4-SO$_2$N(CH$_3$)$_2$ | 5-Br | Br | CH$_3$ | |
| H | 4-SO$_2$N(CH$_3$)$_2$ | 5-Br | Br | OCH$_3$ | |
| H | 4-SO$_2$N(CH$_3$)$_2$ | 5-Br | Br | OCF$_2$CH$_3$ | |

TABLE XIIIb

General Formula XIIIb

| R | R$_1$ | R$_x$ | Q$_2$ | X$_1$ | Y$_2$ | m.p. (°C.) |
|---|---|---|---|---|---|---|
| H | 4-SCH$_3$ | H | CO$_2$CH$_3$ | CH$_3$ | H | |
| H | 4-SCH$_3$ | H | CO$_2$CH$_3$ | OCH$_3$ | H | |
| H | 4-SCH$_3$ | H | CO$_2$CH$_3$ | OCH$_2$CH$_3$ | H | |
| H | 4-SCH$_3$ | H | CO$_2$CH$_3$ | OCF$_2$H | H | |
| H | 4-SCH$_3$ | H | CO$_2$CH$_3$ | CH$_3$ | CH$_3$ | |
| H | 4-SCH$_3$ | H | CO$_2$CH$_3$ | OCH$_3$ | CH$_3$ | |
| H | 4-SCH$_3$ | H | CO$_2$CH$_3$ | OCH$_2$CH$_3$ | CH$_3$ | |
| H | 4-SCH$_3$ | H | CO$_2$CH$_3$ | OCF$_2$H | CH$_3$ | |
| H | 4-SCH$_2$CH$_3$ | H | CO$_2$CH$_3$ | CH$_3$ | H | |
| H | 4-SCH$_2$CH$_3$ | H | CO$_2$CH$_3$ | OCH$_3$ | H | |
| H | 4-SCH$_2$CH$_3$ | H | CO$_2$CH$_3$ | OCH$_2$CH$_3$ | H | |
| H | 4-SCH$_2$CH$_3$ | H | CO$_2$CH$_3$ | OCF$_2$H | H | |
| H | 4-SCH$_2$CH$_3$ | H | CO$_2$CH$_3$ | CH$_3$ | CH$_3$ | |
| H | 4-SCH$_2$CH$_3$ | H | CO$_2$CH$_3$ | OCH$_3$ | CH$_3$ | |
| H | 4-SCH$_2$CH$_3$ | H | CO$_2$CH$_3$ | OCH$_2$CH$_3$ | CH$_3$ | |
| H | 4-SCH$_2$CH$_3$ | H | CO$_2$CH$_3$ | OCF$_2$H | CH$_3$ | |
| H | 4-SCH$_2$CH$_2$CH$_3$ | H | CO$_2$CH$_3$ | CH$_3$ | H | |
| H | 4-SCH$_2$CH$_2$CH$_3$ | H | CO$_2$CH$_3$ | OCH$_3$ | H | |
| H | 4-SCH$_2$CH$_2$CH$_3$ | H | CO$_2$CH$_3$ | OCH$_2$CH$_3$ | H | |
| H | 4-SCH$_2$CH$_2$CH$_3$ | H | CO$_2$CH$_3$ | OCF$_2$H | H | |
| H | 4-SCH$_2$CH$_2$CH$_3$ | H | CO$_2$CH$_3$ | CH$_3$ | CH$_3$ | |
| H | 4-SCH$_2$CH$_2$CH$_3$ | H | CO$_2$CH$_3$ | OCH$_3$ | CH$_3$ | |
| H | 4-SCH$_2$CH$_2$CH$_3$ | H | CO$_2$CH$_3$ | OCH$_2$CH$_3$ | CH$_3$ | |
| H | 4-SCH$_2$CH$_2$CH$_3$ | H | CO$_2$CH$_3$ | OCF$_2$H | CH$_3$ | |
| H | 4-S(O)CH$_2$CH$_2$CH$_3$ | H | CO$_2$CH$_3$ | CH$_3$ | H | |
| H | 4-S(O)CH$_2$CH$_2$CH$_3$ | H | CO$_2$CH$_3$ | OCH$_3$ | H | |
| H | 4-S(O)CH$_2$CH$_2$CH$_3$ | H | CO$_2$CH$_3$ | OCH$_2$CH$_3$ | H | |
| H | 4-S(O)CH$_2$CH$_2$CH$_3$ | H | CO$_2$CH$_3$ | OCF$_2$H | H | |
| H | 4-S(O)CH$_2$CH$_2$CH$_3$ | H | CO$_2$CH$_3$ | CH$_3$ | CH$_3$ | |
| H | 4-S(O)CH$_2$CH$_2$CH$_3$ | H | CO$_2$CH$_3$ | OCH$_3$ | CH$_3$ | |
| H | 4-S(O)CH$_2$CH$_2$CH$_3$ | H | CO$_2$CH$_3$ | OCH$_2$CH$_3$ | CH$_3$ | |
| H | 4-S(O)CH$_2$CH$_2$CH$_3$ | H | CO$_2$CH$_3$ | OCF$_2$H | CH$_3$ | |
| H | 4-S(O)$_2$CH$_2$CH$_2$CH$_3$ | H | CO$_2$CH$_3$ | CH$_3$ | H | |
| H | 4-S(O)$_2$CH$_2$CH$_2$CH$_3$ | H | CO$_2$CH$_3$ | OCH$_3$ | H | |
| H | 4-S(O)$_2$CH$_2$CH$_2$CH$_3$ | H | CO$_2$CH$_3$ | OCH$_2$CH$_3$ | H | |
| H | 4-S(O)$_2$CH$_2$CH$_2$CH$_3$ | H | CO$_2$CH$_3$ | OCF$_2$H | H | |
| H | 4-S(O)$_2$CH$_2$CH$_2$CH$_3$ | H | CO$_2$CH$_3$ | CH$_3$ | CH$_3$ | |
| H | 4-S(O)$_2$CH$_2$CH$_2$CH$_3$ | H | CO$_2$CH$_3$ | OCH$_3$ | CH$_3$ | |
| H | 4-S(O)$_2$CH$_2$CH$_2$CH$_3$ | H | CO$_2$CH$_3$ | OCH$_2$CH$_3$ | CH$_3$ | |
| H | 4-S(O)$_2$CH$_2$CH$_2$CH$_3$ | H | CO$_2$CH$_3$ | OCF$_2$H | CH$_3$ | |

TABLE XIVb

General Formula XIVb

| R | R$_1$ | R$_x$ | Q$_2$ | X$_2$ | Y$_3$ | m.p. (°C.) |
|---|---|---|---|---|---|---|
| H | 4-SCH$_3$ | H | CO$_2$CH$_3$ | CH$_3$ | CH$_3$ | |
| H | 4-SCH$_3$ | H | CO$_2$CH$_3$ | OCH$_3$ | CH$_3$ | |
| H | 4-SCH$_3$ | H | CO$_2$CH$_3$ | SCH$_3$ | CH$_3$ | |
| H | 4-SCH$_3$ | H | CO$_2$CH$_3$ | CH$_3$ | CH$_2$CH$_3$ | |
| H | 4-SCH$_3$ | H | CO$_2$CH$_3$ | SCH$_3$ | CH$_2$CH$_3$ | |
| H | 4-SCH$_3$ | H | CO$_2$CH$_3$ | SCH$_3$ | CH$_2$CF$_3$ | |
| H | 4-SCH$_3$ | H | CO$_2$CH$_3$ | CH$_3$ | CH$_2$CF$_3$ | |
| H | 4-SCH$_3$ | H | CO$_2$CH$_3$ | OCH$_3$ | CH$_2$CF$_3$ | |
| H | 4-SCH$_2$CH$_3$ | H | CO$_2$CH$_3$ | CH$_3$ | CH$_3$ | |
| H | 4-SCH$_2$CH$_3$ | H | CO$_2$CH$_3$ | OCH$_3$ | CH$_3$ | |
| H | 4-SCH$_2$CH$_3$ | H | CO$_2$CH$_3$ | SCH$_3$ | CH$_3$ | |
| H | 4-SCH$_2$CH$_3$ | H | CO$_2$CH$_3$ | CH$_3$ | CH$_2$CH$_3$ | |
| H | 4-SCH$_2$CH$_3$ | H | CO$_2$CH$_3$ | SCH$_3$ | CH$_2$CH$_3$ | |
| H | 4-SCH$_2$CH$_3$ | H | CO$_2$CH$_3$ | SCH$_3$ | CH$_2$CF$_3$ | |

TABLE XIVb-continued

General Formula XIVb

| R | R$_1$ | R$_x$ | Q$_2$ | X$_2$ | Y$_3$ | m.p. (°C.) |
|---|---|---|---|---|---|---|
| H | 4-SCH$_2$CH$_3$ | H | CO$_2$CH$_3$ | CH$_3$ | CH$_2$CF$_3$ | |
| H | 4-SCH$_2$CH$_3$ | H | CO$_2$CH$_3$ | OCH$_3$ | CH$_2$CF$_3$ | |
| H | 4-SCH$_2$CH$_2$CH$_3$ | H | CO$_2$CH$_3$ | CH$_3$ | CH$_3$ | |
| H | 4-SCH$_2$CH$_2$CH$_3$ | H | CO$_2$CH$_3$ | OCH$_3$ | CH$_3$ | |
| H | 4-SCH$_2$CH$_2$CH$_3$ | H | CO$_2$CH$_3$ | SCH$_3$ | CH$_3$ | |
| H | 4-SCH$_2$CH$_2$CH$_3$ | H | CO$_2$CH$_3$ | CH$_3$ | CH$_3$CH$_3$ | |
| H | 4-SCH$_2$CH$_2$CH$_3$ | H | CO$_2$CH$_3$ | SCH$_3$ | CH$_2$CH$_3$ | |
| H | 4-SCH$_2$CH$_2$CH$_3$ | H | CO$_2$CH$_3$ | SCH$_3$ | CH$_2$CF$_3$ | |
| H | 4-SCH$_2$CH$_2$CH$_3$ | H | CO$_2$CH$_3$ | CH$_3$ | CH$_2$CF$_3$ | |
| H | 4-SCH$_2$CH$_2$CH$_3$ | H | CO$_2$CH$_3$ | OCH$_3$ | CH$_2$CF$_3$ | |
| H | 4-S(O)CH$_2$CH$_2$CH$_3$ | H | CO$_2$CH$_3$ | CH$_3$ | CH$_3$ | |
| H | 4-S(O)CH$_2$CH$_2$CH$_3$ | H | CO$_2$CH$_3$ | OCH$_3$ | CH$_3$ | |
| H | 4-S(O)CH$_2$CH$_2$CH$_3$ | H | CO$_2$CH$_3$ | SCH$_3$ | CH$_3$ | |
| H | 4-S(O)CH$_2$CH$_2$CH$_3$ | H | CO$_2$CH$_3$ | CH$_3$ | CH$_2$CH$_3$ | |
| H | 4-S(O)CH$_2$CH$_2$CH$_3$ | H | CO$_2$CH$_3$ | SCH$_3$ | CH$_2$CH$_3$ | |
| H | 4-S(O)CH$_2$CH$_2$CH$_3$ | H | CO$_2$CH$_3$ | SCH$_3$ | CH$_2$CF$_3$ | |
| H | 4-S(O)CH$_2$CH$_2$CH$_3$ | H | CO$_2$CH$_3$ | CH$_3$ | CH$_2$CF$_3$ | |
| H | 4-S(O)CH$_2$CH$_2$CH$_3$ | H | CO$_2$CH$_3$ | OCH$_3$ | CH$_2$CF$_3$ | |
| H | 4-S(O)$_2$CH$_2$CH$_2$CH$_3$ | H | CO$_2$CH$_3$ | CH$_3$ | CH$_3$ | |
| H | 4-S(O)$_2$CH$_2$CH$_2$CH$_3$ | H | CO$_2$CH$_3$ | OCH$_3$ | CH$_3$ | |
| H | 4-S(O)$_2$CH$_2$CH$_2$CH$_3$ | H | CO$_2$CH$_3$ | SCH$_3$ | CH$_3$ | |
| H | 4-S(O)$_2$CH$_2$CH$_2$CH$_3$ | H | CO$_2$CH$_3$ | CH$_3$ | CH$_2$CH$_3$ | |
| H | 4-S(O)$_2$CH$_2$CH$_2$CH$_3$ | H | CO$_2$CH$_3$ | SCH$_3$ | CH$_2$CH$_3$ | |
| H | 4-S(O)$_2$CH$_2$CH$_2$CH$_3$ | H | CO$_2$CH$_3$ | SCH$_3$ | CH$_2$CF$_3$ | |
| H | 4-S(O)$_2$CH$_2$CH$_2$CH$_3$ | H | CO$_2$CH$_3$ | CH$_3$ | CH$_2$CF$_3$ | |
| H | 4-S(O)$_2$CH$_2$CH$_2$CH$_3$ | H | CO$_2$CH$_3$ | OCH$_3$ | CH$_2$CF$_3$ | |

TABLE XVb

General Formula XVb

| R | R$_1$ | R$_x$ | Q$_2$ | X$_3$ | m.p. (°C.) |
|---|---|---|---|---|---|
| H | 4-SCH$_3$ | H | CO$_2$CH$_3$ | CH$_3$ | |
| H | 4-SCH$_3$ | H | CO$_2$CH$_3$ | OCH$_3$ | |
| H | 4-SCH$_2$CH$_3$ | H | CO$_2$CH$_3$ | CH$_3$ | |
| H | 4-SCH$_2$CH$_3$ | H | CO$_2$CH$_3$ | OCH$_3$ | |
| H | 4-SCH$_2$CH$_2$CH$_3$ | H | CO$_2$CH$_3$ | CH$_3$ | |
| H | 4-SCH$_2$CH$_2$CH$_3$ | H | CO$_2$CH$_3$ | OCH$_3$ | |
| H | 4-S(O)CH$_2$CH$_2$CH$_3$ | H | CO$_2$CH$_3$ | CH$_3$ | |
| H | 4-S(O)CH$_2$CH$_2$CH$_3$ | H | CO$_2$CH$_3$ | OCH$_3$ | |
| H | 4-S(O)$_2$CH$_2$CH$_2$CH$_3$ | H | CO$_2$CH$_3$ | CH$_3$ | |
| H | 4-S(O)$_2$CH$_2$CH$_2$CH$_3$ | H | CO$_2$CH$_3$ | OCH$_3$ | |
| H | 4-CO$_2$CH$_3$ | H | CO$_2$CH$_3$ | CH$_3$ | |
| H | 4-CO$_2$CH$_3$ | H | CO$_2$CH$_3$ | OCH$_3$ | |
| H | 4-CO$_2$CH$_3$ | H | SCH$_3$ | CH$_3$ | |
| H | 4-CO$_2$CH$_3$ | H | SCH$_3$ | OCH$_3$ | |
| H | 4-CO$_2$CH$_3$ | H | SCH$_2$CH$_3$ | CH$_3$ | |
| H | 4-CO$_2$CH$_3$ | H | SCH$_2$CH$_3$ | OCH$_3$ | |
| H | 4-CO$_2$CH$_3$ | H | SCH$_2$CH$_2$CH$_3$ | CH$_3$ | |
| H | 4-CO$_2$CH$_3$ | H | SCH$_2$CH$_2$CH$_3$ | OCH$_3$ | |
| H | 4-CO$_2$CH$_3$ | H | S(O)CH$_2$CH$_2$CH$_3$ | CH$_3$ | |
| H | 4-CO$_2$CH$_3$ | H | S(O)CH$_2$CH$_2$CH$_3$ | OCH$_3$ | |
| H | 4-CO$_2$CH$_3$ | H | S(O)$_2$CH$_2$CH$_2$CH$_3$ | CH$_3$ | |
| H | 4-CO$_2$CH$_3$ | H | S(O)$_2$CH$_2$CH$_2$CH$_3$ | OCH$_3$ | |
| H | 4-CO$_2$CH$_3$ | H | CHO | CH$_3$ | |
| H | 4-CO$_2$CH$_3$ | H | CHO | OCH$_3$ | |
| H | 4-SCH$_3$ | H | CHO | CH$_3$ | |
| H | 4-SCH$_3$ | H | CHO | OCH$_3$ | |
| H | 4-SCH$_2$CH$_3$ | H | CHO | CH$_3$ | |
| H | 4-SCH$_2$CH$_3$ | H | CHO | OCH$_3$ | |

TABLE XVb-continued

General Formula XVb

| R | R$_1$ | R$_x$ | Q$_2$ | X$_3$ | m.p. (°C.) |
|---|---|---|---|---|---|
| H | 4-SCH$_2$CH$_2$CH$_3$ | H | CHO | CH$_3$ | |
| H | 4-SCH$_2$CH$_2$CH$_3$ | H | CHO | OCH$_3$ | |
| H | 4-S(O)CH$_2$CH$_2$CH$_3$ | H | CHO | CH$_3$ | |
| H | 4-S(O)CH$_2$CH$_2$CH$_3$ | H | CHO | OCH$_3$ | |
| H | 4-S(O)$_2$CH$_2$CH$_2$CH$_3$ | H | CHO | CH$_3$ | |
| H | 4-S(O)$_2$CH$_2$CH$_2$CH$_3$ | H | CHO | OCH$_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 19

Wettable Powder

| | |
|---|---|
| N—[(4,6-dimethoxypyrimidin-2-yl)aminocarbonyl]-2-[2-(dimethylaminosulfonyl)ethyl]-3-thiophene-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 20

Wettable Powder

| | |
|---|---|
| 2-[2-(dimethylaminosulfonyl)ethyl]—N—[(4-methoxy-6-methyl-1,3,5-triazine-2-yl)aminocarbonyl]3,5-triazin-2-yl)aminocarbonyl]-3-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 21

Granule

| | |
|---|---|
| Wettable Powder of Example 20 | 5% |
| attapulgite granules | 95% |

-continued (U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE 22

Extruded Pellet

| | |
|---|---|
| N—[(4,6-dimethoxypyrimidin-2-yl)aminocarbonyl]-2-(methoxymethyl)-3-thiophenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 23

Low Strength Granule

| | |
|---|---|
| N—[(4-methoxy-6-methyl-1,3,5-triazin-2-yl)-aminocarbonyl]-2-(methoxymethyl)-3-thiophene-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 24

Granule

| | |
|---|---|
| N—[(4,6-dimethoxypyrimidin-2-yl)aminocarbonyl]-2-[2-(dimethylaminosulfonyl)ethyl]-3-thiophene-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 25

Low Strength Granule

| | |
|---|---|
| 2-[2-(dimethylaminosulfonyl)ethyl]-N—[(4-methoxy-6-methyl-1,3,5-triazin-2-yl)aminocarbonyl]-3-thiophenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 26

Aqueous Suspension

| | |
|---|---|
| N—[(4,6-dimethoxypyrimidin-2-yl)aminocarbonyl]-2-(methoxymethyl)-3-thiophenesulfonamide | 40.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 27

Solution

| | |
|---|---|
| N—[(4-methoxy-6-methyl-1,3,5-triazin-2-yl)aminocarbonyl]-2-(methoxymethyl)-3-thiophenesulfonamide, sodium salt | 5% |
| water | 95% |

The salt is added directly to the water with stirring to produce the solution, which may then be packaged for use.

EXAMPLE 28

High Strength Concentrate

| | |
|---|---|
| N—[(4,6-dimethoxypyrimidin-2-yl)aminocarbonyl]-2-2-(dimethylaminosulfonyl)ethyl]-3-thiophene-sulfonamide | 99.0% |
| silica aerogel | 0.5% |
| synthetic amorphous silica | 0.5% |

The ingredients are blended and ground in a hammer-mill to produce a material essentially all passing a U.S. Ser. No. 50 screen (0.3 mm opening). The concentrate may be formulated further if necessary.

EXAMPLE 29

Wettable Powder

| | |
|---|---|
| 2-[2-(dimethylaminosulfonyl)ethyl]-N—[(4-methoxy-6-methyl-1,3,5-triazin-2-yl)aminocarbonyl]-3-thiophenesulfonamide | 90.0% |
| dioctyl sodium sulfosuccinate | 0.1% |

| | |
|---|---|
| synthetic fine silica | 9.9% |

The ingredients are blended and ground in a hammr-mill to produce particles essentially all below 100 microns. The material is sifted through a U.S. Ser. No. 50 screen and then packaged.

EXAMPLE 30

Wettable Powder

| | |
|---|---|
| N—[(4,6-dimethoxypyrimidin-2-yl)aminocarbonyl]-2-(methoxymethyl)-3-thiophenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 31

Oil Suspension

| | |
|---|---|
| N—[(4-methoxy-6-methyl-1,3,5-triazin-2-yl)-aminocarbonyl]-2-(methoxymethyl)-3-thiophene-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 32

Dust

| | |
|---|---|
| N—[(4,6-dimethoxypyrimidin-2-yl)aminocarbonyl]-2-[2-(dimethylaminosulfonyl)ethyl]-3-thiophene-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 33

Oil Suspension

| | |
|---|---|
| 2-[2-(dimethylaminosulfonyl)ethyl]—N—[(4-methoxy-6-methyl-1,3,5-triazin-2-yl)aminocarbonyl]-3-thiophenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 34

Wettable Powder

| | |
|---|---|
| N—[(4,6-dimethoxypyrimidin-2-yl)aminocarbonyl]-2-(methoxymethyl)-3-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

The compounds of the present invention are expected to be highly active preemergent or postemergent herbicides or plant growth regulants. Many of them should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops, such as soybean, corn, wheat, barley and cotton. Alternatively, the subject compounds should be useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required. Those compounds which exhibited no activity at test rates indicated in the biological tables are expected to show activity at higher application rates.

The compounds of the invention may be used in combination with any other commercial herbicide, examples of which are those of the triazine, triazole, uracil, urea, amide, diphenylether, carbamate and bipyridylium types.

Test A

Seeds of crabgrass (Digitaria spp.), barnyardgrass (*Echinochloa crusgalli*), wild oats (*Avena fatua*), morningglory (Ipomoea spp.), cocklebur (*Xanthium pensylvanicum*), velvetleaf (*Abutilon theophrasti*), giant foxtail (*Setaria faberii*), cheatgrass (*Bromus secalinus* L.), sorghum, corn, soybean, sugarbeet, cotton, rice, barley, wheat and purple nutsedge (*Cyperus rotundus*) tubers were planted and treated preemergence with the test chemicals dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment.

The ratings, summarized in Table A, are based on a numerical scale extending from 0=no injury, to 10=complete kill. The accompanying descriptive symbols have the following meanings:

C=chlorosis/necrosis:
B=burn;
D=defoliation;
E=emergence inhibition;
G=growth retardation;
H=formative effect;
U=unusual pigmentation;
X=axillary stimulation;
S=albinism; and
6Y=abscised buds or flowers.

Compounds

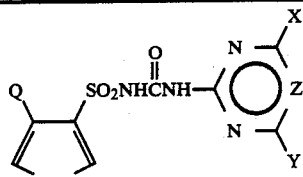

| Compound | Q | X | Y | Z |
|---|---|---|---|---|
| 1 | CN | CH₃ | CH₃ | CH |
| 2 | CN | CH₃ | OCH₃ | CH |
| 3 | CN | CH₃ | OCH₃ | N |
| 4 | CN | OCH₃ | OCH₃ | N |
| 5 | CN | Cl | OCH₃ | CH |

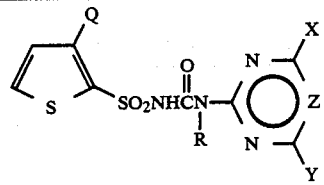

| Compound | Q | R | X | Y | Z |
|---|---|---|---|---|---|
| 6 | CN | H | CH₃ | CH₃ | CH |
| 7 | CN | H | OCH₃ | CH₃ | CH |
| 8 | CN | H | OCH₃ | OCH₃ | CH |
| 9 | CN | H | Cl | OCH₃ | CH |
| 10 | CN | H | OCH₃ | CH₃ | N |
| 11 | CN | H | OCH₃ | OCH₃ | N |
| 12 | CH₂CH₂OCH₃ | H | OCH₃ | OCH₃ | CH |
| 13 | CH₂CH₂OCH₃ | H | OCH₃ | CH₃ | N |
| 14 | CH₂CH₂OCH₃ | H | CH₃ | CH₃ | CH |
| 15 | CH₂CH₂OCH₃ | H | Cl | OCH₃ | CH |
| 16 | CH₂Cl | H | CH₃ | CH₃ | CH |
| 17 | CH₂Cl | H | CH₃ | OCH₃ | CH |
| 18 | CH₂Cl | H | OCH₃ | OCH₃ | CH |
| 19 | CH₂Cl | H | Cl | OCH₃ | CH |
| 20 | CH₂Cl | H | CH₃ | CH₃ | N |
| 21 | CH₂Cl | H | CH₃ | OCH₃ | N |
| 22 | CH₂Cl | H | OCH₃ | OCH₃ | N |
| 23 | CH₂Cl | CH₃ | CH₃ | OCH₃ | N |

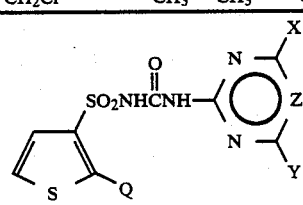

| Compound | Q | X | Y | Z |
|---|---|---|---|---|
| 24 | CH₂Cl | CH₃ | CH₃ | CH |
| 25 | CH₂OCH₃ | CH₃ | CH₃ | CH |
| 26 | CH₂OCH₃ | OCH₃ | OCH₃ | CH |
| 27 | CH₂OCH₃ | Cl | OCH₃ | CH |
| 28 | CH₂OCH₃ | OCH₃ | CH₃ | N |
| 29 | CH₂OCH₃ | OCH₃ | OCH₃ | N |
| 30 | CH₂OCH₂CH₃ | OCH₃ | OCH₃ | CH |
| 31 | CH₂Cl | OCH₃ | CH₃ | CH |
| 32 | CH₂Cl | Cl | OCH₃ | CH |
| 33 | CH₂Cl | OCH₃ | CH₃ | N |
| 34 | CH₂Cl | OCH₃ | OCH₃ | N |

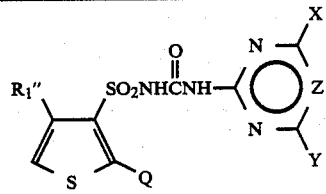

| Compound | Q | R₁″ | X | Y | Z |
|---|---|---|---|---|---|
| 35 | COOCH₃ | SO₂N(CH₃)₂ | OCH₃ | OCH₃ | CH |
| 36 | COOCH₃ | SO₂N(CH₃)₂ | CH₃ | OCH₃ | N |
| 37 | COOCH₃ | SCH₂CH₃ | CH₃ | CH₃ | CH |
| 38 | COOCH₃ | SCH₂CH₃ | CH₃ | OCH₃ | CH |
| 39 | COOCH₃ | SCH₂CH₃ | OCH₃ | OCH₃ | CH |
| 40 | COOCH₃ | SCH₂CH₃ | CH₃ | OCH₃ | N |
| 41 | COOCH₃ | SCH₂CH₃ | OCH₃ | OCH₃ | N |
| 42 | COOCH₃ | SCH₂CH₃ | Cl | OCH₃ | CH |
| 43 | COOCH₃ | S(O)CH₂CH₃ | CH₃ | CH₃ | CH |
| 44 | COOCH₃ | S(O)CH₂CH₃ | CH₃ | OCH₃ | CH |
| 45 | COOCH₃ | S(O)CH₂CH₃ | OCH₃ | OCH₃ | CH |
| 46 | COOCH₃ | S(O)CH₂CH₃ | CH₃ | OCH₃ | N |
| 47 | COOCH₃ | S(O)CH₂CH₃ | OCH₃ | OCH₃ | N |
| 48 | COOCH₃ | S(O)CH₂CH₃ | Cl | OCH₃ | CH |
| 49 | COOCH₃ | SO₂CH₂CH₃ | CH₃ | CH₃ | CH |
| 50 | COOCH₃ | SO₂CH₂CH₃ | CH₃ | OCH₃ | CH |
| 51 | COOCH₃ | SO₂CH₂CH₃ | OCH₃ | OCH₃ | CH |
| 52 | COOCH₃ | SO₂CH₂CH₃ | CH₃ | OCH₃ | N |
| 53 | COOCH₃ | SO₂CH₂CH₃ | OCH₃ | OCH₃ | N |
| 54 | COOCH₃ | SO₂CH₂CH₃ | Cl | OCH₃ | CH |
| 55 | COOCH₃ | SCH₂CH₂CH₃ | CH₃ | CH₃ | CH |
| 56 | COOCH₃ | SCH₂CH₂CH₃ | CH₃ | OCH₃ | CH |
| 57 | COOCH₃ | SCH₂CH₂CH₃ | OCH₃ | OCH₃ | CH |
| 58 | COOCH₃ | SCH₂CH₂CH₃ | CH₃ | OCH₃ | N |
| 59 | COOCH₃ | SCH₂CH₂CH₃ | OCH₃ | OCH₃ | N |
| 60 | COOCH₃ | SCH₂CH₂CH₃ | Cl | OCH₃ | CH |
| 61 | COOCH₃ | SO₂CH₂CH₂CH₃ | CH₃ | CH₃ | CH |
| 62 | COOCH₃ | SO₂CH₂CH₂CH₃ | CH₃ | OCH₃ | CH |
| 63 | COOCH₃ | SO₂CH₂CH₂CH₃ | OCH₃ | OCH₃ | CH |
| 64 | COOCH₃ | SO₂CH₂CH₂CH₃ | CH₃ | OCH₃ | N |
| 65 | COOCH₃ | SO₂CH₂CH₂CH₃ | OCH₃ | OCH₃ | N |
| 66 | COOCH₃ | SO₂CH₂CH₂CH₃ | Cl | OCH₃ | CH |
| 67 | COOCH₃ | S(O)CH₂CH₂CH₃ | CH₃ | CH₃ | CH |
| 68 | COOCH₃ | S(O)CH₂CH₂CH₃ | CH₃ | OCH₃ | CH |
| 69 | COOCH₃ | S(O)CH₂CH₂CH₃ | OCH₃ | OCH₃ | CH |
| 70 | COOCH₃ | S(O)CH₂CH₂CH₃ | CH₃ | OCH₃ | N |
| 71 | COOCH₃ | S(O)CH₂CH₂CH₃ | OCH₃ | OCH₃ | N |
| 72 | COOCH₃ | S(O)CH₂CH₂CH₃ | Cl | OCH₃ | CH |

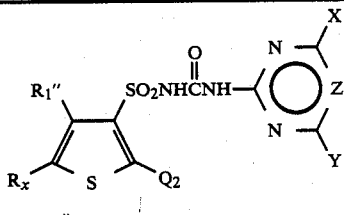

| Compound | Rₓ | R₁″ | Q₂ | X | Y | Z |
|---|---|---|---|---|---|---|
| 73 | Br | SO₂N(CH₃)₂ | Br | CH₃ | CH₃ | CH |
| 74 | Br | SO₂N(CH₃)₂ | Br | CH₃ | OCH₃ | CH |
| 75 | Br | SO₂N(CH₃)₂ | Br | OCH₃ | OCH₃ | CH |
| 76 | Br | SO₂N(CH₃)₂ | Br | CH₃ | OCH₃ | N |
| 77 | Br | SO₂N(CH₃)₂ | Br | OCH₃ | OCH₃ | N |
| 78 | Br | SO₂N(CH₃)₂ | Br | Cl | OCH₃ | CH |
| 79 | Br | SCH₂CH₃ | Br | CH₃ | CH₃ | CH |
| 80 | Br | SCH₂CH₃ | Br | CH₃ | OCH₃ | CH |
| 81 | Br | SCH₂CH₃ | Br | OCH₃ | OCH₃ | CH |
| 82 | Br | SCH₂CH₃ | Br | CH₃ | OCH₃ | N |

-continued
| | | Compounds | | | | |
|---|---|---|---|---|---|---|
| 83 | Br | SCH$_2$CH$_3$ | Br | OCH$_3$ | OCH$_3$ | N |
| 84 | Br | SCH$_2$CH$_3$ | Br | Cl | OCH$_3$ | CH |
-continued
Compounds
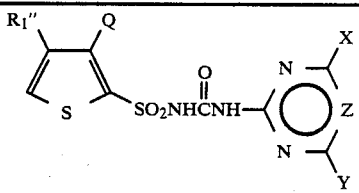
| Compound | Q | R$_1''$ | X | Y | Z |
|---|---|---|---|---|---|
| 85 | COOCH$_3$ | SCH$_2$CH$_2$CH$_3$ | CH$_3$ | OCH$_3$ | CH |
| 86 | COOCH$_3$ | SCH$_2$CH$_2$CH$_3$ | OCH$_3$ | OCH$_3$ | CH |
| 87 | COOCH$_3$ | SCH$_2$CH$_2$CH$_3$ | OCH$_3$ | OCH$_3$ | N |
| 88 | COOCH$_3$ | SCH$_2$CH$_2$CH$_3$ | Cl | OCH$_3$ | CH |

TABLE A

| | Compound 1 | | Compound 2 | | Compound 3 | | Compound 4 | | Compound 5 | | Compound 6 | | Compound 7 | | Compound 8 | | Compound 9 | | Compound 10 | |
|---|---|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | POSTEMERGENCE | | | | | | | | | | | |
| Morningglory | 9C | 9H | 10C | 5C,9G | 9C | 5C,9G | 4C,9H | 5G | 10C | 10C | 9C | 3G | 10C | 9C | 10C | 10C | 10C | 5C,9G | FC,9G | 2C,4G |
| Cocklebur | 10C | 2C,9G | 10C | 9C | 9C | 5C,9G | 5C,9G | 0 | 10C | 5G | 10C | 8H | 10C | 2C,8G | 10C | 10C | 10C | 9H | 5C,9G | 3C,8H |
| Velvetleaf | 10C | 9C | 10C | 9C | 9C | 3C,7H | 5C,9G | 4G | 9C | 3C,8H | 9C | 9C | 10C | 10C | 10C | 10C | 10C | 10C | 9C | 2C,7G |
| Nutsedge | 9C | 3C,9G | 4C,9G | 8G | 9C | 2G | 0 | 0 | 4C,8G | 5G | 7G | 3G | 10C | 7G | 10C | 2C,8G | 5C,9G | 2C,6G | 0 | 0 |
| Crabgrass | 8G | 7G | 3C,8G | 2C,7G | 9C | 0 | 0 | 0 | 2G | 0 | 0 | 0 | 2C,6G | 0 | 3H | 0 | 0 | 0 | 0 | 0 |
| Giant Foxtail | 3C,6G | 1H | 3C,8H | 2C,6H | 9C | 0 | 0 | 0 | 3G | 0 | 0 | 0 | 2C,6H | 2G | 6G | 5G | 2C,5G | 0 | 0 | 0 |
| Barnyardgrass | 9C | 2C,5H | 3C,8H | 2C,8H | 9C | 3C,9H | 3C,8H | 0 | 4C,9H | 3C,8H | 0 | 0 | 3C,7H | 2H | 3C,8H | 4G | 5H | 0 | 3G | 0 |
| Cheatgrass | 6C,9G | 8G | 9C | 2C,8G | 9C | 2G | 2G | 0 | 2C,7G | 0 | 0 | 0 | 9C | 5G | 9C | 2C,8G | 4G | 0 | 0 | 0 |
| Wild Oats | 9C | 3C,9G | 6C,9G | 2C,6G | 3C,7G | 0 | 2C | 0 | 0 | 0 | 0 | 0 | 2C,5G | 0 | 2G | 9C | 0 | 0 | 0 | 0 |
| Wheat | 9G | 2G | 4C,9G | 3C,6G | 3C,9G | 4G | 3G | 0 | 5C,9G | 0 | 5C,9G | 2C,7H | 3C,5G | 5G | 2G | 2C,8G | 0 | 0 | 2C,7H | 0 |
| Corn | 10C | 5U,9G | 4C,9G | 5G | 3C,9G | 9H | 9H | 0 | 2C | 0 | 0 | 0 | 3C,5G | 0 | 3C,8H | 5H | 5H | 0 | 3C,9G | 2G |
| Barley | 5C,9G | 5G | 3C,9H | 4U,9C | 5C,9G | 0 | 0 | 0 | 4C,8G | 9H | 6H | 0 | 3C,5G | 3C,9H | 2G | 5C,9G | 5H | 0 | 3C,9G | 0 |
| Soybean | 9C | 9C | 9C | 8G | 5C,9G | 5C,9G | 5C,9G | 4C,9G | 9C | 4C,8G | 2C,8H | 6H | 4C,9G | 4C,9G | 5C,9G | 6G | 3C,8G | 5G | 3G | 2G |
| Rice | 5C,9G | 4C,9G | 5C,9G | 9C | 9C | 9G | 2C,9G | 6G | 9C | 2C,7G | 9C | 4C,6G | 3C,8G | 3C,8G | 8G | 8H | 8H | 4G | 2C,3G | 0 |
| Sorghum | 2U,9G | 2C,8G | 10C | 5C,9G | 3C,8G | 3C,8G | 5G | 0 | 4C,9H | 3C,9H | 0 | 2C,6G | 4C,9G | 4C,9G | 9H | 8H | 9C | 5G | 9C | 10C |
| Sugar beet | 9C | 9C | 10C | 2C,8G | 9C | 9C | 9C | 4C,5G | 9C | 10C | 10C | 10C | 9C | 9C | 10C | 10C | 10C | 5G | 9C | 5G |
| Cotton | 9C | 10C | 10C | 10C | 3C,8G | 3C,8G | 4C,9H | 2C,5G | 9C | 5C,9G | 10C | 4C,9G | 10C | 9C | 10C | 10C | 6C,9G | 4C,8G | 8G | 0 |
| | | | | | | | | | PREEMERGENCE | | | | | | | | | | | |
| Morningglory | 9G | 9G | 9G | 8G | 7H | 0 | 8H | 0 | 9G | 7G | 6G | 4G | 9G | 9G | 9C | 9G | 8G | 4G | 7G | 0 |
| Cocklebur | 7H | 4G | 3C,7H | 1H | 0 | 0 | 0 | 0 | 0 | — | 5G | 4G | 8G | 9H | 5G | 9H | 5G | 8G | 0 | 0 |
| Velvetleaf | 8G | 3G | 8G | 7G | 0 | 0 | 0 | 0 | 3G | 2G | 6G | 2G | 9G | 9G | 7G | 9G | 7G | 5G | 0 | 0 |
| Nutsedge | 10E | 10E | 10E | 2C,9G | 0 | 0 | 0 | 0 | 9G | 9G | 0 | 0 | 10C | 0 | 5G | 10E | 9G | 0 | 9H | 0 |
| Crabgrass | 9G | 3G | 3C,8G | 6G | 0 | 0 | 0 | 0 | 0 | 0 | 0 | 0 | 8G | 0 | 5G | 0 | 9G | 0 | 0 | 0 |
| Giant Foxtail | 0 | 0 | 7G | 0 | 0 | 0 | 0 | 0 | 0 | 0 | 0 | 0 | 5G | 0 | 0 | 0 | 5G | 0 | 0 | 0 |
| Barnyardgrass | 8G | 2G | 9H | 3G | 0 | 0 | 0 | 0 | 8H | 4G | 0 | 0 | 5G | 5G | 5G | 5G | 4G | 0 | 8G | 2G |
| Cheatgrass | 9H | 8H | 4C,9H | 8G | 0 | 0 | 0 | 0 | 7G | 0 | 0 | 0 | 5G | 0 | 6G | 4G | 3G | 0 | 0 | 0 |
| Wild Oats | 2C,8H | 7G | 4C,8H | 5G | 0 | 0 | 0 | 0 | 0 | 0 | 0 | 0 | 10E | 5G | 8G | 7G | 0 | 0 | 0 | 0 |
| Wheat | 9H | 7G | 8G | 5G | 0 | 0 | 6G | 0 | 7G | 0 | 0 | 0 | 5G | 5G | 6G | 7G | 7G | 0 | 0 | 0 |
| Corn | 9G | 8G | 9G | 9G | 0 | 0 | 7G | 0 | 8G | 5G | 4G | 2C,7G | 8H | 9H | 5G | 4G | 4G | 0 | 9H | 2G |
| Barley | 9G | 6G | 9G | 5G | 7H | 0 | 0 | 0 | 4G | 0 | 4G | 5G | 9G | 9H | 9G | 3G | 2C | 0 | 0 | 0 |
| Soybean | 3C,9H | 6H | 6G | 3C,7H | 3C,4H | 0 | 3C,6H | 0 | 2C,6G | 2C,7H | 0 | 2C,3H | 10E | 9H | 8G | 3C,8H | 3C,8H | 6G | 8G | 2G |
| Rice | 10E | 9H | 10E | 9H | 6G | 0 | 9H | 0 | 10E | 1H | 2C,7H | 7G | 9H | 9H | 5G | 5G | 3C,8G | 2G | 8G | 0 |
| Sorghum | 9H | 2C,9G | 10E | 10E | 3G | 0 | 2G | 0 | 9H | 9H | 10E | 0 | 9H | 9H | 3G | 10C | 2C,8G | 8G | 8G | 5G |
| Sugar beet | 9H | 5G | 5C,9G | 9G | 2H | 0 | 3G | 0 | 9H | 7G | 2G | 7G | 4C,9G | 9G | 5C,9G | 10C | 2C,8G | 8G | 8G | 5G |
| Cotton | 9G | 8G | 9G | 9G | 2G | 0 | 6G | 0 | 8G | 6G | 4C,9G | 9G | 9C | 9C | 10C | 10C | 7G | 4H | 4G | 0 |

| | Compound 11 | | Compound 12 | | Compound 13 | | Compound 14 | | Compound 15 | | Compound 16 | | Compound 17 | | Compound 18 | | Compound 19 | | Compound 20 | |
|---|---|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | POSTEMERGENCE | | | | | | | | | | | |
| Morningglory | 2C,6G | 0 | 10C | 5C,9G | 10C | 10C | 10C | 5C,9G | 10C | 4C,9G | 1C | 0 | 3C,6G | 3C,6G | 3C,8G | 2G | 2C,2H | 0 | 0 | 0 |
| Cocklebur | 4H | 0 | 9C | 9C | 9C | 9C | 10C | 9C | 9C | 3G | 5G | 0 | 9H | 2H | 3H | 2H | 2H | 0 | 0 | 0 |
| Velvetleaf | 3H | 0 | 10C | 10C | 10C | 10C | 9C | 9C | 10C | 4C,9G | 3C,8G | 0 | 5C,9G | 5C,9G | 9C | 2C,7H | 0 | 0 | 0 | 0 |
| Nutsedge | 0 | 0 | 10C | 6C,9G | 10C | 2C,5G | 4C,9G | 3C,5G | 4C,9G | 5G | 0 | 0 | 3C,6G | 3G | 9G | 0 | 0 | 0 | 0 | 0 |
| Crabgrass | 0 | 0 | 2C,5G | 4G | 0 | 0 | 0 | 0 | 0 | 0 | 5G | 0 | 2C,7G | 3G | 9G | 0 | 0 | 0 | 0 | 0 |
| Giant Foxtail | 0 | 0 | 9C | 0 | 0 | 0 | 2G | 2G | 2G | 0 | 5G | 0 | 7G | 3H | 3G | 0 | 0 | 0 | 0 | 0 |
| Barnyardgrass | 0 | 0 | 9C | 3C,7G | 0 | 0 | 2G | 3C,8H | 2G | 5G | 3G | 0 | 9H | 3H | 4H | 0 | 0 | 0 | 0 | 0 |
| Cheatgrass | 0 | 0 | 5C,9G | 3C,9H | 0 | 0 | 4C,9H | 6G | 0 | 0 | 0 | 0 | 5G | 3G | 2G | 0 | 0 | 0 | 0 | 0 |
| Wild Oats | 0 | 0 | 4G | 5G | 0 | 0 | 8G | 0 | 5G | 0 | 0 | 0 | 6G | 0 | 0 | 0 | 0 | 0 | 0 | 0 |
| Wheat | 0 | 0 | 2G | 9G | 0 | 0 | 2C,5G | 0 | 0 | 0 | 0 | 0 | 2G | 0 | 0 | 0 | 0 | 0 | 0 | 0 |

TABLE A-continued

| | Compound 21 | | Compound 22 | | Compound 23 | | Compound 24 | | Compound 25 | | Compound 26 | | Compound 27 | | Compound 28 | | Compound 29 | | Compound 30 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Corn | 0 | 0 | 9G | 2C,6H | 3C,8H | 0 | 3C,9H | 2C,7G | 3G | 0 | 0 | 0 | 9G | 3C,7H | 2C,5H | 5G | 0 | 0 | 0 | 0 |
| Barley | 0 | 0 | 4G | 2C,3G | 0 | 0 | 2C,5G | 2C,8G | 2H,4G | 0 | 0 | 0 | 3G | 3C,3G | 4C,9G | 2C,5G | 0 | 0 | 0 | 0 |
| Soybean | 2C,7G | 1C | 9C | 9C | 9C | 0 | 4C,9G | 4C,9G | 8G | 0 | 0 | 0 | 3C,8H | 6G | 2C,2H | 2G | 0 | 0 | 0 | 0 |
| Rice | 0 | 1H | 5C,9G | 8G | 3C,5G | 3C,9G | 9C | 3C,7H | 3C,9H | 1C | 0 | 0 | 8G | 2C,4G | 9G | 2C,4G | 0 | 0 | 0 | 0 |
| Sorghum | 2G | 4G | 4C,9H | 4C,9H | 3G | 3G | 4C,9H | 2C,8G | 9C | 5G | 0 | 0 | 2C,8H | 2C,7G | 5C,9G | 0 | 0 | 0 | 0 | 0 |
| Sugar beet | 4C,9G | 2C,6G | 10C | 9C | 8G | 10C | 9C | 4C,9G | 9C | 4G | 0 | 1H | 3C,9H | 3C,8G | 2C,9G | 0 | 7G | 0 | 0 | 0 |
| Cotton | 3C,7G | 3G | 10C | 9C | 10C | 9C | 9C | 4C,9G | 5C,9G | 3C,7G | 0 | 0 | 4C,9G | 0 | 2C,5G | 0 | 7G | 1H | 0 | 0 |
| | | | | | | | | | PREEMERGENCE | | | | | | | | | | | |
| Morningglory | 0 | 0 | 9G | 3C,9G | 9C | 8G | 9G | 8G | 9C | 0 | 0 | 0 | 3G | 3G | 8G | 2C,6H | 2G | 5C,9G | 2G | 1H |
| Cocklebur | 0 | 0 | 9H | 8H | — | 8H | 9H | — | 5H | 0 | 0 | 0 | — | 2H | 5G | 5H | 2G | 6G | 2G | 8G |
| Velvetleaf | 0 | 0 | 9G | 9G | 4C,8G | 3H | 4C,9G | 8G | 5H | 0 | 0 | 0 | 2G | 0 | 0 | 8G | 5G | 5C,9H | 10C | 10C |
| Nutsedge | 0 | 0 | 10E | 10E | 2C | 0 | 3C,7G | 0 | 10E | 0 | 0 | 0 | 5G | 0 | 0 | 4G | 2G | 0 | 9G | 2C,9G |
| Crabgrass | 0 | 0 | 5G | 2G | 0 | 0 | 3C,3H | 0 | 3G | 0 | 0 | 0 | 5G | 3G | 0 | 0 | 2G | 0 | 3G | 0 |
| Giant Foxtail | 0 | 0 | 6G | 2G | 0 | 0 | 3C,3H | 0 | 3C,3H | 0 | 0 | 0 | 7G | 3G | 4G | 0 | 7H | 0 | 5G | 0 |
| Barnyardgrass | 0 | 0 | 3C,9H | 3C,8H | 0 | 0 | 4C,8H | 3C,7G | 4C,8H | 0 | 0 | 0 | 5G | 0 | 2C,7G | 0 | 3C,9H | 4C,9G | 6G | 2G |
| Cheatgrass | 0 | 0 | 8G | 7G | 0 | 0 | 4C,9H | 5G | 4C,9H | 0 | 0 | 0 | 3H | 0 | 3C,9H | 5H | 0 | 0 | 7G | 2G |
| Wild Oats | 0 | 0 | 5G | 2C,4G | 0 | 0 | 2C,9G | 0 | 4C,9G | 0 | 0 | 0 | 2G | 0 | 0 | 0 | 0 | 0 | 0 | 0 |
| Wheat | 0 | 0 | 3G | 0 | 0 | 0 | 7G | 0 | 7G | 0 | 0 | 0 | 4G | 0 | 2G | 0 | 0 | 0 | 0 | 0 |
| Corn | 0 | 0 | 3C,9H | 7G | 2C,8G | 0 | 4C,9H | 3C,7G | 5G | 0 | 0 | 0 | 0 | 2C,2G | 2G | 8H | 3C,9H | 0 | 0 | 2G |
| Barley | 0 | 0 | 7G | 6G | 0 | 0 | 8G | 4G | 3G | 0 | 0 | 0 | 2C,5H | 2C,2H | 2G | 0 | 0 | 0 | 0 | 0 |
| Soybean | 2C,8G | 3G | 3C,8H | 7H | 0 | 7H | 3C,7H | 3G | 0 | 0 | 0 | 0 | 8G | 4G | 1C,5G | 0 | 0 | 0 | 0 | 0 |
| Rice | 3C,7G | 2H | 2C,9G | 3C,8G | 8H | 0 | 3C,8H | 3C,5G | 2C,7G | 5G | 0 | 0 | 3C,6G | 3G | 7G | 0 | 6G | 0 | 0 | 2C,6H |
| Sorghum | 0 | 0 | 2C,9H | 3C,8H | 7G | 0 | 3C,9H | 3C,8H | 2C,7G | 3G | 0 | 0 | 5H | 4C,9G | 2C,5G | 0 | 2C,7G | 4C,9G | 2C,8G | 3G |
| Sugar beet | 2C | 0 | 9C | 9C | 5G | 4C,9G | 3C,7G | 6G | 4C,9G | 5G | 0 | 0 | 3C,8G | 7G | 3H | 5C,9G | 0 | 0 | 8G | 2C,9G |
| Cotton | 4C,9G | 3C,6G | 9C | 9C | 5C,9G | 2C,8G | 3C,7G | 9G | 9C | 8G | 0 | 0 | 5H | 0 | 3G | 0 | 2C,4H | 9C | 1C,6G | 10C |
| | 3C,6G | 0 | 9C | 9C | 4C,9G | | 4C,9G | | 9C | 0 | 0 | 0 | 2G | 4C,9G | 0 | 9C | 10C | 9C | 10C | 10C |
| | 0 | 0 | 0 | 0 | 0 | 0 | 0 | 0 | 0 | 0 | 0 | 0 | 0 | 0 | 0 | 0 | 0 | 0 | 0 | 0 |

| Rate kg/ha | Compound 21 | | Compound 22 | | Compound 23 | | Compound 24 | | Compound 25 | | Compound 26 | | Compound 27 | | Compound 28 | | Compound 29 | | Compound 30 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | POSTEMERGENCE | | | | | | | | | | | | | | |
| Morningglory | 1C | 1C | 0 | 0 | 0 | 0 | 0 | 0 | 2G | 0 | 3G | 3G | 3C,8G | 3H | 10C | 2C,6G | 10C | 5C,9G | 2C,8G | 1H |
| Cocklebur | 2C,5H | 1H | 0 | 0 | 0 | 0 | 0 | 0 | 2C,8G | 0 | 2G | — | 8H | 1H | 10C | 5H | 1H | 6G | 2C,9G | 8G |
| Velvetleaf | 3C,9G | 4G | 0 | 0 | 0 | 0 | 0 | 0 | 10C | 6G | 10C | 3H | 5C,9G | 5G | 10C | 8G | 10C | 5C,9H | 10C | 10C |
| Nutsedge | 0 | 0 | 0 | 0 | 0 | 0 | 0 | 0 | 3C,8G | 5G | 3C,8G | 9G | 8G | 7G | 0 | 4G | 4G | 0 | 9G | 2C,9G |
| Crabgrass | 0 | 0 | 0 | 0 | 0 | 0 | 0 | 0 | 7G | 5G | 5G | 5G | 3G | 0 | 4G | 0 | 0 | 0 | 3G | 0 |
| Giant Foxtail | 0 | 0 | 0 | 0 | 0 | 0 | 0 | 0 | 4G | 5G | 4G | 2C,6H | 3G | 0 | 2C,7G | 0 | 2G | 0 | 5G | 0 |
| Barnyardgrass | 0 | 0 | 0 | 0 | 0 | 0 | 0 | 0 | 2G | 4G | 2C,5H | 5G | 4G | 0 | 3C,9H | 0 | 7H | 0 | 6G | 2G |
| Cheatgrass | 0 | 0 | 0 | 0 | 0 | 0 | 0 | 0 | 9H | 2C,5H | 4C,9H | 7H | 3H | 0 | 0 | 5H | 0 | 0 | 7G | 0 |
| Wild Oats | 0 | 0 | 0 | 0 | 0 | 0 | 1C | 0 | 7G | 9H | 3G | 6G | 2G | 0 | 0 | 0 | 0 | 0 | 0 | 2G |
| Wheat | 0 | 0 | 0 | 0 | 0 | 0 | 2H | 0 | 2C,7G | 2C,3G | 8G | 2G | 4G | 0 | 0 | 8H | 3C,9H | 0 | 0 | 0 |
| Corn | 2C,8G | 3G | 0 | 0 | 0 | 0 | 3G | 0 | 4G | 0 | 6G | 1H | 0 | 0 | 0 | 0 | 0 | 4C,9G | 2C,8H | 2C,6H |
| Barley | 3C,7G | 2H | 3C,3H | 0 | 0 | 0 | 3H | 0 | 9G | 5H | 9G | 0 | 5H | 0 | 3C,9H | 8H | 3C,6G | 2G | 8G | 3G |
| Soybean | 0 | 0 | 0 | 0 | 0 | 0 | 5G | 0 | 4C,9G | 3C,7G | 3C,6G | 2G | 8G | 5G | 5C,9G | 5C,9G | 9C | 5C,9H | 10C | 2C,9G |
| Rice | 3C,7G | 0 | 3C,3H | 0 | 0 | 0 | 1H | 0 | 5C,9G | 3C,6H | 3C,6G | 2C,3G | 5C,9G | 0 | 5G | 5G | 7G | 2G | 9G | 3G |
| Sorghum | 0 | 0 | 0 | 0 | 0 | 0 | 2C,7G | 0 | 9H | 4C,9H | 2C | 0 | 8G | 5G | 3C,9H | 0 | 2C,4H | 4C,9G | 2C,8H | 2C,8G |
| Sugar beet | 2C | 0 | 0 | 0 | 0 | 0 | 3C,7G | 2C | 3C,9H | 2G | 9C | 3C,8G | 9C | 4C,9G | 10C | 9C | 10C | 9C | 1C,6G | 9C |
| Cotton | 4C,9G | 3C,6G | 3C,7G | 4C,9G | 4C,9G | 2C,8G | 3C,7G | 3G | 10C | 9C | 5C,9G | 3C,8G | 9C | 7G | 5C,9G | 10C | 10C | 9C | 10C | 10C |
| | 3C,6G | 0 | 0 | 0 | 0 | 0 | 0 | 0 | 9C | 0 | 9C | 0 | 9C | 0 | 9C | 10C | 3C,7H | 9C | 10C | |
| | | | | | | | | | PREEMERGENCE | | | | | | | | | | | |
| Morningglory | 0 | 0 | 0 | 0 | 0 | 0 | 0 | 0 | 5G | 3G | 3G | 3G | 5G | 3G | 9G | 9G | 5H | 8G | 5G |
| Cocklebur | 0 | 0 | 0 | 0 | 0 | 0 | 4G | 0 | 8H | — | 2H | — | 2H | 0 | 4G | 4G | 0 | 2C,7G | 6H |
| Velvetleaf | 0 | 0 | 3C,3H | 0 | 0 | 0 | 4C,9G | 5H | 5G | 3H | 5G | 0 | 5G | 4C,9G | 3C,6G | 1C | 3G | 2G |
| Nutsedge | 0 | 0 | 3C,7G | 0 | 0 | 0 | 5G | 0 | 9G | 9G | 10E | 0 | 9G | 4G | 4G | 0 | 5G |
| Crabgrass | 0 | 0 | 0 | 0 | 0 | 0 | 0 | 0 | 0 | 0 | 0 | 0 | 0 | 4G | 0 | 0 |

TABLE A-continued

| | Compound 31 | | Compound 32 | | Compound 33 | | Compound 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Giant Foxtail | 0 | 0 | 0 | 0 | 0 | 0 | 0 | 0 | 2G | 0 | 5G | 0 | 0 | 0 | 3G | 0 | 0 | 0 | 7G | 5G |
| Barnyardgrass | 0 | 0 | 0 | 0 | 0 | 0 | 0 | 0 | 9H | 3C,8H | 3C,9H | 3G | 3G | 3G | 3C,7G | 0 | 0 | 0 | 2C,6G | 2G |
| Cheatgrass | 0 | 0 | 0 | 0 | 0 | 0 | 0 | 0 | 8G | 7G | 7G | 0 | 2G | 0 | 0 | 0 | 0 | 0 | 6G | 4G |
| Wild Oats | 0 | 0 | 0 | 0 | 0 | 0 | 0 | 0 | 5G | 3G | 2G | 0 | 0 | 0 | 0 | 0 | 0 | 0 | 0 | 0 |
| Wheat | 0 | 0 | 0 | 0 | 0 | 0 | 0 | 0 | 6G | 0 | 2G | 0 | 0 | 0 | 0 | 0 | 0 | 0 | 0 | 0 |
| Corn | 0 | 0 | 0 | 0 | 2C,3G | 0 | 0 | 0 | 3C,7G | 3C,3H | 3C,8G | 0 | 0 | 0 | 2C,7G | 2C,7G | 3G | 0 | 1C | 0 |
| Barley | 0 | 0 | 0 | 0 | 6G | 0 | 0 | 0 | 8G | 5G | 1C | 0 | 3G | 3G | 2C,5H | 0 | 0 | 0 | 1C | 0 |
| Soybean | 0 | 0 | 0 | 0 | 0 | 0 | 0 | 0 | 1H | 1C | 3C,7H | 2C,2H | 0 | 0 | 3C,7H | 2C,5H | 2C,2H | 0 | 2G | 0 |
| Rice | 0 | 0 | 0 | 0 | 4G | 0 | 0 | 0 | 9H | 9H | 5G | 5G | 4G | 0 | 3C,8G | 6G | 3G | 0 | 2C,7G | 0 |
| Sorghum | 0 | 0 | 0 | 0 | 3G | 0 | 0 | 0 | 9H | 1C | 6G | 0 | 2G | 0 | 2C,5C | 3C,6G | 1C | 0 | 2C,6G | 0 |
| Sugar beet | 0 | 0 | 0 | 0 | 3H | 0 | 0 | 0 | 8G | 3C,5H | 9G | 5G | 5G | 0 | 2C,9G | 9G | 3C,5H | 0 | 8G | 0 |
| Cotton | 0 | 0 | 0 | 0 | 0 | 0 | 0 | 0 | 7G | 2G | 3G | 2G | 2G | 5G | 2C,9G | 8G | 3H | 0 | 6G | 5G |

| | CMPD 41 | | CMPD 42 | | CMPD 43 | | CMPD 44 | | CMPD 45 | | CMPD 46 | | CMPD 47 | | CMPD 48 | | CMPD 49 | | CMPD 50 | |
|---|---|---|---|---|---|---|---|---|---|---|---|---|---|---|---|---|---|---|---|---|
| | | | | | | | | | POSTEMERGENCE | | | | | | | | | | | |
| Morningglory | 3C,6G | 8G | 1H | 0 | 0 | 0 | 3G | 0 | 0 | 0 | | | 10C | 10C | 10C | 10C | 10C | 2G | 4C,8H | 2G |
| Cocklebur | 3C,8H | 9H | 1H | 0 | 3C,8H | 0 | 0 | 0 | 0 | 0 | | | 10C | 9C | 10C | 10C | 10C | 3C,5H | 10C | 10C |
| Velvetleaf | 5C,9G | 8G | 1H | 0 | 3C,6G | 0 | 2H | 0 | 0 | 0 | | | 9C | 9C | 10C | 10C | 9C | 6H | 9C | 9C |
| Nutsedge | 3C,9G | 3G | 2C,6G | 3G | 0 | 0 | 0 | 0 | 0 | 0 | | | 2C,5G | 3C,8G | 2C,8G | 9C | 3C,7G | 9G | 3C,3G | 9C |
| Crabgrass | 4C,9G | 5G | 3G | 0 | 0 | 0 | 0 | 0 | 0 | 0 | | | 3C,6G | 2G | 3C,8G | 4C,9G | 0 | 0 | 5G | 3C,5G |
| Giant Foxtail | 3C,7G | 5G | 2G | 0 | 0 | 0 | 0 | 0 | 0 | 0 | | | 2G | 3C,8G | 5C,9G | 9C | 5C,9H | 3C,6G | 5C,9H | 3C,7G |
| Barnyardgrass | 4C,9G | 8G | 2G | 0 | 5C,9H | 5G | 0 | 0 | 0 | 0 | | | 10C | 9C | 10C | 9C | 0 | 3C,7G | 9C | 3C,8G |
| Cheatgrass | 5C,9H | 9H | 3G | 0 | 0 | 0 | 0 | 0 | 0 | 0 | | | 9C | 4C,9G | 9C | 4C,9G | 4C,9G | 9G | 4C,9G | 3C,8G |
| Wild Oats | 7G | 2G | 0 | 0 | 6G | 5G | 0 | 0 | 0 | 0 | | | 4C,9G | 9C | 9C | 9C | 9G | 5G | 9C | 5C,9G |
| Wheat | 3C,9G | 3C,5G | 0 | 0 | 0 | 0 | 0 | 0 | 0 | 0 | | | 9G | 3C,7G | 3C,8G | 3C,9G | 3C,5G | 4G | 3C,9G | 4G |
| Corn | 3C,6G | 2G | 5H | 0 | 2C,9H | 6H | 2H | 0 | 0 | 0 | | | 3C,9H | 2C,5G | 4C,9G | 4C,9G | 6G | 3C,6G | 3C,9G | 5G |
| Barley | 8G | 9H | 0 | 0 | 0 | 0 | 0 | 0 | 0 | 0 | | | 9G | 3C,7H | 3C,8G | 7G | 2C,8H | 2G | 2C,8G | 2C,8H |
| Soybean | 3C,8H | 3C,3H | 2H | 0 | 3C,4H | 1H | 3C,3H | 1C,1H | 0 | 0 | | | 4C,9H | 2C,5G | 5C,9G | 5G | 2C,8H | 3C,5H | 3G | 3G |
| Rice | 3C,9H | 4C,8H | 0 | 0 | 4G | 2G | 3G | 0 | 0 | 0 | | | 9G | 4C,9G | 5C,9G | 5C,9G | 5G | 6H | 3C,8H | 2H |
| Sorghum | 5C,9G | 4C,8G | 3C,8G | 3G | 4C,7G | 5G | 3G | 0 | 0 | 0 | | | 4C,9G | 3C,9H | 5C,9G | 5C,9G | 4C,9G | 3C,7G | 5C,9G | 3C,8G |
| Sugar beet | 4C,9G | 4C,8H | 3C,8G | 2G | 3C,8H | 2G | 3C,7G | 4G | 0 | 0 | | | 10C | 9C | 10C | 10C | 10C | 3C,7G | 5C,9G | 3C,8H |
| Cotton | 4C,9H | 3C,6G | 3G | 0 | 2C,5G | 5G | 3C,3H | 2G | 0 | 0 | | | 9C | 9C | 9C | 9C | 4C,9G | 0 | 5C,9G | 2C,3G |
| | | | | | | | | | PREEMERGENCE | | | | | | | | | | | |
| Morningglory | 9G | 8G | 3H | 0 | 0 | 0 | 0 | 0 | 0 | 0 | | | 9G | 9G | 8H | 7H | 2G | 0 | 5G | 0 |
| Cocklebur | 9H | 9H | 6G | 0 | 0 | 0 | 3G | 0 | 0 | 0 | | | 9H | 8H | 3H | 8H | 3C,5H | 2G | 7G | 2G |
| Velvetleaf | 3C,9G | 8G | 5G | 0 | 0 | 0 | 0 | 0 | 0 | 0 | | | 3C,8H | 3C,6H | 3C,7H | 4C,8G | 6H | 3C,6G | 4G | 10C |
| Nutsedge | 3C,9G | 3G | 3C,8G | 0 | 0 | 0 | 0 | 0 | 0 | 0 | | | 10E | 10E | 10E | 10E | 9G | 0 | 0 | 9C |
| Crabgrass | 6G | 5G | 0 | 0 | 0 | 0 | 0 | 0 | 0 | 0 | | | 4G | 4G | 2G | 3G | 0 | 4G | 0 | 0 |
| Giant Foxtail | 3C,8G | 5G | 0 | 0 | 0 | 0 | 0 | 0 | 0 | 0 | | | 3C,8H | 2G | 3C,8H | 4C,9H | 3C,6G | 3G | 3G | 3C,5G |
| Barnyardgrass | 3C,9H | 3C,7G | 0 | 0 | 6G | 0 | 0 | 0 | 0 | 0 | | | 9H | 8G | 3C,5H | 9H | 3C,7G | 5G | 5G | 5G |
| Cheatgrass | 6G | 4G | 0 | 0 | 0 | 0 | 5G | 0 | 0 | 0 | | | 3C,8H | 3C,4G | 5C,9H | 4C,9H | 9G | 4G | 4G | 4G |
| Wild Oats | 2C,8G | 3C,6G | 0 | 0 | 5G | 0 | 0 | 0 | 0 | 0 | | | 3C,8H | 1C | 3C,5G | 3C,5G | 1C | 2G | 0 | 0 |
| Wheat | 7G | 5G | 0 | 0 | 3C,6G | 2C,2G | 0 | 0 | 0 | 0 | | | 2C,9G | 3C,4G | 2C,8G | 2C,8G | 2G | 2C,8G | 3C,6G | 0 |
| Corn | 3C,9H | 2C,7G | 3H | 0 | 0 | 0 | 4G | 0 | 0 | 0 | | | 9G | 1C | 3C,9G | 2C,9G | 2G | 0 | 0 | 0 |
| Barley | 9G | 8G | 6G | 0 | 2C,2G | 0 | 0 | 0 | 0 | 0 | | | 3C,8H | 3C,3H | 3C,8G | 2C,5G | 0 | 2C,5G | 0 | 0 |
| Soybean | 7H | 7H | 5G | 0 | 0 | 0 | 2C | 0 | 0 | 0 | | | 4C,6H | 3C,3H | 3C,6G | 3C,6H | 2C,5G | 7G | 4G | 2H |
| Rice | 9H | 9H | 2H | 0 | 6G | 0 | 1C | 0 | 0 | 0 | | | 4C,9H | 3C,8H | 3C,7G | 3C,7G | 7G | 3C,9G | 3C,7G | 2C |
| Sorghum | 3C,9H | 3C,9H | 2C,5G | 0 | 3C,9H | 2G | 2C,4G | 0 | 0 | 0 | | | 9H | 9H | 9H | 9H | 3C,9G | 10C | 10C | 7G |
| Sugar beet | 3C,9G | 3C,8G | 8G | 4G | 4G | 4G | 3H | 3G | 0 | 0 | | | 10H | 9H | 10H | 5C,9G | 10C | 7G | 3C,7G | 2C |
| Cotton | 9G | 9G | 7G | 0 | 2G | 2G | 3G | 2G | 0 | 0 | | | 9C | 2C,7H | 4C,8H | 2C,8G | 7G | 0 | 0 | 0 |

TABLE A-continued

POSTEMERGENCE

| Rate kg/ha | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 7G | 0 | 5C,9G | 10C | 4C,9G | 4C,9H | 5C,9G | 3C,9H | 5C,9G | 4C,9G | 0 | 0 | 0 | 0 | 9C | 7G | 10C | 3C,9H | 10C | 3C,8G |
| Morningglory | 3C,8H | 2C | 10C | 10C | 10C | 4C,8G | 10C | 10C | 10C | 10C | 3C,5H | 1H | 3C,5H | 1H | 10C | 10C | 10C | 10C | 10C | 9C |
| Cocklebur | 10C | 10C | 10C | 10C | 10C | 4C,8G | 10C | 9C | 10C | 10C | 3C,5H | 2G | 3C,6H | 0 | 10C | 9C | 10C | 10C | 10C | 10C |
| Nutsedge | 2G | 0 | 3C,8G | 3C,7G | 3C,9G | 0 | 3C,9G | 2C,5G | 3C,8G | 3C,8G | 3C,6G | 0 | 3C,6G | 0 | 2C,8G | 4C,9H | 4C,8G | 4C,8G | 4C,9G | 4C,8G |
| Crabgrass | 2G | 0 | 9G | 0 | 3C,5G | 0 | 4G | 0 | 3C,6G | 1C | 3C,6G | 3C,8H | 0 | 3C,8H | 0 | 2C,5G | 2C,8G | 10C | 4G | 9H |
| Barnyardgrass | 5C,9G | 3C,7H | 9C | 10C | 10C | 9H | 9C | 9H | 5C,9H | 5C,9H | 9C | 2G | 9C | 2G | 10C | 9C | 10C | 10C | 9C | 9C |
| Wild Oats | 2C,5G | 2G | 2G | 0 | 3C,5G | 3C,5G | 2G | 2C | 2G | 3C,9G | 2G | 2G | 2G | 9C | 2G | 9C | 2C,9G | 4G | 7G | 5G |
| Wheat | 9G | 3C,9G | 5G | 0 | 2C,9G | 3C,5G | 2G | 3G | 2G | 7G | 7G | 3G | 7G | 8G | 2G | 0 | 3C,9G | 9G | 7G | 2C,9G |
| Corn | 3C,9G | 9G | 3C,6H | 1C,2G | 3C,5H | 2C,3G | 3C,5G | 3C,3G | 3C,8G | 3C,9G | 3C,6G | 3C,9G | 3C,6G | 0 | 3C,8G | 3C,8H | 2C,9G | 4C,9G | 3C,9G | 4C,9G |
| Soybean | 3C,4G | 3C,3H | 3C,8H | 2C,4H | 4C,9G | 3C,8G | 3C,8G | 3C,9H | 4C,9G | 0 | 2C,9G | 3C,9H | 2C,9G | 0 | 3C,5H | 2C,2H | 3C,9G | 6C,9G | 2C,8H | 3G |
| Rice | 5C,9G | 7G | 4C,9G | 2G | 6C,9G | 7G | 4C,9G | 7G | 3C,9G | 0 | 4C,9G | 3C,8G | 4C,9G | 3C,8G | 3C,7G | 3G | 9C | 4C,9G | 6C,9G | 3C,9G |
| Sorghum | 5C,9G | 3C,8G | 4C,9G | 9G | 3C,9G | 3C,8G | 3C,9G | 4G | 2C,8G | 8G | 5C,9G | 7G | 5C,9G | 7G | 4C,9H | 5G | 10C | 10C | 10C | 3C,9G |
| Cheatgrass | 6C,9G | 3C,7G | 3C,7G | 2C,4G | 5C,9G | 3C,7G | 5C,9G | 6G | 4C,9G | 6G | 4C,9G | 7G | 4C,9G | 7G | 8H | 7G | 9C | 10C | 9C | 9C |
| Sugar beet | 10C | 10C | 10C | 9C | 10C | 10C | 10C | 9C | 3C,8G | 1C | 3C,5H | 1C | 3C,5H | 1C | 9C | 9G | 9C | 10C | 9C | 3C,9G |
| Velvetleaf | 4C,8H | 3G | 9C | 3C,8H | 10C | 4C,9H | 10C | 4C,9H | 3C,7H | 9C | 5C,9G | 3C,6G | 5C,9G | 2C,8G | 3C,7G | 2C | 3C,9G | 2C,7H | 3C,9G | 0 |
| Giant Foxtail | 4C,9G | 3C,7G | 3C,8G | 3C,4G | 4C,8G | 0 | 3C,8G | 2C,6G | 3C,8G | 3C,4G | 2C,9G | 3C,5G | 2C,9G | 3C,5G | 3C,9G | 3C,3G | 3C,9G | 3C,9G | 3C,9G | 2C,8G |
| Barley | 9G | 2C,8G | 7G | 0 | 7G | 0 | 3C,5G | 3G | 3C,5G | 5G | 2C,5G | 3C,6G | 2C,5G | 3C,6G | 3C,5G | 3G | 5C,9G | 3C,9G | 3C,9G | 7G |

PREEMERGENCE

| Rate kg/ha | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Cotton | 0 | 0 | 3C,8H | 2G | 7H | 3G | 3C,7G | 3H | 5G | 5G | 0 | 0 | 0 | 0 | 7G | 3G | 9G | 8G | 2C,9G | 2G |
| Morningglory | 0 | 0 | 8G | 4C,9G | 8G | 2H | 2G | 1H | 5G | 5G | 0 | 2H | 0 | 1H | 9G | 7H | 9H | 9H | 7G | 7G |
| Cocklebur | 0 | 0 | 7H | 3C,3H | — | 5G | 8H | — | — | — | — | — | — | — | — | 3C,5H | 3C,7H | 3C,8H | 9H | 8H |
| Nutsedge | 0 | 0 | 10E | 2C,5G | 10E | 3G | 10E | 6G | 5G | 5G | — | — | — | — | 10E | 6G | 10E | 10E | 9G | 9G |
| Crabgrass | 0 | 0 | 4G | 3C,6G | 4G | 3G | 3G | 6G | 3G | 4G | 0 | 0 | 0 | 0 | 0 | 0 | 0 | 0 | 3C,9G | 3C,9G |
| Barnyardgrass | 4G | 0 | 3C,8H | 3C,6H | 9H | 2C,5G | 9H | 2C,5G | 3C,7H | 3C,7H | 3G | 0 | 3G | 0 | 3C,9H | 3C,7G | 2C,8G | 2C,8G | 5G | 5G |
| Wild Oats | 1C | 0 | 4G | 3C,2H | 7H | 2C | 3C,6G | 2C | 2G | 2G | 0 | 0 | 0 | 0 | 10H | 0 | 10H | 9H | 9H | 9H |
| Wheat | 6G | 0 | 5G | 3G | 3C,7H | 1H | 5G | 3G | 4G | 4G | 0 | 0 | 0 | 0 | 8G | 0 | 2C,7G | 7G | 5G | 4G |
| Corn | 3C,8G | 0 | 8G | 3C,5G | 3C,7H | 2C,2G | 3C,9G | 2C | 3C,8G | 3C,8G | 0 | 0 | 0 | 0 | 3C,8G | 3C,3G | 3C,9H | 3C,8H | 2C,6H | 4G |
| Soybean | 2G | 4G | 3C,5H | 3C,2H | 3C,6H | 2C,4G | 3C,5H | 2C,4H | 3C,5H | 4H | 2C,5G | 3C,8H | 2C,5G | 3C,8H | 3C,5H | 2C,2H | 4C,9G | 3C,6G | 2C,3G | 2C,3G |
| Rice | 2C,5G | 0 | 8H | 3G | 10E | 3C,7G | 3C,8G | 1C | 9H | 7G | 2C,5G | 3C,9H | 2C,5G | 3C,9H | 9H | 2C,6G | 10E | 10E | 5C,9H | 5C,9H |
| Sorghum | 2C,7G | 0 | 3C,8H | 3C,8H | 10E | 3C,7G | 8G | 3G | 3C,9H | 3C,8H | 3C,8G | 3C,9H | 3C,8G | 3C,9H | 10E | 3C,9H | 10H | 10E | 10H | 10H |
| Cheatgrass | 6G | 0 | 9G | 6G | 4C,9H | 8G | 3C,7H | 7G | 9H | 8H | 0 | 0 | 0 | 0 | 8H | 7G | 9H | 9H | 9H | 9H |
| Sugar beet | 9G | 4G | 9C | 0 | 9C | 9C | 3C,7H | 9C | 10C | 4C,9G | 3H | 0 | 3H | 0 | 9C | 9G | 4C,9G | 4C,9G | 5C,9G | 5C,9G |
| Velvetleaf | 0 | 0 | 6G | 2H | 3C,7H | 3C,4G | 3C,7H | 2C,2H | 4C,9G | 2C | 0 | 0 | 0 | 0 | 3C,7G | 2C | 3C,9G | 3C,9G | 6C,9G | 2C,7G |
| Giant Foxtail | 4G | 0 | 4G | 3C,4G | 3C,8H | 3C,4G | 3C,8H | 5G | 2C,9G | 6G | 3C,7G | 3C,3G | 3C,7G | 3C,3G | 3C,7G | 3G | 9H | 2C,7G | 9H | 5G |
| Barley | 6G | 0 | 9C | 3C,9G | 9H | 6G | 3C,5G | 5G | 3C,5G | 1C | 3C,5G | 0 | 3C,5G | 0 | 3C,9G | 3G | 9G | 8G | 0 | 0 |

POSTEMERGENCE

| Rate kg/ha | CMPD 57 | | CMPD 58 | | CMPD 59 | | CMPD 60 | |
|---|---|---|---|---|---|---|---|---|
| | 0.05 | 0.01 | 0.05 | 0.01 | 0.05 | 0.01 | 0.05 | 0.01 |
| Cotton | 9C | 10C | 10C | 7G | 8G | 7G | 10C | 7G |
| Morningglory | 10C | 10C | 4C,8H | 1C | 4C,8H | 1H | 10C | 4C,9G |
| Cocklebur | 10C | 10C | 10C | 4C,9G | 10C | 9C | 10C | 9C |
| Nutsedge | 10C | 10C | 5G | 2C,3G | 5G | 0 | 6G | 3G |
| Crabgrass | 6G | 4G | 5G | 3C,8H | 5G | 2G | 3G | 0 |
| Barnyardgrass | 9C | 9C | 4C,9H | 2C,9G | 4C,9H | 3C,7H | 4C,9H | 7H |
| Wild Oats | 4G | 2G | 9G | 4G | 7G | 8G | 7G | 4G |
| Wheat | 4G | 2C,9G | 9G | 9G | 9G | 9G | 4G | 4G |
| Corn | 3C,9G | 9G | 3C,5G | 3G | 3C,5G | 0 | 0 | 0 |
| Soybean | 4C,9G | 4C,9G | 2C,6G | 3G | 2C,3G | 1H | 3G | 2G |
| Rice | 5C,9G | 2C,8G | 5C,9G | 3C,4G | 4C,9H | 7G | 8G | 3G |

TABLE A-continued

| Rate kg/ha | CMPD 61 | | CMPD 62 | | CMPD 63 | | CMPD 64 | | CMPD 65 | | CMPD 66 | | CMPD 67 | | CMPD 68 | | CMPD 69 | | CMPD 70 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Sorghum | 9C | 8G | 5C,9G | 3C,8H | 4C,9G | 2C,5H | 3C,9G | 9G | 3C,9G | 3C,9G | 3C,9G | 3C,9G | 3C,9G | 3C,9G | 4C,9G | 4C,9H | 5C,9G | 5C,9G | 3C,9G | 3C,9H |
| Cheatgrass | 10C | 9C | 3C,9H | 8G | 3C,9G | 8G | 9C | 9G | 6C,9G | 3C,9G | 4C,9G | 4C,9G | 5C,9G | 3C,6G | 4C,8G | 3C,7G | 3C,8G | 8G | 8G | 3C,5G |
| Sugar beet | 9C | 3C,8H | 3C,6H | 2C,3G | 3C,7G | 2C,3G | 9C | 9C | 9C | 9C | 9C | 9C | 9C | 9C | 9C | 9C | 3C,8G | 9C | 9C | 3C |
| Velvetleaf | 10C | 10C | 2C | 0 | 9C | 0 | 5C,9H | 5C,9H | 10C | 9 | 9C | 5G | 10C | 5G | 5C,9G | 5C,9G | 2C,7G | 3G | 10C | 4C,9H |
| Giant Foxtail | 9C | 9C | 3C,9G | 3C,8G | 9C | 6G | 7G | 0 | 5C,9G | 2C,8G | 5G | 5G | 4C,9G | 9C | 9C | 5C,9G | 6G | 7G | 7G | 2G |
| Barley | 9G | 5G | 9G | 5G | 2C,8G | 8G | 0 | 0 | 2C,8G | 4G | 4G | 5G | 3C,9G | 5G | 2C,8G | 8G | 3C,5G | 0 | 2C,5G | 0 |
| | | | | | | | | PREEMERGENCE | | | | | | | | | | | | |
| Cotton | 9C | 0 | 0 | 0 | 0 | 0 | 3C,9G | 2C,8G | 9G | 6G | 3G | 3G | 8G | 4G | 5G | 5G | 7G | 7G | 3C,6G | 7G |
| Morningglory | 9H | 8G | 0 | 0 | 0 | 0 | 9G | 9G | 9G | 3G | 3C,7G | 1H | 9G | 1H | 5G | 2G | 2G | 2G | 7H | 3C,3H |
| Cocklebur | — | 7G | 10E | 0 | 0 | 0 | 8H | 2C | — | — | 4C,9H | 2C,3G | 8H | 2C,3G | — | 4G | — | 4G | 8H | 3C |
| Nutsedge | 9G | 9G | 2G | 0 | 0 | 0 | 9G | 9G | 5G | 2C,5H | 0 | 10E | 9G | 10E | 10E | 0 | 0 | 0 | 0 | 0 |
| Crabgrass | 3C,8G | 2G | 5G | 0 | 2G | 0 | 10E | 0 | 0 | 0 | 3C,7H | 3G | 3C,8H | 3G | 3G | 2G | 2C | 3G | 3C,8H | 0 |
| Barnyardgrass | 9H | 2G | 3G | 0 | 3G | 0 | 10H | 3C,6H | 8H | 3G | 0 | 0 | 2C,6G | 0 | 5G | 5G | 2C | 3G | 3G | 4G |
| Wild Oats | 5G | 3G | 5G | 0 | 0 | 0 | 10H | 0 | 5G | 2C | 3C,7G | 2G | 7G | 2G | 8G | 2C | 8G | 6C,9G | 3C,8G | 0 |
| Wheat | 9G | 0 | 0 | 0 | 0 | 0 | 9H | 9H | 0 | 1C | 0 | 2G | 8G | 2G | 8G | 8G | 6G | 2G | 3G | 0 |
| Corn | 3C,8G | 0 | 3C,7G | 3C,6H | 3C,6H | 0 | 1C,4G | 2C,4G | 1C,4G | 6G | 3C,7G | 2C,2G | 3C,8G | 2C,2G | 3C,7G | 4C,9H | 2C,5G | 9G | 2C,5G | 2G |
| Soybean | 2C,6G | 5G | 0 | 0 | 0 | 0 | 3C,6H | 3C,6H | 3C,5H | 1C | 3C,6H | 3G | 5H | 3G | 3C,3G | 3H | 2C,2H | 2H | 2C,2H | 0 |
| Rice | 9H | 8G | 2C,7H | 0 | 3G | 0 | 10H | 3C,9G | 9H | 0 | 4C,6H | 0 | 9H | 0 | 0 | 8G | 4C,9G | 2G | 7G | 4G |
| Sorghum | 10H | 8G | 9H | 0 | 3C,8H | 0 | 10H | 3C,9H | 9H | 4G | 3C,9H | 3C,7G | 10H | 3C,7G | 7G | 3C,5G | 3C,9H | 4C,9H | 3C,9H | 3C,7H |
| Cheatgrass | 3C,9G | 9G | 7G | 0 | 3G | 0 | 9H | 5G | 5G | 3C,7G | 3C,9H | 6G | 8G | 6G | 3C,9H | 0 | 3C,7G | 9G | 3C,7G | 3G |
| Sugar beet | 3C,9G | 5G | 5G | 0 | 5G | 0 | 3C,8H | 8G | 5G | 5G | 5G | 5C,9G | 8G | 5C,9G | 5H | 5H | 5H | 9G | 4C,9G | 5H |
| Velvetleaf | 5C,9G | 7G | 0 | 0 | 10C | 0 | 3C,8H | 2C | 9G | 8G | 9G | 3G | 4C,8H | 3G | 3G | 3G | 0 | 5C,9H | 3C,6G | 0 |
| Giant Foxtail | 3C,9H | 3G | 3C,9H | 0 | 3C,7G | 2C,8H | 9H | 3C,8H | 6G | 2C,5H | 4C,9G | 3G | 5G | 3G | 9G | 3C,9G | 3C,9H | 3G | 4G | 2G |
| Barley | 8G | 0 | 2C,3G | 0 | 2C,6G | 0 | 8G | 5G | 9G | 3C,9G | 0 | 3G | 7G | 3G | 2G | 2G | 3C,9G | 4G | 2C,5G | 0 |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | POSTEMERGENCE | | | | | | | | | | | | |
| Cotton | 10C | 9H | 9C | 3C,8H | 10C | 3C,7H | 0 | 0 | 2H | 0 | 2G | 2G | 4C,8H | 4C,8G | 9H | 5C,9G | 2C,4G | 5C,9G | 7H | 1C |
| Morningglory | 10C | 3C,8G | 10C | 10C | 10C | 3C,5G | 3C,6H | 3C,6H | 3C,6H | 3C,7G | 3C,7G | 2G | 3C,7H | 10C | 10C | 10C | 7G | 10C | 4C,9H | 2C,3H |
| Cocklebur | 10C | 4C,9H | 10C | 10C | 10C | 10C | 4C,9H | 3C,8G | 3C,8G | 4C,9H | 9C | 9C | 9C | 10C | 10C | 10C | 10C | 10C | 4C,9H | 2C,2G |
| Nutsedge | 4C,9G | 5G | 4C,9G | 5G | 9C | 3C,9G | 4G | 4G | 0 | 0 | 3C,7H | 2G | 2G | 8G | 5G | 3C,9G | 2C,6G | 3C,9G | 3G | 0 |
| Crabgrass | 5G | 0 | 2G | 0 | 10C | 0 | 0 | 5C,9G | 2C | 0 | 0 | 0 | 9G | 9G | 5G | 8G | 9C | 9C | 2G | 0 |
| Barnyardgrass | 9C | 2C | 5C,9G | 5C,9H | 10C | 9C | 2C | 5G | 2C | 3C,8H | 3C,7H | 0 | 9G | 9G | 3C,8H | 4C,9G | 5C,9H | 9C | 9C | 3C,8H |
| Wild Oats | 3C,8G | 2G | 9C | 9C | 2G | 0 | 3C,3G | 5G | 9C | 2C | 0 | 0 | 4C,9G | 4C,9G | 3C,3G | 5C,9G | 3G | 3G | 2G | 9G |
| Wheat | 9G | 7G | 3C,9G | 8G | 9C | 5G | 9C | 5G | 3C,5G | 3C,8G | 0 | 2G | 9G | 5G | 3C,6G | 3G | 6G | 9C | 6C,9G | 3C,7G |
| Corn | 4C,9H | 2H | 4C,9H | 1H | 2C,9G | 7H | 4C,9H | 4C,9G | 4C,9G | 2C | 2G | 0 | 9H | 3C,6H | 4C,8H | 6G | 2G | 2G | 2C,9G | 3C,6H |
| Soybean | 4C,9G | 6H | 4C,9G | 3C,7G | 3C,8H | 3H | 3H | 3H | 3H | 0 | 0 | 5H | 9C | 5H | 6H | 3C,7G | 4C,9H | 4C,9H | 2H | 3C,7G |
| Rice | 9C | 9C | 9C | 4C,9G | 2C,9G | 3C,9G | 4C,9G | 4C,9G | 5C,9G | 2C,9G | 4G | 4G | 5H | 4C,9G | 5G | 9G | 3H | 9G | 8G | 9G |
| Sorghum | 9C | 4C,9G | 4C,9G | 2C,9G | 2C,3G | 3C,9G | 2C,6H | 4C,9G | 4C,9G | 4C,8G | 3C,8G | 2C,6G | 5C,9G | 5C,9G | 4C,9G | 4C,9G | 9G | 9G | 4C,9G | 3G |
| Cheatgrass | 9C | 6C,9G | 9C | 2C,9G | 3C,9G | 3C,9G | 2C,6H | 4C,9G | 4C,9G | 2C,6H | 3C,8G | 4C,8G | 5C,9G | 8G | 5C,9G | 5C,9G | 9G | 9G | 9G | 3G |
| Sugar beet | 9C | 9C | 10C | 10C | 2C | 2C,3G | 3C,5G | 0 | 3C,7H | 3C,7H | 3C,7G | 4C,9H | 9C | 4C,9H | 9C | 9C | 10C | 5C,9G | 3C,8G | 3C,7H |
| Velvetleaf | 10C | 9C | 10C | 10C | 10C | 8G | 0 | 0 | 5C,9G | 2C,8G | 0 | 4G | 9C | 4G | 9C | 9C | 3G | 3G | 9C | 0 |
| Giant Foxtail | 3C,8G | 3C,6G | 3C,8G | 5G | 3C,7G | 4G | 9H | 6G | 2H | 3C,9G | 0 | 4G | 3C,9G | 4G | 6C | 3C,7G | 5C,9H | 3C,7G | 3C,4H | 3C,8G |
| Barley | 4C,8G | 4C,8G | 4C,9G | 2C,5G | 3C,9G | 5G | 8G | 5G | 9G | 3C,9G | 0 | 4G | 3C,9G | 3C,6G | 3C,6G | 3C,6G | 4G | 3C,7G | 3C,7G | 2G |
| | | | | | | | | PREEMERGENCE | | | | | | | | | | | | |
| Cotton | 3C,8G | 4G | 8H | 7G | 3C,8H | 6G | 4G | 0 | 4G | 0 | 0 | 2G | 2G | 0 | 8H | 5G | 5G | 0 | 0 | 0 |
| Morningglory | — | 8G | 9G | 9G | — | 2G | 9G | 0 | 9G | 0 | 0 | 2G | 2G | 5G | 5G | 2G | 2G | 1C | 0 | 0 |
| Cocklebur | 9H | 8H | 8H | — | 9H | 2C,5H | 2C,3H | 0 | 2H | 0 | — | 8H | 8H | 9H | — | 7H | 7H | 2C,5H | 0 | 0 |
| Nutsedge | 0 | 0 | 4C,9G | 0 | 9G | 8G | 0 | 0 | 0 | 0 | 0 | 0 | 0 | 0 | 4G | — | 4G | 0 | 0 | 0 |
| Crabgrass | 0 | 0 | 3G | 2G | 2G | 0 | 3C,8H | 0 | 0 | 0 | 0 | 2G | 2H | 2G | 2G | 4G | 9H | 0 | 0 | 0 |
| Barnyardgrass | 8H | 5G | 9H | 3H | 9H | 9H | 0 | 0 | 0 | 0 | 0 | 2H | 2H | 9H | 9H | 9H | 0 | 0 | 0 | 0 |

TABLE A-continued

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| Wild Oats | 3C,7G | 3C,3G | 3C,5G | 0 | 0 | 0 | 1C | 0 | — | 0 | 0 | 0 | 3C,6G | 0 | 3C,3G | 2C,4G | 0 | 0 | 3C,7G | 0 |
| Wheat | 8G | 8G | 3C,9H | 6G | 7G | 3G | 6G | 0 | — | 0 | 0 | 0 | 3G | 0 | 3G | 7G | 0 | 2G | 2C,7G | 0 |
| Corn | 3C,8G | 0 | 3C,9H | 0 | 3C,7G | 0 | 3C,6G | 2G | — | 4G | 0 | 0 | 3C,8H | 0 | 2G | 3C,8G | 2G | 0 | 3C,7G | 0 |
| Soybean | 3C,7H | 5H | 3C,7H | 3C,6H | 7H | 5G | 0 | 0 | — | 0 | 0 | 0 | 3C,7H | 0 | 2C,4H | 5H | 5G | 2G | 2H | 0 |
| Rice | 9H | 9H | 9H | 8G | 9H | 8H | 8H | 2G | — | 0 | 2G | 0 | 8H | 0 | 4G | 8G | 4G | 4G | 9H | 0 |
| Sorghum | 9H | 9H | 10H | 2C,7G | 9H | 7G | 3C,9H | 3C,5G | 2C,7G | 0 | 4G | 2G | 2G | 0 | 3C,8H | 9H | 3C,7G | 5G | 9H | 0 |
| Cheatgrass | 9G | 6G | 9G | 9H | 9H | 8H | 8G | 0 | 0 | 0 | 0 | 0 | 6G | 0 | 7G | 9G | 6G | 7H | 2C,6G | 0 |
| Sugar beet | 9G | 9G | 9G | 8G | 9H | 8G | 3H | 0 | 0 | 0 | 3G | 0 | 7H | 0 | 3H | 9G | 7H | 5H | 2H | 0 |
| Velvetleaf | 7H | 2G | 4C,9G | 7H | 8H | 3H | 0 | 0 | 0 | 0 | 0 | 0 | 5C,9G | 0 | 1H | 8H | 0 | 0 | 0 | 0 |
| Giant Foxtail | 5G | 3G | 8H | 6G | 8G | 3G | 3C,9H | 0 | 2C,9G | 0 | 6G | 0 | 3C,8H | 0 | 3C,5G | 4G | 5G | 5G | 0 | 0 |
| Barley | 9G | 8H | 3C,9G | 7G | 9G | 5G | 2C,9G | 3G | 2C,9G | 0 | 8G | 0 | 9G | 6G | 9G | 9G | 5G | 5G | 2C,9G | 9G |
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

POSTEMERGENCE

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| Cotton | 9H | 2G | 0 | 0 | 5C,9G | 4C,8H | 9C | 5C,9G | 4C,9G | 5C,9G | 3C,8G | 3C,8G | 3C,8H | 3C,8H | 3C,9H | 3C,9H | 1C | 1C | 4C,9G | 3C,7H |
| Morningglory | 9C | 9C | 3C,6H | 3G | 10C | 5H | 3C,8G | 2C,2H | 9C | 4C,9G | 4C,8G | 4C,8G | 3C,8H | 3G | 10C | 2C,5G | 0 | 0 | 4C,8H | 2C,4H |
| Cocklebur | 10C | 9C | 3C,8H | 1C | 10C | 3C,8H | 10C | 0 | 10C | 10C | 2G | 2G | 5C,9G | 0 | 10C | 3C,7G | 4G | 4G | 5C,9G | 4C,9G |
| Nutsedge | 7G | 2G | 0 | 0 | 3C,8G | 3C,7G | 9C | 3C,8G | 3C,8G | 2C,5G | 2G | 2C | 0 | 4G | 3C,8G | 2C | 0 | 0 | 36,9G | — |
| Crabgrass | 0 | 0 | 6G | 0 | 2G | 0 | 3C,8G | 0 | 3C,7G | 3C,5G | 5C,9H | 5C,9H | 4G | 4G | 2G | 9H | 0 | 0 | 0 | 0 |
| Barnyardgrass | 5C,9G | 2C,5H | 5C,9H | 3C,8H | 4C,9H | 3C,6G | 9H | 3C,8H | 3C,7H | 5C,9H | 0 | 0 | 3C,7H | 4G | 3C,7H | 1C,2H | 3H | 3H | 0 | 3H |
| Wild Oats | 2C,4G | 0 | 9G | 9G | 3C,8H | 3G | 2C,6G | 0 | 3C,7H | 2C,3G | 5C,9H | 5C,9H | 3C,9H | 0 | 1H | 0 | 6G | 0 | 3H | 0 |
| Wheat | 2G | 0 | 9C | 0 | 8G | 3G | 8G | 2G | 4G | 5G | 3C,8G | 3C,8G | 0 | 0 | 2G | 3G | 7H | 0 | 0 | 0 |
| Corn | 8H | 0 | 4C,9G | 3C,8H | 2C,5H | 3G | 9H | 7H | 2C,6H | 4C,9G | 3C,8G | 3C,8G | 3C,7H | 0 | 2C,6G | 0 | 0 | 2C | 2H | 0 |
| Soybean | 3C,5H | 0 | 2H | 2H | 3C,8H | 2G | 4C,9G | 4C,9G | 4C,9G | 3C,9H | 4G | 4G | 3C,7H | 0 | 3C,7H | 3G | 0 | 0 | 3C,6G | 2C,2H |
| Rice | 8G | 0 | 9C | 9C | 5C,9G | 3G | 3C,8G | 2C,8G | 3C,9H | 3C,8G | 5C,9H | 5C,9H | 3G | 3G | 4G | 0 | 0 | 0 | 3C,7G | 2G |
| Sorghum | 4C,9G | 3C,9G | 9C | 4C,9G | 5C,9G | 3C,7G | 4C,9G | 4C,9G | 4C,9H | 9C | 4G | 4G | 3C,9H | 3G | 2C,9H | 2C,5G | 2C | 2C | 3C,7G | 2G |
| Cheatgrass | 8G | 5G | 4C,9G | 9G | 2C,8G | 3C,7G | 2C,7G | 3C,4G | 8G | 3C,8G | 5C,9H | 5C,9H | 3G | 3G | 2C,5G | 3C,8H | 0 | 0 | 2C,5G | 2G |
| Sugar beet | 9G | 5C,9G | 4C,8H | 3C,6H | 9C | 3C,8G | 9C | 9C | 4C,8H | 9C | 9C | 9C | 4C,6H | 3C,7G | 3C,7G | 4C,8G | 1C | 1C | 3C,4G | 2C,5G |
| Velvetleaf | 9C | 6G | 0 | 0 | 10C | 9C | 9C | 10C | 4C,8H | 10C | 5C,8H | 5C,8H | 3C,7G | 3C,7G | 10C | 2G | 2G | 2G | 5C,9G | 3C,7G |
| Giant Foxtail | 2C,6G | 0 | 4C,9G | 3C,7H | 3C,5G | 2C,3G | 2C,5G | 2G | 4C,9G | 2G | 3C,6G | 3C,6G | 2C,3G | 2C,3G | 1H | 0 | 1C | 1C | 0 | 0 |
| Barley | 3G | 0 | 4C,9G | 3C,7G | 3C,8G | 2C,5G | 2C,8G | 7G | 2C,3H | 2C,3G | 0 | 0 | 0 | 2G | 2G | 0 | 0 | 0 | 0 | 0 |

PREEMERGENCE

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| Cotton | 7G | 3G | 0 | 0 | 0 | 0 | 2C,4G | 3G | 3G | 0 | | | 2C,3G | 2C,3G | 3G | 1H | 0 | 0 | 0 | 0 |
| Morningglory | 9G | 3G | 3G | 0 | 3C,8H | 0 | 0 | 0 | 4G | 0 | 1C | 1C | 2C,4G | 2C,4G | 2H | | 0 | 0 | 0 | 0 |
| Cocklebur | 8H | 3H | 2C,3G | 0 | 3C,4H | 0 | 9H | 3C,4H | 8H | — | 3C,3H | 3C,3H | — | — | 3C,3H | 3C,8H | 0 | 0 | 0 | 0 |
| Nutsedge | 0 | 0 | 0 | 0 | 3C,4H | 0 | 3C,8H | 2C,5G | 3C,5H | 0 | 3G | 3G | 3C,9H | 3C,9H | 2C,8G | 3C,7G | 0 | 0 | 0 | 0 |
| Crabgrass | 9H | 0 | 9H | 0 | 9H | 0 | 5G | 4G | 9H | 0 | 3C,6G | 3C,6G | 8G | 8G | 7G | 2C | 0 | 0 | 0 | 0 |
| Barnyardgrass | 4G | 3G | 0 | 0 | 5G | 0 | 5G | 3C,8G | 3C,7G | 8H | 3C,6G | 3C,6G | 3C,9H | 3C,9H | 0 | 0 | 0 | 0 | 0 | 0 |
| Wild Oats | 3G | 0 | 0 | 0 | 4C,9H | 3C,6G | 4C,9H | 3C,8H | 9H | 8H | 0 | 0 | 0 | 0 | 3G | 0 | 0 | 0 | 0 | 0 |
| Wheat | 4G | 0 | 7G | 0 | 3C,8H | 3G | 3C,8H | 3C,8G | 3G | 3G | 3C,5G | 3C,5G | 7G | 7G | 0 | 0 | 0 | 0 | 0 | 0 |
| Corn | 3G | 0 | 4G | 0 | 8H | 4G | 3C,7H | 3C,6G | 3C,9H | 5G | 3C,7G | 3C,7G | 3C,7G | 3C,7G | 2G | 0 | 0 | 0 | 0 | 0 |
| Soybean | 5G | 0 | 1C | 0 | 3C,8H | 2G | 2C,8G | 2C,6G | 3C,9H | 3C,6H | 3C,5G | 3C,5G | 3C,7G | 3C,7G | 2C,5G | 3C,7G | 0 | 0 | 0 | 0 |
| Rice | 8H | 7G | 7H | 0 | 3C,8G | 2C,4H | 3C,7G | 2C,5G | 3C,7H | 3C,5G | 3C,5G | 3C,5G | 3C,7G | 3C,7G | 2C,2H | 3C,5H | 0 | 2C | 0 | 0 |
| Sorghum | 9H | 3C,9H | 3C,9H | 0 | 9H | 3C,8H | 3C,8G | 8G | 9H | 9H | 7G | 7G | 3C,9H | 3C,9H | 7H | 9G | 0 | 0 | 0 | 0 |
| Cheatgrass | 7G | 5G | 0 | 0 | 8G | 8G | 3C,9H | 4C,9G | 5C,9G | 5C,9H | 9G | 9G | 3C,9H | 3C,9H | 3C | 9G | 0 | 0 | 0 | 0 |
| Sugar beet | 9G | 5H | 0 | 0 | 10C | 8H | 4C,9G | 9G | 8G | 9G | 4G | 4G | 3C,9H | 3C,9H | 7G | 9G | 2C | 5G | 5G | 3H |
| Velvetleaf | 8H | 2H | 0 | 0 | 4C,9G | 0 | 2H | 3H | 5H | 5H | 2H | 2H | 9C | 9C | 5H | 7G | 0 | 0 | 0 | 0 |
| Giant Foxtail | 7H | 0 | 2G | 0 | 4C,8G | 0 | 3C,6G | 3G | 3C,7H | 0 | 3C,7H | 3C,7H | 0 | 0 | 2H | 4G | 2C | 0 | 0 | 0 |
| Barley | 9G | 3G | 9G | 5G | 8G | 4G | 3C,5G | 2C,5G | 3C,4G | 2G | 3C,6G | 3C,6G | 2G | 2G | 0 | 5G | 0 | 0 | 0 | 0 |
| | CMPD 81 | | CMPD 82 | | CMPD 83 | | CMPD 84 | | CMPD 85 | | CMPD 86 | | CMPD 87 | | CMPD 88 | | | |

TABLE A-continued

| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 |
|---|---|---|---|---|---|---|---|---|---|---|---|---|---|---|
| | | | | | POSTEMERGENCE | | | | | | | | | |
| Cotton | — | 3C,7G | 2G | 3C,7G | 2C,5G | 2G | 1C | 0 | 1C | 0 | 0 | 0 | 0 | 0 |
| Morningglory | — | 2C,5G | 0 | 1H | 0 | 2C,4G | 2H | 0 | 1C,2G | 0 | 0 | 0 | 0 | 0 |
| Cocklebur | — | 9C | 5C,9G | 5C,9H | 3C,8G | 4C,9G | 2C,7G | 0 | 1C | 0 | 0 | 0 | 0 | 0 |
| Nutsedge | — | 9G | 0 | 0 | 0 | 2C,8G | — | 0 | 0 | 0 | 0 | 0 | 0 | 0 |
| Crabgrass | — | 0 | 0 | 0 | 0 | 0 | 0 | 0 | 0 | 0 | 0 | 0 | 0 | 0 |
| Barnyardgrass | — | 0 | 3C,4H | 3C,6H | 0 | 2H | 0 | 0 | 0 | 0 | 0 | 0 | 0 | 0 |
| Wild Oats | — | 0 | 0 | 2G | 0 | 0 | 0 | 0 | 0 | 0 | 0 | 0 | 0 | 0 |
| Wheat | — | 0 | 0 | 7G | 0 | 0 | 0 | 0 | 0 | 0 | 0 | 0 | 0 | 0 |
| Corn | — | 0 | 0 | 0 | 0 | 0 | 0 | 0 | 0 | 0 | 0 | 0 | 0 | 0 |
| Soybean | — | 3C,7G | 1H | 4C,9G | 2H | 0 | 0 | 0 | 1C | 0 | 0 | 0 | 0 | 0 |
| Rice | — | 0 | 0 | 0 | 0 | 0 | 0 | 0 | 0 | 0 | 0 | 0 | 0 | 0 |
| Sorghum | — | 3C,8G | 3C,7H | 3C,9H | 3C,8H | 3C,4G | 0 | 0 | 0 | 0 | 0 | 0 | 0 | 0 |
| Cheatgrass | — | 0 | 0 | 0 | 0 | 0 | 0 | 0 | 0 | 0 | 0 | 0 | 0 | 0 |
| Sugar beet | — | 2C,5G | 3G | 3C,7G | 2H | 1C | 2C,7G | 0 | 0 | 0 | 0 | 0 | 0 | 0 |
| Velvetleaf | — | 5C,9G | 3C,7G | 3G | 0 | 1C | 1C | 0 | 0 | 0 | 0 | 0 | 0 | 0 |
| Giant Foxtail | — | 3C,4H | 3C,3G | 1C | 0 | 0 | 0 | 0 | 0 | 0 | 0 | 0 | 0 | 0 |
| Barley | — | 0 | 0 | 0 | 0 | 0 | 0 | 0 | 0 | 0 | 0 | 0 | 0 | 0 |
| | | | | | PREEMERGENCE | | | | | | | | | |
| Cotton | — | 1C | 0 | 0 | 0 | 1C | 0 | 3G | 0 | 0 | 0 | 0 | 0 | 0 |
| Morningglory | — | 0 | 0 | 0 | 0 | 1C | 0 | 0 | 0 | 0 | 0 | 0 | 0 | 0 |
| Cocklebur | — | 0 | 0 | — | 0 | 1C | 0 | — | — | — | — | — | — | — |
| Nutsedge | — | 0 | 0 | 0 | 0 | 0 | 0 | 0 | 0 | 0 | 0 | 0 | 0 | 0 |
| Crabgrass | — | 0 | 0 | 0 | 0 | 0 | 0 | 0 | 0 | 0 | 0 | 0 | 0 | 0 |
| Barnyardgrass | — | 0 | 0 | 0 | 0 | 3G | 0 | 0 | 0 | 0 | 0 | 0 | 0 | 0 |
| Wild Oats | — | 0 | 0 | 0 | 0 | 0 | 0 | 0 | 0 | 0 | 0 | 0 | 0 | 0 |
| Wheat | — | 0 | 0 | 0 | 0 | 0 | 0 | 0 | 0 | 0 | 0 | 0 | 0 | 0 |
| Corn | — | 1H | 0 | 0 | 0 | 0 | 0 | 0 | 0 | 0 | 0 | 0 | 0 | 0 |
| Soybean | — | 3C,2G | 0 | 0 | 0 | 2C | 0 | 0 | 0 | 0 | 0 | 0 | 0 | 0 |
| Rice | — | 2G | 0 | 0 | 0 | 0 | 0 | 3G | 0 | 0 | 0 | 2G | 0 | 0 |
| Sorghum | — | 3C,7G | 0 | 2C,5G | 0 | 2C,7G | 0 | 0 | 0 | 0 | 0 | 0 | 0 | 0 |
| Cheatgrass | — | 0 | 0 | 0 | 0 | 3G | 0 | 0 | 0 | 0 | 0 | 0 | 0 | 0 |
| Sugar beet | — | 7G | 3G | 3G | 0 | 3G | 0 | 3G | 7G | 0 | 0 | 0 | 0 | 0 |
| Velvetleaf | — | 0 | 0 | 0 | 0 | 0 | 0 | 0 | 0 | 0 | 0 | 0 | 0 | 0 |
| Giant Foxtail | — | 0 | 0 | 0 | 0 | 0 | 0 | 0 | 0 | 0 | 0 | 0 | 0 | 0 |
| Barley | — | 2G | 0 | 0 | 0 | 0 | 0 | 0 | 0 | 0 | 0 | 0 | 0 | 0 |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oat (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (—) response means no test.

Response ratings are contained in Table B.

TABLE B

| RATE = G/HA | CMPD 55 | | | | CMPD 56 | | | | CMPD 57 | | | | CMPD 58 | | | | CMPD 59 | | | | CMPD 68 | | | | CMPD 61 | | | |
|---|---|---|---|---|---|---|---|---|---|---|---|---|---|---|---|---|---|---|---|---|---|---|---|---|---|---|---|---|
| RATE | 1. | 4. | 16. | 62. | 1. | 4. | 16. | 62. | 1. | 4. | 16. | 62. | 1. | 4. | 16. | 62. | 1. | 4. | 16. | 62. | 1. | 4. | 16. | 62. | 1. | 4. | 16. | 62. |
| | | | | | | | | | POSTEMERGENCE | | | | | | | | | | | | | | | | | | | |
| GIANT FOXTAIL | 0 | 0 | 30 | 50 | 0 | 0 | 30 | 60 | 0 | 30 | 50 | 70 | | 30 | 50 | 70 | 0 | 30 | 50 | 80 | 0 | 30 | 0 | 40 | 0 | 0 | 30 | — |
| VELVETLEAF | 50 | 70 | 100 | 100 | 70 | 50 | 70 | 100 | 30 | 100 | 100 | 100 | | 50 | 70 | 100 | 30 | 30 | 60 | 100 | 30 | 60 | 90 | 100 | 30 | 80 | 100 | 100 |
| SUGAR BEETS | 50 | 90 | 100 | 0 | 100 | 90 | 100 | 100 | 70 | 100 | 100 | 100 | | 90 | 100 | 100 | 50 | 70 | 100 | 100 | 70 | 70 | 100 | 100 | 70 | 100 | 100 | 50 |
| CRABGRASS | 0 | 0 | 0 | 60 | 0 | 30 | 60 | 80 | 0 | 30 | 30 | 70 | | 0 | 30 | 50 | 0 | 0 | 30 | 50 | 0 | 0 | 30 | 60 | 0 | 0 | 30 | 50 |
| TEAWEED | 0 | 20 | 30 | 70 | 0 | 30 | 50 | 70 | 0 | 30 | 50 | 70 | | 50 | 70 | 90 | 0 | 50 | 30 | 50 | 30 | 50 | 60 | 60 | 30 | 50 | 70 | 90 |
| JIMSONWEED | 0 | 0 | 30 | 60 | 0 | 30 | 70 | 80 | 30 | 30 | 50 | 80 | | 30 | 30 | 90 | 30 | 50 | 70 | 50 | 0 | 70 | 60 | 70 | 0 | 40 | 100 | 100 |
| RICE | 0 | 30 | 60 | 100 | 0 | 30 | 70 | 100 | 30 | 30 | 50 | 70 | | 30 | 70 | 90 | 0 | 30 | 70 | 100 | 0 | 30 | 30 | 50 | 30 | 50 | 100 | 100 |
| COCKLEBUR | 60 | 90 | 100 | 100 | 70 | 70 | 100 | 100 | 30 | 100 | 100 | 100 | | 30 | 70 | 100 | 50 | 50 | 100 | 100 | 60 | 70 | 90 | 70 | 30 | 100 | 100 | 100 |
| COTTON | 0 | 30 | 60 | 90 | 0 | 30 | 50 | 70 | 30 | 30 | 60 | 100 | | 30 | 30 | 30 | 0 | 0 | 0 | 30 | 0 | 0 | 0 | 40 | 0 | 30 | 70 | 90 |
| SOYBEAN | 0 | 30 | 60 | 100 | 70 | 100 | 100 | 100 | 50 | 80 | 100 | 100 | | 60 | 100 | 100 | 30 | 70 | 70 | 100 | 30 | 70 | 30 | 30 | 30 | 50 | 100 | 100 |
| BARNYARD GRASS | 0 | 30 | 30 | 90 | 0 | 40 | 50 | 70 | 0 | 30 | 50 | 70 | | 0 | 20 | 30 | 0 | 0 | 0 | 30 | 0 | 30 | 0 | 0 | 0 | 30 | 70 | — |
| WILD OATS | 0 | 30 | 30 | 100 | 0 | 40 | 70 | 100 | 30 50 | 80 | 70 | 70 | | 0 | 70 | 70 | 0 | 0 | 30 | 30 | 30 | 30 | 30 | 30 | 30 | 30 | 60 | — |
| MORNINGGLORY | 30 | 50 | 70 | 90 | 30 | 0 | 30 | 70 | 0 | 0 | 0 | 30 | | 90 | 90 | 90 | 0 | 30 | 50 | 70 | 50 | 70 | 100 | 100 | 0 | 50 | 70 | 50 |
| WHEAT | 0 | 0 | 0 | 20 | 0 | 0 | 30 | 50 | 0 | 0 | 0 | 40 | | 0 | 0 | 30 | 0 | 0 | 30 | 30 | 0 | 0 | 0 | 30 | 0 | 0 | 0 | — |
| CASSIA | 0 | 30 | 60 | 60 | 30 | 30 | 70 | 100 | 50 | 70 | 90 | 100 | | 60 | 90 | 100 | 30 | 30 | 50 | 40 | 50 | 70 | 60 | 50 | 30 | 30 | 30 | — |
| JOHNSONGRASS | 30 | 50 | 70 | 90 | 0 | 0 | 30 | 90 | 0 | 30 | 30 | 30 | | 60 | 60 | 70 | 0 | 30 | 30 | 60 | 0 | 30 | 30 | 50 | 0 | 30 | 70 | 70 |
| NUTSEDGE | 0 | 0 | 0 | 50 | 30 | 30 | 50 | 70 | 50 | 70 | 70 | 100 | | 30 | 30 | 50 | 30 | 30 | 50 | 70 | 30 | 30 | 30 | 30 | 30 | 30 | 100 | 100 |
| CORN | 0 | 30 | 30 | 40 | 0 | 0 | 30 | 60 | 0 | 0 | 0 | 40 | | 0 | 0 | 30 | 0 | 0 | 30 | 30 | 0 | 0 | 0 | 30 | 0 | 0 | 0 | 50 |
| WILD BUCKWHEAT | 0 | 0 | 60 | 100 | 0 | 30 | 60 | 90 | 50 | 70 | 90 | 90 | | 50 | 70 | 100 | 0 | 30 | 30 | 60 | 30 | 30 | 60 | 70 | 30 | 30 | 50 | — |
| BLACK GRASS | 0 | 30 | 30 | 80 | 0 | 30 | 40 | 100 | 30 | 50 | 70 | 100 | | 30 | 70 | 100 | 0 | 0 | 50 | 100 | 0 | 0 | 30 | 70 | 0 | 0 | 30 | — |
| RAPESEED | 60 | 100 | 100 | 100 | 60 | 100 | 100 | 100 | 70 | 100 | 100 | 100 | | 100 | 100 | 100 | 0 | 30 | 80 | 100 | 30 | 30 | 50 | 100 | 30 | 100 | 100 | 100 |
| BARLEY | 0 | 0 | 0 | 40 | 0 | 0 | 30 | 70 | 0 | 30 | 20 | 40 | | 0 | 30 | 30 | 0 | 0 | 30 | 30 | 0 | 0 | 30 | 20 | 0 | 0 | 30 | — |
| GREEN FOXTAIL | 0 | 30 | 30 | 50 | 0 | 30 | 30 | 70 | 0 | 50 | 50 | 70 | | 30 | 30 | 50 | 0 | 0 | 30 | 60 | 0 | 0 | 30 | 70 | 0 | 0 | 30 | — |
| CHEAT GRASS | 30 | 60 | 70 | 70 | 30 | 30 | 50 | 100 | 0 | 70 | 70 | 100 | | 30 | 30 | 60 | 30 | 0 | 30 | 70 | 30 | 30 | 50 | 90 | 0 | 60 | 80 | 100 |
| VIOLA | 0 | 0 | 0 | 80 | 0 | 0 | 30 | 100 | 30 | 50 | 70 | 100 | | 30 | 70 | 100 | 0 | 30 | 60 | 100 | 30 | 30 | 70 | 80 | 30 | 30 | 30 | — |
| LAMBSQUARTER | 50 | 70 | 100 | 100 | 30 | 30 | 60 | 80 | 50 | 50 | 70 | 70 | | 30 | 50 | 70 | 30 | 0 | 50 | 60 | 30 | 50 | 30 | 60 | 0 | 50 | 70 | 100 |
| | | | | | | | | | PREEMERGENCE | | | | | | | | | | | | | | | | | | | |
| GIANT FOXTAIL | — | — | 30 | 60 | — | — | 50 | 70 | — | — | 50 | 70 | | 0 | 30 | 70 | — | — | 70 | 60 | — | — | 30 | 70 | — | — | 60 | 60 |
| VELVETLEAF | — | 30 | 60 | 90 | — | — | 30 | 80 | — | — | 50 | 80 | | 30 | 30 | 50 | — | — | 60 | 60 | — | — | 50 | 50 | — | — | 30 | 50 |
| SUGAR BEETS | — | 30 | 60 | 0 | — | — | 60 | 100 | — | — | 90 | 100 | | 70 | 70 | 90 | — | — | 80 | 90 | — | — | 70 | 80 | — | — | 80 | 80 |
| CRABGRASS | — | 0 | 0 | 70 | — | — | 50 | 70 | — | — | 30 | 50 | | 0 | 0 | 30 | — | — | 0 | 0 | — | — | 30 | 30 | — | — | 60 | 60 |
| TEAWEED | — | 30 | 40 | 70 | — | — | 50 | 60 | — | — | 50 | 80 | | 30 | 30 | 60 | — | — | 30 | 30 | — | — | 30 | 30 | — | — | 30 | 30 |
| JIMSONWEED | — | 30 | 50 | 80 | — | — | 50 | 70 | — | — | 60 | 80 | | 30 | 30 | 60 | — | — | 60 | 60 | — | — | 50 | 50 | — | — | 30 | 50 |
| RICE | — | — | 50 | 70 | — | — | 30 | 80 | — | — | 50 | 80 | | 30 | 0 | 30 | — | — | 30 | 30 | — | — | 30 | 70 | — | — | 30 | 70 |
| COCKLEBUR | — | — | 30 | 100 | — | — | 50 | 70 | — | — | 60 | 80 | | 30 | 30 | 50 | — | — | 50 | 60 | — | — | 30 | 50 | — | — | 30 | 50 |
| COTTON | — | — | 60 | 90 | — | — | 0 | 80 | — | — | 30 | 30 | | 0 | 0 | 30 | — | — | 0 | 20 | — | — | 30 | 30 | — | — | 20 | 70 |
| SOYBEAN | — | — | 0 | 0 | — | — | 0 | 20 | — | — | 30 | 50 | | 0 | 0 | 0 | — | — | 0 | 0 | — | — | 0 | 30 | — | — | 0 | 50 |
| BARNYARD GRASS | — | — | 60 | 90 | — | — | 40 | 80 | — | — | 60 | 80 | | 30 | 30 | 60 | — | — | 30 | 60 | — | — | 30 | 60 | — | — | 60 | 60 |
| WILD OATS | — | — | 30 | 50 | — | — | 20 | 40 | — | — | 50 | 0 | | 0 | 0 | 30 | — | — | 0 | 30 | — | — | 30 | 30 | — | — | 30 | 30 |
| MORNINGGLORY | — | — | 0 | 70 | — | — | 30 | 50 | — | — | 30 | 60 | | 0 | 0 | 30 | — | — | 0 | 60 | — | — | 50 | 70 | — | — | 70 | 70 |
| WHEAT | — | — | 0 | 0 | — | — | 0 | 30 | — | — | 50 | 30 | | 30 | 0 | 30 | — | — | 30 | 30 | — | — | 0 | 70 | — | — | 50 | 50 |
| CASSIA | — | — | 30 | 60 | — | — | 50 | 30 | — | — | 50 | 70 | | 30 | 0 | 50 | — | — | 30 | 50 | — | — | 30 | 50 | — | — | 30 | 60 |
| JOHNSONGRASS | — | — | 60 | 90 | — | — | 0 | 0 | — | — | 30 | 30 | | 0 | 0 | 30 | — | — | 0 | 0 | — | — | 30 | 70 | — | — | 30 | 50 |
| NUTSEDGE | — | — | 0 | 30 | — | — | 50 | 80 | — | — | 70 | 80 | | 30 | 50 | 80 | — | — | 50 | 80 | — | — | 70 | 80 | — | — | 50 | 70 |
| CORN | — | — | 0 | 70 | — | — | 0 | 0 | — | — | 30 | 30 | | 0 | 0 | 0 | — | — | 0 | 0 | — | — | 40 | 0 | — | — | 60 | 0 |
| WILD BUCKWHEAT | — | 30 | 50 | 70 | — | — | 30 | 80 | — | 50 | 70 | 100 | | 30 | 30 | 70 | — | — | 30 | 60 | — | — | 70 | — | 60 | 70 | 80 | — |
| BLACK GRASS | — | 30 | 50 | 70 | — | 30 | 60 | 100 | — | 70 | 90 | 100 | | 0 | 40 | 80 | — | 30 | 50 | 90 | — | 30 | 50 | 70 | — | 30 | 50 | 70 |
| RAPESEED | — | 30 | 70 | 90 | — | 30 | 70 | 100 | — | 50 | 70 | 100 | | 0 | 30 | 60 | — | 0 | 50 | 70 | — | 50 | 70 | 90 | — | 50 | 70 | 80 |

TABLE B-continued

| | CMPD 62 | | | | CMPD 63 | | | | CMPD 67 | | | | CMPD 68 | | | | CMPD 69 | | | | CMPD 71 | | | |
|---|---|---|---|---|---|---|---|---|---|---|---|---|---|---|---|---|---|---|---|---|---|---|---|---|
| RATE = G/HA | 1. | 4. | 16. | 62. | 1. | 4. | 16. | 62. | 1. | 4. | 16. | 62. | 1. | 4. | 16. | 62. | 1. | 4. | 16. | 62. | 1. | 4. | 16. | 62. |
| BARLEY | — | — | 0 | 0 | — | — | 0 | — | 0 | 0 | 0 | 0 | — | — | 0 | 0 | — | 0 | 0 | 0 | — | 0 | 30 | 50 |
| GREEN FOXTAIL | — | — | 0 | 30 | — | — | 0 | 30 | 30 | 60 | 30 | 30 | — | — | 30 | 50 | — | 30 | 50 | 70 | — | 30 | 50 | 70 |
| CHEAT GRASS | — | — | 30 | 50 | — | — | 50 | 50 | 70 | 100 | 100 | 70 | — | — | 50 | 80 | — | 30 | 100 | 80 | 30 | 50 | 50 | 70 |
| VIOLA | — | — | 50 | 90 | — | — | 80 | 100 | 100 | 100 | 100 | 100 | — | — | 70 | 100 | — | 0 | 50 | 100 | 0 | 0 | 30 | 50 |
| LAMBSQUARTER | — | — | 70 | 100 | — | — | 100 | 100 | 100 | 100 | 90 | 100 | — | — | 100 | 70 | — | 70 | 100 | — | 70 | 100 | 90 | 100 |

POSTEMERGENCE

| | CMPD 62 | | | | CMPD 63 | | | | CMPD 67 | | | | CMPD 68 | | | | CMPD 69 | | | | CMPD 71 | | | |
|---|---|---|---|---|---|---|---|---|---|---|---|---|---|---|---|---|---|---|---|---|---|---|---|---|
| RATE = G/HA | 1. | 4. | 16. | 62. | 1. | 4. | 16. | 62. | 1. | 4. | 16. | 62. | 1. | 4. | 16. | 62. | 1. | 4. | 16. | 62. | 1. | 4. | 16. | 62. |
| GIANT FOXTAIL | 0 | 0 | 30 | — | 0 | 0 | 30 | — | 0 | 0 | 30 | — | 0 | 0 | 30 | — | 0 | 0 | 0 | — | 0 | 0 | 0 | — |
| VELVETLEAF | 40 | 70 | 100 | 100 | 30 | 60 | 100 | 100 | 30 | 60 | 100 | 100 | 30 | 50 | 70 | 100 | 30 | 60 | 90 | 100 | 30 | 0 | 30 | 30 |
| SUGAR BEETS | 70 | 100 | 100 | — | 50 | 70 | 80 | — | 100 | 100 | 100 | — | 100 | 100 | 100 | — | 70 | 100 | 100 | — | 30 | 60 | 30 | 30 |
| CRABGRASS | 0 | 30 | 40 | 50 | 0 | 0 | 50 | 70 | 0 | 0 | 30 | 50 | 0 | 30 | 30 | 70 | 0 | 0 | 0 | 0 | 0 | 0 | 0 | 0 |
| TEAWEED | 0 | 20 | 40 | 60 | 30 | 0 | 30 | 60 | 30 | 60 | 50 | 70 | 30 | 50 | 50 | 60 | 30 | 30 | 30 | 50 | 0 | 0 | 30 | 30 |
| JIMSONWEED | 0 | 30 | 60 | 80 | 0 | 0 | 70 | 50 | 0 | 20 | 40 | 60 | 0 | 50 | 100 | 100 | 0 | 0 | 40 | 30 | 0 | 0 | 30 | 50 |
| RICE | 30 | 50 | 70 | 90 | 30 | 50 | 100 | 90 | 50 | 50 | 60 | 100 | 30 | 30 | 100 | 60 | 30 | 30 | 70 | 100 | 30 | 30 | 70 | 100 |
| COCKLEBUR | 30 | 50 | 70 | 100 | 70 | 100 | 100 | 100 | 50 | 50 | 50 | 90 | 30 | 50 | 100 | 100 | 30 | 50 | 0 | 20 | 0 | 0 | 30 | 30 |
| COTTON | 0 | 30 | 60 | 60 | 30 | 50 | 50 | 100 | 50 | 50 | 30 | 70 | 30 | 30 | 70 | — | 30 | 50 | 70 | 100 | 30 | 50 | 70 | — |
| SOYBEAN | 30 | 30 | 70 | — | 30 | 0 | 40 | — | 20 | 30 | 50 | 90 | 30 | 30 | 30 | 100 | 30 | 30 | 20 | — | 30 | 0 | 30 | 60 |
| BARNYARD GRASS | 0 | 0 | 0 | 100 | 0 | 0 | 70 | 100 | 40 | 0 | 40 | — | 0 | 30 | 50 | — | 0 | 30 | 90 | 100 | 0 | 30 | 70 | — |
| WILD OATS | 0 | 0 | 30 | — | 30 | 0 | 50 | — | 20 | 30 | 30 | 90 | 30 | 0 | 30 | 90 | 30 | 50 | 100 | 60 | 30 | 30 | 30 | 60 |
| MORNINGGLORY | 30 | 30 | 70 | 70 | 30 | 30 | 70 | 70 | 30 | 30 | 70 | 90 | 30 | 30 | 70 | — | 30 | 50 | 70 | — | 30 | 50 | 70 | — |
| WHEAT | 0 | 0 | 0 | — | 0 | 0 | 0 | — | 0 | 0 | 0 | 70 | 0 | 30 | 30 | 60 | 0 | 30 | 30 | — | 30 | 0 | 0 | 0 |
| CASSIA | 30 | 50 | 70 | 90 | 30 | 30 | 70 | 90 | 30 | 30 | 30 | 100 | 30 | 30 | 30 | 100 | 30 | 50 | 30 | 80 | 0 | 0 | 0 | 60 |
| JOHNSONGRASS | 0 | 0 | 60 | 100 | 30 | 50 | 60 | 100 | 0 | 0 | 60 | 50 | 50 | 50 | 70 | 50 | 70 | 60 | 70 | 70 | 0 | 30 | 70 | 80 |
| NUTSEDGE | 0 | 0 | 0 | 50 | 0 | 0 | 0 | — | 0 | 0 | 30 | — | 0 | 0 | 30 | — | 0 | 0 | 20 | 100 | 0 | 30 | 30 | — |
| CORN | 0 | 50 | 70 | — | 30 | 30 | 70 | — | 30 | 50 | 30 | — | 30 | 50 | 50 | — | 30 | 50 | 70 | — | 0 | 30 | 30 | 60 |
| WILD BUCKWHEAT | 30 | 50 | 70 | — | 50 | 70 | 100 | 50 | 30 | 30 | 60 | 50 | 30 | 0 | 70 | 50 | 30 | 60 | 90 | — | 30 | 30 | 70 | — |
| BLACK GRASS | 30 | 50 | 100 | — | 50 | 100 | 100 | — | 30 | 90 | 100 | — | 50 | 100 | 100 | 100 | 70 | 90 | 100 | — | 30 | 60 | 100 | 0 |
| RAPESEED | 100 | 100 | 100 | 50 | 100 | 100 | 100 | 50 | 100 | 50 | 70 | — | 100 | 0 | 0 | — | 100 | 0 | 0 | 30 | 30 | 30 | 100 | — |
| BARLEY | 0 | 0 | 0 | — | 0 | 0 | 0 | — | 0 | 0 | 30 | — | 0 | 30 | 30 | 50 | 0 | 0 | 50 | 30 | 0 | 30 | 0 | — |
| GREEN FOXTAIL | 30 | 50 | 70 | 90 | 30 | 50 | 70 | 90 | 30 | 60 | 60 | 100 | 30 | 50 | 70 | 100 | 30 | 50 | 70 | — | 30 | 50 | 50 | 50 |
| CHEAT GRASS | 0 | 0 | 0 | — | 0 | 0 | 0 | — | 0 | 0 | 0 | — | 0 | 0 | 20 | — | 0 | 30 | 30 | 30 | 0 | 0 | 30 | — |
| VIOLA | 30 | 50 | 70 | 70 | 30 | 50 | 70 | 90 | 70 | 90 | 100 | 90 | 70 | 60 | 70 | 90 | 30 | 50 | 70 | 70 | 30 | 50 | 50 | — |
| LAMBSQUARTER | 30 | 60 | 90 | 100 | 30 | 50 | 70 | 60 | 30 | 60 | 100 | 100 | 50 | 50 | 70 | 100 | 50 | 60 | 90 | 100 | 50 | 30 | 70 | 50 |

PREEMERGENCE

| | CMPD 62 | | | | CMPD 63 | | | | CMPD 67 | | | | CMPD 68 | | | | CMPD 69 | | | | CMPD 71 | | | |
|---|---|---|---|---|---|---|---|---|---|---|---|---|---|---|---|---|---|---|---|---|---|---|---|---|
| RATE = G/HA | 1. | 4. | 16. | 62. | 1. | 4. | 16. | 62. | 1. | 4. | 16. | 62. | 1. | 4. | 16. | 62. | 1. | 4. | 16. | 62. | 1. | 4. | 16. | 62. |
| GIANT FOXTAIL | — | 0 | 30 | 60 | — | 0 | 30 | 30 | — | 0 | 30 | 50 | — | 30 | 50 | 70 | — | 30 | 50 | 70 | — | 30 | 50 | 70 |
| VELVETLEAF | — | 30 | 50 | 70 | — | 50 | 30 | 60 | — | 0 | 30 | 60 | — | 50 | 100 | 60 | — | 30 | 30 | 50 | — | 0 | 30 | 50 |
| SUGAR BEETS | — | 50 | 70 | 90 | — | 70 | 70 | 80 | — | 30 | 50 | 70 | — | 100 | 100 | 100 | — | 60 | 70 | 80 | — | 50 | 70 | 80 |
| CRABGRASS | — | 0 | 30 | 50 | — | 30 | 30 | 50 | — | 0 | 30 | 50 | — | 30 | 30 | 50 | — | 0 | 0 | 0 | — | 0 | 0 | 0 |
| TEAWEED | — | 30 | 50 | 70 | — | 30 | 30 | 50 | — | 0 | 30 | 50 | — | 30 | 50 | 70 | — | 30 | 30 | 50 | — | 0 | 30 | 30 |
| JIMSONWEED | — | 30 | 30 | 50 | — | 30 | 70 | 30 | — | 30 | 60 | 70 | — | 50 | 100 | 60 | — | 30 | 50 | 70 | — | 30 | 50 | 50 |
| RICE | — | 30 | 50 | 70 | — | 30 | 50 | 30 | — | 30 | 60 | 90 | — | 50 | 100 | 70 | — | 30 | 70 | 100 | — | 30 | 70 | 70 |
| COCKLEBUR | — | 30 | 30 | 30 | — | 60 | 90 | 30 | — | 0 | 30 | 30 | — | 30 | 30 | 30 | — | 30 | 20 | 30 | — | 30 | 30 | 30 |
| COTTON | — | 20 | 30 | 20 | — | 0 | 20 | 20 | — | 0 | 60 | 30 | — | 50 | 50 | 30 | — | 30 | 70 | 50 | — | 30 | 50 | 50 |
| SOYBEAN | — | 30 | 60 | 90 | — | 30 | 30 | 70 | — | 0 | 30 | 30 | — | 30 | 40 | 60 | — | 50 | 70 | 70 | — | 30 | 50 | 70 |
| BARNYARD GRASS | — | 30 | 0 | 30 | — | 0 | 30 | 0 | — | 30 | 30 | 0 | — | 60 | 30 | 30 | — | 70 | 70 | 50 | — | 30 | 50 | 30 |
| WILD OATS | — | 0 | 50 | 70 | — | 0 | 0 | 70 | — | 0 | 0 | 30 | — | 0 | 60 | 30 | — | 0 | 0 | 0 | — | 0 | 50 | 50 |
| MORNINGGLORY | — | 30 | 70 | 30 | — | 30 | 50 | 30 | — | 30 | 50 | 30 | — | 30 | 40 | 30 | — | 50 | 50 | 70 | — | 30 | 50 | 70 |
| WHEAT | — | 0 | 0 | 0 | — | 30 | 50 | 70 | — | 0 | 0 | 0 | — | 0 | 0 | 0 | — | 0 | 0 | 30 | — | 0 | 30 | 30 |
| CASSIA | — | 50 | 50 | 30 | — | 50 | 70 | 60 | — | 30 | 50 | 30 | — | 50 | 50 | 30 | — | 50 | 50 | 30 | — | 30 | 50 | 30 |
| JOHNSONGRASS | — | 30 | 50 | 70 | — | 0 | 30 | 60 | — | 30 | 50 | 70 | — | 30 | 70 | 70 | — | 30 | 50 | 30 | — | 30 | 50 | 70 |

TABLE B-continued

| | | | | | | | | | | | | | | | | | | | | |
|---|---|---|---|---|---|---|---|---|---|---|---|---|---|---|---|---|---|---|---|---|
| NUTSEDGE | — | — | 0 | 30 | 50 | — | 0 | 30 | 50 | — | 0 | 0 | 0 | 0 | 30 | — | 0 | 30 | — | 50 |
| CORN | — | — | 0 | 0 | 0 | — | 0 | 0 | 0 | — | 0 | 0 | 0 | 20 | 0 | — | 0 | 0 | — | 0 |
| WILD BUCKWHEAT | — | — | 30 | 50 | 70 | — | 30 | 50 | 70 | — | 50 | 70 | 50 | 80 | 70 | — | 50 | 70 | 30 | 70 |
| BLACK GRASS | — | — | 30 | 50 | 70 | — | 50 | 70 | 80 | — | 100 | 100 | 100 | 100 | 100 | — | 100 | 100 | 60 | 90 |
| RAPESEED | — | — | 50 | 70 | 80 | — | 70 | 80 | 80 | — | 50 | 70 | 90 | 90 | 70 | — | 50 | 70 | 50 | 80 |
| BARLEY | — | — | 0 | 0 | 30 | — | 0 | 0 | 30 | — | 0 | 0 | 30 | 30 | 0 | — | 0 | 0 | 0 | 0 |
| GREEN FOXTAIL | — | — | 30 | 60 | 90 | — | 30 | 50 | 60 | — | 50 | 60 | 50 | 90 | 50 | — | 30 | 50 | 30 | 70 |
| CHEAT GRASS | — | — | 30 | 50 | 70 | — | 30 | 70 | 70 | — | 100 | 70 | 100 | 100 | 100 | — | 80 | 90 | 50 | 80 |
| VIOLA | — | — | 50 | 70 | 100 | — | 50 | 80 | 90 | — | 100 | 100 | 100 | 100 | 100 | — | 70 | 100 | 50 | 90 |
| LAMBSQUARTER | — | — | 80 | 90 | 100 | — | 70 | 90 | 90 | — | 90 | 100 | 100 | 100 | 100 | — | 100 | 100 | 30 | 100 |

Test C

Procedure

Plastic trays were lined with polyethylene liners and filled with pasturized Sassafras loamy sand soil (pH 6.5, 1% OM). One tray was planted with wheat (*Triticum aestivum*), barley (*Hordeum vulgare*), wild oat (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*), and rapeseed (*Brassica napus*). A second tray was planted with *Matricaria inodora*, cleavers bedstraw (*Galium aparine*), Russian thistle (*Salsola kali*), shepherdspurse (*Capsella bursapastoris*), kochia (*Kochia scoparia*), black nightshade (*Solanum nigrum*), speedwell (*Veronica persica*), wild buckwheat (*Polygonum convolvulus*), and sugarbeet (*Beta vulgaris*). For postemergence treatments, the first tray was planted 14 days before spraying, and the second tray was planted 24 days before treatment. Plants in the postemergence treatments ranged in height from 1 to 15 cm depending on specie. Wheat, barley, and wild oats were in the 2-leaf stage of development (Zadoks stage 11). A second set of trays was prepared in an identical manner before spraying to serve as preemergence treatments. Herbicides were diluted in a non-phytotoxic solvent and were applied to the trays using a belt sprayer.

Plants were grown in the greenhouse for 21 days at which time visual ratings were made by comparing to an untreated control planting. Ratings were based on a scale of 0=no effect to 100=complete kill. The results are in Table C.

TABLE C

| | CMPD 69 | | | | |
|---|---|---|---|---|---|
| RATE KG/HA | 0.004 | 0.008 | 0.016 | 0.032 | 0.064 |
| POSTEMERGENCE | | | | | |
| WHEAT | 10 | 30 | 40 | 60 | 90 |
| BARLEY | 0 | 10 | 20 | 50 | 50 |
| WILD OATS | 0 | 0 | 0 | 0 | 20 |
| CHEATGRASS | 0 | 20 | 40 | 70 | 90 |
| BLACKGRASS | 20 | 40 | 60 | 70 | 90 |
| ANN. BLUEGRASS | 0 | 0 | 10 | 20 | 40 |
| GREEN FOXTAIL | 0 | 0 | 20 | 40 | 60 |
| ITAL. RYEGRASS | 0 | 0 | 0 | 0 | 20 |
| RAPESEED | 100 | 100 | 100 | 100 | 100 |
| WINTER WHEAT | 0 | 20 | 30 | 50 | 70 |
| WINTER BARLEY | 0 | 0 | 30 | 50 | 70 |
| GOATGRASS | 0 | 10 | 20 | 30 | 40 |
| WILD OATS STG 2 | 0 | 0 | 0 | 0 | 20 |
| BLACKGRASS STG 2 | 0 | 40 | 50 | 60 | 90 |

| | CMPD 69 | | | | |
|---|---|---|---|---|---|
| RATE KG/HA | 0.004 | 0.008 | 0.016 | 0.032 | 0.064 |
| PREEMERGENCE | | | | | |
| WHEAT | 0 | 0 | 10 | 30 | 40 |
| BARLEY | 0 | 20 | 30 | 40 | 50 |
| WILD OATS | 0 | 0 | 0 | 0 | 20 |
| CHEATGRASS | 0 | 30 | 30 | 90 | 90 |
| BLACKGRASS | 0 | 20 | 50 | 60 | 80 |
| ANN. BLUEGRASS | 0 | 0 | 10 | 30 | 70 |
| GREEN FOXTAIL | 0 | 0 | 0 | 20 | 40 |
| ITAL. RYEGRASS | 0 | 0 | 10 | 20 | 30 |
| RAPESEED | 60 | 80 | 90 | 100 | 100 |
| WINTER WHEAT | 0 | 0 | 20 | 20 | 30 |
| WINTER BARLEY | 0 | 20 | 30 | 40 | 50 |
| GOATGRASS | 0 | 0 | 0 | 20 | 40 |

| | CMPD 69 | | | | |
|---|---|---|---|---|---|
| RATE RATE = KG/HA | 0.004 | 0.008 | 0.016 | 0.032 | 0.064 |
| POSTEMERGENCE | | | | | |
| GALIUM | 10 | 50 | 50 | 70 | 70 |
| WILD BUCKWHEAT | 0 | 0 | 20 | 30 | 60 |
| KOCHIA | 0 | 10 | 20 | 30 | 70 |
| FALSE CHAMOMILE | 30 | 60 | 90 | 90 | 100 |
| BLK. NIGHTSHADE | 20 | 20 | 40 | 70 | 70 |
| RUSSIAN THISTLE | 50 | 60 | 80 | 90 | 90 |
| SPEEDWELL | 0 | 0 | 20 | 50 | 60 |
| SUGARBEETS | 80 | 100 | 100 | 100 | 100 |
| VRNCA HDRAFOLIA | 0 | 10 | 30 | 60 | 90 |
| LAMBSQUARTER | 0 | 20 | 40 | 100 | 100 |
| FIELD PENNYCRES | 40 | 70 | 90 | 90 | 90 |
| VIOLA | 0 | 0 | 20 | 50 | 50 |

| | CMPD 69 | | | | |
|---|---|---|---|---|---|
| RATE KG/HA | 0.004 | 0.008 | 0.016 | 0.032 | 0.064 |
| PREEMERGENCE | | | | | |
| GALIUM | 0 | 0 | 20 | 50 | 50 |
| WILD BUCKWHEAT | 0 | 0 | 10 | 20 | 60 |
| KOCHIA | 0 | 0 | 0 | 20 | 70 |
| FALSE CAMOMILE | 20 | 60 | 70 | 70 | 90 |
| BLK. NIGHTSHADE | 10 | 20 | 50 | 70 | 70 |
| RUSSIAN THISTLE | 0 | 0 | 0 | 10 | 60 |
| SPEEDWELL | 0 | 0 | 0 | 40 | 40 |
| SUGARBEETS | 80 | 80 | 100 | 100 | 100 |
| VRNCA HDRAFOLIA | 0 | 0 | 30 | 50 | 70 |
| LAMBSQUARTER | 0 | 10 | 30 | 60 | 80 |
| FIELD PENNYCRES | 0 | 10 | 20 | 50 | 70 |
| VIOLA | 0 | 10 | 60 | 90 | 100 |

What is claimed is:

1. A compound having the formula:

$$LSO_2NHCNA \text{ with } W \text{ double bonded to } C, R \text{ on } N$$

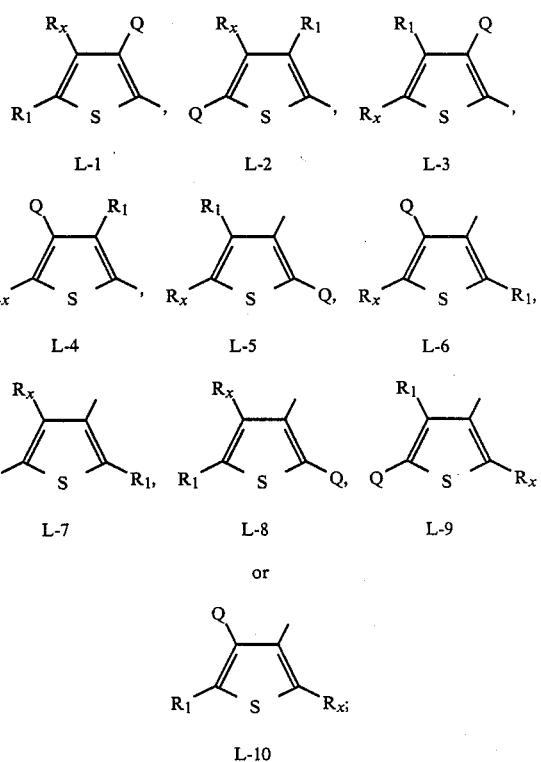

wherein
L is

L-1, L-2, L-3, L-4, L-5, L-6, L-7, L-8, L-9 or

L-10

R is H or $CH_3$;
W is O or S;
$R_1$ is $R_1'$ or $R''_1$;

$R_x$ is H or halogen;

$R_1'$ is H, $C_1$-$C_3$ alkyl, $C_1$-$C_3$ haloalkyl, halogen, nitro, $C_1$-$C_3$ alkoxy, CN, $C_1$-$C_3$ haloalkoxy or $C_1$-$C_3$ haloalkylthio;

$R_1''$ is $SO_2NR_aR_b$, $C_1$-$C_3$ alkylthio, $C_1$-$C_3$ alkylsulfinyl, $C_1$-$C_3$ alkylsulfonyl, $CO_2R_c$ or $C(O)NR_gR_h$;

$R_a$ is H, $C_1$-$C_4$ alkyl, $C_2$-$C_3$ cyanoalkyl, methoxy, ethoxy or $C_3$-$C_4$ alkenyl;

$R_b$ is H or $C_1$-$C_3$ alkyl; or $R_a$ and $R_b$ may be taken together to form $(CH_2)_3$, $(CH_2)_4$, $(CH_2)_5$ or $CH_2CH_2OCH_2CH_2$;

$R_c$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, cyclopropylmethyl or $C_2$-$C_4$ alkoxyalkyl;

$R_g$ is H or $C_1$-$C_3$ alkyl;

$R_h$ is $C_1$-$C_3$ alkyl;

Q is $Q_1$ or $Q_2$;

$Q_1$ is $ER_2$, $NR_3R_4$, $$\overset{W_1}{\underset{}{\|}}\!\!\!JPR_5R_6,$$

$OSO_2R_7$, CN, $SO_2NHR_{21}$, $SO_2N\!\!\overset{\triangle}{\phantom{X}}$, $SO_2N\!\!\overset{\square}{\phantom{X}}$, $SO_2NR_{22}NR_{23}R_{24}$ or $C_1$-$C_4$ alkyl substituted with $R_8$;

E is O, S, SO or $SO_2$;

$W_1$ is O or S;

J is O, S, NH, $NCH_3$, $CH_2$ or a single bond;

$Q_2$ is $SO_2NH_2$, $SO_2NR_iR_j$, $CO_2R_k$, $C(O)NR_mR_n$, $C_1$-$C_3$ alkylthio, $C_1$-$C_3$ alkylsulfinyl, $C_1$-$C_3$ alkylsulfonyl, halogen, CHO or $CR_p=NOR_q$;

$R_i$ is $C_1$-$C_4$ alkyl, $C_2$-$C_3$ cyanoalkyl, methoxy, ethoxy or $C_3$-$C_4$ alkenyl;

$R_j$ is $C_1$-$C_3$ alkyl or $R_i$ and $R_j$ may be taken together to form $(CH_2)_5$ or $CH_2CH_2OCH_2CH_2$;

$R_k$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, cyclopropylmethyl or $C_2$-$C_4$ alkoxyalkyl;

$R_m$ is H or $C_1$-$C_3$ alkyl;

$R_n$ is $C_1$-$C_3$ alkyl;

$R_p$ is H, $C_1$-$C_4$ alkyl or $C_1$-$C_4$ haloalkyl;

$R_q$ is H, $C_1$-$C_4$ alkyl, $C_3$-$C_4$ alkenyl or $C_3$-$C_4$ alkynyl;

$R_2$ is $C_1$-$C_6$ alkyl substituted with $R_8$, $C_2$-$C_6$ alkenyl substituted with $R_8$, $C_3$-$C_6$ alkynyl, $C_3$-$C_6$ alkynyl substituted with $R_8$, $C_1$-$C_6$ haloalkyl, $C_2$-$C_6$ haloalkenyl or $C_3$-$C_6$ haloalkynyl;

$R_3$ is $C_1$-$C_4$ alkyl;

$R_4$ is H or $C_1$-$C_4$ alkyl; or $R_3$ and $R_4$ may be taken together to form $(CH_2)_4$, $(CH_2)_5$ or $CH_2CH_2OCH_2CH_2$;

$R_5$ and $R_6$ are independently $C_1$-$C_2$ alkyl, $C_1$-$C_2$ alkoxy, $C_1$-$C_2$ alkylthio, $C_1$-$C_2$ alkylamino or di($C_1$-$C_2$ alkyl)amino;

$R_7$ is $C_1$-$C_4$ alkyl, $C_1$-$C_4$ haloalkyl, $C_3$-$C_4$ alkenyl, $C_3$-$C_4$ haloalkenyl, $C_3$-$C_4$ alkynyl, $C_3$-$C_4$ haloalkynyl or $NR_{19}R_{20}$;

$R_8$ is $OR_9$, $S(O)_nR_{10}$, $CO_2R_{10}$, $SO_2NR_{11}R_{12}$, $NR_{11}R_{12}$, $CONR_{11}R_{12}$, $C(O)R_{13}$, $C(W_2R_{14})_2$, $\underset{R_{13}}{\overset{W_2}{\underset{|}{C}}}\!\overset{\displaystyle (}{\underset{\displaystyle W_3}{\Big\rangle}_{\!\!m}}\!\underset{R_{15}}{\phantom{X}}$, $\underset{R_{13}}{\overset{}{C}}\!\!=\!\!NOR_{16}$, $\overset{W}{\underset{\|}{S}}CR_{17}$, CN, SCN, SH, $NO_2$ or $N_3$;

$R_9$ is H, $C_1$-$C_4$ alkyl, $C_3$-$C_4$ alkenyl, $C_3$-$C_4$ alkynyl, $C_1$-$C_4$ haloalkyl, $C_3$-$C_4$ haloalkenyl, $C_3$-$C_4$ haloalkynyl, $C_2$-$C_4$ alkylcarbonyl, $C_1$-$C_4$ alkylsulfonyl, $C_2$-$C_4$ alkoxyalkyl, $C_2$-$C_4$ alkylthioalkyl or $C_2$-$C_4$ cyanoalkyl;

$R_{10}$ is $C_1$-$C_4$ alkyl, $C_3$-$C_4$ alkenyl, $C_3$-$C_4$ alkynyl, $C_1$-$C_4$ haloalkyl, $C_3$-$C_4$ haloalkenyl, $C_3$-$C_4$ haloalkynyl, $C_2$-$C_4$ alkoxyalkyl, $C_2$-$C_4$ alkylthioalkyl or $C_2$-$C_4$ cyanoalkyl;

$R_{11}$ is H or $C_1$-$C_3$ alkyl;

$R_{12}$ is H, $C_1$-$C_4$ alkyl, $C_1$-$C_4$ haloalkyl, $C_3$-$C_6$ cycloalkyl, $C_2$-$C_4$ alkoxyalkyl, $C_2$-$C_4$ alkylthioalkyl, $C_2$-$C_4$ cyanoalkyl, $C_1$-$C_3$ alkoxy, $C_3$-$C_4$ alkenyl or $C_3$-$C_4$ alkynyl; or $R_{11}$ and $R_{12}$ may be taken together to form $(CH_2)_3$, $(CH_2)_4$, $(CH_2)_5$ or $CH_2CH_2OCH_2CH_2$;

$R_{13}$ is H, $C_1$-$C_4$ alkyl or $C_1$-$C_4$ haloalkyl;

$R_{14}$ is $C_1$-$C_2$ alkyl;

$R_{15}$ is H or $CH_3$;

$R_{16}$ is H, $C_1$-$C_4$ alkyl, $C_3$-$C_4$ alkenyl or $C_3$-$C_4$ alkynyl;

$R_{17}$ is $C_1$-$C_4$ alkyl, $C_1$-$C_4$ alkoxy, $C_1$-$C_4$ alkylthio, $C_1$-$C_4$ alkylamino or di($C_1$-$C_4$ alkyl)amino;

$R_{19}$ is H, $C_1$-$C_3$ alkyl, $C_3$-$C_4$ alkenyl or $C_3$-$C_4$ alkynyl;

$R_{20}$ is H or $C_1$-$C_3$ alkyl; or $R_{19}$ and $R_{20}$ may be taken together to form $(CH_2)_4$, $(CH_2)_5$ or $CH_2CH_2OCH_2CH_2$;

$R_{21}$ is $C_1$-$C_4$ alkyl, $C_1$-$C_3$ haloalkyl, $C_2$-$C_3$ cyanoalkyl, cyclopropyl, $C_3$-$C_4$ alkenyl, $C_3$-$C_4$ alkynyl, $C_2$-$C_4$ alkoxyalkyl or $C_1$-$C_2$ alkoxy;

$R_{22}$ is H or $C_1$-$C_4$ alkyl;

$R_{≦}$ is H or $C_1$-$C_4$ alkyl;

$R_{24}$ is H, $C_1$-$C_4$ alkyl, $C_3$-$C_4$ alkenyl, $C_3$-$C_4$ alkynyl, $C_1$-$C_4$ haloalkyl or phenyl which may be optionally substituted with $R_{25}$; or $R_{23}$ and $R_{24}$ may be taken together to form $(CH_2)_4$, $(CH_2)_5$ or $CH_2CH_2OCH_2CH_2$;

$R_{25}$ is H, $CH_3$, Cl, F, Br, $NO_2$, $CF_3$, CH or $OCH_3$;

m is 1 or 2;

n is 0, 1 or 2;

$W_2$ and $W_3$ are independently O or S;

A is

A-1, A-6

X is H, $C_1$-$C_4$ alkyl, $C_1$-$C_4$ alkoxy, $C_2$-$C_4$ haloalkoxy, $C_1$-$C_4$ haloalkyl, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_2$-$C_4$ haloalkoxy, $C_1$-$C_4$ haloalkylthio, $C_1$-$C_4$ alkylthio, $C_2$-$C_5$ alkoxyalkyl, $C_2-C_5$ alkoxyalkoxy, amino, $C_1-C_3$ alkylamino, di($C_1-C_3$alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_4-C_5$ cycloalkyl, $C_2-C_4$ alkynyl, cyano,

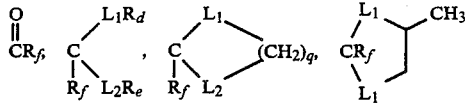

or $N(OCH_3)CH_3$;
q is 2 or 3;
$L_1$ and $L_2$ are independently O or S;
$R_d$ and $R_e$ are independently $C_1-C_2$ alkyl;
$R_f$ is H or $CH_3$;
z is N;
$X_3$ is $CH_3$ or $OCH_3$;
and their agriculturally suitable salts; provided that
(a) when E is O or S and $R_9$ is H, then $R_2$ is other than $CH_2OR_9$;
(b) when W is S, then A is A-1, R is H and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

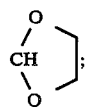

(c) the total number of carbon atoms in $R_1$ and Q is less than or equal to 10;
(d) when Q is

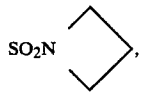

then X and Y are other than $SCF_2H$;
(e) when $R_1$ is $R_1'$ then L is L-1, L-3, L-5, L-6, L-8 or L-10;
(f) the total number of carbon atoms in $R_{22}$, $R_{23}$ and $R_{24}$ is less than or equal to 10;
(g) when $R_{21}$ is $C_1-C_4$ alkyl, $C_2-C_3$ cyanoalkyl, $C_1-C_2$ alkoxy or $C_3-C_4$ alkenyl, then X and Y are other than $SCF_2H$;
(h) when Y is CN and $R_1'$ is H, F, Cl or $CH_3$, then $R_{21}$ is other than $C_1-C_3$ alkyl;
(i) when $R_1$ is $R_1'$ then Q is $Q_1$;
(j) when $R_1$ is $R_1''$ then Q is $Q_1$ or $Q_2$;
(k) when $Q_2$ is halogen then $R_x$ is halogen;
(l) when $R_1''$ is $SO_2NR_aR_b$, $CO_2R_c$ or $C(O)NR_gR_h$ when Q is $SO_2NHR_{21}$,

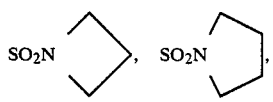

$SO_2NR_{22}NR_{23}R_{24}$, $SO_2NH_2$, $SO_2NR_iR_j$, $CO_2R_k$, $C(O)NR_mR_n$ or CHO then L is L-1, L-2, L-5 or L-6; and (m) when $Q_2$ is halogen then L is L-2, L-4, L-5, L-6, L-7 or L-9.

2. A compound of claim 1 wherein Q is $Q_1$.
3. A compound of claim 1 wherein
$R_1$ is $R_1'$;
$R_1$ is H, $CH_3$, Cl, Br, $OCH_3$ or $C_1$ haloalkyl;
X is $CH_3$, $OCH_3$, $OCH_2CH_3$, $CH_2F$, $CF_3$, $OCH_2CH_2F$, $OCH_2CHF_2$, $OCH_2CF_3$, $CH_2Cl$ or $CH_2Br$; and
Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $CH_2SCH_2CH_3$, $OCH_2CH_2OCH_3$,

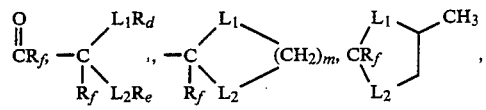

$SCF_2H$, $C\equiv CH$ or $C\equiv CCH_3$.
4. A compound of claim 3 where A is A-1 and W is O.
5. A compound of claim 4 where L is L-1 or L-3.
6. A compound of claim 4 where L is L-5, L-6, L-8 or L-10.
7. A compound of claim 5 where
$Q_1$ is $ER_2$,

$C_1-C_2$ alkyl substituted with $R_8$, CN, $SO_2NH-C_1-C_2$ alkyl, $SO_2NH$cyclopropyl or

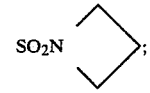

$R_2$ is $C_1-C_3$ alkyl substituted with $R_8$, $C_1-C_3$ haloalkyl, $C_2-C_3$ haloalkenyl or $C_3-C_4$ alkynyl;
$R_5$ and $R_6$ are independently $CH_3$, $OCH_3$ or $SCH_3$;
$R_8$ is $OR_9$, $C_1-C_2$ alkylthio, $C_1-C_2$ alkylsulfinyl, $C_1-C_2$ alkylsulfonyl, $CO_2(C_1-C_2$ alkyl), $SO_2N(-C_1-C_2$ alkyl$)_2$, $C(O)CH_3$, CN or $C(O)N(CH_3)_2$; and
$R_9$ is H, $C_1-C_2$ alkyl or $C_2-C_3$ cyanoalkyl.
8. A compound of claim 7 where
X is $CH_3$, $OCH_3$, $OCH_2CH_3$ or $OCH_2CF_3$;
Y is $CH_3$, $OCH_3$, $C_2H_5$, $CH_2OCH_3$, $NHCH_3$ or $CH(OCH_3)_2$;
$Q_1$ is $ER_2$, $C_1-C_2$ alkyl substituted with $R_8$, CN or $SO_2NHC_1-C_2$ alkyl;
E is S or $SO_2$;
$R_2$ is $C_1-C_2$ alkyl substituted with $R_8$ or $C_1-C_2$ haloalkyl; and
$R_8$ is $CH_3O$, $CH_3CH_2O$, $CH_3S$, $CH_3SO_2$, $SO_2N(CH_3)_2$ or $CO_2CH_3$.
9. A compound of claim 6 where
$Q_1$ is $ER_2$,

$C_1-C_2$ alkyl substituted with $R_8$, CN, $SO_2NH-C_1-C_2$ alkyl, $SO_2NH$cyclopropyl or

R$_2$ is C$_1$-C$_3$ alkyl substituted with R$_8$, C$_1$-C$_3$ haloalkyl, C$_2$-C$_3$ haloalkenyl or C$_3$-C$_4$ alkynyl;

R$_5$ and R$_6$ are independently CH$_3$, OCH$_3$ or SCH$_3$;

R$_8$ is OR$_9$, C$_1$-C$_2$ alkylthio, C$_1$-C$_2$ alkylsulfinyl, C$_1$-C$_2$ alkylsulfonyl, CO$_2$(C$_1$-C$_2$ alkyl), SO$_2$N(-C$_1$-C$_2$ alkyl)$_2$, C(O)CH$_3$, CN or C(O)N(CH$_3$)$_2$; and R$_9$ is H, C$_1$-C$_2$ alkyl or C$_2$-C$_3$ cyanoalkyl.

10. A compound of claim 9 where

X is CH$_3$, OCH$_3$, OCH$_2$CH$_3$ or OCH$_3$CF$_3$;

Y is CH$_3$, OCH$_3$, C$_2$H$_5$, CH$_2$OCH$_3$, NHCH$_3$ or CH(OCH$_3$)$_2$;

Q$_1$ is ER$_2$, C$_1$-C$_2$ alkyl substituted with R$_8$, CN or SO$_2$NHC$_1$-C$_2$ alkyl;

E is S or SO$_2$;

R$_2$ is C$_1$-C$_2$ alkyl substituted with R$_8$ or C$_1$-C$_2$ haloalkyl; and

R$_8$ is CH$_3$O, CH$_3$CH$_2$O, CH$_3$S, CH$_3$SO$_2$, SO$_2$N(CH$_3$)$_2$ or CO$_2$CH$_3$.

11. A compound of claim 1 wherein

R$_1$ is R$_1''$;

X is CH$_3$, OCH$_3$, OCH$_2$CH$_3$, CH$_2$F, CF$_3$, OCH$_2$CH$_2$F, OCH$_2$CHF$_2$, OCH$_2$CF$_3$, CH$_2$Cl or CH$_2$Br; and Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$, OCH$_2$CH$_2$OCH$_3$,

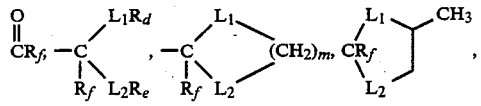

SCF$_2$H, C≡CH or C≡CCH$_3$.

12. A compound of claim 11 where W is O.
13. A compound of claim 12 where L is L-1.
14. A compound of claim 12 where L is L-2.
15. A compound of claim 12 where L is L-3.
16. A compound of claim 12 where L is L-4.
17. A compound of claim 12 where L is L-5.
18. A compound of claim 12 where L is L-6.
19. A compound of claim 12 where L is L-7.
20. A compound of claim 12 where L is L-8.
21. A compound of claim 12 where L is L-9.
22. A compound of claim 12 where L is L-10.
23. A compound of claim 13 where Q$_1$ is ER$_2$,

C$_1$-C$_2$ alkyl substituted with R$_8$, CN, SO$_2$NH-C$_1$-C$_2$ alkyl, SO$_2$NHcyclopropyl or

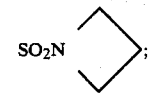

R$_2$ is C$_1$-C$_3$ alkyl substituted with R$_8$, C$_1$-C$_3$ haloalkyl, C$_2$-C$_3$ haloalkenyl or C$_3$-C$_4$ alkynyl;

R$_5$ and R$_6$ are independently CH$_3$, OCH$_3$ or SCH$_3$;

R$_8$ is OR$_9$, C$_1$-C$_2$ alkylthio, C$_1$-C$_2$ alkysulfinyl, C$_1$-C$_2$ alkylsulfonyl, CO$_2$(C$_1$-C$_2$ alkyl), SO$_2$N(-C$_1$-C$_2$ alkyl)$_2$, C(O)CH$_3$, CN or C(O)N(CH$_3$)$_2$; and R$_9$ is H, C$_1$-C$_2$ alkyl or C$_2$-C$_3$ cyanoalkyl.

24. A compound of claim 23 where

Q$_1$ is ER$_2$, C$_1$-C$_2$ alkyl substituted with R$_8$, CN or SO$_2$NHC$_1$-C$_2$ alkyl;

E is S or SO$_2$;

R$_2$ is C$_1$-C$_2$ alkyl substituted with R$_8$ or C$_1$-C$_2$ haloalkyl;

R$_8$ is CH$_3$O, CH$_3$CH$_2$O, CH$_3$S, CH$_3$SO$_2$, SO$_2$N(CH$_3$)$_2$ or CO$_2$CH$_3$;

Q$_2$ is SO$_2$NR$_i$R$_j$, CO$_2$R$_k$, C(O)NR$_m$R$_n$, C$_1$-C$_3$ alkylthio, C$_1$-C$_3$ alkylsulfinyl or C$_1$-C$_3$ alkylsulfonyl;

R$_a$ is H or C$_1$-C$_2$ alkyl;

R$_b$ is C$_1$-C$_2$ alkyl;

R$_c$ and R$_k$ are independently C$_1$-C$_3$ alkyl, allyl, CH$_2$CH$_2$Cl or CH$_2$CH$_2$OCH$_3$;

R$_g$ is H or C$_1$-C$_2$ alkyl;

R$_h$ is CH$_3$;

R$_i$ is C$_1$-C$_2$ alkyl; and

R$_j$ is C$_1$-C$_2$ alkyl.

25. A compound of claim 24 where

A is A-1;

X is CH$_3$, OCH$_3$, OCH$_2$CH$_3$ or OCH$_2$CF$_3$; and

Y is CH$_3$, OCH$_3$, C$_2$H$_5$, CH$_2$OCH$_3$, NHCH$_3$ or CH(OCH$_3$)$_2$.

26. A compound of claim 14 where

Q$_1$ is ER$_2$,

C$_1$-C$_2$ alkyl substituted with R$_8$, CN, SO$_2$NH-C$_1$-C$_2$ alkyl, SO$_2$NHcyclopropyl or

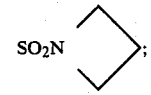

R$_2$ is C$_1$-C$_3$ alkyl substituted with R$_8$, C$_1$-C$_3$ haloalkyl, C$_2$C$_3$ haloalkenyl or C$_3$-C$_4$ alkynyl;

R$_5$ and R$_6$ are independently CH$_3$, OCH$_3$ or SCH$_3$;

R$_8$ is OR$_9$, C$_1$-C$_2$ alkylthio, C$_1$-C$_2$ alkylsulfinyl, C$_1$-C$_2$ alkylsulfonyl, CO$_2$(C$_1$-C$_2$ alkyl), SO$_2$N(-C$_1$-C$_2$ alkyl)$_2$, C(O)CH$_3$, CN or C(O)N(CH$_3$)$_2$; and R$_9$ is H, C$_1$-C$_2$ alkyl or C$_2$-C$_3$ cyanoalkyl.

27. A compound of claim 26 where

Q$_1$ is ER$_2$, C$_1$-C$_2$ alkyl substituted with R$_8$, CN or SO$_2$NHC$_1$-C$_2$ alkyl;

E is S or SO$_2$;

R$_2$ is C$_1$-C$_2$ alkyl substituted with R$_8$ or C$_1$-C$_2$ haloalkyl;

R$_8$ is CH$_3$O, CH$_3$CH$_2$O, CH$_3$S, CH$_3$SO$_2$, SO$_2$N(CH$_3$)$_2$ or CO$_2$CH$_3$;

$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

28. A compound of claim 27 where
A is A-1;
X is $CH_3$, $OCH_3$, $OCH_2CH_3$ or $OCH_2CF_3$; and
Y is $CH_3$, $OCH_3$, $C_2H_5$, $CH_2OCH_3$, $NHCH_3$ or $CH(OCH_3)_2$.

29. A compound of claim 15 where
$Q_1$ is $ER_2$,

$C_1$-$C_2$ alkyl substituted with $R_8$, CN, $SO_2NH$-$C_1$-$C_2$ alkyl, $SO_2NH$cyclopropyl or

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

30. A compound of claim 29 where
$Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

31. A compound of claim 30 where
A is A-1;
X is $CH_3$, $OCH_3$, $OCH_2CH_3$ or $OCH_2CF_3$; and
Y is $CH_3$, $OCH_3$, $C_2H_5$, $CH_2OCH_3$, $NHCH_3$ or $CH(OCH_3)_2$.

32. A compound of claim 16 where
$Q_1$ is $ER_2$,

$C_1$-$C_2$ alkyl substituted with $R_8$, CN, $SO_2NH$-$C_1$-$C_2$ alkyl, $SO_2NH$cyclopropyl or

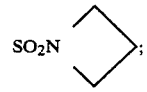

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

33. A compound of claim 32 where
$Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

34. A compound of claim 33 where
A is A-1;
X is $CH_3$, $OCH_3$, $OCH_2CH_3$ or $OCH_2CF_3$; and
Y is $CH_3$, $OCH_3$, $C_2H_5$, $CH_2OCH_3$, $NHCH_3$ or $CH(OCH_3)_2$.

35. A compound of claim 17 where
$Q_1$ is $ER_2$,

$C_1$-$C_2$ alkyl substituted with $R_8$, CN, $SO_2NH$-$C_1$-$C_2$ alkyl, $SO_2NH$cyclopropyl or

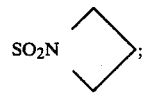

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

36. A compound of claim 35 where
$Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;

$R_8$ is $CH_3O$, $CH_3CH_2O$, $CH_3S$, $CH_3SO_2$, $SO_2N(CH_3)_2$ or $CO_2CH_3$;

$Q_2$ is $SO_2NR_iR_j$, $CO_2R_k$, $C(O)NR_mR_n$, $C_1$–$C_3$ alkylthio, $C_1$–$C_3$ alkylsulfinyl or $C_1$–$C_3$ alkylsulfonyl;

$R_a$ is H or $C_1$–$C_2$ alkyl;

$R_b$ is $C_1$–$C_2$ alkyl;

$R_c$ and $R_k$ are independently $C_1$–$C_3$ alkyl, allyl, $CH_2CH_2Cl$ or $CH_2CH_2OCH_3$;

$R_g$ is H or $C_1$–$C_2$ alkyl;

$R_h$ is $CH_3$;

$R_i$ is $C_1$–$C_2$ alkyl; and $R_j$ is $C_1$–$C_2$ alkyl.

37. A compound of claim 36 where

A is A-1;

X is $CH_3$, $OCH_3$, $OCH_2CH_3$ or $OCH_2CF_3$; and

Y is $CH_3$, $OCH_3$, $C_2H_5$, $CH_2OCH_3$, $NHCH_3$ or $CH(OCH_3)_2$.

38. A compound of claim 18 where $Q_1$ is $ER_2$,

$C_1$–$C_2$ alkyl substituted with $R_8$, CN, $SO_2NH$-$C_1$–$C_2$ alkyl, $SO_2NH$cyclopropyl or

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;

$R_5$ and $R_6$ are independently $CH_3$, $OCH_3$ or $SCH_3$;

$R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and $R_9$ is H, $C_1$–$C_2$ alkyl or $C_2$–$C_3$ cyanoalkyl.

39. A compound of claim 38 where $Q_1$ is $ER_2$, $C_1$–$C_2$ alkyl substituted with $R_8$, CN or $SO_2NHC_1$–$C_2$ alkyl;

E is S or $SO_2$;

$R_2$ is $C_1$–$C_2$ alkyl substituted with $R_8$ or $C_1$–$C_2$ haloalkyl;

$R_8$ is $CH_3O$, $CH_3CH_2O$, $CH_3S$, $CH_3SO_2$, $SO_2N(CH_3)_2$ or $CO_2CH_3$;

$Q_2$ is $SO_2NR_iR_j$, $CO_2R_k$, $C(O)NR_mR_n$, $C_1$–$C_3$ alkylthio, $C_1$–$C_3$ alkylsulfinyl or $C_1$–$C_3$ alkylsulfonyl;

$R_a$ is H or $C_1$–$C_2$ alkyl;

$R_b$ is $C_1$–$C_2$ alkyl;

$R_c$ and $R_k$ are independently $C_1$–$C_3$ alkyl, allyl, $CH_2CH_2Cl$ or $CH_2CH_2OCH_3$;

$R_g$ is H or $C_1$–$C_2$ alkyl;

$R_h$ is $CH_3$;

$R_i$ is $C_1$–$C_2$ alkyl; and $R_j$ is $C_1$–$C_2$ alkyl.

40. A compound of claim 39 where

A is A-1;

X is $CH_3$, $OCH_3$, $OCH_2CH_3$ or $OCH_2CF_3$; and

Y is $CH_3$, $OCH_3$, $C_2H_5$, $CH_2OCH_3$, $NHCH_3$ or $CH(OCH_3)_2$.

41. A compound of claim 19 where $Q_1$ is $ER_2$,

$C_1$–$C_2$ alkyl substituted with $R_8$, CN, $SO_2NH$-$C_1$–$C_2$ alkyl, $SO_2NH$cyclopropyl or

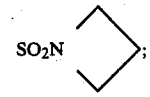

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;

$R_5$ and $R_6$ are independently $CH_3$, $OCH_3$ or $SCH_3$;

$R_8$ is $OR_9$, $C_1$–$C_2$ alkylthio, $C_1$–$C_2$ alkylsulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and $R_9$ is H, $C_1$–$C_2$ alkyl or $C_2$–$C_3$ cyanoalkyl.

42. A compound of claim 41 where $Q_1$ is $ER_2$, $C_1$–$C_2$ alkyl substituted with $R_8$, CN or $SO_2NHC_1$–$C_2$ alkyl;

E is S or $SO_2$;

$R_2$ is $C_1$–$C_2$ alkyl substituted with $R_8$ or $C_1$–$C_2$ haloalkyl;

$R_8$ is $CH_3O$, $CH_3CH_2O$, $CH_3S$, $CH_3SO_2$, $SO_2N(CH_3)_2$ or $CO_2CH_3$;

$Q_2$ is $SO_2NR_iR_j$, $CO_2R_k$, $C(O)NR_mR_n$, $C_1$–$C_3$ alkylthio, $C_1$–$C_3$ alkylsulfinyl or $C_1$–$C_3$ alkylsulfonyl;

$R_a$ is H or $C_1$–$C_2$ alkyl;

$R_b$ is $C_1$–$C_2$ alkyl;

$R_c$ and $R_k$ are independently $C_1$–$C_3$ alkyl, allyl, $CH_2CH_2Cl$ or $CH_2CH_2OCH_3$;

$R_g$ is H or $C_1$–$C_2$ alkyl;

$R_h$ is $CH_3$;

$R_i$ is $C_1$–$C_2$ alkyl; and $R_j$ is $C_1$–$C_2$ alkyl.

43. A compound of claim 42 where

A is A-1;

X is $CH_3$, $OCH_3$, $OCH_2CH_3$ or $OCH_2CF_3$; and

Y is $CH_3$, $OCH_3$, $C_2H_5$, $CH_2OCH_3$, $NHCH_3$ or $CH(OCH_3)_2$.

44. A compound of claim 20 where $Q_1$ is $ER_2$,

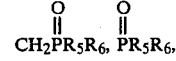

$C_1$–$C_2$ alkyl substituted with $R_8$, CN, $SO_2NH$-$C_1$–$C_2$ alkyl, $SO_2NH$cyclopropyl or

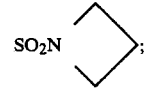

$R_2$ is $C_1$–$C_3$ alkyl substituted with $R_8$, $C_1$–$C_3$ haloalkyl, $C_2$–$C_3$ haloalkenyl or $C_3$–$C_4$ alkynyl;

$R_5$ and $R_6$ are independently $CH_3$, $OCH_3$ or $SCH_3$;

$R_8$ is $OR_9$, $C_1$–$C_2$ alkylthio, $C_1$–$C_2$ alkysulfinyl, $C_1$–$C_2$ alkylsulfonyl, $CO_2(C_1$–$C_2$ alkyl), $SO_2N(C_1$–$C_2$ alkyl)$_2$, $C(O)CH_3$, CN or $C(O)N(CH_3)_2$; and $R_9$ is H, $C_1$–$C_2$ alkyl or $C_2$–$C_3$ cyanoalkyl.

45. A compound of claim 44 where $Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

46. A compound of claim 45 where
A is A-1;
X is $CH_3$, $OCH_3$, $OCH_2CH_3$ or $OCH_2CF_3$; and
Y is $CH_3$, $OCH_3$, $C_2H_5$, $CH_2OCH_3$, $NHCH_3$ or $CH(OCH_3)_2$.

47. A compound of claim 21 where
$Q_1$ is $ER_2$,

$C_1$-$C_2$ alkyl substituted with $R_8$, CN, $SO_2NH$-$C_1$-$C_2$ alkyl, $SO_2NH$cyclopropyl or

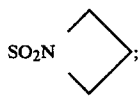

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

48. A compound of claim 47 where
$Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

49. A compound of claim 48 where
A is A-1;
X is $CH_3$, $OCH_3$, $OCH_2CH_3$ or $OCH_2CF_3$; and
Y is $CH_3$, $OCH_3$, $C_2H_5$, $CH_2OCH_3$, $NHCH_3$ or $CH(OCH_3)_2$.

50. A compound of claim 22 where
$Q_1$ is $ER_2$,

$C_1$-$C_2$ alkyl substituted with $R_8$, CN, $SO_2NH$-$C_1$-$C_2$ alkyl, $SO_2NH$cyclopropyl or

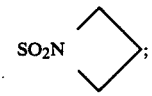

$R_2$ is $C_1$-$C_3$ alkyl substituted with $R_8$, $C_1$-$C_3$ haloalkyl, $C_2$-$C_3$ haloalkenyl or $C_3$-$C_4$ alkynyl;
$R_5$ and $R_6$ are independently $CH_3$, $OCH_3$ or $SCH_3$;
$R_8$ is $OR_9$, $C_1$-$C_2$ alkylthio, $C_1$-$C_2$ alkylsulfinyl, $C_1$-$C_2$ alkylsulfonyl, $CO_2(C_1$-$C_2$ alkyl), $SO_2N(C_1$-$C_2$ alkyl)$_2$, $C(O)CH_3$, CN or $C(O)N(CH_3)_2$; and
$R_9$ is H, $C_1$-$C_2$ alkyl or $C_2$-$C_3$ cyanoalkyl.

51. A compound of claim 50 where
$Q_1$ is $ER_2$, $C_1$-$C_2$ alkyl substituted with $R_8$, CN or $SO_2NHC_1$-$C_2$ alkyl;
E is S or $SO_2$;
$R_2$ is $C_1$-$C_2$ alkyl substituted with $R_8$ or $C_1$-$C_2$ haloalkyl;
$R_8$ is $CH_3O$, $CH_3CH_2O$, $CH_3S$, $CH_3SO_2$, $SO_2N(CH_3)_2$ or $CO_2CH_3$;
$Q_2$ is $SO_2NR_iR_j$, $CO_2R_k$, $C(O)NR_mR_n$, $C_1$-$C_3$ alkylthio, $C_1$-$C_3$ alkylsulfinyl or $C_1$-$C_3$ alkylsulfonyl;
$R_a$ is H or $C_1$-$C_2$ alkyl;
$R_b$ is $C_1$-$C_2$ alkyl;
$R_c$ and $R_k$ are independently $C_1$-$C_3$ alkyl, allyl, $CH_2CH_2Cl$ or $CH_2CH_2OCH_3$;
$R_g$ is H or $C_1$-$C_2$ alkyl;
$R_h$ is $CH_3$;
$R_i$ is $C_1$-$C_2$ alkyl; and
$R_j$ is $C_1$-$C_2$ alkyl.

52. A compound of claim 51 where
A is A-1;
X is $CH_3$, $OCH_3$, $OCH_2CH_3$ or $OCH_2CF$; and
Y is $CH_3$, $OCH_3$, $C_2H_5$, $CH_2OCH_3$, $NHCH_3$ or $CH(OCH_3)_2$.

53. The compound of claim 1 which is N-[(4-methoxy-6-methyl-1,3,5-triazin-2-yl)aminocarbonyl]-2-(methoxymethyl)-3-thiophenesulfonamide.

54. A composition suitable for controlling the growth of undesired vegetation which comprises an effective amount of a compound of claim 1 and at least one of the following: surfactant, solid or liquid diluent.

55. A composition suitable for controlling the growth of undesired vegetation which comprises an effective amount of a compound of claim 2 and at least one of the following: surfactant, solid or liquid diluent.

56. A composition suitable for controlling the growth of undesired vegetation which comprises an effective amount of a compound of claim 3 and at least one of the following: surfactant, solid or liquid diluent.

57. A composition suitable for controlling the growth of undesired vegetation which comprises an effective amount of a compound of claim 4 and at least one of the following: surfactant, solid or liquid diluent.

58. A composition suitable for controlling the growth of undesired vegetation which comprises an effective amount of a compound of claim 5 and at least one of the following: surfactant, solid or liquid diluent.

59. A composition suitable for controlling the growth of undesired vegetation which comprises an effective amount of a compound of claim 6 and at least one of the following: surfactant, solid or liquid diluent.

60. A composition suitable for controlling the growth of undesired vegetation which comprises an effective amount of a compound of claim 7 and at least one of the following: surfactant, solid or liquid diluent.

61. A composition suitable for controlling the growth of undesired vegetation which comprises an effective amount of a compound of claim 8 and at least one of the following: surfactant, solid or liquid diluent.

62. A composition suitable for controlling the growth of undesired vegetation which comprises an effective amount of a compound of claim 9 and at least one of the following: surfactant, solid or liquid diluent.

63. A composition suitable for controlling the growth of undesired vegetation which comprises an effective amount of a compound of claim 10 and at least one of the following: surfactant, solid or liquid diluent.

64. A composition suitable for controlling the growth of undesired vegetation which comprises an effective amount of a compound of claim 11 and at least one of the following: surfactant, solid or liquid diluent.

65. A composition suitable for controlling the growth of undesired vegetation which comprises an effective amount of a compound of claim 53 and at least one of the following: surfactant, solid or liquid diluent.

66. A method for controlling the growth of undesired vegetation which comprises applying to the locus to be protected an effective amount of a compound of claim 1.

67. A method for controlling the growth of undesired vegetation which comprises applying to the locus to be protected an effective amount of a compound of claim 2.

68. A method for controlling the growth of undesired vegetation which comprises applying to the locus to be protected an effective amount of a compound of claim 3.

69. A method for controlling the growth of undesired vegetation which comprises applying to the locus to be protected an effective amount of a compound of claim 4.

70. A method for controlling the growth of undesired vegetation which comprises applying to the locus to be protected an effective amount of a compound of claim 5.

71. A method for controlling the growth of undesired vegetation which comprises applying to the locus to be protected an effective amount of a compound of claim 6.

72. A method for controlling the growth of undesired vegetation which comprises applying to the locus to be protected an effective amount of a compound of claim 7.

73. A method for controlling the growth of undesired vegetation which comprises applying to the locus to be protected an effective amount of a compound of claim 8.

74. A method for controlling the growth of undesired vegetation which comprises applying to the locus to be protected an effective amount of a compound of claim 9.

75. A method of controlling the growth of undesired vegetation which comprises applying to the locus to be protected an effective amount of a compound of claim 10.

76. A method for controlling the growth of undesired vegetation which comprises applying to the locus to be protected an effective amount of a compound of claim 11.

77. A method for controlling the growth of undesired vegetation which comprises applying to the locus to be protected an effective amount of a compound of claim 53.

* * * * *